US008420784B2

(12) United States Patent
Kato et al.

(10) Patent No.: US 8,420,784 B2
(45) Date of Patent: Apr. 16, 2013

(54) INTERLEUKIN 10 RECEPTOR, (IL-10R) ANTIBODIES

(75) Inventors: Shinichiro Kato, Tokyo (JP); Rachel Soloff Nugent, La Jolla, CA (US); Tomoyuki Tahara, Tokyo (JP); Paul Rogers, La Jolla, CA (US); Aihua Song, La Jolla, CA (US)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 0 days.

(21) Appl. No.: 12/994,789

(22) PCT Filed: May 27, 2009

(86) PCT No.: PCT/US2009/045322
§ 371 (c)(1),
(2), (4) Date: Nov. 26, 2010

(87) PCT Pub. No.: WO2009/154995
PCT Pub. Date: Dec. 23, 2009

(65) Prior Publication Data
US 2011/0144312 A1 Jun. 16, 2011

Related U.S. Application Data

(60) Provisional application No. 61/056,299, filed on May 27, 2008.

(51) Int. Cl.
*A61K 39/395* (2006.01)
*C07K 16/28* (2006.01)
*C12P 21/08* (2006.01)
*G01N 33/53* (2006.01)

(52) U.S. Cl.
USPC .................. 530/387.1; 530/388.1; 530/389.1; 435/7.2; 424/139.1; 424/144.1

(58) Field of Classification Search .................. None
See application file for complete search history.

(56) References Cited

U.S. PATENT DOCUMENTS

| 2003/0040044 A1 | 2/2003 | Heavner et al. |
| 2005/0054019 A1 | 3/2005 | Michaud et al. |
| 2005/0196386 A1 | 9/2005 | Blazar et al. |
| 2005/0287150 A1 | 12/2005 | Ambrosino et al. |

FOREIGN PATENT DOCUMENTS

| EP | 1439223 A1 | 7/2004 |
| WO | 00/56356 A2 | 9/2000 |
| WO | 2004/067697 A2 | 8/2004 |

OTHER PUBLICATIONS

Paul, Fundamental Immunology, 3rd Edition, 1993, pp. 292-295.*
Brummell et al. Biochemistry, 1993, vol. 32, pp. 1180-1187.*
Kobayashi et al. Protein Engineering, 1999, vol. 12, pp. 879-844.*
Coleman, Research in Immunol, 1994, vol. 145, pp. 33-36.*
International Search Report (PCT/ISA/210) issued in PCT/US09/045322, dated May 25, 2010.
Written Opinion of the International Searching Authority (PCT/ISA/237) issued in PCT/US09/45322, dated May 25, 2010.
Stella Redpath, et al.; "Immune Checkpoints in Viral Latency"; Annu. Rev. Microbiol, 2001 vol. 55; pp. 531-560.
Raymond P. Donnelly, et al.; "The Interleukin-10 Signal Transduction Pathway and Regulation of Gene Expression in Mononeuclear Phagocytes"; Journal of Interferon and Cytokine Research, 1999; vol. 19; pp. 563-573.
Anne-Marie O'Farrell, et al; " IL-10 inhibits macrophage activation and proliferation by distinct signaling mechanisms evidence for Stat3-dependent and -independent pathways"; the EMBO Journal 1998; vol. 17 No. 4; pp. 1006-1018.
Kevin W. Moore, et al.; "Interleukin-10 and the Interleukin-10 Receptor"; Annu. Rev. Immunol 2001; vol. 19; pp. 683-765.
Ali Akbar Rahim Rahimi, et al.; "STAT-1 Mediates the Stimulatory Effect of IL-10 on CD14 Expression in Human Monocytic Cells"; J Immunol 2005; vol. 174; pp. 7823-7832.
Peter Brossart, et al.; "Tumor Necrosis Factor α and CD40 Ligand Antagonize the Inhibitory Effects of Interleukin 10 on T-Cell Stimulatory Capacity of Dendritic Cells"; Cancer Research 60, 4485-92 (2000).
Stella Redpath; "Hijacking and exploitation if IL-10 by intracellular pathogens"; Trends in Microbiology vol. 9 No. 2; Feb. 2001; pp. 86-92.
Antonio G. Castro, et al.; "anti-Interleukin 10 Receptor Monoclonal Antibody is an Adjuvant for T Helper Cell Type 1 Responses to Soluble Antigen Only in the Presence of Lipopolysaccharide"; Journal Exp. Med. Nov. 20, 2000; vol. 192 No. 10; pp. 1529-1534.
Henry W. Murray; "Interleukin 10 receptor blockade-pentavalent antimony treatment in experimental visceral leishmaniasis" ACTA Tropica 2005, vol. 93; pp. 295-301.
David Brooks, et al.; "Interleukin-10 determines viral clearance or persistence in vivo"; Nature Medicine Nov. 2006; vol. 12 No. 11; pp. 1301-1309.
Mette Ejrnaes, et al.; "Resolution of a chronic viral infection after interleukin-10 receptor blockade" J. Exp. Med. Oct. 30, 2006; vol. 203 No. 11; pp. 2461-2472.
Mette Ejrnaes, et al.; "Cure of chronic viral infection and virus-induced type 1 diabetes by neutralizing antibodies"; Clinical & Development Immunology, 2006; vol. 13(2-4); pp. 337-347.
Mette Ejrnaes, et al; "Cure of chronic viral infection by neutralizing antibody treatment"; Autoimmunity Reviews 2007, vol. 6; pp. 267-271.

(Continued)

*Primary Examiner* — Bridget E Bunner
*Assistant Examiner* — Fozia Hamud
(74) *Attorney, Agent, or Firm* — Sughrue Mion, PLLC

(57) ABSTRACT

The invention relates to IL-1O Receptor alpha (IL-1ORα) antibodies and subsequences thereof, human and humanized IL-10 Receptor alpha (IL-IORα) antibodies and subsequences thereof, isolated and purified IL-10 Receptor alpha (IL-1ORα) antibodies and subsequences thereof, compositions including IL-10 Receptor alpha (IL-1ORα) antibodies and subsequences thereof, and methods that employ IL-10 Receptor alpha (IL-1ORα) antibodies and subsequences thereof. The invention includes among other things, methods of treating a pathogen infection, pathogen reactivation, and methods of vaccinating or immunizing against a pathogen infection, which include, for example, administering an IL-10 Receptor alpha (IL-1ORα) antibody or subsequence, to treat a pathogen infection, pathogen reactivation or for vaccination or immunization.

13 Claims, 13 Drawing Sheets

OTHER PUBLICATIONS

David G. Brooks, et al.; "IL-10 blockade resurrects T cell activity and eliminates a persistent viral infection"; the Journal of Immunology, 2007; vol. 178, Abstract.

David G. Brooks, et al; "IL-10 blockade facilitates DNA vaccine-induced T cell responses and enhances clearance of persistent virus infection"; J. Exp. Med. Mar. 2008; vol. 205 No. 3; pp. 533-541.

L. Geng, et al.; "B7-H1 expression is upregulated in peripheral blood CD14+ Monocytes of patients with chronic hepatitis B virus infection, which correlates with higher serum IL-10 levels."; Journal of Viral Hepatitis 2006; vol. 13, pp. 725-733.

Alain P. Vicari; et al.; "Interleukin-10 in viral diseases and cancer: existing in labyrinth"; Immunological Reviews 2004, vol. 202; pp. 223-236.

Eirini I. Rigopoulou, et al., "Blocking of IL-10 Receptor—A Novel Approach to Stimulate Virus-specific T Cell reactivity in Chronic Hepatitis C virus (HCV) Infection," ASSLD Abstracts:#577, 304A, Oct. 2000.

Eirini I. Rigopoulou, et al.; "Lamivudine Plus Interleukin-12 Combination Therapy in Chronic Hepatitis B: Antiviril and Immunological Activity"; Heptatology 2005; vol. 42 No. 5; pp. 1028-1036.

Mario Clerici , et al.; "Role of Interleukin-10 in T Helper Cell Dysfunction in Asymptomatic Individuals Infected with the Human Immunodeficiency Virus"; Journal of Clinical Investigation Inc., 1994; vol. 93; pp. 768-775.

Mark A. Brockman, et al.; "IL-10 is up-regulated in multiple cell types during viremic HIV infection and reversibly inhibits virus-specific T cells"; Blood, Jul. 2009; vol. 114 No. 2; pp. 346-356.

Khusru Asadullah; et al.; "Interleukin-10: An Important Immunoregulatory Cytokine with Major Impact on Psoriasis" Current Drug Targets—Inflammation & Allergy, 2004; vol. 4; pp. 185-192.

Ying Liu, et al.; "The EBV IL-10 Homologue Is a Selective Agonist with Impaired Binding to the II-10 Receptor"; The American Association of Immunologists, 1997; vol. 158; pp. 604-613.

Ulrich Reineke, et al.; "Mapping of the Interleukin-10/Interleukin-10 receptor combining site"; Protein Science 1998, vol. 7; pp. 951-960.

Naoto Yoshino, et al.; "Upgrading of Flow Cytometric Analysis for Absolute Counts, Cytokines and other Antigenic Molecules of Cynomolgus Monkeys (*Macaca fascicularis*) by Using Anti-Human Cross-Reactive Antibodies" Exp Amin. 2000, vol. 49 No. 2, pp. 97-110.

Arnaud Marchant, et al.; "Interleukiin-10 controls interferon-γ and tumor necrosis factor production during experimental endotoxemia"; Eur. Journal Immunol. 1994; vol. 24; pp. 1167-1171.

European Patent Office, Extended Search Report issued Jun. 20, 2012, in counterpart European Application No. 09767307.3 (in the name of Kyowa Hakko Kirin Co., Ltd.).

Levings, Megan K. et al. "Differentiation of Tr1 cells by immature dendritic cells requires IL-10 but not CD25 $^+$CD4$^+$ Tr cells", Blood, Feb. 1, 2005, vol. 105, No. 3, pp. 1162-1169.

Goodier, Martin R. et al. "Lipopolysaccharide Stimulates the Proliferation of Human CD56 $^+$CD3$^-$ NK Cells: A Regulatory Role of Monocytes and IL-10", The Journal of Immunology, 2000, vol. 165, pp. 139-147.

Hulse, Kathryn E. et al. "Targeting Fel d 1 to FcγRl induces a novel variation of the $T_H2$ response in subjects with cat allergy", Journal of Allergy Clinical Immunology, Mar. 1, 2008, vol. 121, No. 3, pp. 756-762.

Rigopoulou, Eirini I. et al. "Blocking of interleukin-10 receptor—a novel approach to stimulate T-helper cell type 1 responses to hepatitis C virus", Clinical Immunology, Oct. 1, 2005, vol. 117, No. 1. pp. 57-64.

Silva, Regina A. et al. "Blocking the Receptor for IL-10 Improves Antimycobacterial Chemotherapy and Vaccination", The Journal of Immunology, Aug. 1, 2001, vol. 167, No. 3, pp. 1535-1541.

Silva, Regina A. et al. "Blocking the Receptor for Interleukin 10 Protects Mice from Lethal Listeriosis", Antimicrobial Agents and Chemotherapy, Apr. 1, 2001, vol. 45, No. 4, pp. 1312-1314.

Vicari, Alain P. et al. "Reversal of Tumor-induced Dendritic Cell Paralysis by CpG Immunostimulatory Oligonucleotide and Anti-Intereukin 10 Receptor Antibody" The Journal of Experimental Medicine, Aug. 19, 2002, vol. 196. No. 4, pp. 541-549.

\* cited by examiner

136C5   136C8   136D29   3F9   37607

A.

B.

C.

SEQUENCE LISTING

```
<160> NUMBER OF SEQ ID NOS: 87

<210> SEQ ID NO 1
<211> LENGTH: 1737
<212> TYPE: DNA
<213> ORGANISM: Homo sapiens

<400> SEQUENCE: 1
atgctgccgt gcctcgtagt gctgctggcg gcgctcctca gcctccgtct tggctcagac      60
gctcatggga cagagctgcc cagccctccg tctgtgtggt ttgaagcaga attttccac     120 cacatcctcc actggacacc catcccaaat cagtctgaaa gtacctgcta tgaagtggca    180
ctcctgaggt atggaataga gtcctggaac tccatctcca actgtagcca gaccctgtcc    240
```

```
tatgacctta ccgcagtgac cttggacctg taccacagca atggctaccg ggccagagtg    300
cgggctgtgg acggcagccg gcactccaac tggaccgtca ccaacacccg cttctctgtg    360
gatgaagtga ctctgacagt tggcagtgtg aacctagaga tccacaatgg cttcatcctc    420
gggaagattc agctacccag gcccaagatg gcccccgcaa atgacacata tgaaagcatc    480
ttcagtcact tccgagagta tgagattgcc attcgcaagg tgccgggaaa cttcacgttc    540
acacacaaga agtaaaaaca tgaaaacttc agcctcctaa cctctggaga agtgggagag    600
ttctgtgtcc aggtgaaacc atctgtcgct tcccgaagta caaggggat gtggtctaaa     660 gaggagtgca tctccctcac caggcagtat ttcaccgtga ccaacgtcat catcttcttt    720
gcctttgtcc tgctgctctc cggagccctc gcctactgcc tggccctcca gctgtatgtg    780
cggcgccgaa agaagctacc cagtgtcctg ctcttcaaga agcccagccc cttcatcttc    840
atcagccagc gtccctcccc agagacccaa gacaccatcc acccgcttga tgaggaggcc    900
tttttgaagg tgtccccaga gctgaagaac ttggacctgc acggcagcac agacagtggc    960
tttggcagca ccaagccatc cctgcagact gaagagcccc agttcctcct ccctgaccct   1020
cacccccagg ctgacagaac gctgggaaac ggggagcccc tgtgctgggg gacagctgc   1080 agtagtggca gcagcaatag cacagacagc gggatctgcc tgcaggagcc cagcctgagc   1140
cccagcacag ggcccacctg ggagcaacag gtggggagca acagcagggg ccaggatgac   1200
agtggcattg acttagttca aaactctgag gccgggctg gggacacaca gggtggctcg    1260
gccttgggcc accacagtcc cccggagcct gaggtgcctg gggaagaaga cccagctgct   1320
gtggcattcc agggttacct gaggcagacc agatgtgctg aagagaaggc aaccaagaca   1380
ggctgcctgg aggaagaatc gcccttgaca gatggccttg cccccaaatt cgggagatgc   1440
ctggttgatg aggcaggctt gcatccacca gccctggcca agggctattt gaaacaggat   1500
cctctagaaa tgactctggc ttcctcaggg gccccaacgg acagtggaa ccagcccact    1560 gaggaatggt cactcctggc cttgagcagc tgcagtgacc tgggaatatc tgactggagc   1620
tttgcccatg accttgcccc tctaggctgt gtggcagccc caggtggtct cctgggcagc   1680
tttaactcag acctggtcac cctgcccctc atctctagcc tgcagtcaag tgagtga      1737
```

<210> SEQ ID NO 2
<211> LENGTH: 578
<212> TYPE: PRT
<213> ORGANISM: Homo sapiens

<400> SEQUENCE: 2

Met Leu Pro Cys Leu Val Val Leu Ala Ala Leu Leu Ser Leu Arg
1               5                   10                  15

Leu Gly Ser Asp Ala His Gly Thr Glu Leu Pro Ser Pro Ser Val
            20                  25                  30

Trp Phe Glu Ala Glu Phe Phe His His Ile Leu His Trp Thr Pro Ile
        35                  40                  45

Pro Asn Gln Ser Glu Ser Thr Cys Tyr Glu Val Ala Leu Leu Arg Tyr
    50                  55                  60

Gly Ile Glu Ser Trp Asn Ser Ile Ser Asn Cys Ser Gln Thr Leu Ser
65                  70                  75                  80

Tyr Asp Leu Thr Ala Val Thr Leu Asp Leu Tyr His Ser Asn Gly Tyr
                85                  90                  95

Arg Ala Arg Val Arg Ala Val Asp Gly Ser Arg His Ser Asn Trp Thr
                100                 105                 110

Val Thr Asn Thr Arg Phe Ser Val Asp Glu Val Thr Leu Thr Val Gly

```
                115                 120                 125
Ser Val Asn Leu Glu Ile His Asn Gly Phe Ile Leu Gly Lys Ile Gln
            130                 135                 140
Leu Pro Arg Pro Lys Met Ala Pro Ala Asn Asp Thr Tyr Glu Ser Ile
145                 150                 155                 160
Phe Ser His Phe Arg Glu Tyr Glu Ile Ala Ile Arg Lys Val Pro Gly
                165                 170                 175
Asn Phe Thr Phe Thr His Lys Lys Val Lys His Glu Asn Phe Ser Leu
            180                 185                 190
Leu Thr Ser Gly Glu Val Gly Glu Phe Cys Val Gln Val Lys Pro Ser
                195                 200                 205
Val Ala Ser Arg Ser Asn Lys Gly Met Trp Ser Lys Glu Glu Cys Ile
            210                 215                 220
Ser Leu Thr Arg Gln Tyr Phe Thr Val Thr Asn Val Ile Ile Phe Phe
225                 230                 235                 240
Ala Phe Val Leu Leu Leu Ser Gly Ala Leu Ala Tyr Cys Leu Ala Leu
                245                 250                 255
Gln Leu Tyr Val Arg Arg Arg Lys Lys Leu Pro Ser Val Leu Leu Phe
            260                 265                 270
Lys Lys Pro Ser Pro Phe Ile Phe Ile Ser Gln Arg Pro Ser Pro Glu
                275                 280                 285
Thr Gln Asp Thr Ile His Pro Leu Asp Glu Glu Ala Phe Leu Lys Val
            290                 295                 300
Ser Pro Glu Leu Lys Asn Leu Asp Leu His Gly Ser Thr Asp Ser Gly
305                 310                 315                 320
Phe Gly Ser Thr Lys Pro Ser Leu Gln Thr Glu Glu Pro Gln Phe Leu
                325                 330                 335
Leu Pro Asp Pro His Pro Gln Ala Asp Arg Thr Leu Gly Asn Gly Glu
            340                 345                 350
Pro Pro Val Leu Gly Asp Ser Cys Ser Ser Gly Ser Ser Asn Ser Thr
                355                 360                 365
Asp Ser Gly Ile Cys Leu Gln Glu Pro Ser Leu Ser Pro Ser Thr Gly
            370                 375                 380
Pro Thr Trp Glu Gln Gln Val Gly Ser Asn Ser Arg Gly Gln Asp Asp
385                 390                 395                 400
Ser Gly Ile Asp Leu Val Gln Asn Ser Glu Gly Arg Ala Gly Asp Thr
                405                 410                 415
Gln Gly Gly Ser Ala Leu Gly His His Ser Pro Pro Glu Pro Glu Val
            420                 425                 430
Pro Gly Glu Glu Asp Pro Ala Ala Val Ala Phe Gln Gly Tyr Leu Arg
            435                 440                 445
Gln Thr Arg Cys Ala Glu Glu Lys Ala Thr Lys Thr Gly Cys Leu Glu
            450                 455                 460
Glu Glu Ser Pro Leu Thr Asp Gly Leu Gly Pro Lys Phe Gly Arg Cys
465                 470                 475                 480
Leu Val Asp Glu Ala Gly Leu His Pro Pro Ala Leu Ala Lys Gly Tyr
                485                 490                 495
Leu Lys Gln Asp Pro Leu Glu Met Thr Leu Ala Ser Ser Gly Ala Pro
            500                 505                 510
Thr Gly Gln Trp Asn Gln Pro Thr Glu Glu Trp Ser Leu Leu Ala Leu
            515                 520                 525
Ser Ser Cys Ser Asp Leu Gly Ile Ser Asp Trp Ser Phe Ala His Asp
            530                 535                 540
```

```
Leu Ala Pro Leu Gly Cys Val Ala Ala Pro Gly Gly Leu Leu Gly Ser
545                 550                 555                 560

Phe Asn Ser Asp Leu Val Thr Leu Pro Leu Ile Ser Ser Leu Gln Ser
                565                 570                 575

Ser Glu

<210> SEQ ID NO 3
<211> LENGTH: 1398
<212> TYPE: DNA
<213> ORGANISM: Homo sapiens

<400> SEQUENCE: 3
atggtgccgt gcctcgtagt gctgctggcg gcgctcctca gcctccgtct tggctcagac      60
gctcatggga cagagctgcc cagccctccg tctgtgtggt ttgaagcaga atttttccac     120
cacatcctcc actggacacc catcccaaat cagtctgaaa gtacctgcta tgaagtggcg     180
ctcctgaggt atggaataga gtcctggaac tccatctcca actgtagcca gaccctgtcc     240
tatgacctta ccgcagtgac cttggacctg taccacagca atggctaccg ggccagagtg     300
cgggctgtgg acggcagccg gcactccaac tggaccgtca ccaacacccg cttctctgtg     360
gatgaagtga ctctgacagt tggcagtgtg aacctagaga tccacaatgg cttcatcctc     420
gggaagattc agctacccag gcccaagatg gccccgcga atgacacata tgaaagcatc     480
ttcagtcact tccgagagta tgagattgcc attcgcaagg tgccgggaaa cttcacgttc     540
acacacaaga agtaaaaca tgaaaacttc agcctcctaa cctctggaga agtgggagag     600
ttctgtgtcc aggtgaaacc atctgtcgct tcccgaagta caaggggat gtggtctaaa     660 gaggagtgca tctccctcac caggcagtat ttcaccgtga ccaacagatc ttgtgacaaa     720
actcacacat gcccaccgtg cccagcacct gaactcctgg ggggaccgtc agtcttcctc     780
ttccccccaa aacccaagga caccctcatg atctcccgga cccctgaggt cacatgcgtg     840
gtggtggacg tgagccacga agaccctgag gtcaagttca actggtacgt ggacggcgtg     900
gaggtgcata atgccaagac aaagccgcgg gaggagcagt acaacagcac gtaccgtgtg     960
gtcagcgtcc tcaccgtcct gcaccaggac tggctgaatg gcaaggagta caagtgcaag    1020
gtctccaaca aagcccctccc agcccccatc gagaaaacca tctccaaagc caagggcag    1080 ccccgagaac cacaggtgta caccctgccc ccatcccggg atgagctgac caagaaccag    1140
gtcagcctga cctgcctggt caaaggcttc tatcccagcg acatcgccgt ggagtgggag    1200
agcaatgggc agccggagaa caactacaag accacgcctc ccgtgctgga ctccgacggc    1260
tccttcttcc tctacagcaa gctcaccgtg gacaagagca ggtggcagca ggggaacgtc    1320
ttctcatgct ccgtgatgca tgaggctctg cacaaccact acacgcagaa gagcctctcc    1380
ctgtctccgg gtaaatga                                                  1398

<210> SEQ ID NO 4
<211> LENGTH: 465
<212> TYPE: PRT
<213> ORGANISM: Homo sapiens

<400> SEQUENCE: 4

Met Val Pro Cys Leu Val Val Leu Leu Ala Ala Leu Leu Ser Leu Arg
1               5                   10                  15

Leu Gly Ser Asp Ala His Gly Thr Glu Leu Pro Ser Pro Pro Ser Val
                20                  25                  30

Trp Phe Glu Ala Glu Phe Phe His His Ile Leu His Trp Thr Pro Ile
            35                  40                  45
```

-continued

```
Pro Asn Gln Ser Glu Ser Thr Cys Tyr Glu Val Ala Leu Leu Arg Tyr
    50                  55                  60

Gly Ile Glu Ser Trp Asn Ser Ile Ser Asn Cys Ser Gln Thr Leu Ser
65                  70                  75                  80

Tyr Asp Leu Thr Ala Val Thr Leu Asp Leu Tyr His Ser Asn Gly Tyr
                85                  90                  95

Arg Ala Arg Val Arg Ala Val Asp Gly Ser Arg His Ser Asn Trp Thr
                100                 105                 110

Val Thr Asn Thr Arg Phe Ser Val Asp Glu Val Thr Leu Thr Val Gly
                115                 120                 125

Ser Val Asn Leu Glu Ile His Asn Gly Phe Ile Leu Gly Lys Ile Gln
            130                 135                 140

Leu Pro Arg Pro Lys Met Ala Pro Ala Asn Asp Thr Tyr Glu Ser Ile
145                 150                 155                 160

Phe Ser His Phe Arg Glu Tyr Glu Ile Ala Ile Arg Lys Val Pro Gly
                165                 170                 175

Asn Phe Thr Phe Thr His Lys Lys Val Lys His Glu Asn Phe Ser Leu
                180                 185                 190

Leu Thr Ser Gly Glu Val Gly Glu Phe Cys Val Gln Val Lys Pro Ser
            195                 200                 205

Val Ala Ser Arg Ser Asn Lys Gly Met Trp Ser Lys Glu Glu Cys Ile
210                 215                 220

Ser Leu Thr Arg Gln Tyr Phe Thr Val Thr Asn Arg Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
                260                 265                 270

Arg Thr Pro Glu Val Thr Cys Val Val Asp Val Ser His Glu Asp
            275                 280                 285

Pro Glu Val Lys Phe Asn Trp Tyr Val Asp Gly Val Glu Val His Asn
            290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
                340                 345                 350

Thr Ile Ser Lys Ala Lys Gly Gln Pro Arg Glu Pro Gln Val Tyr Thr
            355                 360                 365

Leu Pro Pro Ser Arg Asp Glu Leu Thr Lys Asn Gln Val Ser Leu Thr
370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
                420                 425                 430

Ser Arg Trp Gln Gln Gly Asn Val Phe Ser Cys Ser Val Met His Glu
            435                 440                 445

Ala Leu His Asn His Tyr Thr Gln Lys Ser Leu Ser Leu Ser Pro Gly
450                 455                 460

Lys
```

<210> SEQ ID NO 5
<211> LENGTH: 1398
<212> TYPE: DNA
<213> ORGANISM: Artificial Sequence
<220> FEATURE:
<223> OTHER INFORMATION: Description of Artificial Sequence: Artificial Fusion construct

<400> SEQUENCE: 5

| | | | | | |
|---|---|---|---|---|---|
| atggtgccgt | gcctcgtagt | gctgctggcg | gcgctcctca | gcctccgtct | tggctcagac | 60 |
| gctcatggga | cagagctgcc | cagccctccg | tctgtgtggt | ttgaagcaga | attttccac | 120 |
| cacatcctcc | actggacacc | catcccaaat | cagtctgaaa | gtacctgcta | tgaagtggca | 180 |
| ctcctgaggt | atggaataga | gtcctggaac | tccatctcca | actgtagcca | gaccctgtcc | 240 |
| tatgacctta | ccgcagtgac | cttggacctg | taccgcagca | atggctaccg | ggccagagtg | 300 |
| cgggctgtgg | acggcagccg | gcactccaac | tggaccgtca | ccaacacccg | cttctctgtg | 360 |
| gatgaagtga | ctctgacagt | tggcagtgtg | aacctagaga | tccacaatgg | cttcatcctc | 420 |
| gggaagattc | agctacccag | gcccaagatg | gcccccgcaa | atgacacata | tgaaagcatc | 480 |
| ttcagtcact | ccgagagta | tgagattgcc | attcgcaagg | tgccgggaaa | cttcacgttc | 540 |
| acacacaaga | agtaaaaaca | tgaaaacttc | agcctcctaa | cctctggaga | agtgggagag | 600 |
| ttctgtgtcc | aggtgaaacc | atctgtcgct | tcccgaagta | caaggggat | gtggtctaaa | 660 |
| gaggagtgcg | tctccctcac | caggcagtat | ttcaccgtga | ccaacagatc | ttgtgacaaa | 720 |
| actcacacat | gcccaccgtg | cccagcacct | gaactcctgg | ggggaccgtc | agtcttcctc | 780 |
| ttccccccaa | aacccaagga | caccctcatg | atctcccgga | cccctgaggt | cacatgcgtg | 840 |
| gtggtggacg | tgagccacga | agaccctgag | gtcaagttca | actggtacgt | ggacggcgtg | 900 |
| gaggtgcata | atgccaagac | aaagccgcgg | gaggagcagt | acaacagcac | gtaccgtgtg | 960 |
| gtcagcgtcc | tcaccgtcct | gcaccaggac | tggctgaatg | gcaaggagta | caagtgcaag | 1020 |
| gtctccaaca | aagccctccc | agcccccatc | gagaaaacca | tctccaaagc | caagggcag | 1080 |
| ccccgagaac | cacaggtgta | caccctgccc | ccatcccggg | aggagatgac | caagaaccag | 1140 |
| gtcagcctga | cctgcctggt | caaaggcttc | tatcccagcg | acatcgccgt | ggagtgggag | 1200 |
| agcaatgggc | agccggagaa | caactacaag | accacgcctc | ccgtgctgga | ctccgacggc | 1260 |
| tccttcttcc | tctatagcaa | gctcaccgtg | gacaagagca | ggtggcagca | ggggaacgtc | 1320 |
| ttctcatgct | ccgtgatgca | tgaggctctg | cacaaccact | acacgcagaa | gagcctctcc | 1380 |
| ctgtctccgg | gtaaatga | | | | | 1398 |

<210> SEQ ID NO 6
<211> LENGTH: 465
<212> TYPE: PRT
<213> ORGANISM: Artificial Sequence
<220> FEATURE:
<223> OTHER INFORMATION: Description of Artificial Sequence: Synthetic Fusion construct

<400> SEQUENCE: 6

Met Val Pro Cys Leu Val Val Leu Leu Ala Ala Leu Leu Ser Leu Arg
1               5                   10                  15

Leu Gly Ser Asp Ala His Gly Thr Glu Leu Pro Ser Pro Pro Ser Val
                20                  25                  30

Trp Phe Glu Ala Glu Phe Phe His His Ile Leu His Trp Thr Pro Ile
            35                  40                  45

-continued

```
Pro Asn Gln Ser Glu Ser Thr Cys Tyr Glu Val Ala Leu Leu Arg Tyr
     50                  55                  60

Gly Ile Glu Ser Trp Asn Ser Ile Ser Asn Cys Ser Gln Thr Leu Ser
 65                  70                  75                  80

Tyr Asp Leu Thr Ala Val Thr Leu Asp Leu Tyr Arg Ser Asn Gly Tyr
                 85                  90                  95

Arg Ala Arg Val Arg Ala Val Asp Gly Ser Arg His Ser Asn Trp Thr
                100                 105                 110

Val Thr Asn Thr Arg Phe Ser Val Asp Glu Val Thr Leu Thr Val Gly
             115                 120                 125

Ser Val Asn Leu Glu Ile His Asn Gly Phe Ile Leu Gly Lys Ile Gln
         130                 135                 140

Leu Pro Arg Pro Lys Met Ala Pro Ala Asn Asp Thr Tyr Glu Ser Ile
145                 150                 155                 160

Phe Ser His Phe Arg Glu Tyr Glu Ile Ala Ile Arg Lys Val Pro Gly
                 165                 170                 175

Asn Phe Thr Phe Thr His Lys Lys Val Lys His Glu Asn Phe Ser Leu
                180                 185                 190

Leu Thr Ser Gly Glu Val Gly Glu Phe Cys Val Gln Val Lys Pro Ser
            195                 200                 205

Val Ala Ser Arg Ser Asn Lys Gly Met Trp Ser Lys Glu Glu Cys Val
        210                 215                 220

Ser Leu Thr Arg Gln Tyr Phe Thr Val Thr Asn Arg Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Asp Val Ser His Glu Asp
        275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Arg Glu Glu Met Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

Lys
```

<210> SEQ ID NO 7
<211> LENGTH: 1743
<212> TYPE: DNA
<213> ORGANISM: Cynomolgus

<400> SEQUENCE: 7

| | | | | | |
|---|---|---|---|---|---|
| atgctgccgt | gcctcgtagt | gctgctggcg | gcgttcctca | gtcgccgtct | tggctcagac | 60 |
| gctcatggga | cagagctgcc | cagcccgcca | tctgtgtggt | ttgaagcaga | attttccac | 120 |
| cacatcctcc | actggacacc | catcccaaat | cagtctgaaa | gtacctgcta | tgaagtggca | 180 |
| ctcctgaggt | atggaacagg | gcgctggaac | tccatctcca | actgtagcca | ggccctgtcc | 240 |
| tatgacctta | ccgcggtgac | cttggacctg | taccgcagca | atggctaccg | ggccagagtg | 300 |
| cgtgctgtgg | acggcagccg | gcactccaac | tggaccgtca | ccaacacccg | cttctctttg | 360 |
| gatgaagtga | ctctgacagt | tggcagtgtg | aagctagaga | tccacaatgg | cttcatcctt | 420 |
| gggaagattc | agccccccag | gcccaagatg | gctcctgcaa | atgacacata | tgaaagcatc | 480 |
| ttcagtcact | tccgagagta | tgagattgcc | attcgcaagg | tgccgggaaa | ctttacgttc | 540 |
| acacacaaga | agtaaaaca | tgaaaacttc | agcctcctaa | cctctggaga | agtgggagag | 600 |
| ttctgtgtcc | aggtgaaacc | atctgtcact | tcccgaacca | caaggggat | gtggtctaaa | 660 |
| gaggagtgcg | tctccctcac | caggcagtat | ttcaccgtga | ccaacgtcat | catcttcttt | 720 |
| gcctttgtcc | tgctgctctc | cggagccctg | gcctactgcc | tggccctcca | gctgtatgtg | 780 |
| cggcgccgaa | agaagctgcc | cagggtcctg | ctcttcaaga | agcccaacgc | cttcatcttc | 840 |
| atcagccagc | gtcccteccc | agagacccaa | gacaccatcc | acccgcttga | tgaggaggcc | 900 |
| ttcctgaagg | tgtcaccaga | gctgaggaac | tcggacctgc | atggcagcac | ggacagtggc | 960 |
| tttggcagta | ccaaaccatc | cctgcagacc | gaagagcccc | agttcctcct | ccctgaccct | 1020 |
| cacccccagg | ctgacagaac | gctgggaaac | ggagagcccc | tgagctggg | cgacagctgc | 1080 |
| agtagtggca | gcagcaatag | cacggacagc | gggatctgcc | tgcaggagcc | cagcctgagc | 1140 |
| cccagcactg | ggcccacctg | ggagcagcag | gtggggagcg | acagcagggg | ccaggatgac | 1200 |
| agtggcattg | gcctagttca | aaactctgag | ggccaggctg | gggacacaca | gggtggctca | 1260 |
| gccttgggcc | acgacagtcc | cccagagcct | gaggtgcctg | cggaacaaga | cccaactgct | 1320 |
| gtggtattcc | gggctacct | gaggcagacc | agatgcgctg | aggagaaggc | aaccaagaca | 1380 |
| ggctgcctgg | aggaagaatt | gcccctgaca | ggtggccttg | gcccaaatt | cagggatgc | 1440 |
| ctggatgacg | aagcaggctt | gcatccatca | gccctggcca | agggctattt | gaaacaggat | 1500 |
| cccctagaaa | tgactctggc | ttcctcgggg | gccccagctg | aacagtggaa | ccagcccact | 1560 |
| gaggaatggt | cactcctggc | cttgagcagc | tgcagtgacc | tgggaacatc | tgactggagc | 1620 |
| tttgcccatg | accttgcccc | tctaggctgt | gtggcagccc | cagatggtct | cctgggcagc | 1680 |
| tttaactcag | acctggtcac | cctgcccctc | atctctagcc | tgcactcgag | tgactcgagc | 1740 |
| tga | | | | | | 1743 |

<210> SEQ ID NO 8
<211> LENGTH: 580
<212> TYPE: PRT
<213> ORGANISM: Cynomolgus Macaque

<400> SEQUENCE: 8

Met Leu Pro Cys Leu Val Val Leu Leu Ala Ala Phe Leu Ser Arg Arg
1               5                   10                  15

Leu Gly Ser Asp Ala His Gly Thr Glu Leu Pro Ser Pro Pro Ser Val
            20                  25                  30

Trp Phe Glu Ala Glu Phe Phe His His Ile Leu His Trp Thr Pro Ile
            35                  40                  45

Pro Asn Gln Ser Glu Ser Thr Cys Tyr Glu Val Ala Leu Leu Arg Tyr
        50                  55                  60

Gly Thr Gly Arg Trp Asn Ser Ile Ser Asn Cys Ser Gln Ala Leu Ser
65                  70                  75                  80

Tyr Asp Leu Thr Ala Val Thr Leu Asp Leu Tyr Arg Ser Asn Gly Tyr
                85                  90                  95

Arg Ala Arg Val Arg Ala Val Asp Gly Ser Arg His Ser Asn Trp Thr
            100                 105                 110

Val Thr Asn Thr Arg Phe Ser Leu Asp Glu Val Thr Leu Thr Val Gly
            115                 120                 125

Ser Val Lys Leu Glu Ile His Asn Gly Phe Ile Leu Gly Lys Ile Gln
130                 135                 140

Pro Pro Arg Pro Lys Met Ala Pro Ala Asn Asp Thr Tyr Glu Ser Ile
145                 150                 155                 160

Phe Ser His Phe Arg Glu Tyr Glu Ile Ala Ile Arg Lys Val Pro Gly
                165                 170                 175

Asn Phe Thr Phe Thr His Lys Lys Val Lys His Glu Asn Phe Ser Leu
            180                 185                 190

Leu Thr Ser Gly Glu Val Gly Glu Phe Cys Val Gln Val Lys Pro Ser
            195                 200                 205

Val Thr Ser Arg Thr Asn Lys Gly Met Trp Ser Lys Glu Glu Cys Val
210                 215                 220

Ser Leu Thr Arg Gln Tyr Phe Thr Val Thr Asn Val Ile Ile Phe Phe
225                 230                 235                 240

Ala Phe Val Leu Leu Leu Ser Gly Ala Leu Ala Tyr Cys Leu Ala Leu
                245                 250                 255

Gln Leu Tyr Val Arg Arg Arg Lys Lys Leu Pro Arg Val Leu Leu Phe
            260                 265                 270

Lys Lys Pro Asn Ala Phe Ile Phe Ile Ser Gln Arg Pro Ser Pro Glu
            275                 280                 285

Thr Gln Asp Thr Ile His Pro Leu Asp Glu Glu Ala Phe Leu Lys Val
290                 295                 300

Ser Pro Glu Leu Arg Asn Ser Asp Leu His Gly Ser Thr Asp Ser Gly
305                 310                 315                 320

Phe Gly Ser Thr Lys Pro Ser Leu Gln Thr Glu Glu Pro Gln Phe Leu
                325                 330                 335

Leu Pro Asp Pro His Pro Gln Ala Asp Arg Thr Leu Gly Asn Gly Glu
            340                 345                 350

Pro Pro Glu Leu Gly Asp Ser Cys Ser Ser Gly Ser Ser Asn Ser Thr
            355                 360                 365

Asp Ser Gly Ile Cys Leu Gln Glu Pro Ser Leu Ser Pro Ser Thr Gly
370                 375                 380

Pro Thr Trp Glu Gln Gln Val Gly Ser Asp Ser Arg Gly Gln Asp Asp
385                 390                 395                 400

Ser Gly Ile Gly Leu Val Gln Asn Ser Glu Gly Gln Ala Gly Asp Thr
                405                 410                 415

Gln Gly Gly Ser Ala Leu Gly His Asp Ser Pro Pro Glu Pro Glu Val
            420                 425                 430

Pro Ala Glu Gln Asp Pro Thr Ala Val Val Phe Arg Gly Tyr Leu Arg

|   | 435 |   |   | 440 |   |   |   | 445 |   |   |   |
|---|---|---|---|---|---|---|---|---|---|---|---|

Gln Thr Arg Cys Ala Glu Glu Lys Ala Thr Lys Thr Gly Cys Leu Glu
                450                 455                 460

Glu Glu Leu Pro Leu Thr Gly Gly Leu Gly Pro Lys Phe Arg Gly Cys
465                 470                 475                 480

Leu Asp Asp Glu Ala Gly Leu His Pro Ser Ala Leu Ala Lys Gly Tyr
                    485                 490                 495

Leu Lys Gln Asp Pro Leu Glu Met Thr Leu Ala Ser Ser Gly Ala Pro
                500                 505                 510

Ala Glu Gln Trp Asn Gln Pro Thr Glu Glu Trp Ser Leu Leu Ala Leu
                515                 520                 525

Ser Ser Cys Ser Asp Leu Gly Thr Ser Asp Trp Ser Phe Ala His Asp
                530                 535                 540

Leu Ala Pro Leu Gly Cys Val Ala Ala Pro Asp Gly Leu Leu Gly Ser
545                 550                 555                 560

Phe Asn Ser Asp Leu Val Thr Leu Pro Leu Ile Ser Ser Leu His Ser
                    565                 570                 575

Ser Asp Ser Ser
            580

<210> SEQ ID NO 9
<211> LENGTH: 1398
<212> TYPE: DNA
<213> ORGANISM: Artificial Sequence
<220> FEATURE:
<223> OTHER INFORMATION: Description of Artificial Sequence: Synthetic
      Fusion construct

<400> SEQUENCE: 9

| atggtgccgt gcctcgtagt gctgctggcg gcgttcctca gtcgccgtct tggctcagac | 60 |
|---|---|
| gctcatggga cagagctgcc cagcccgcca tctgtgtggt ttgaagcaga attttccac | 120 |
| cacatcctcc actggacacc catcccaaat cagtctgaaa gtacctgcta tgaagtggca | 180 |
| ctcctgaggt atggaacagg cgctggaac tccatctcca actgtagcca ggccctgtcc | 240 |
| tatgaccttta ccgcggtgac cttggacctg taccgcagca atggctaccg ggccagagtg | 300 |
| cgtgctgtgg acggcagccg gcactccaac tggaccgtca ccaacacccg cttctctttg | 360 |
| gatgaagtga ctctgacagt tggcagtgtg aagctagaga tccacaatgg cttcatcctt | 420 |
| gggaagattc agccccccag gcccaagatg gctcctgcaa atgacacata tgaaagcatc | 480 |
| ttcagtcact ccgagagta tgagattgcc attcgcaagg tgccgggaaa ctttacgttc | 540 |
| acacacaaga agtaaaaaca tgaaaacttc agcctcctaa cctctggaga agtgggagag | 600 |
| ttctgtgtcc aggtgaaacc atctgtcact tcccgaacca acaagggat gtggtctaaa | 660 |
| gaggagtgcg tctcccctcac caggcagtat ttcaccgtga ccaacagatc ttgtgacaaa | 720 |
| actcacacat gcccaccgtg cccagcacct gaactcctgg ggggaccgtc agtcttcctc | 780 |
| ttcccccaa acccaagga caccctcatg atctcccgga cccctgaggt cacatgcgtg | 840 |
| gtggtggacg tgagccacga agaccctgag gtcaagttca actggtacgt ggacggcgtg | 900 |
| gaggtgcata atgccaagac aaagccgcgg gaggagcagt acaacagcac gtaccgtgtg | 960 |
| gtcagcgtcc tcaccgtcct gcaccaggac tggctgaatg gcaaggagta caagtgcaag | 1020 |
| gtctccaaca aagccctccc agcccccatc gagaaaacca tctccaaagc caaagggcag | 1080 |
| ccccgagaac cacaggtgta caccctgccc ccatcccggg aggagatgac caagaaccag | 1140 |
| gtcagcctga cctgcctggt caaaggcttc tatcccagcg acatcgccgt ggagtgggag | 1200 |

-continued

```
agcaatgggc agccggagaa caactacaag accacgcctc ccgtgctgga ctccgacggc    1260
tccttcttcc tctatagcaa gctcaccgtg acaagagca ggtggcagca ggggaacgtc     1320
ttctcatgct ccgtgatgca tgaggctctg cacaaccact acacgcagaa gagcctctcc    1380
ctgtctccgg gtaaatga                                                   1398
```

<210> SEQ ID NO 10
<211> LENGTH: 465
<212> TYPE: PRT
<213> ORGANISM: Artificial Sequence
<220> FEATURE:
<223> OTHER INFORMATION: Description of Artificial Sequence: Synthetic Fusion construct

<400> SEQUENCE: 10

```
Met Val Pro Cys Leu Val Leu Leu Ala Ala Phe Leu Ser Arg Arg
1               5                   10                  15

Leu Gly Ser Asp Ala His Gly Thr Glu Leu Pro Ser Pro Pro Ser Val
            20                  25                  30

Trp Phe Glu Ala Glu Phe Phe His His Ile Leu His Trp Thr Pro Ile
        35                  40                  45

Pro Asn Gln Ser Glu Ser Thr Cys Tyr Glu Val Ala Leu Leu Arg Tyr
    50                  55                  60

Gly Thr Gly Arg Trp Asn Ser Ile Ser Asn Cys Ser Gln Ala Leu Ser
65                  70                  75                  80

Tyr Asp Leu Thr Ala Val Thr Leu Asp Leu Tyr Arg Ser Asn Gly Tyr
                85                  90                  95

Arg Ala Arg Val Arg Ala Val Asp Gly Ser Arg His Ser Asn Trp Thr
            100                 105                 110

Val Thr Asn Thr Arg Phe Ser Leu Asp Glu Val Thr Leu Thr Val Gly
        115                 120                 125

Ser Val Lys Leu Glu Ile His Asn Gly Phe Ile Leu Gly Lys Ile Gln
    130                 135                 140

Pro Pro Arg Pro Lys Met Ala Pro Ala Asn Asp Thr Tyr Glu Ser Ile
145                 150                 155                 160

Phe Ser His Phe Arg Glu Tyr Glu Ile Ala Ile Arg Lys Val Pro Gly
                165                 170                 175

Asn Phe Thr Phe Thr His Lys Lys Val Lys His Glu Asn Phe Ser Leu
            180                 185                 190

Leu Thr Ser Gly Glu Val Gly Glu Phe Cys Val Gln Val Lys Pro Ser
        195                 200                 205

Val Thr Ser Arg Thr Asn Lys Gly Met Trp Ser Lys Glu Glu Cys Val
    210                 215                 220

Ser Leu Thr Arg Gln Tyr Phe Thr Val Thr Asn Arg Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
```

```
                   325                 330                 335
Tyr Lys Cys Lys Val Ser Asn Lys Ala Leu Pro Ala Pro Ile Glu Lys
                340                 345                 350

Thr Ile Ser Lys Ala Lys Gly Gln Pro Arg Glu Pro Gln Val Tyr Thr
            355                 360                 365

Leu Pro Pro Ser Arg Glu Glu Met Thr Lys Asn Gln Val Ser Leu Thr
        370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

Lys
465

<210> SEQ ID NO 11
<211> LENGTH: 35
<212> TYPE: DNA
<213> ORGANISM: Artificial Sequence
<220> FEATURE:
<223> OTHER INFORMATION: Description of Artificial Sequence: DNA Primer

<400> SEQUENCE: 11
gagagagaga gaattcgccc aggatgctgc cgtgc                              35

<210> SEQ ID NO 12
<211> LENGTH: 37
<212> TYPE: DNA
<213> ORGANISM: Artificial Sequence
<220> FEATURE:
<223> OTHER INFORMATION: Description of Artificial Sequence: DNA Primer

<400> SEQUENCE: 12
agagagagag cggccgcggc agaggagcag gcatggc                            37

<210> SEQ ID NO 13
<211> LENGTH: 41
<212> TYPE: DNA
<213> ORGANISM: Artificial Sequence
<220> FEATURE:
<223> OTHER INFORMATION: Description of Artificial Sequence: DNA Primer

<400> SEQUENCE: 13
aaaccggaat tcccaccatg gtgccgtgcc tcgtagtgct g                       41

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence: DNA Primer

<400> SEQUENCE: 14
aaaggaagat ctgttggtca cggtgaaata ctgcct                             36

<210> SEQ ID NO 15
<211> LENGTH: 31
```

```
<212> TYPE: DNA
<213> ORGANISM: Artificial Sequence
<220> FEATURE:
<223> OTHER INFORMATION: Description of Artificial Sequence: DNA Primer

<400> SEQUENCE: 15
ccttggacct gtaccgcagc aatggctacc g                                31

<210> SEQ ID NO 16
<211> LENGTH: 31
<212> TYPE: DNA
<213> ORGANISM: Artificial Sequence
<220> FEATURE:
<223> OTHER INFORMATION: Description of Artificial Sequence: DNA Primer

<400> SEQUENCE: 16
cggtagccat tgctgcggta caggtccaag g                                31

<210> SEQ ID NO 17
<211> LENGTH: 31
<212> TYPE: DNA
<213> ORGANISM: Artificial Sequence
<220> FEATURE:
<223> OTHER INFORMATION: Description of Artificial Sequence: DNA Primer

<400> SEQUENCE: 17
tctaaagagg agtgcgtctc cctcaccagg c                                31

<210> SEQ ID NO 18
<211> LENGTH: 31
<212> TYPE: DNA
<213> ORGANISM: Artificial Sequence
<220> FEATURE:
<223> OTHER INFORMATION: Description of Artificial Sequence: DNA Primer

<400> SEQUENCE: 18
gcctggtgag ggagacgcac tcctctttag a                                31

<210> SEQ ID NO 19
<211> LENGTH: 50
<212> TYPE: DNA
<213> ORGANISM: Artificial Sequence
<220> FEATURE:
<223> OTHER INFORMATION: Description of Artificial Sequence: DNA Primer

<400> SEQUENCE: 19
acacagatct gttggtcacg gtgaaatact gcctggtgag ggagatgcac             50

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: DNA Primer

<400> SEQUENCE: 20
atgctgccgt gcctcgtagt gctgc                                       25

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: DNA Primer

<400> SEQUENCE: 21
atggttcccc tgagcaaata atcc                                        24
```

<210> SEQ ID NO 22
<211> LENGTH: 17
<212> TYPE: DNA
<213> ORGANISM: Artificial Sequence
<220> FEATURE:
<223> OTHER INFORMATION: Description of Artificial Sequence: DNA Primer

<400> SEQUENCE: 22
caggaaacag ctatgac                                                    17

<210> SEQ ID NO 23
<211> LENGTH: 429
<212> TYPE: DNA
<213> ORGANISM: Homo sapiens

<400> SEQUENCE: 23
atggacttgg ggctgtgctg ggttttcctt gttgctattt tagaaggtgt ccagtgtgag      60
gtgcagctgg tggagtctgg gggaggcttg gtacagcctg gggggtccct gagactctcc    120
tgtgcagcct ctggattcac cttcagtagc tatagcatga actgggtccg ccaggctcca    180 gggaagggc tggagtgggt ttcatacatt agtactggta gtagtaccat atactacgca     240
gactctgtga agggccgatt caccatctcc agagacaatg ccaagaactc actgtatctg    300
caaatgaaca gcctgagaga cgaggacacg gctgtgtatt actgtgcgag agagaattac    360
tatggttcgg ggagttatga agactacttt gactactggg gccagggaac cctggtcacc    420
gtctcctca                                                            429

<210> SEQ ID NO 24
<211> LENGTH: 384
<212> TYPE: DNA
<213> ORGANISM: Homo sapiens

<400> SEQUENCE: 24
atggaagccc cagctcagct tctcttcctc ctgctactct ggctcccaga taccaccgga     60
gaaattgtgt tgacacagtc tccagccacc ctgtctttgt ctccagggga aagagccacc    120
ctctcctgca gggccagtca gagtgttagc agctacttag cctggtacca acagaaacct    180
ggccaggctc ccaggctcct catctatgat gcatccaaca gggccactgg catcccagcc    240
aggttcagtg gcagtgggtc tgggacagac ttcactctca ccatcagcag cctagagcct    300
gaagattttg cagtttatta ctgtcagcag cgtagcaact ggcccatatt cactttcggc    360
cctgggacca aagtggatat caaa                                           384

<210> SEQ ID NO 25
<211> LENGTH: 429
<212> TYPE: DNA
<213> ORGANISM: Homo sapiens

<400> SEQUENCE: 25
atggagttgg ggctgtgctg ggttttcctt gttgctattt tagaaggtgt ccagtgtgag      60
gtgcagctgg tggagtctgg gggaggctta gtacagcctg gggggtccct gagactctcc    120
tgtgcagcct ctggattcac cttcagtagc tatagcatga actgggtccg ccaggctcca    180 gggaagggc tggagtgggt ttcatacatt agtactagga gtagtaccat atactacgca     240
gactctgtga agggccgatt caccatctcc agagacaatg ccaagaactc actgtatctg    300
caaatgaaca gcctgagaga cgaggacacg gctgtgtatt actgtgcgag agagaattac    360
tatggttcgg ggagttatga agactacttt gactactggg gccagggaac cctggtcacc    420

```
gtctcctca                                                              429

<210> SEQ ID NO 26
<211> LENGTH: 384
<212> TYPE: DNA
<213> ORGANISM: Homo sapiens

<400> SEQUENCE: 26
atggaagccc cagctcagct tctcttcctc ctgctactct ggctcccaga taccaccgga      60
gaaattgtgt tgacacagtc tccagccacc ctgtctttgt ctccagggga aagagccacc     120
ctctcctgca gggccagtca gagtgttagc agctacttag cctggtacca acagaaacct     180
ggccaggctc ccaggctcct catctatgat gcatccaaca gggccactgg catcccagcc     240
aggttcagtg gcagtgggtc tgggacagac ttcactctca ccatcagcag cctagagcct     300
gaagattttg cagtttatta ctgtcagcag cgtagcaact ggcccatatt cactttcggc     360
cctgggacca aagtggatat caaa                                             384

<210> SEQ ID NO 27
<211> LENGTH: 417
<212> TYPE: DNA
<213> ORGANISM: Homo sapiens

<400> SEQUENCE: 27
atggactgca cctggaggat cctcttcttg gtggcagcag ctacaggcac ccacgcccag      60
gtccagctgg tacaatctgg ggctgaggtg aagaagcctg ggcctcagt gaaggtctcc     120 tgcaaggttt ccggattcac cctcactgaa ttatccatgc actgggtgcg acaggctcct     180
ggaaaagggc ttgaatggat gggaggtttt gatcctgacg atggtgaaac aatctacgca     240
cagaagttcc agggcagagt ctccatgacc gaggacacat ctacagacac agcctacatg     300
gagctgagca gcctgagatc tgaggacacg gccgtgtatt actgtgcaac aggggggtac     360
tatggtcctg tcggtatgga cgtctggggc caagggacca cggtcaccgt ctcctca       417

<210> SEQ ID NO 28
<211> LENGTH: 387
<212> TYPE: DNA
<213> ORGANISM: Homo sapiens

<400> SEQUENCE: 28
atggacatga gggtcctcgc tcagctcctg gggctcctgc tgctctgttt cccaggtgcc      60
agatgtgaca tccagatgac ccagtctcca tcctcactgt ctgcatctgt aggagacaga     120
gtcaccatca cttgtcgggc gagtcagggt attagcatct ggttagcctg gtatcagcag     180
aaaccagaga aagcccctaa gtccctgatc tatgctgcat ccagtttgca aagtggggtc     240
ccatcaaggt tcagcggcag tggatctggg acagatttca ctctcaccat cagcagcctg     300
cagcctgaag attttgcaac ttattactgc aacagtata atagttaccc gctcactttc     360
ggcggaggga ccaaggtgga gatcaaa                                          387

<210> SEQ ID NO 29
<211> LENGTH: 143
<212> TYPE: PRT
<213> ORGANISM: Homo sapiens

<400> SEQUENCE: 29

Met Asp Leu Gly Leu Cys Trp Val Phe Leu Val Ala Ile Leu Glu Gly
1               5                   10                  15
```

```
Val Gln Cys Glu Val Gln Leu Val Glu Ser Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ser Met Asn Trp Val Arg Gln Ala Pro Gly Lys Gly Leu
    50                  55                  60

Glu Trp Val Ser Tyr Ile Ser Thr Gly Ser Ser Thr Ile Tyr Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Asp Glu Thr Ala Val
            100                 105                 110

Tyr Tyr Cys Ala Arg Glu Asn Tyr Tyr Gly Ser Gly Ser Tyr Glu Asp
        115                 120                 125

Tyr Phe Asp Tyr Trp Gly Gln Gly Thr Leu Val Thr Val Ser Ser
        130                 135                 140

<210> SEQ ID NO 30
<211> LENGTH: 128
<212> TYPE: PRT
<213> ORGANISM: Homo sapiens

<400> SEQUENCE: 30

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

Asn Trp Pro Ile Phe Thr Phe Gly Pro Gly Thr Lys Val Asp Ile Lys
        115                 120                 125

<210> SEQ ID NO 31
<211> LENGTH: 143
<212> TYPE: PRT
<213> ORGANISM: Homo sapiens

<400> SEQUENCE: 31

Met Glu Leu Gly Leu Cys Trp Val Phe Leu Val Ala Ile Leu Glu Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ser Met Asn Trp Val Arg Gln Ala Pro Gly Lys Gly Leu
    50                  55                  60

Glu Trp Val Ser Tyr Ile Ser Thr Arg Ser Ser Thr Ile Tyr Tyr Ala
65                  70                  75                  80

Asp Ser Val Lys Gly Arg Phe Thr Ile Ser Arg Asp Asn Ala Lys Asn
```

```
                    85                  90                  95
Ser Leu Tyr Leu Gln Met Asn Ser Leu Arg Asp Glu Asp Thr Ala Val
            100                 105                 110

Tyr Tyr Cys Ala Arg Glu Asn Tyr Tyr Gly Ser Gly Ser Tyr Glu Asp
        115                 120                 125

Tyr Phe Asp Tyr Trp Gly Gln Gly Thr Leu Val Thr Val Ser Ser
    130                 135                 140

<210> SEQ ID NO 32
<211> LENGTH: 128
<212> TYPE: PRT
<213> ORGANISM: Homo sapiens

<400> SEQUENCE: 32

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

Asn Trp Pro Ile Phe Thr Phe Gly Pro Gly Thr Lys Val Asp Ile Lys
        115                 120                 125

<210> SEQ ID NO 33
<211> LENGTH: 139
<212> TYPE: PRT
<213> ORGANISM: Homo sapiens

<400> SEQUENCE: 33

Met Asp Cys Thr Trp Arg Ile Leu Phe Leu Val Ala Ala Ala Thr Gly
1               5                   10                  15

Thr His Ala Gln Val Gln Leu Val Gln Ser Gly Ala Glu Val Lys Lys
            20                  25                  30

Pro Gly Ala Ser Val Lys Val Ser Cys Lys Val Ser Gly Phe Thr Leu
        35                  40                  45

Thr Glu Leu Ser Met His Trp Val Arg Gln Ala Pro Gly Lys Gly Leu
    50                  55                  60

Glu Trp Met Gly Gly Phe Asp Pro Asp Gly Glu Thr Ile Tyr Ala
65                  70                  75                  80

Gln Lys Phe Gln Gly Arg Val Ser Met Thr Glu Asp Thr Ser Thr Asp
                85                  90                  95

Thr Ala Tyr Met Glu Leu Ser Ser Leu Arg Ser Glu Asp Thr Ala Val
            100                 105                 110

Tyr Tyr Cys Ala Thr Gly Gly Tyr Tyr Gly Pro Val Gly Met Asp Val
        115                 120                 125

Trp Gly Gln Gly Thr Thr Val Thr Val Ser Ser
    130                 135

<210> SEQ ID NO 34
```

```
<211> LENGTH: 129
<212> TYPE: PRT
<213> ORGANISM: Homo sapiens

<400> SEQUENCE: 34

Met Asp Met Arg Val Leu Ala Gln Leu Gly Leu Leu Leu Leu Cys
1               5                   10                  15

Phe Pro Gly Ala Arg Cys Asp Ile Gln Met Thr Gln Ser Pro Ser
                20                  25                  30

Leu Ser Ala Ser Val Gly Asp Arg Val Thr Ile Thr Cys Arg Ala Ser
            35                  40                  45

Gln Gly Ile Ser Ile Trp Leu Ala Trp Tyr Gln Gln Lys Pro Glu Lys
50                      55                  60

Ala Pro Lys Ser Leu Ile Tyr Ala Ala Ser Ser Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Tyr Asn Ser Tyr Pro Leu Thr Phe Gly Gly Gly Thr Lys Val Glu Ile
        115                 120                 125

Lys

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 35
ctaatacgac tcactatagg gc                                          22

<210> SEQ ID NO 36
<211> LENGTH: 31
<212> TYPE: DNA
<213> ORGANISM: Artificial Sequence
<220> FEATURE:
<223> OTHER INFORMATION: Description of Artificial Sequence:  Primer

<400> SEQUENCE: 36
tcttgtccac cttggtgttg ctgggcttgt g                                31

<210> SEQ ID NO 37
<211> LENGTH: 30
<212> TYPE: DNA
<213> ORGANISM: Artificial Sequence
<220> FEATURE:
<223> OTHER INFORMATION: Description of Artificial Sequence:  Primer

<400> SEQUENCE: 37
aggcacacaa cagaggcagt tccagatttc                                  30

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence:  Primer

<400> SEQUENCE: 38
gtaaaacgac ggccagtg                                               18
```

```
<210> SEQ ID NO 39
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 39
caggaaacag ctatgac                                                    17

<210> SEQ ID NO 40
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 40
agagagagag gtcgactcac catggacttg gggctgtg                             38

<210> SEQ ID NO 41
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 41
agagagagag gctagctgag gagacggtga ccagggttc                            39

<210> SEQ ID NO 42
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 42
agagagagag agatctgaac catggaagcc ccagctca                             38

<210> SEQ ID NO 43
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 43
agagagagag cgtacgtttg atatccactt tggtcccagg                           40

<210> SEQ ID NO 44
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 44
agagagagag gtcgactcac catggagttg gggctgtg                             38

<210> SEQ ID NO 45
<211> LENGTH: 38
<212> TYPE: DNA
<213> ORGANISM: Artificial Sequence
<220> FEATURE:
<223> OTHER INFORMATION: Description of Artificial Sequence: Primer
```

```
<400> SEQUENCE: 45
agagagagag gtcgactcac catggactgc acctggag                    38

<210> SEQ ID NO 46
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 46
agagagagag gctagctgag gagacggtga ccgtggt                     37

<210> SEQ ID NO 47
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 47
agagagagag agatctacag catggacatg agggtcc                     37

<210> SEQ ID NO 48
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 48
agagagagag cgtacgtttg atctccacct tggtccctcc                  40

<210> SEQ ID NO 49
<211> LENGTH: 5
<212> TYPE: PRT
<213> ORGANISM: Homo sapiens

<400> SEQUENCE: 49

Ser Tyr Ser Met Asn
1               5

<210> SEQ ID NO 50
<211> LENGTH: 17
<212> TYPE: PRT
<213> ORGANISM: Homo sapiens

<400> SEQUENCE: 50

Tyr Ile Ser Thr Gly Ser Ser Thr Ile Tyr Tyr Ala Asp Ser Val Lys
1               5                   10                  15

Gly

<210> SEQ ID NO 51
<211> LENGTH: 15
<212> TYPE: PRT
<213> ORGANISM: Homo sapiens

<400> SEQUENCE: 51

Glu Asn Tyr Tyr Gly Ser Gly Ser Tyr Glu Asp Tyr Phe Asp Tyr
1               5                   10                  15

<210> SEQ ID NO 52
<211> LENGTH: 17
<212> TYPE: PRT
<213> ORGANISM: Homo sapiens
```

<400> SEQUENCE: 52

Tyr Ile Ser Thr Arg Ser Ser Thr Ile Tyr Tyr Ala Asp Ser Val Lys
1               5                   10                  15
Gly

<210> SEQ ID NO 53
<211> LENGTH: 5
<212> TYPE: PRT
<213> ORGANISM: Homo sapiens

<400> SEQUENCE: 53

Glu Leu Ser Met His
1               5

<210> SEQ ID NO 54
<211> LENGTH: 17
<212> TYPE: PRT
<213> ORGANISM: Homo sapiens

<400> SEQUENCE: 54

Gly Phe Asp Pro Asp Asp Gly Glu Thr Ile Tyr Ala Gln Lys Phe Gln
1               5                   10                  15
Gly

<210> SEQ ID NO 55
<211> LENGTH: 11
<212> TYPE: PRT
<213> ORGANISM: Homo sapiens

<400> SEQUENCE: 55

Gly Gly Tyr Tyr Gly Pro Val Gly Met Asp Val
1               5                   10

<210> SEQ ID NO 56
<211> LENGTH: 11
<212> TYPE: PRT
<213> ORGANISM: Homo sapiens

<400> SEQUENCE: 56

Arg Ala Ser Gln Ser Val Ser Ser Tyr Leu Ala
1               5                   10

<210> SEQ ID NO 57
<211> LENGTH: 7
<212> TYPE: PRT
<213> ORGANISM: Homo sapiens

<400> SEQUENCE: 57

Asp Ala Ser Asn Arg Ala Thr
1               5

<210> SEQ ID NO 58
<211> LENGTH: 10
<212> TYPE: PRT
<213> ORGANISM: Homo sapiens

<400> SEQUENCE: 58

Gln Gln Arg Ser Asn Trp Pro Ile Phe Thr
1               5                   10

<210> SEQ ID NO 59
<211> LENGTH: 11
<212> TYPE: PRT

<213> ORGANISM: Homo sapiens

<400> SEQUENCE: 59

Arg Ala Ser Gln Gly Ile Ser Ile Trp Leu Ala
1               5                   10

<210> SEQ ID NO 60
<211> LENGTH: 7
<212> TYPE: PRT
<213> ORGANISM: Homo sapiens

<400> SEQUENCE: 60

Ala Ala Ser Ser Leu Gln Ser
1               5

<210> SEQ ID NO 61
<211> LENGTH: 9
<212> TYPE: PRT
<213> ORGANISM: Homo sapiens

<400> SEQUENCE: 61

Gln Gln Tyr Asn Ser Tyr Pro Leu Thr
1               5

<210> SEQ ID NO 62
<211> LENGTH: 1398
<212> TYPE: DNA
<213> ORGANISM: Homo sapiens

<400> SEQUENCE: 62

| | | |
|---|---|---|
| atggtgccgt gcctcgtagt gctgctggcg gcgctcctca gcctccgtct tggctcagac | 60 |
| gctcatggga cagagctgcc cagccctccg tctgtgtggt ttgaagcaga atttttccac | 120 |
| cacatcctcc actggacacc catcccaaat cagtctgaaa gtacctgcta tgaagtggcg | 180 |
| gtcctgaggt atggaataga gtcctggaac tccatctcca actgtagcca gaccctgtcc | 240 |
| tatgacctta ccgcagtgac cttggacctg taccacagca atggctaccg ggccagagtg | 300 |
| cgggctgtgg acggcagccg gcactccaac tggaccgtca ccaacacccg cttctctgtg | 360 |
| gatgaagtga ctctgacagt tggcagtgtg aacctagaga tccacaatgg cttcatcctc | 420 |
| gggaagattc agctacccag gcccaagatg gcccccgcga tgacacata tgaaagcatc | 480 |
| ttcagtcact tccgagagta tgagattgcc attcgcaagg tgccgggaaa cttcacgttc | 540 |
| acacacaaga agtaaaaaca tgaaaacttc agcctcctaa cctctggaga agtgggagag | 600 |
| ttctgtgtcc aggtgaaacc atctgtcgct tcccgaagta caaggggat gtggtctaaa | 660 |
| gaggagtgca tctcccctcac caggcagtat ttcaccgtga ccaacagatc ttgtgacaaa | 720 |
| actcacacat gcccaccgtg cccagcacct gaactcctgg ggggaccgtc agtcttcctc | 780 |
| ttccccccaa aacccaagga caccctcatg atctcccgga cccctgaggt cacatgcgtg | 840 |
| gtggtggacg tgagccacga agaccctgag gtcaagttca actggtacgt ggacggcgtg | 900 |
| gaggtgcata atgccaagac aaagccgcgg gaggagcagt acaacagcac gtaccgtgtg | 960 |
| gtcagcgtcc tcaccgtcct gcaccaggac tggctgaatg gcaaggagta caagtgcaag | 1020 |
| gtctccaaca aagccctccc agcccccatc gagaaaacca tctccaaagc caagggcag | 1080 |
| ccccgagaac cacaggtgta caccctgccc ccatcccggg atgagctgac caagaaccag | 1140 |
| gtcagcctga cctgcctggt caaaggcttc tatcccagcg acatcgccgt ggagtgggag | 1200 |
| agcaatgggc agccggagaa caactacaag accacgcctc ccgtgctgga ctccgacggc | 1260 |
| tccttcttcc tctacagcaa gctcaccgtg gacaagagca ggtggcagca ggggaacgtc | 1320 |

```
ttctcatgct ccgtgatgca tgaggctctg cacaaccact acacgcagaa gagcctctcc    1380
ctgtctccgg gtaaatga                                                  1398
```

<210> SEQ ID NO 63
<211> LENGTH: 465
<212> TYPE: PRT
<213> ORGANISM: Homo sapiens

<400> SEQUENCE: 63

```
Met Val Pro Cys Leu Val Val Leu Leu Ala Leu Leu Ser Leu Arg
1               5                   10                  15

Leu Gly Ser Asp Ala His Gly Thr Glu Leu Pro Ser Pro Ser Val
                20                  25                  30

Trp Phe Glu Ala Glu Phe Phe His His Ile Leu His Trp Thr Pro Ile
                35                  40                  45

Pro Asn Gln Ser Glu Ser Thr Cys Tyr Glu Val Ala Val Leu Arg Tyr
    50                  55                  60

Gly Ile Glu Ser Trp Asn Ser Ile Ser Asn Cys Ser Gln Thr Leu Ser
65                  70                  75                  80

Tyr Asp Leu Thr Ala Val Thr Leu Asp Leu Tyr His Ser Asn Gly Tyr
                85                  90                  95

Arg Ala Arg Val Arg Ala Val Asp Gly Ser Arg His Ser Asn Trp Thr
                100                 105                 110

Val Thr Asn Thr Arg Phe Ser Val Asp Glu Val Thr Leu Thr Val Gly
                115                 120                 125

Ser Val Asn Leu Glu Ile His Asn Gly Phe Ile Leu Gly Lys Ile Gln
    130                 135                 140

Leu Pro Arg Pro Lys Met Ala Pro Ala Asn Asp Thr Tyr Glu Ser Ile
145                 150                 155                 160

Phe Ser His Phe Arg Glu Tyr Glu Ile Ala Ile Arg Lys Val Pro Gly
                165                 170                 175

Asn Phe Thr Phe Thr His Lys Lys Val Lys His Glu Asn Phe Ser Leu
                180                 185                 190

Leu Thr Ser Gly Glu Val Gly Glu Phe Cys Val Gln Val Lys Pro Ser
                195                 200                 205

Val Ala Ser Arg Ser Asn Lys Gly Met Trp Ser Lys Glu Glu Cys Ile
    210                 215                 220

Ser Leu Thr Arg Gln Tyr Phe Thr Val Thr Asn Arg Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
                260                 265                 270

Arg Thr Pro Glu Val Thr Cys Val Val Asp Val Ser His Glu Asp
                275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
                340                 345                 350

Thr Ile Ser Lys Ala Lys Gly Gln Pro Arg Glu Pro Gln Val Tyr Thr
```

```
                  355                 360                 365
Leu Pro Pro Ser Arg Asp Glu Leu Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
            435                 440                 445

Ala Leu His Asn His Tyr Thr Gln Lys Ser Leu Ser Leu Ser Pro Gly
    450                 455                 460

Lys
465

<210> SEQ ID NO 64
<211> LENGTH: 1398
<212> TYPE: DNA
<213> ORGANISM: Homo sapiens

<400> SEQUENCE: 64
atggtgccgt gcctcgtagt gctgctggcg gcgctcctca gcctccgtct tggctcagac      60
gctcatggga cagagctgcc cagccctccg tctgtgtggt ttgaagcaga atttttccac     120
cacatcctcc actggacacc catcccaaat cagtctgaaa gtacctgcta tgaagtggcg     180
ctcctgaggt atggaataga gtcctggaac tccatctcca actgtagcca gaccctgtcc     240
tatgacctta ccgcagtgac cttggacctg taccacagca atggctaccg ggccagagtg     300
cgggctgtgg acggcagccg gcactccaac tggaccatca ccaacacccg cttctctgtg     360
gatgaagtga ctctgacagt tggcagtgtg aacctagaga tccacaatgg cttcatcctc     420
gggaagattc agctacccag gcccaagatg gccccgcga atgacacata tgaaagcatc     480
ttcagtcact ccgagagta tgagattgcc attcgcaagg tgccgggaaa cttcacgttc     540
acacacaaga agtaaaaaca tgaaaacttc agcctcctaa cctctggaga agtgggagag     600
ttctgtgtcc aggtgaaacc atctgtcgct cccgaagta caaggggat gtggtctaaa     660 gaggagtgca tctccctcac caggcagtat ttcaccgtga ccaacagatc ttgtgacaaa     720
actcacacat gcccaccgtg cccagcacct gaactcctgg ggggaccgtc agtcttcctc     780 ttcccccaa acccaagga caccctcatg atctcccgga cccctgaggt cacatgcgtg     840
gtggtggacg tgagccacga agaccctgag gtcaagttca actggtacgt ggacggcgtg     900
gaggtgcata atgccaagac aaagccgcgg gaggagcagt acaacagcac gtaccgtgtg     960
gtcagcgtcc tcaccgtcct gcaccaggac tggctgaatg gcaaggagta caagtgcaag    1020
gtctccaaca agccctcccc agcccccatc gagaaaacca tctccaaagc caagggcag    1080 ccccgagaac cacaggtgta caccctgccc ccatcccggg atgagctgac caagaaccag    1140
gtcagcctga cctgcctggt caaaggcttc tatcccagcg acatcgccgt ggagtgggag    1200
agcaatgggc agccggagaa caactacaag accacgcctc ccgtgctgga ctccgacggc    1260
tccttcttcc tctacagcaa gctcaccgtg gacaagagca ggtggcagca ggggaacgtc    1320
ttctcatgct ccgtgatgca tgaggctctg cacaaccact acacgcagaa gagcctctcc    1380
ctgtctccgg gtaaatga                                                  1398
```

```
<210> SEQ ID NO 65
<211> LENGTH: 465
<212> TYPE: PRT
<213> ORGANISM: Homo sapiens

<400> SEQUENCE: 65
```

| | | | | | | | | | | | | | | | |
|---|---|---|---|---|---|---|---|---|---|---|---|---|---|---|---|
| Met | Val | Pro | Cys | Leu | Val | Val | Leu | Ala | Ala | Leu | Leu | Ser | Leu | Arg | |
| 1 | | | | 5 | | | | | 10 | | | | | 15 | |

Leu Gly Ser Asp Ala His Gly Thr Glu Leu Pro Ser Pro Ser Val
               20                    25                    30

Trp Phe Glu Ala Glu Phe Phe His Ile Leu His Trp Thr Pro Ile
        35                    40                    45

Pro Asn Gln Ser Glu Ser Thr Cys Tyr Glu Val Ala Leu Leu Arg Tyr
50                   55                   60

Gly Ile Glu Ser Trp Asn Ser Ile Ser Asn Cys Ser Gln Thr Leu Ser
65                   70                   75                   80

Tyr Asp Leu Thr Ala Val Thr Leu Asp Leu Tyr His Ser Asn Gly Tyr
                    85                   90                   95

Arg Ala Arg Val Arg Ala Val Asp Gly Ser Arg His Ser Asn Trp Thr
                    100                  105                  110

Ile Thr Asn Thr Arg Phe Ser Val Asp Glu Val Thr Leu Thr Val Gly
                    115                  120                  125

Ser Val Asn Leu Glu Ile His Asn Gly Phe Ile Leu Gly Lys Ile Gln
130                  135                  140

Leu Pro Arg Pro Lys Met Ala Pro Ala Asn Asp Thr Tyr Glu Ser Ile
145                  150                  155                  160

Phe Ser His Phe Arg Glu Tyr Glu Ile Ala Ile Arg Lys Val Pro Gly
                    165                  170                  175

Asn Phe Thr Phe Thr His Lys Lys Val Lys His Glu Asn Phe Ser Leu
                    180                  185                  190

Leu Thr Ser Gly Glu Val Gly Glu Phe Cys Val Gln Val Lys Pro Ser
                    195                  200                  205

Val Ala Ser Arg Ser Asn Lys Gly Met Trp Ser Lys Glu Glu Cys Ile
210                  215                  220

Ser Leu Thr Arg Gln Tyr Phe Thr Val Thr Asn Arg Ser Cys Asp Lys
225                  230                  235                  240

Thr His Thr Cys Pro Pro Cys Pro Ala Pro Glu Leu Leu Gly Gly Pro
                    245                  250                  255

Ser Val Phe Leu Phe Pro Pro Lys Pro Lys Asp Thr Leu Met Ile Ser
                    260                  265                  270

Arg Thr Pro Glu Val Thr Cys Val Val Val Asp Val Ser His Glu Asp
                    275                  280                  285

Pro Glu Val Lys Phe Asn Trp Tyr Val Asp Gly Val Glu Val His Asn
                    290                  295                  300

Ala Lys Thr Lys Pro Arg Glu Glu Gln Tyr Asn Ser Thr Tyr Arg Val
305                  310                  315                  320

Val Ser Val Leu Thr Val Leu His Gln Asp Trp Leu Asn Gly Lys Glu
                    325                  330                  335

Tyr Lys Cys Lys Val Ser Asn Lys Ala Leu Pro Ala Pro Ile Glu Lys
                    340                  345                  350

Thr Ile Ser Lys Ala Lys Gly Gln Pro Arg Glu Pro Gln Val Tyr Thr
                    355                  360                  365

Leu Pro Pro Ser Arg Asp Glu Leu Thr Lys Asn Gln Val Ser Leu Thr
370                  375                  380

Cys Leu Val Lys Gly Phe Tyr Pro Ser Asp Ile Ala Val Glu Trp Glu

|  | | | | | |
|---|---|---|---|---|---|
| 385 | | 390 | 395 | | 400 |
| Ser Asn Gly Gln Pro Glu Asn Asn Tyr Lys Thr Thr Pro Val Leu | | | | | |
| | | 405 | 410 | | 415 |
| Asp Ser Asp Gly Ser Phe Phe Leu Tyr Ser Lys Leu Thr Val Asp Lys | | | | | |
| | 420 | | 425 | 430 | |
| Ser Arg Trp Gln Gln Gly Asn Val Phe Ser Cys Ser Val Met His Glu | | | | | |
| | 435 | | 440 | 445 | |
| Ala Leu His Asn His Tyr Thr Gln Lys Ser Leu Ser Leu Ser Pro Gly | | | | | |
| | 450 | | 455 | 460 | |
| Lys | | | | | |
| 465 | | | | | |

<210> SEQ ID NO 66
<211> LENGTH: 1398
<212> TYPE: DNA
<213> ORGANISM: Homo sapiens

<400> SEQUENCE: 66

| | | | | | |
|---|---|---|---|---|---|
| atggtgccgt | gcctcgtagt | gctgctggcg | gcgctcctca | gcctccgtct | tggctcagac | 60 |
| gctcatggga | cagagctgcc | cagccctccg | tctgtgtggt | ttgaagcaga | atttttccac | 120 |
| cacatcctcc | actggacacc | catcccaaat | cagtctgaaa | gtacctgcta | tgaagtggcg | 180 |
| ctcctgaggt | atgaatagaa | gtcctggaac | tccatctcca | actgtagcca | gaccctgtcc | 240 |
| tatgacctta | ccgcagtgac | cttggacctg | taccacagca | atggctaccg | ggccagagtg | 300 |
| cgggctgtgg | acgcagccg | gcactccaac | tggaccgtca | ccaacacccg | cttctctgtg | 360 |
| gatgaagtga | ctctgacagt | tggcagtgtg | aacctagaga | tccacaatgg | cttcatcctc | 420 |
| ggaagattc | agctacccag | gcccaagatg | gcccccgcga | atgacacata | tgaaggcatc | 480 |
| ttcagtcact | tccgagagta | tgagattgcc | attcgcaagg | tgccgggaaa | cttcacgttc | 540 |
| acacacaaga | agtaaaaaca | tgaaaacttc | agcctcctaa | cctctggaga | agtgggagag | 600 |
| ttctgtgtcc | aggtgaaacc | atctgtcgct | tcccgaagta | caaggggat | gtggtctaaa | 660 |
| gaggagtgca | tctccctcac | caggcagtat | tcaccgtga | ccaacagatc | ttgtgacaaa | 720 |
| actcacacat | gcccaccgtg | cccagcacct | gaactcctgg | ggggaccgtc | agtcttcctc | 780 |
| ttcccccca | aacccaagga | caccctcatg | atctcccgga | cccctgaggt | cacatgcgtg | 840 |
| gtggtggacg | tgagccacga | agaccctgag | gtcaagttca | actggtacgt | ggacggcgtg | 900 |
| gaggtgcata | atgccaagac | aaagccgcgg | gaggagcagt | acaacagcac | gtaccgtgtg | 960 |
| gtcagcgtcc | tcaccgtcct | gcaccaggac | tggctgaatg | gcaaggagta | caagtgcaag | 1020 |
| gtctccaaca | aagccctccc | agcccccatc | gagaaaacca | tctccaaagc | caaagggcag | 1080 |
| ccccgagaac | cacaggtgta | caccctgccc | ccatcccggg | atgagctgac | caagaaccag | 1140 |
| gtcagcctga | cctgcctggt | caaaggcttc | tatcccagcg | acatcgccgt | ggagtgggag | 1200 |
| agcaatgggc | agccggagaa | caactacaag | accacgcctc | ccgtgctgga | ctccgacggc | 1260 |
| tccttcttcc | tctacagcaa | gctcaccgtg | gacaagagca | ggtggcagca | ggggaacgtc | 1320 |
| ttctcatgct | ccgtgatgca | tgaggctctg | cacaaccact | acacgcagaa | gagcctctcc | 1380 |
| ctgtctccgg | gtaaatga | | | | | 1398 |

<210> SEQ ID NO 67
<211> LENGTH: 465
<212> TYPE: PRT
<213> ORGANISM: Homo sapiens

<400> SEQUENCE: 67

-continued

```
Met Val Pro Cys Leu Val Val Leu Ala Leu Leu Ser Leu Arg
1               5                   10                  15

Leu Gly Ser Asp Ala His Gly Thr Glu Leu Pro Ser Pro Ser Val
                20              25              30

Trp Phe Glu Ala Glu Phe Phe His His Ile Leu His Trp Thr Pro Ile
                35                  40                  45

Pro Asn Gln Ser Glu Ser Thr Cys Tyr Glu Val Ala Leu Leu Arg Tyr
        50                  55                  60

Gly Ile Glu Ser Trp Asn Ser Ile Ser Asn Cys Ser Gln Thr Leu Ser
65                  70                  75                  80

Tyr Asp Leu Thr Ala Val Thr Leu Asp Leu Tyr His Ser Asn Gly Tyr
                85                  90                  95

Arg Ala Arg Val Arg Ala Val Asp Gly Ser Arg His Ser Asn Trp Thr
                100                 105                 110

Val Thr Asn Thr Arg Phe Ser Val Asp Glu Val Thr Leu Thr Val Gly
            115                 120                 125

Ser Val Asn Leu Glu Ile His Asn Gly Phe Ile Leu Gly Lys Ile Gln
        130                 135                 140

Leu Pro Arg Pro Lys Met Ala Pro Ala Asn Asp Thr Tyr Glu Gly Ile
145                 150                 155                 160

Phe Ser His Phe Arg Glu Tyr Glu Ile Ala Ile Arg Lys Val Pro Gly
                165                 170                 175

Asn Phe Thr Phe Thr His Lys Lys Val Lys His Glu Asn Phe Ser Leu
            180                 185                 190

Leu Thr Ser Gly Glu Val Gly Glu Phe Cys Val Gln Val Lys Pro Ser
        195                 200                 205

Val Ala Ser Arg Ser Asn Lys Gly Met Trp Ser Lys Glu Glu Cys Ile
    210                 215                 220

Ser Leu Thr Arg Gln Tyr Phe Thr Val Thr Asn Arg Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
                260                 265                 270

Arg Thr Pro Glu Val Thr Cys Val Val Val Asp Val Ser His Glu Asp
                275                 280                 285

Pro Glu Val Lys Phe Asn Trp Tyr Val Asp Gly Val Glu Val His Asn
        290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Arg Asp Glu Leu Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
```

```
                420            425            430
Ser Arg Trp Gln Gln Gly Asn Val Phe Ser Cys Ser Val Met His Glu
            435                 440                 445

Ala Leu His Asn His Tyr Thr Gln Lys Ser Leu Ser Leu Ser Pro Gly
    450                 455                 460

Lys
465

<210> SEQ ID NO 68
<211> LENGTH: 1398
<212> TYPE: DNA
<213> ORGANISM: Homo sapiens

<400> SEQUENCE: 68
atggtgccgt gcctcgtagt gctgctggcg gcgctcctca gcctccgtct tggctcagac      60
gctcatggga cagagctgcc cagccctccg tctgtgtggt ttgaagcaga attttttccac    120 cacatcctcc actggacacc catcccaaat cagtctgaaa gtacctgcta tgaagtggcg    180
ctcctgaggt atggaataga gtcctggaac tccatctcca actgtagcca gaccctgtcc    240
tatgacctta ccgcagtgac cttggacctg taccacagca tggctaccg ggccagagtg     300 cgggctgtgg acggcagccg gcactccaac tggaccgtca ccaacacccg cttctctgtg    360
gatgaagtga ctctgacagt tggcagtgtg aacctagaga tccacaatgg cttcatcctc    420
gggaagattc agctacccag gccaagatg gcccccgcga tgacacata tgaaagcatc      480 ttcagtcact ccgagagta tgagattgcc attcgcaagg tgccgggaaa cttcacgttc     540
acacacaaga agtaaaaaca tgaaaacttc agcctcctaa cctctggaga agtgggagag    600
ttctgtgtcc aggtgaaacc atctgtcgct tccgaaagta caaggggat gtggtctaaa     660 gaggagtgca tctcccctca caggcagtat ttcaccgtga ccaacagatc ttgtgacaaa    720
actcacacat gcccaccgtg cccagcacct gaactcctgg ggggaccgtc agtcttcctc    780
ttccccccaa aacccaagga caccctcatg atctcccgga cccctgaggt cacatgcgtg    840
gtggtggacg tgagccacga agaccctgag gtcaagttca actggtacgt ggacggcgtg    900
gaggtgcata atgccaagac aaagccgcgg gaggagcagt acaacagcac gtaccgtgtg    960
gtcagcgtcc tcaccgtcct gcaccaggac tggctgaatg gcaaggagta caagtgcaag   1020
gtctccaaca aagccctccc agcccccatc gagaaaacca tctccaaagc caaagggcag   1080
ccccgagaac cacaggtgta caccctgccc ccatcccggg atgagctgac caagaaccag   1140
gtcagcctga cctgcctggt caaaggcttc tatcccagcg acatcgccgt ggagtgggag   1200
agcaatgggc agccggagaa caactacaag accacgcctc ccgtgctgga ctccgacggc   1260
tccttcttcc tctacagcaa gctcaccgtg gacaagagca ggtggcagca ggggaacgtc   1320
ttctcatgct ccgtgatgca tgaggctctg cacaaccact acacgcagaa gagcctctcc   1380
ctgtctccgg gtaaatga                                                  1398

<210> SEQ ID NO 69
<211> LENGTH: 465
<212> TYPE: PRT
<213> ORGANISM: Homo sapiens

<400> SEQUENCE: 69

Met Val Pro Cys Leu Val Val Leu Ala Ala Leu Leu Ser Leu Arg
1                5                   10                  15

Leu Gly Ser Asp Ala His Gly Thr Glu Leu Pro Ser Pro Pro Ser Val
                20                  25                  30
```

-continued

Trp Phe Glu Ala Glu Phe Phe His His Ile Leu His Trp Thr Pro Ile
         35                  40                  45

Pro Asn Gln Ser Glu Ser Thr Cys Tyr Glu Val Ala Leu Leu Arg Tyr
 50                  55                  60

Gly Ile Glu Ser Trp Asn Ser Ile Ser Asn Cys Ser Gln Thr Leu Ser
65                  70                  75                  80

Tyr Asp Leu Thr Ala Val Thr Leu Asp Leu Tyr His Ser Asn Gly Tyr
             85                  90                  95

Arg Ala Arg Val Arg Ala Val Asp Gly Ser Arg His Ser Asn Trp Thr
             100                 105                 110

Val Thr Asn Thr Arg Phe Ser Val Asp Glu Val Thr Leu Thr Val Gly
         115                 120                 125

Ser Val Asn Leu Glu Ile His Asn Gly Phe Ile Leu Gly Lys Ile Gln
     130                 135                 140

Leu Pro Arg Pro Lys Met Ala Pro Ala Asn Asp Thr Tyr Glu Ser Ile
145                 150                 155                 160

Phe Ser His Phe Arg Glu Tyr Glu Ile Ala Ile Arg Lys Val Pro Gly
                 165                 170                 175

Asn Phe Thr Phe Thr His Lys Lys Val Lys His Glu Asn Phe Ser Leu
             180                 185                 190

Leu Thr Ser Gly Glu Val Gly Glu Phe Cys Val Gln Val Lys Pro Ser
         195                 200                 205

Val Ala Ser Glu Ser Asn Lys Gly Met Trp Ser Lys Glu Glu Cys Ile
     210                 215                 220

Ser Leu Thr Arg Gln Tyr Phe Thr Val Thr Asn Arg Ser Cys Asp Lys
225                 230                 235                 240

Thr His Thr Cys Pro Pro Cys Pro Ala Pro Glu Leu Leu Gly Gly Pro
                 245                 250                 255

Ser Val Phe Leu Phe Pro Pro Lys Pro Lys Asp Thr Leu Met Ile Ser
             260                 265                 270

Arg Thr Pro Glu Val Thr Cys Val Val Val Asp Val Ser His Glu Asp
         275                 280                 285

Pro Glu Val Lys Phe Asn Trp Tyr Val Asp Gly Val Glu Val His Asn
     290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                 325                 330                 335

Tyr Lys Cys Lys Val Ser Asn Lys Ala Leu Pro Ala Pro Ile Glu Lys
             340                 345                 350

Thr Ile Ser Lys Ala Lys Gly Gln Pro Arg Glu Pro Gln Val Tyr Thr
         355                 360                 365

Leu Pro Pro Ser Arg Asp Glu Leu Thr Lys Asn Gln Val Ser Leu Thr
     370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                 405                 410                 415

Asp Ser Asp Gly Ser Phe Phe Leu Tyr Ser Lys Leu Thr Val Asp Lys
             420                 425                 430

Ser Arg Trp Gln Gln Gly Asn Val Phe Ser Cys Ser Val Met His Glu
         435                 440                 445

Ala Leu His Asn His Tyr Thr Gln Lys Ser Leu Ser Leu Ser Pro Gly

<210> SEQ ID NO 70
<211> LENGTH: 1398
<212> TYPE: DNA
<213> ORGANISM: Homo sapiens

<400> SEQUENCE: 70

```
atggtgccgt gcctcgtagt gctgctggcg gcgctcctca gcctccgtct tggctcagac      60
gctcatggga cagagctgcc cagccctccg tctgtgtggt ttgaagcaga attttccac     120
cacatcctcc actggacacc catcccaaat cagtctgaaa gtacctgcta tgaagtggcg    180
ctcctgaggt atgaataga gtcctggaac tccatctcca actgtagcca gaccctgtcc    240
tatgacctta ccgcagtgac cttggacctg taccacagca atggctaccg ggccagagtg    300
cgggctgtgg acggcagccg gcactccaac tggaccgtca ccaacacccg cttctctgtg    360
gatgaagtga ctctgacagt tggcagtgtg aacctagaga tccacaatgg cttcatcctc    420
gggaagattc agctacccag gcccaagatg ccccccgcga atgacacata tgaaagcatc    480
ttcagtcact tccgagagta tgagattgcc attcgcaagg tgccgggaaa cttcacgttc    540
acacacaaga agtaaaaaca tgaaaacttc agcctcctaa cctctggaga agtgggagag    600
ttctgtgtcc aggtgaaacc atctgtcgct tcccgaagta caaggggat gtggtctaaa    660
gaggagtgca tctccctcac caggcagtat ttcaccatga ccaacagatc ttgtgacaaa    720
actcacacat gcccaccgtg cccagcacct gaactcctgg ggggaccgtc agtcttcctc    780
ttcccccaa aacccaagga caccctcatg atctcccgga cccctgaggt cacatgcgtg    840
gtggtggacg tgagccacga agaccctgag gtcaagttca actggtacgt ggacggcgtg    900
gaggtgcata atgccaagac aaagccgcgg gaggagcagt acaacagcac gtaccgtgtg    960
gtcagcgtcc tcaccgtcct gcaccaggac tggctgaatg gcaaggagta caagtgcaag   1020
gtctccaaca aagccctccc agcccccatc gagaaaacca tctccaaagc caaagggcag   1080
ccccgagaac cacaggtgta caccctgccc ccatcccggg atgagctgac caagaaccag   1140
gtcagcctga cctgcctggt caaaggcttc tatcccagcg acatcgccgt ggagtgggag   1200
agcaatgggc agccggagaa caactacaag accacgcctc ccgtgctgga ctccgacggc   1260
tccttcttcc tctacagcaa gctcaccgtg gacaagagca ggtggcagca ggggaacgtc   1320
ttctcatgct ccgtgatgca tgaggctctg cacaaccact acacgcagaa gagcctctcc   1380
ctgtctccgg gtaaatga                                                 1398
```

<210> SEQ ID NO 71
<211> LENGTH: 465
<212> TYPE: PRT
<213> ORGANISM: Homo sapiens

<400> SEQUENCE: 71

```
Met Val Pro Cys Leu Val Val Leu Leu Ala Ala Leu Leu Ser Leu Arg
1               5                   10                  15

Leu Gly Ser Asp Ala His Gly Thr Glu Leu Pro Ser Pro Ser Val
            20                  25                  30

Trp Phe Glu Ala Glu Phe Phe His His Ile Leu His Trp Thr Pro Ile
        35                  40                  45

Pro Asn Gln Ser Glu Ser Thr Cys Tyr Glu Val Ala Leu Leu Arg Tyr
    50                  55                  60
```

```
Gly Ile Glu Ser Trp Asn Ser Ile Ser Asn Cys Ser Gln Thr Leu Ser
65                  70                  75                  80

Tyr Asp Leu Thr Ala Val Thr Leu Asp Leu Tyr His Ser Asn Gly Tyr
                85                  90                  95

Arg Ala Arg Val Arg Ala Val Asp Gly Ser Arg His Ser Asn Trp Thr
            100                 105                 110

Val Thr Asn Thr Arg Phe Ser Val Asp Glu Val Thr Leu Thr Val Gly
        115                 120                 125

Ser Val Asn Leu Glu Ile His Asn Gly Phe Ile Leu Gly Lys Ile Gln
    130                 135                 140

Leu Pro Arg Pro Lys Met Ala Pro Ala Asn Asp Thr Tyr Glu Ser Ile
145                 150                 155                 160

Phe Ser His Phe Arg Glu Tyr Glu Ile Ala Ile Arg Lys Val Pro Gly
                165                 170                 175

Asn Phe Thr Phe Thr His Lys Lys Val Lys His Glu Asn Phe Ser Leu
            180                 185                 190

Leu Thr Ser Gly Glu Val Gly Glu Phe Cys Val Gln Val Lys Pro Ser
        195                 200                 205

Val Ala Ser Arg Ser Asn Lys Gly Met Trp Ser Lys Glu Glu Cys Ile
    210                 215                 220

Ser Leu Thr Arg Gln Tyr Phe Thr Met Thr Asn Arg Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Arg Asp Glu Leu Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

Lys
465
```

```
<210> SEQ ID NO 72
<211> LENGTH: 27
<212> TYPE: DNA
<213> ORGANISM: Artificial Sequence
<220> FEATURE:
<223> OTHER INFORMATION: Description of Artificial Sequence:  Primer

<400> SEQUENCE: 72
ctatgaagtg gcggtcctga ggtatgg                                        27

<210> SEQ ID NO 73
<211> LENGTH: 27
<212> TYPE: DNA
<213> ORGANISM: Artificial Sequence
<220> FEATURE:
<223> OTHER INFORMATION: Description of Artificial Sequence:  Primer

<400> SEQUENCE: 73
ccatacctca ggaccgccac ttcatag                                        27

<210> SEQ ID NO 74
<211> LENGTH: 26
<212> TYPE: DNA
<213> ORGANISM: Artificial Sequence
<220> FEATURE:
<223> OTHER INFORMATION: Description of Artificial Sequence:  Primer

<400> SEQUENCE: 74
ctccaactgg accatcacca acaccc                                         26

<210> SEQ ID NO 75
<211> LENGTH: 26
<212> TYPE: DNA
<213> ORGANISM: Artificial Sequence
<220> FEATURE:
<223> OTHER INFORMATION: Description of Artificial Sequence:  Primer

<400> SEQUENCE: 75
gggtgttggt gatggtccag ttggag                                         26

<210> SEQ ID NO 76
<211> LENGTH: 35
<212> TYPE: DNA
<213> ORGANISM: Artificial Sequence
<220> FEATURE:
<223> OTHER INFORMATION: Description of Artificial Sequence:  Primer

<400> SEQUENCE: 76
caaatgacac atatgaaggc atcttcagtc acttc                               35

<210> SEQ ID NO 77
<211> LENGTH: 35
<212> TYPE: DNA
<213> ORGANISM: Artificial Sequence
<220> FEATURE:
<223> OTHER INFORMATION: Description of Artificial Sequence:  Primer

<400> SEQUENCE: 77
gaagtgactg aagatgcctt catatgtgtc atttg                               35

<210> SEQ ID NO 78
<211> LENGTH: 33
<212> TYPE: DNA
<213> ORGANISM: Artificial Sequence
<220> FEATURE:
<223> OTHER INFORMATION: Description of Artificial Sequence:  Primer

<400> SEQUENCE: 78
```
ccatctgtcg cttccgaaag taacaagggg atg                                    33

<210> SEQ ID NO 79
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 79
catccccttg ttactttcgg aagcgacaga tgg                                    33

<210> SEQ ID NO 80
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 80
gtcacaagat ctgttggtca tggtgaaata ctgcctgg                               38

<210> SEQ ID NO 81
<211> LENGTH: 12
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 81

Tyr His Ser Asn Gly Tyr Arg Ala Arg Val Arg Ala
1               5                   10

<210> SEQ ID NO 82
<211> LENGTH: 10
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 82

Thr Val Thr Asn Thr Arg Phe Ser Val Asp
1               5                   10

<210> SEQ ID NO 83
<211> LENGTH: 10
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 83

Ser Ile Phe Ser His Phe Arg Glu Tyr Glu
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 84

```
Gly Asn Phe Thr Phe Thr His Lys Lys Val
1               5                   10

<210> SEQ ID NO 85
<211> LENGTH: 10
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 85

Ser Val Ala Ser Arg Ser Asn Lys Gly Met
1               5                   10

<210> SEQ ID NO 86
<211> LENGTH: 22
<212> TYPE: PRT
<213> ORGANISM: Artificial Sequence
<220> FEATURE:
<223> OTHER INFORMATION: Description of Artificial Sequence: Synthetic
      construct of Biotinylated peptide

<400> SEQUENCE: 86

Ser Gly Ser Thr Leu Asp Leu Tyr His Ser Asn Gly Tyr Arg Ala Arg
1               5                   10                  15

Val Arg Ala Val Asp Gly
            20

<210> SEQ ID NO 87
<211> LENGTH: 21
<212> TYPE: PRT
<213> ORGANISM: Artificial Sequence
<220> FEATURE:
<223> OTHER INFORMATION: Description of Artificial Sequence: Synthetic
      construct of Biotinylated peptide

<400> SEQUENCE: 87

Ser Gly Ser Thr Tyr Ser Ile Phe Ser His Phe Arg Glu Tyr Glu Ile
1               5                   10                  15

Ala Ile Arg Lys Val
            20
```

INTERLEUKIN 10 RECEPTOR, (IL-10R) ANTIBODIES

RELATED APPLICATIONS

This application claims priority to application Ser. No. 61/056,299, filed May 27, 2008, and is expressly incorporated by reference in its entirety.

INTRODUCTION

Interleukin 10 (IL-10) or cytokine synthesis inhibitory factor (CSIF) is secreted by dendritic cells (DC), macrophages, T cells, B cells, mast cells and keratinocytes at the late stage of an immune response to a pathogen, and has potent anti-inflammatory and immunosuppressive effects on hematopoietic cells (Redpath, et al., *Annu Rev Microbiol* 55:531 (2001)). IL-10 can inhibit the production of many cytokines, including IL-2, IFN-γ, TNF-α, IL-1, IL-4 and GM-CSF (Donnelly, et al., *J Interferon Cytokine Res* 19:563 (1999); Redpath, et al., *Annu Rev Microbiol* 55:531 (2001)). It can also downregulate the expression of MHC class II, ICAM-1, CD80 and CD86 on monocytes, thus reducing the T cell activating capacity of monocyte APC(O'Farrell, et al., *Embo J* 17:1006 (1998); Donnelly, et al., *J Interferon Cytokine Res* 19:563 (1999); Moore, et al., *Annu Rev Immunol* 19:683 (2001)), while also increasing CD14 expression and responses to LPS (Rahimi, et al., *J Immunol* 174:7823 (2005)). IL-10 inhibits DC maturation and IL-12 production (Brossart, et al., *Cancer Res* 60:4485 (2000)), thus suppressing their capacity to induce a Th1 response. Furthermore, IL-10 promotes the generation of regulatory T cells (Tregs) (Moore, et al., *Annu Rev Immunol* 19:683 (2001)).

Given it's substantial immunosuppressive activity, aberrant expression of IL-10 has been implicated in the pathogenesis of many chronic or progressive infectious diseases. Monocytes and macrophages are a major source of IL-10 production, and intracellular pathogens usually target macrophages at the site of infection (Redpath, et al., *Trends Microbiol* 9:86 (2001)). There is extensive evidence that excessive IL-10 usually results in impaired APC function in priming and sustaining adaptive Th1 response, thus decreasing the effectiveness of anti-pathogen immune responses. Based on mouse models, both innate and adaptive immune responses are enhanced or impaired by experimental depletion or elevation of IL-10 in vivo, respectively. These events are reflected by the augmented or reduced clearance, respectively, of intracellular pathogens, such as *Listeria monocytogenes* (Castro, et al., *J Exp Med* 192:1529 (2000)), *Streptococcus pneumoniae*, *Staphylococcus aureus*, *Mycobacterium avium*, *Candida albicans*, *Leishmania major* (Moore, et al., *Annu Rev Immunol* 19:683 (2001); Murray, *Acta Trop* 93:295 (2005)), and lymphocytic choriomeningitis virus (LCMV) (Brooks, et al., *Nat Med* 12:1301 (2006); Ejrnaes, et al., *J Exp Med* 203:2461 (2006); Ejrnaes, et al., *Clin Dev Immunol* 13:337 (2006); Brooks, et al., *Journal of Immunology* 178 (2007); Ejrnaes, et al., *Autoimmun Rev* 6:267 (2007); Brooks, et al., *J Exp Med* 205:533 (2008)).

In humans, elevated IL-10 levels correlate with a number of chronic or progressive infectious diseases caused by intracellular pathogens, such as visceral leishmaniasis and mycobacteria. In addition, it has been reported that anti-IL-10 monoclonal antibodies can restore responses of pathogen-specific T cells from infected patients in vitro (Moore, et al., *Annu Rev Immunol* 19:683 (2001)), suggesting that IL-10 mediates the T cell unresponsiveness or anergy in these chronic diseases. Elevated IL-10 serum levels have also been associated with several chronic viral infectious diseases, including Hepatitis B virus (HBV) (Geng, L., et al., *J Viral Hepat* 13:725 (2006)), Hepatitis C virus (HCV) (Vicari, et al., *Immunol Rev* 202:223 (2004)), HIV (Redpath, et al., *Trends Microbiol* 9:86 (2001)), and Cytomegalovirus (CMV) (Redpath, et al., *Trends Microbiol* 9:86 (2001)). IL-10 is one strategy viruses exploit to evade the immune response. Some viruses infect macrophages and induce cellular IL-10 production, whereas other viruses encode an IL-10 homolog (vIL-10), such as CMV and Epstein-Barr virus (EBV) (Liu, et al., *J Immunol* 158:604 (1997); Moore, et al., *Annu Rev Immunol* 19:683 (2001)). The exact molecular mechanisms by which persistent viral infection causes increased IL-10 secretion have not been determined. However, elevated IL-10 levels result in local and/or systemic suppression of inflammatory responses. In HBV and HCV chronically infected patients, increased IL-10 levels lead to diminished T cell activity, evidenced by the loss of proliferation and cytokine production in the presence of viral antigens in vitro. Moreover, this phenotype in HCV patients can be reversed with anti-IL-10R antibody in vitro (Rigopoulou, et al., *AASLD Abstracts:* 304A (2000); Rigopoulou, et al., *Hepatology* 42:1028 (2005)). Similar responses to IL-10 neutralization have been observed in vitro by PBMC from HIV infected patients (Clerici, et al., *J Clin Invest* 93:768 (1994); Brockman, et al., *Blood* (2009)).

IL-10 mediates its immunosuppressive activities through binding to the cellular IL-10 receptor (IL-10R). IL-10R is composed of two subunits, IL-10Rα (IL-10Ralpha or IL-10R1, CD210) and IL-10Rβ (IL-10Rbeta, IL-10R2), which are members of the class II cytokine receptor family (Donnelly, et al., *J Interferon Cytokine Res* 19:563 (1999); Moore, et al., *Annu Rev Immunol* 19:683 (2001)). Although not wishing to be bound by theory, binding of IL-10 to the heterodimeric IL-10R results in the activation of receptor-associated Jak1 and Tyk2 protein tyrosine kinases, and subsequent tyrosine phosphorylation and activation of DNA binding of signal transducer and activator of transcription 3 (STAT3) and STAT1. This signaling pathway ultimately results in suppression of proinflammatory cytokine production, the negative regulation of T cell, dendritic cell and macrophage activation and other immune suppressive effects.

IL-10Rα is the ligand binding subunit, and it binds IL-10 with high affinity (Kd~35-200 pM). Human IL-10Rα contains 578 amino acids with a molecular size of 90-110 kDa, and it shares 60% homology with mouse IL-10Rα. IL-10Rα is primarily expressed by hematopoietic cells, such as B cells, T cells, NK cells, natural Killer T (NKT) cells, monocytes and macrophages, although generally at levels of only a few hundred per cell (Donnelly, et al., *J Interferon Cytokine Res* 19:563 (1999)). IL-10Rα expression on T cells is downregulated by activation, while it is upregulated on monocytes upon activation, consistent with the idea that IL-10 inhibits the function of those cells after the onset of an immune response (Moore, et al., *Annu Rev Immunol* 19:683 (2001)). This also supports the observation that naïve CD4 T cells are targeted by IL-10, while activated and memory T cells seem to be rather insensitive toward this cytokine. IL-10Rα expression has also been observed on nonhematopoietic cells, although it is more often induced rather than constitutive, such as on LPS treated fibroblasts.

IL-10Rβ contributes little to IL-10 binding affinity, and it is an accessory subunit of IL-10R for signaling (Donnelly, et al., *J Inteiferon Cytokine Res* 19:563 (1999)). IL-10Rβ is part of multiple cytokine receptor complexes, including IL-22 (Asadullah, et al., *Curr Drug Targets Inflamm Allergy* 3:185 (2004)), IL-28, and IL-29. Human IL-10Rβ contains 325 amino acids and is approximately 69% identical to the mouse homologue. In the presence of IL-10, IL-10Rα associates with IL-10Rβ to form tetrameric IL-10R complexes consisting of two of each subunit, which is required for signal transduction. Hence, IL-10Rβ knockout mice develop chronic severe enterocolitis, resembling IL-10 knockout animals. In contrast to cell type restricted expression of IL-10Rα, IL-10Rβ is constitutively expressed in most cells and tissues examined. Unlike IL-10Rα, IL-10Rβ expression in immune cells has not been found to change upon activation. Thus, any stimulus upregulating IL-10Rα expression is sufficient to render the cell responsive to IL-10.

The combining site of human IL-10 and human IL-10Rα has been mapped and shown to be discontinuous. One neutralizing anti-IL-10Rα monoclonal antibody (#MAB274, clone 37607, R&D Systems) has been found to recognize discontinuous epitopes that overlap with some of the IL-10/IL-10R binding regions (Reineke, et al., *Protein Sci* 7:951 (1998)), suggesting that the natural conformation of IL-10R might be important for the generation of neutralizing antibody. Commercially available neutralizing anti-IL-10Rα monoclonal antibodies block all known cellular and viral IL-10 activities (Moore, et al., *Annu Rev Immunol* 19:683 (2001)). Neutralizing anti-IL-10Rβ monoclonal antibodies can also abrogate IL-10 response with perhaps additional effects through other receptor complexes using IL-10Rβ.

SUMMARY

The invention is based, at least in part, on the generation of anti-human Interleukin-10 receptor alpha (IL10Rα) antibodies. Anti-human IL-10Rα antibodies disclosed herein specifically bind to human IL-10Rα. In particular, for example, exemplary IL-10Rα monoclonal antibodies, denoted 136C5 (antibody producing hybridoma deposited on Apr. 8, 2008, with deposit designation of PTA-9131, ATCC 10801 University Blvd., Manassas, Va. 20110-2209), 136C8 (antibody producing hybridoma deposited on Apr. 8, 2008, with deposit designation of PTA-9132, ATCC 10801 University Blvd., Manassas, Va. 20110-2209), and 136D29 (antibody producing hybridoma deposited on Apr. 8, 2008, with deposit designation of PTA-9133, ATCC 10801 University Blvd., Manassas, Va. 20110-2209), bind to IL-10R expressing monocytes and lymphocytes. The exemplary IL-10Rα monoclonal antibodies also bind to human IL-10Rα stably transfected cell lines, EL4-hIL-10Rα and CHO-hIL-10Rα, but not to non-transfected parental cell lines. Moreover, the antibodies are blocked from binding to endogenous IL-10Rα by pre-bound human IL-10. Incubation of IL-10Rα antibodies with human peripheral blood mononuclear cells (PBMC) treated with lipopolysaccharide and IL-10 neutralizes (i.e., inhibits, reduces, antagonizes, prevents or blocks) both exogenous and endogenous IL-10 inhibition of LPS-induced TNF-α secretion (i.e., modulate human IL-10R/IL-10 signaling activity).

Exemplary IL-10Rα antibodies recognize two "epitopes" on IL-10Rα, as determined by cross-blocking studies, human IL-10Rα single nucleotide polymorphism (SNP) variant binding, and cross-reactivity with macaque IL-10Rα. Two of the exemplary antibodies, namely 136C5 and 136C8 bind to all known IL-10Rα SNP variants (e.g., SEQ ID NOs:6, 63, 65, 67, 69 and 71). All exemplary IL-10Rα antibodies bind to chimpanzee IL-10Rα (e.g. SEQ ID NO: 6) and inhibit IL-10R/IL-10 signaling activity, and therefore functionally modulate chimpanzee IL-10Rα activity (i.e., modulate IL-10R/IL-10 signaling activity). Two of the exemplary IL-10Rα antibodies, namely 136C5 and 136C8, bind to chimpanzee IL-10Rα and cynomolgus macaque IL-10Rα (SEQ ID NOs: 8 and 10), and inhibit IL-10R/IL-10 signaling activity, and therefore functionally modulate chimpanzee IL-10Rα and cynomolgus macaque IL-10Rα activity (i.e., modulate IL-10R/IL-10 signaling activity). In comparison to commercially available antibodies 3F9 (#308806, Biolegend), SPM466 (#E8574, Spring Biosciences) and 37607 (#MAB274, R&D Systems), the IL-10Rα antibodies disclosed herein are unique in the ability to functionally modulate both chimpanzee and macaque IL-10Rα activity and to recognize all known IL-10Rα extracellular SNP variants (e.g., SEQ ID NOs:6, 63, 65, 67, 69 and 71).

In accordance with the invention, there are provided antibodies and subsequences thereof that specifically bind to IL-10 Receptor alpha protein (IL-10Rα). In one embodiment, an antibody or subsequence thereof specifically binds to IL-10 Receptor alpha protein, and reduces, inhibits or competes for binding of an antibody designated 136C5, 136C8, or 136D29 to the IL-10 Receptor alpha protein. In another embodiment, an antibody or subsequence thereof specifically binds to IL-10 Receptor alpha protein, and reduces, inhibits or competes for binding of an antibody or subsequence thereof comprising a heavy chain variable region sequence of any of SEQ ID NOs:29, 31 or 33, and a light chain variable region sequence of any of SEQ ID NOs:30, 32, or 34, to the IL-10 Receptor alpha protein. In a further embodiment, an antibody or subsequence thereof specifically binds to IL-10 Receptor alpha protein, and does not detectably reduce, inhibit or compete for binding of antibody designated 3F9, SPM466, or 37607 to the IL-10 Receptor alpha protein. In an additional embodiment, an antibody or subsequence thereof specifically binds to IL-10 Receptor alpha protein, and binds to an epitope distinct from the epitope to which antibody designated 3F9, SPM466, or 37607 binds. In still a further embodiment, an antibody or subsequence thereof binds to or recognizes a conformational epitope (e.g., of IL-10Rα), and not a linear epitope (e.g., of IL-10Rα).

In accordance with the invention, there are also provided antibodies and subsequences thereof that specifically bind to IL-10 Receptor alpha protein (IL-10Rα) and modulate an IL-10R/IL-10 signaling activity. In one embodiment, an antibody or subsequence thereof specifically binds to IL-10Rα, and reduces, inhibits, decreases, suppresses or limits an IL-10R/IL-10 signaling activity. In particular aspects, an antibody or subsequence thereof specifically binds to a human IL-10Rα and a chimpanzee or cynomolgus macaque IL-10Rα, and reduces, inhibits, decreases, suppresses or limits an IL-10R/IL-10 signaling activity. In further particular aspects, an antibody or subsequence thereof specifically binds to a human IL-10Rα, a chimpanzee IL-10Rα and a cynomolgus macaque IL-10Rα, and reduces, inhibits, decreases, suppresses or limits an IL-10R/IL-10 signaling activity. Exemplary IL-10R/IL-10 signaling activities include reducing, decreasing or suppressing TNF-alpha, IL-6, IL-1β or IFN-gamma expression or secretion by peripheral blood mononuclear cells PBMC treated with LPS. In particular, TNF-alpha, IL-6, or TN-gamma expression or secretion by PBMCs (e.g., human, chimpanzee or macaque) increases when PBMCs are treated with LPS in vitro—addition of IL-10 reduces, decreases or suppresses TNF-alpha, IL-6, IL-1β or IFN-gamma expression or secretion by PBMCs (e.g., human, chimpanzee or macaque) treated with LPS. Thus, an invention antibody or subsequence thereof that reverses or limits IL-10 suppression, inhibition or reduction of TNF-alpha, IL-6, IL-1β or TN-gamma expression or secretion by PBMCs will in turn increase, stimulate or induce TNF-alpha, IL-6, IL-1β or TN-gamma expression or secretion by PBMCs (e.g., human, chimpanzee or macaque)

treated with LPS in vitro. Such antibodies and subsequences thereof are considered to functionally modulate IL-10R/IL-10 signaling. Additional Exemplary IL-10R/IL-10 signaling activities include reducing, decreasing or suppressing TNF-alpha or IFN-gamma expression or secretion by a human natural killer T (NKT) cell line stimulated with the antigen α-galactosylcermaide. In particular, TNF-alpha or TN-gamma expression or secretion by NKT cells increases when they are treated with a synthetic α-galactosylceramide, KRN700, in vitro—addition of IL-10 reduces, decreases or suppresses TNF-alpha or IFN-gamma expression or secretion by NKT cells with KRN7000 (Kawano, et al., *Science,* 278: 1626 (1997); Kobayashi, et al., *Oncol Res* 7:259 (1995)). Thus, an invention antibody or subsequence thereof that reverses or limits IL-10 suppression, inhibition or reduction of TNF-alpha or IFN-gamma expression or secretion by NKT cells will in turn increase, stimulate or induce TNF-alpha or IFN-gamma expression or secretion by NKT cells treated with KRN7000 in vitro. Such antibodies and subsequences thereof are considered to functionally modulate IL-10R/IL-10 signaling.

IL-10 receptor alpha (IL-10R alpha) antibodies and subsequences (monoclonal or polyclonal) thereof bind to IL-10 receptor (IL-10R). Antibodies include mammalian, primatized, humanized and fully human antibody. Antibodies can be monoclonal (a single monoclonal or pool of two or more monoclonal) or polyclonal immunoglobulins that belong to any class such as IgM, IgG, IgA, IgE, IgD, and any subclass thereof. Exemplary subclasses for IgG are $IgG_1$, $IgG_2$, $IgG_3$ and $IgG_4$.

Specific non-limiting examples of IL-10R antibody include antibodies set forth herein as 136C5 (antibody producing hybridoma deposited on Apr. 8, 2008, with deposit designation of PTA-9131, ATCC 10801 University Blvd., Manassas, Va. 20110-2209), 136C8 (antibody producing hybridoma deposited on Apr. 8, 2008, with deposit designation of PTA-9132, ATCC 10801 University Blvd., Manassas, Va. 20110-2209), and 136D29 (antibody producing hybridoma deposited on Apr. 8, 2008, with deposit designation of PTA-9133, ATCC 10801 University Blvd., Manassas, Va. 20110-2209), subsequences and variants thereof. Specific non-limiting examples of IL-10 antibody include antibodies with a heavy and light chain variable region amino acid sequences of each of 136C5, 136C8 and 136D29 as set forth herein in Example 2, as SEQ ID NOs:29, 31, and 33; and SEQ ID NOs:30, 32, and 34.

IL-10Rα antibodies also include antibodies that specifically bind to more than one species type of IL-10Rα such as human IL-10Rα, chimpanzee IL-10Rα and cynomolgus macaque IL-10Rα. Exemplary invention antibodies include IL-10Rα antibodies that bind to human IL-10Rα, and chimpanzee IL-10Rα and/or macaque IL-10Rα. In contrast, a commercially available antibody that binds to human IL-10Rα, 37607, fails to detectably bind to chimpanzee IL-10Rα or macaque IL-10Rα.

IL-10Rα antibodies further include antibodies that specifically bind to one or more human IL-10Rα SNP variants. In particular embodiments, an antibody or subsequence thereof specifically binds to one or more of IL-10Rα variants set forth as SEQ ID NOs.:6, 63, 65, 67, 69 or 71. In further particular embodiments, an antibody or subsequence thereof specifically binds with greater affinity to one or more of IL-10Rα variant set forth as SEQ ID NOs.:6, 63, 65, 67, 69 or 71 than binding of 136D29, 3F9, SPM466 or 37607 antibody to IL-10Rα variant set forth as SEQ ID NOs.:6, 63, 65, 67, 69 or 71.

IL-10 receptor (IL-10R) antibody subsequences (antibody fragments) include functional subsequences, which exhibit at least partial IL-10R binding. Such "functional" subsequences or fragments include but are not limited to Fab, Fab', F(ab')$_2$, Fv, Fd, single-chain Fv (scFv), disulfide-linked Fvs (sdFv), light chain variable region $V_L$, heavy chain variable region $V_H$, trispecific (Fab$_3$), bispecific (Fab$_2$), diabody (($V_L$-$V_H$)$_2$ or ($V_H$-$V_L$)$_2$), triabody (trivalent), tetrabody (tetravalent), minibody ((scF$_v$-$C_H$3)$_2$), bispecific single-chain Fv (Bis-scFv), IgGdeltaCH2, scFv-Fc and (scFv)$_2$-Fc. Functional fragments and subsequences also include all or a portion of a full length antibody heavy or light chain, or a heavy or light chain variable region, which includes one or more CDRs of a heavy or light chain variable region sequence (e.g., 1, 2 or all 3 of each of the heavy and light chain variable region CDRs optionally including flanking framework regions, FRs). In various aspects, a functional fragment or a subsequence of a full length antibody heavy or light chain, or a heavy or light chain variable region, has a length from about 20-30, 30-50, 50-100, 100-150, 150-200, 200-250, 250-300, 300-400, or 400-500, amino acid residues.

IL-10 receptor (IL-10R) antibody variants include functional variants, which exhibit at least partial IL-10R binding. In various embodiments, an antibody variant includes one or more amino acid substitutions, deletions or insertions of an antibody constant or variable region sequence set forth herein as 136C5, 136C8 or 136D29, or a heavy or light chain variable regions sequence of 136C5, 136C8 or 136D29, e.g., SEQ ID NOs:29, 31 or 33, or e.g., SEQ ID NOs:30, 32, or 34.

In accordance with the invention, there are also provided methods of treating a subject for a pathogen infection (chronic or acute). In one embodiment, a method includes administering to a subject in need thereof an amount of an IL-10 receptor alpha (IL-10R alpha) antibody or subsequence thereof sufficient to treat the subject for the pathogen infection.

In accordance with the invention, there are also provided prophylactic methods including methods of vaccinating and immunizing a subject against a pathogen infection (chronic or acute), for example, to protect the subject from a pathogen infection (e.g., provide the subject with some protection against pathogen infection), to decrease or reduce the probability of a pathogen infection in a subject, to decrease or reduce susceptibility of a subject to a pathogen infection, or to inhibit or prevent a pathogen infection in a subject. In one embodiment, a method includes administering to a subject an amount of an IL-10 receptor alpha (IL-10R alpha) antibody or subsequence thereof prior to, substantially contemporaneously with or following administration of a pathogen antigen, live or attenuated pathogen, or a nucleic acid encoding all or a portion (e.g., an epitope) of any protein or proteinaceous pathogen antigen sufficient to vaccinate or immunize the subject against the pathogen infection (chronic or acute).

In various aspects, a method is sufficient to protect the subject from the pathogen infection (e.g., provide the subject with some protection against pathogen infection), to decrease or reduce the probability of pathogen infection in the subject, to decrease or reduce susceptibility of a subject to a pathogen infection, or to inhibit or prevent a pathogen infection, or to decrease, reduce, inhibit or prevent pathogen reactivation in a subject.

Methods of the invention include administering the IL-10 receptor (IL-10R) antibody or subsequence thereof at various times and in various quantities. In particular embodiments, IL-10 receptor (IL-10R) antibody or subsequence thereof is administered prior to, substantially contemporaneously with or following contact, exposure to or infection with a pathogen. In other embodiments, IL-10 receptor (IL-10R) antibody or subsequence thereof is administered prior to, substantially contemporaneously with or following exposure to, contact with or infection (chronic or acute) of the subject with a pathogen. In additional embodiments, IL-10 receptor (IL-10R) antibody or subsequence thereof is administered prior to, substantially contemporaneously with or following pathogen infection, development of a symptom associated with or caused by a pathogen (e.g., inflammation), pathogen replication or proliferation, or pathogen reactivation from latency. In further embodiments, an IL-10 receptor alpha (IL-10R alpha) antibody or subsequence thereof, and a pathogen antigen, live or attenuated pathogen, or nucleic acid encoding all or a portion (e.g., an epitope) of any protein or proteinaceous pathogen antigen are administered as a combination composition, or are administered separately, such as concurrently or sequentially, to a subject in order to effect vaccination or immunization, prior to, substantially contemporaneously with or following pathogen infection, development of a symptom associated with or caused by a pathogen (e.g., inflammation), pathogen replication or proliferation, or pathogen reactivation from latency.

Pathogens treated, or vaccinated or immunized against include any pathogen which may respond to an IL-10 receptor antibody or subsequence thereof. In various embodiments, a pathogen is a virus, bacterium, parasite or a fungus.

Exemplary viruses include poxvirus, herpesvirus, hepatitis virus, immunodeficiency virus, flavivirus, papilloma virus (PV), polyoma virus, rhabdovirus, a myxovirus, an arenavirus, a coronavirus, adenovirus, reovirus, picornavirus, togavirus, bunyavirus, parvovirus or retrovirus.

Poxviruses include a vaccinia virus, Molluscum contagiosum, variola major smallpox virus, variola minor smallpox virus, cow pox, camel pox, sheep pox, and monkey pox. Herpesviruses include alpha-herpesvirus, beta-herpesvirus, gamma-herpesvirus, Epstein Bar Virus (EBV), Cytomegalovirus (CMV), varicella zoster virus (VZV/HHV-3), and human herpes virus 1, 2, 4, 5, 6, 7, and 8 (HHV-8, Kaposi's sarcoma-associated virus). Hepatitis viruses include hepatitis A, B, C, D, E and G. Immunodeficiency viruses include human immunodeficiency virus (HIV), such as HIV-1, HIV-2 and HIV-3. Flaviviruses include Hepatitis C virus, Yellow Fever virus, Dengue virus, and Japanese Encephalitis and West Nile viruses. Papilloma viruses include human papilloma virus (HPV), such as HPV strain 1, 6, 11, 16, 18, 30, 31, 42, 43, 44, 45, 51, 52, and 54. Polyoma viruses include BK virus (BKV) and JC virus (JCV). Rhabdoviruses include rabies virus and vesiculovirus. Myxoviruses include paramyxovirus (e.g., measles, mumps, pneumovirus and respiratory syncytial virus (RSV) and orthomyxovirus (e.g., influenza virus, such as influenza A, influenza B and influenza C). Arenaviruses include lymphocytic choriomeningitis virus (LCMV), Junin virus, Lassa virus, Guanarito virus, Sabia virus and Machupo virus. Coronaviruses include viruses that cause a common cold or severe acute respiratory syndrome (SARS). Adenoviruses include viral infections of the bronchii, lung, stomach, intestine (gastroenteritis), eye (conjunctivitis), bladder (cystitis) and skin. Reoviruses include a rotavirus, cypovirus and orbivirus. Picornaviruses include rhinovirus (e.g., causing a common cold), apthovirus, hepatovirus, enterovirus, coxsackie B virus and cardiovirus. Togaviruses include alphavirus, sindbus virus, and rubellavirus. Bunyaviruses include hantavirus, phlebovirus and nairovirus. Retroviruses include alpha, beta, delta, gamma, epsilon, lentivirus, spumavirus and human T-cell leukemia virus, such as human T-cell leukemia virus 1 and 2 (HTLV-1 and HTLV-2). Lentiviruses include immunodeficiency virus, such as bovine, porcine, equine, canine, feline and primate virus.

Exemplary bacteria include a mycobacterium (e.g., tuberculosis and atypical mycobacterium), *listeria monocytogenes, helicobacter, bordetella, streptococcus, salmonella* and *chlamydia*. Exemplary parasites include a protozoa or nematode. Exemplary protozoa include a *Toxoplasma gondii, Leishmania, Plasmodium*, or *Trypanosoma cruzi*. Exemplary nematodes include a *Schistosoma mansoni*, or a *Heligmosomoides polygyrus*. Exemplary fungus includes *Candida albicans*.

Pathogen antigens useful in accordance with the invention can be any antigen, live or attenuated pathogen, or nucleic acid encoding all or a portion (e.g., an epitope) of any protein or proteinaceous pathogen antigen. Particular non-limiting types of pathogen antigens, live or attenuated pathogen, and nucleic acid encoding all or a portion of a pathogen antigen include viral, bacterial, parasite and fungal antigens. Such antigens can be from any pathogen set forth herein or known to one of skill in the art, and can include an antigen that increases, stimulates, enhances, promotes, augments or induces a proinflammatory or adaptive immune response, numbers or activation of an immune cell (e.g., T cell, natural killer T (NKT) cell, dendritic cell (DC), macrophage, neutrophil, eosinophil, mast cell, CD4+ or a CD8+ cell, CD14+, CD11b+ or CD11c+ cells), an anti-pathogen CD4+ or CD8+ T cell response, production of a Th1 cytokine, or a T cell mediated immune response.

In additional various methods embodiments, an antibody or subsequence thereof and a second active, such as a different antibody, an agent or a drug are administered to a subject, one or more times, as a combination (e.g., an IL-10R antibody or subsequence thereof is administered as a combination composition with another antibody, agent or drug to a subject). In further various methods embodiments, an antibody or subsequence thereof and a second active, such as a different antibody, an agent or a drug are administered to a subject, one or more times, sequentially (e.g., an IL-10R antibody or subsequence thereof and an agent or drug are administered separately to a subject, in a sequence). Additional method embodiments include, for example, second actives such as type I interferons, toll receptor ligands, T cell costimulatory molecules such as OX40, 4-1BB and antagonists to inhibitory receptors or ligands such as antibodies that bind to CTLA4, PD-1, PD-L1, CD160 and LAGS.

Methods of the invention also include increasing numbers or activation of an immune cell in a subject with or at risk of a pathogen infection. In one embodiment, a method includes administering to a subject an amount of IL-10 receptor (IL-10R) antibody or subsequence thereof sufficient to increase numbers or activation of the immune cell in the subject. In another embodiment, a method includes administering to a subject an amount of an IL-10 receptor alpha (IL-10R alpha) antibody or subsequence thereof and administering a pathogen antigen, live or attenuated pathogen, or a nucleic acid encoding all or a portion (e.g., an epitope) of any protein or proteinaceous pathogen antigen sufficient to increase numbers or activation of the immune cell in the subject. In particular aspects, the immune cell is a T cell, NKT cell, dendritic cell (DC), macrophage, neutrophil, eosinophil, mast cell, CD4+ or a CD8+ cell, CD14+, CD11b+ or CD11c+ cells.

Methods of the invention further include, among other things, increasing or inducing an anti-pathogen CD8+ or CD4+ T cell response in a subject with or at risk of a pathogen infection. In one embodiment, a method includes administering to a subject in need thereof an amount of IL-10 receptor (IL-10R) antibody or subsequence thereof sufficient to increase or induce an anti-pathogen CD8+ or CD4+ T cell response, including proliferation, cytokine secretion or cytotoxicity, or chemokine expression or production in the subject. In another embodiment, a method includes administering to a subject an amount of an IL-10 receptor alpha (IL-10R alpha) antibody or subsequence thereof and administering a pathogen antigen, live or attenuated pathogen, or a nucleic acid encoding all or a portion (e.g., an epitope) of any protein or proteinaceous pathogen antigen sufficient to increase or induce an anti-pathogen CD8+ or CD4+ T cell response, including proliferation, cytokine secretion or cytotoxicity, or chemokine expression or production in the subject.

Methods of the invention additionally include, among other things, increasing production of a Th1 cytokine (e.g., interferon gamma, IL-1alpha, IL-1beta, IL-2, TNF-alpha, IL-6, IL-9, IL-12, IL-18, GM-CSF, etc.) or a chemokine (e.g., MCP1, MCP5, RANTES, IL-8, 1P-10, MIP-2, etc.). In one embodiment, a method includes administering to a subject in need thereof an amount of IL-10 receptor (IL-10R) antibody or subsequence thereof sufficient to increase production of a Th1 cytokine (e.g., interferon gamma, IL-1alpha, IL-1beta, IL-2, TNF-alpha, IL-6, IL-12, GM-CSF, etc.) or a chemokine (e.g., MCP1, MCP5, RANTES, IL-8, IP-10, MIP-2, etc.) in the subject. In another embodiment, a method includes administering to a subject an amount of an IL-10 receptor alpha (IL-10R alpha) antibody or subsequence thereof and administering a pathogen antigen, live or attenuated pathogen, or a nucleic acid encoding all or a portion (e.g., an epitope) of any protein or proteinaceous pathogen antigen sufficient to increase production of a Th1 cytokine (e.g., interferon gamma, IL-1alpha, IL-1beta, IL-2, TNF-alpha, IL-6, IL-12, GM-CSF, etc.) or a chemokine (e.g., MCP1, MCP5, RANTES, IL-8, W-10, MIP-2, etc.) in the subject.

Methods of the invention include, among other things, methods that provide a therapeutic or beneficial effect to a subject. In various non-limiting embodiments, a method decreases, reduces, inhibits, suppresses, controls or limits pathogen numbers or titer; decreases, reduces, inhibits, suppresses, prevents, controls or limits pathogen proliferation or replication; decreases, reduces, inhibits, suppresses, prevents, controls or limits the amount of a pathogen protein; or decreases, reduces, inhibits, suppresses, prevents, controls or limits the amount of a pathogen nucleic acid. In additional embodiments, a method increases, stimulates, enhances, promotes, augments or induces pathogen clearance or removal; increases, induces, enhances, augments, promotes or stimulates an immune response against a pathogen; decreases, reduces, inhibits, suppresses, prevents, controls or limits pathogen pathology; decreases, reduces, inhibits, suppresses, prevents, controls or limits increases in pathogen numbers or titer; decreases, reduces, inhibits, suppresses, prevents, controls or limits increases in pathogen proliferation or replication, a pathogen protein, or a pathogen nucleic acid. In further embodiments, a method decreases, reduces, inhibits, suppresses, prevents, controls or limits pathogen reactivation from latency, or decreases, reduces, inhibits, suppresses, prevents, controls or limits transmission of pathogen to a host (e.g., transmission of a pathogen from an infected subject to an uninfected subject or susceptible subject). In yet additional embodiments, a method decreases, reduces, inhibits, suppresses, prevents, controls, limits or improves one or more adverse (e.g., physical or physiological) symptoms, disorders, illnesses, diseases or complications associated with or caused by pathogen infection, reactivation from latency or pathology. In still further embodiments, a method provides a subject with protection against a pathogen infection, reactivation from latency, or pathology, or decreases, reduces, inhibits, or limits susceptibility or probability of a subject to a pathogen infection, reactivation from latency, or pathology.

In various additional non-limiting embodiments, pathogen infection, proliferation or pathogenesis or reactivation from latency, is reduced, decreased, inhibited, limited, delayed or prevented, or a method decreases, reduces, inhibits, suppresses, prevents, controls or limits one or more adverse (e.g., physical or physiological) symptoms, disorders, illnesses, diseases or complications caused by or associated with chronic or acute pathogen infection, proliferation or replication, pathology or reactivation from latency. In additional various non-limiting embodiments, a method reduces, decreases, inhibits, delays or prevents onset, progression, frequency, duration, severity, probability or susceptibility of one or more adverse symptoms, disorders, illnesses, diseases or complications caused by or associated with chronic or acute pathogen infection, proliferation or replication, pathology or reactivation from latency. In further various non-limiting embodiments, a method accelerates, facilitates, enhances, augments, or hastens recovery of a subject from a pathogen infection, reactivation from latency or pathogenesis, or one or more adverse symptoms, disorders, illnesses, diseases or complications caused by or associated with chronic or acute pathogen infection, proliferation or replication, pathology or reactivation from latency. In yet additional non-limiting embodiments, a method stabilizes a pathogen infection, proliferation, replication, pathogenesis, or an adverse symptom, disorder, illness, disease or complication caused by or associated with chronic or acute pathogen infection, proliferation or replication, pathology or reactivation from latency, or decreases, reduces, inhibits, suppresses, prevents, limits or controls transmission of a pathogen from an infected host to an uninfected host.

The invention also provides kits that include an IL-10 receptor (IL-10R) antibody or subsequence thereof. Such kits optionally include a pathogen antigen, live or attenuated pathogen, and further optionally include instructions for treating (prophylactic or therapeutic), vaccinating or immunizing a subject against a pathogen infection, or treating (prophylactic or therapeutic) a subject having or at risk of having a pathogen infection, proliferation, reactivation or pathogenesis. Exemplary non-limiting IL-10 receptor (IL-10R) antibody or subsequence thereof for inclusion in kits include antibody (polyclonal or monoclonal), as set forth herein.

DESCRIPTION OF DRAWINGS

FIGS. 6A-6C show data indicating cross-reactivity with non-human primate IL-10Rα. PBMC from humans (A), chimpanzees (B), and cynomolgus macaques (C) were stained with anti-human IL-10Rα antibodies in the absence (filled) or presence (shaded) of recombinant human IL-10Rα, or with an isotype control antibody (open histograms). Histograms represent staining of IL-10Rα on cells in the lymphocyte gate based on forward and side scatter properties. Staining on monocytes was similar.

DETAILED DESCRIPTION

Figures 1A, 1B:
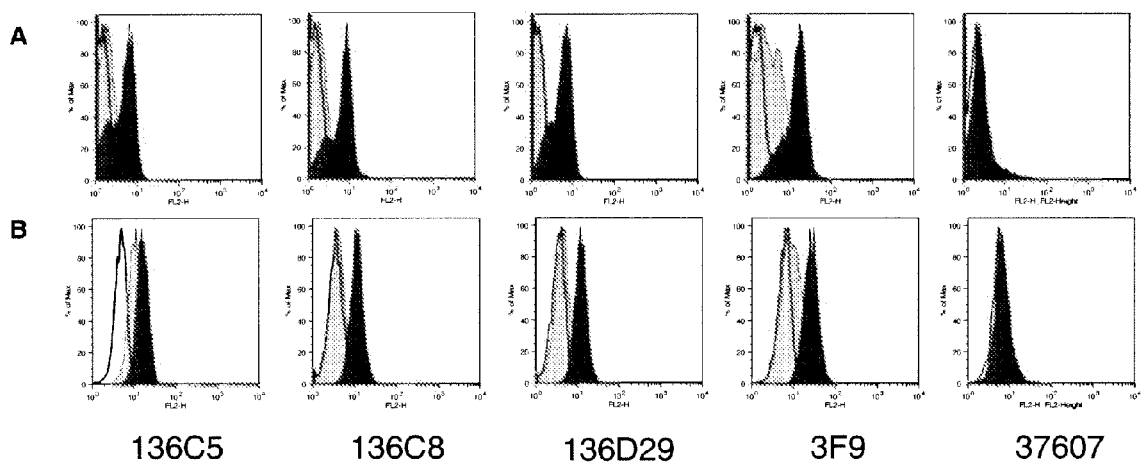
FIGS. 1A-1B show flow cytometric analysis with human anti-human IL-10Rα antibodies. Total human PBMC were stained with biotinylated anti-human IL-10Rα antibodies in the presence (shaded histograms) or absence (filled histograms) of soluble human IL-10Rα protein. Binding of antibodies was detected with streptavidin-PE. The open histogram represents staining with isotype control antibodies. The lymphocyte (A) and monocyte (B) gates were set based on the forward and side scatter profile.

The invention is based at least in part on antibodies and subsequences thereof that specifically bind to IL-10 Receptor alpha protein (IL-10Rα). Invention antibodies and subsequences, including human monoclonal antibodies, are useful in treatment, detection and diagnostic methods. For example, invention antibodies and subsequences are useful in methods of treating a subject for a pathogen infection (chronic or acute). Such treatment methods include therapeutic (following pathogen infection) and prophylactic (prior to pathogen infection) methods including, for example, methods of treating a subject with a pathogen infection, and methods of protecting a subject from a pathogen infection (e.g., provide the subject with protection against pathogen infection), to decrease or reduce the probability of a pathogen infection in a subject, to decrease or reduce susceptibility of a subject to a pathogen infection, or to inhibit or prevent a pathogen infection in a subject, and to decrease, reduce, inhibit or suppress transmission of the pathogen from one subject to another subject.

In accordance with the invention, there are provided antibodies and subsequences thereof that specifically bind to IL-10 Receptor alpha protein (IL-10Rα). In one embodiment, an antibody or subsequence thereof specifically binds to IL-10 Receptor alpha protein, and reduces, inhibits or competes for binding of an antibody designated 136C5, 136C8, or 136D29 to the IL-10 Receptor alpha protein. In another embodiment, an antibody or subsequence thereof specifically binds to IL-10 Receptor alpha protein, and reduces, inhibits or competes for binding of an antibody or subsequence thereof comprising a heavy chain variable region sequence of any of SEQ ID NOs:29, 31 or 33, and a light chain variable region sequence of any of SEQ ID NOs:30, 32, or 34, to the IL-10 Receptor alpha protein. In a further embodiment, an antibody or subsequence thereof specifically binds to IL-10 Receptor alpha protein, and does not detectably reduce, inhibit or compete for binding of antibody designated 3F9, SPM466, or 37607 to the EL-10 Receptor alpha protein.

In accordance with the invention, there are provided antibodies and subsequences thereof that specifically bind to more than one species type of IL-10Rα. In one embodiment, an antibody or subsequence thereof specifically binds to human IL-10Rα, and optionally also binds to chimpanzee IL-10Rα or binds to cynomolgus macaque IL-10Rα. In another embodiment, an antibody or subsequence thereof specifically binds to human IL-10Rα, and binds to chimpanzee IL-10Rα or binds to cynomolgus macaque IL-10Rα. In a further embodiment, an antibody or subsequence thereof specifically binds to human IL-10Rα, to chimpanzee IL-10Rα and to cynomolgus macaque IL-10Rα.

In further embodiments, antibodies and subsequences thereof specifically bind to IL-10 Receptor alpha protein (IL-10Rα) and modulate an IL-10R/IL-10 signaling activity. In one aspect, an antibody or subsequence thereof reduces, inhibits, decreases, suppresses or limits an IL-10R/IL-10 signaling activity. In another aspect an antibody or subsequence thereof reduces, inhibits, decreases, suppresses or limits an IL-10R/IL-10 signaling activity greater than the reduction or inhibition of IL-10 signaling activity by any of 3F9, SPM466 or 37607 antibodies.

In further aspects, an antibody or subsequence thereof specifically binds to a human, a chimpanzee or cynomolgus macaque IL-10Rα, and reduces, inhibits, decreases, suppresses or limits an activity of human, chimpanzee or cynomolgus macaque IL-10Rα (e.g., IL-10R/IL-10 signaling). In still further particular aspects, an antibody or subsequence thereof specifically binds to a human IL-10Rα, and one or both of a chimpanzee IL-10Rα and cynomolgus macaque IL-10Rα, and reduces, inhibits, decreases, suppresses or limits an activity of human, chimpanzee or cynomolgus macaque IL-10Rα (e.g., IL-10R/IL-10 signaling). In another embodiment, an invention antibody or subsequence thereof reverses or limits IL-10 suppression, inhibition, or reduction of TNF-alpha, IL-6, IL-1β or IFN gamma expression or secretion by PBMCs, which is reflected by an increase in TNF-alpha, IL-6, IL-1β or IFN gamma expression or secretion by PBMCs (e.g., human, chimpanzee or macaque) treated with LPS in vitro in the presence of IL-10. In still another embodiment, an invention antibody or subsequence thereof increases or induces TNF-alpha or IFN-gamma expression by NKT cells in the presence of IL-10 and the antigen KRN7000, at least partially restores expression of the HLA-DR MHC class II molecule in the presence of IL-10, or inhibits or reduces IL-10 induced phosphorylation of STAT3. In particular aspects, an invention antibody or subsequence thereof increases or induces TNF-alpha or IFN-gamma expression by PBMC or NKT cells in the presence of IL-10, restores expression of the HLA-DR MHC class II molecule in the presence of IL-10, or inhibits or reduces IL-10 induced phosphorylation of STAT3 greater than another reference antibody, such as any of 3F9, SPM466 or 37607 antibodies.

In an additional embodiment, an antibody or subsequence thereof specifically binds to IL-10 Receptor alpha protein, and binds to an epitope distinct from the epitope to which antibody designated 3F9, SPM466, or 37607 binds. In particular aspects, antibodies and subsequences thereof may reduce or inhibit binding of a reference antibody to IL-10R by less than 50%, by about 50% or more, e.g., 50-70% or, by about 70% or more.

In accordance with the invention, there are also provided antibodies and subsequences thereof that specifically bind to IL-10 Receptor alpha protein (IL-10Rα), and that exhibit sequence identity to a heavy or light chain variable region sequence of antibody designated 136C5, 136C8, or 136D29, or a heavy chain variable region sequence of any of SEQ ID NOs:29, 31 or 33, or a light chain variable region sequence of any of SEQ ID NOs:30, 32, or 34. In one embodiment, an antibody or subsequence thereof that specifically binds to IL-10Rα includes a sequence at least 60% or more (e.g., 65%, 70%, 75%, 80%, 85%, 90%, 95%, etc.) identical to any heavy chain variable region sequence set forth as SEQ ID NOs:29, 31 or 33, and a sequence at least 60% or more (e.g., 65%, 70%, 75%, 80%, 85%, 90%, 95%, etc.) identical to any light chain variable region sequence set forth as SEQ ID NOs:30, 32, or 34.

In another embodiment, an antibody or subsequence thereof that specifically binds to IL-10Rα includes any heavy chain variable region sequence set forth as SEQ ID NOs:29, 31 or 33 and any light chain variable region sequence set forth as SEQ ID NOs:30, 32, or 34, wherein the antibody or subsequence has one or more amino acid additions, deletions or substitutions of SEQ ID NOs:29, 31 or 33, or SEQ ID NOs: 30, 32, or 34. In particular aspects, a sequence is at least 80% or more, e.g., 80-85%, 85-90%, 90-95%, 95-100% identical to any heavy chain variable region sequence set forth as SEQ ID NOs:29, 31 or 33, or any light chain variable region sequence set forth as SEQ ID NOs:30, 32, or 34. In further aspects, an antibody that specifically binds to IL-10Rα includes or consists of any one of a heavy chain variable region sequence set forth as SEQ ID NOs:29, 31 or 33, or a light chain variable region sequence set forth as SEQ ID NOs:30, 32, or 34. In particular aspects, antibodies and subsequences thereof may reduce or inhibit binding of a reference antibody to IL-10R by about 50% or more, e.g., 70% or more.

The term "antibody" refers to a protein that binds to other molecules (antigens) via heavy and light chain variable domains, $V_H$ and $V_L$, respectively. Antibodies include full-length antibodies that include two heavy and two light chain sequences. Antibodies can have kappa or lambda light chain sequences, either full length as in naturally occurring antibodies, mixtures thereof (i.e., fusions of kappa and lambda chain sequences), and subsequences/fragments thereof. Naturally occurring antibody molecules contain two kappa or two lambda light chains.

Antibodies include monoclonal or polyclonal immunoglobulin molecules that belong to any class such as IgM, IgG, IgA, IgE, IgD, and any subclass thereof. Exemplary subclasses for IgG are $IgG_1$, $IgG_2$, $IgG_3$ and $IgG_4$. A "monoclonal" antibody refers to an antibody that is based upon, obtained from or derived from a single clone, including any eukaryotic, prokaryotic, or phage clone. A "monoclonal" antibody is therefore defined structurally, and not the method by which it is produced.

An IL-10 receptor (IL-10R) antibody or subsequence thereof, which can also be referred to as "IL-10R antibody," "anti-IL-10R" and "anti-IL-10R antibody" refers to a polyclonal or monoclonal antibody that specifically binds to IL-10 receptor (IL-10R). The term "bind," or "binding," when used in reference to an antibody, means that the antibody or subsequence thereof interacts at the molecular level with a corresponding epitope (antigenic determinant) present on an antigen. Thus, an antibody specifically binds to all or a part of sequence or an antigenic epitope present on IL-10R. Specific binding is that which is selective for an epitope present in IL-10R. Antibodies and subsequences thereof include specific or selective binding to IL-10R alpha or beta subunits, or an epitope comprising both alpha and beta subunits of IL-10R. Specific and selective binding can be distinguished from non-specific binding using assays known in the art (e.g., immunoprecipitation, ELISA, flow cytometry, Western blotting).

Epitopes typically are short amino acid sequences, e.g. about five to 15 amino acids in length. Epitopes can be contiguous or non-contiguous. A non-contiguous amino acid sequence epitope forms due to protein folding. For example, an epitope can include a non-contiguous amino acid sequence, such as a 5 amino acid sequence and an 8 amino acid sequence, which are not contiguous with each other, but form an epitope due to protein folding. Techniques for identifying epitopes are known to the skilled artisan and include screening overlapping oligopeptides for binding to antibody (for example, U.S. Pat. No. 4,708,871), phage display peptide library kits, which are commercially available for epitope mapping (New England BioLabs). Epitopes may also be identified by inference when epitope length peptide sequences are used to immunize animals from which antibodies that bind to the peptide sequence are obtained and can be predicted using computer programs, such as BEPITOPE (Odorico et al., *J. Mol. Recognit.* 16:20 (2003)).

IL-10 receptor (IL-10R) antibodies and subsequences thereof bind to IL-10R in solution or in solid phase, on cells in vitro or in vivo or in situ. IL-10R can also be present in vivo, such as on one or more cells in vivo, in vitro, in primary cell isolates, passaged cells, cultured cells, immortalized cells and cells ex vivo. Antibody binding to wild type IL-10R expressed by cells typically bind to IL-10R extracellular domain (see, e.g., SEQ ID NO:3). Specific non-limiting cell types that can express IL-10R include activated and other T cells (e.g., naïve, effector, memory or regulatory T cells, CD4+ and CD8+ T cells, NKT cells) and non-T cells. Examples of non-T cells include natural killer (NK) cells, granulocytes (neutrophils), eosinophils, monocytes, macrophages, mast cells and dendritic cells (DC). Cells that do not naturally express IL-10R can be made to express IL-10R, for example, by transfecting or transforming cells with an IL-10R encoding nucleic acid. IL-10 receptor (IL-10R) antibodies and subsequences thereof can bind to one or more transfected or transformed cells that express or produce IL-10R.

IL-10 may, but need not, reduce, decrease or inhibit binding of antibodies to IL-10R. In certain embodiments, binding of an antibody or subsequence thereof to IL-10R is reduced, decreased or inhibited by binding of IL-10 to IL-10R. In other embodiments, binding of antibody or subsequence thereof to IL-10R is not detectably blocked, prevented, reduced, decreased or inhibited by binding of IL-10 to IL-10R.

IL-10 receptor (IL-10R) antibodies and subsequences thereof bind to IL-10 receptor (IL-10R), including mammalian (e.g., primate, such as chimp, macaque and human) forms of IL-10 receptor (IL-10R). IL-10 receptor (IL-10R) antibodies and subsequences thereof may bind to primate IL-10R, such as human IL-10R, but may not detectably bind to chimp IL-10R, or macaque IL-10R. A non-limiting example of IL-10 receptor alpha chain (IL-10Rα) is a human sequence set forth as:

```
                                                          SEQ ID NO: 2
MLPCLVVLLA ALLSLRLGSD AHGTELPSPP SVWFEAEFFH HILHWTPIPN QSESTCYEVA

LLRYGIESWN SISNCSQTLS YDLTAVTLDL YHSNGYRARV RAVDGSRHSN WTVTNTRFSV

DEVTLTVGSV NLEIHNGFIL GKIQLPRPKM APANDTYESI FSHFREYEIA IRKVPGNFTF

THKKVKHENF SLLTSGEVGE FCVQVKPSVA SRSNKGMWSK EECISLTRQY FTVTNVIIFF

AFVLLLSGAL AYCLALQLYV RRRKKLPSVL LFKKPSPFIF ISQRPSPETQ DTIHPLDEEA

FLKVSPELKN LDLHGSTDSG FGSTKPSLQT EEPQFLLPDP HPQADRTLGN GEPPVLGDSC

SSGSSNSTDS GICLQEPSLS PSTGPTWEQQ VGSNSRGQDD SGIDLVQNSE GRAGDTQGGS

ALGHHSPPEP EVPGEEDPAA VAFQGYLRQT RCAEEKATKT GCLEEESPLT DGLGPKFGRC

LVDEAGLHPP ALAKGYLKQD PLEMTLASSG APTGQWNQPT EEWSLLALSS CSDLGISDWS

FAHDLAPLGC VAAPGGLLGS FNSDLVTLPL ISSLQSSE,
```

The term "isolated," when used as a modifier of a composition (e.g., antibodies, subsequences, modified forms, nucleic acids encoding same, etc.), means that the compositions are made by the hand of man or are separated, completely or at least in part, from their naturally occurring in vivo environment. Generally, isolated compositions are substantially free of one or more materials with which they normally associate with in nature, for example, one or more protein, nucleic acid, lipid, carbohydrate, cell membrane. The term "isolated" does not exclude alternative physical forms of the composition, such as fusions/chimeras, multimers/oligomers, modifications (e.g., phosphorylation, glycosylation, lipidation) or derivatized forms, or forms expressed in host cells produced by the hand of man.

An "isolated" composition (e.g., an antibody) can also be "substantially pure" or "purified" when free of most or all of the materials with which it typically associates with in nature. Thus, an isolated antibody that also is substantially pure or purified does not include polypeptides or polynucleotides present among millions of other sequences, such as antibodies of an antibody library or nucleic acids in a genomic or cDNA library, for example. A "substantially pure" or "purified" composition can be combined with one or more other molecules. Thus, "substantially pure" or "purified" does not exclude combinations of compositions, such as combinations of IL-10R antibodies or subsequences, and other antibodies, agents, drugs or therapies.

Antibodies include mammalian, primatized, humanized, fully human antibodies and chimeras. A mammalian antibody is an antibody which is produced by a mammal, transgenic or non-transgenic, or a non-mammalian organism engineered to produce a mammalian antibody, such as a non-mammalian cell (bacteria, yeast, insect cell), animal or plant.

The term "human" when used in reference to an antibody, means that the amino acid sequence of the antibody is fully human, i.e., human heavy and human light chain variable and human constant regions. Thus, all of the amino acids are human or exist in a human antibody. An antibody that is non-human may be made fully human by substituting the non-human amino acid residues with amino acid residues that exist in a human antibody. Amino acid residues present in human antibodies, CDR region maps and human antibody consensus residues are known in the art (see, e.g., Kabat, Sequences of Proteins of Immunological Interest, 4$^{th}$ Ed. US Department of Health and Human Services. Public Health Service (1987); Chothia and Lesk (1987). A consensus sequence of human $V_H$ subgroup III, based on a survey of 22 known human $V_H$ III sequences, and a consensus sequence of human $V_L$ kappa-chain subgroup I, based on a survey of 30 known human kappa I sequences is described in Padlan Mol. Immunol. 31:169 (1994); and Padlan Mol. Immunol. 28:489 (1991). Human antibodies therefore include antibodies in which one or more amino acid residues have been substituted with one or more amino acids present in any other human antibody.

The term "humanized" when used in reference to an antibody, means that the amino acid sequence of the antibody has non-human amino acid residues (e.g., mouse, rat, goat, rabbit, etc.) of one or more complementarity determining regions (CDRs) that specifically bind to the desired antigen in an acceptor human immunoglobulin molecule, and one or more human amino acid residues in the Fv framework region (FR), which are amino acid residues that flank the CDRs. Such antibodies typically have reduced immunogenicity and therefore a longer half-life in humans as compared to the non-human parent antibody from which one or more CDRs were obtained or are based upon.

Antibodies referred to as "primatized" are "humanized" except that the acceptor human immunoglobulin molecule and framework region amino acid residues may be any primate amino acid residue (e.g., ape, gibbon, gorilla, chimpanzees orangutan, macaque), in addition to any human residue. Human FR residues of the immunoglobulin can be replaced with corresponding non-human residues. Residues in the CDR or human framework regions can therefore be substituted with a corresponding residue from the non-human CDR or framework region donor antibody to alter, generally to improve, antigen affinity or specificity, for example. A humanized antibody may include residues, which are found neither in the human antibody nor in the donor CDR or framework sequences. For example, a FR substitution at a particular position that is not found in a human antibody or the donor non-human antibody may be predicted to improve binding affinity or specificity human antibody at that position. Antibody framework and CDR substitutions based upon molecular modeling are well known in the art, e.g., by modeling of the interactions of the CDR and framework residues to identify framework residues important for antigen binding and sequence comparison to identify unusual framework residues at particular positions (see, e.g., U.S. Pat. No. 5,585,089; and Riechmann et al., Nature 332:323 (1988)).

The term "chimeric" and grammatical variations thereof, when used in reference to an antibody, means that the amino acid sequence of the antibody contains one or more portions that are derived from, obtained or isolated from, or based upon two or more different species. For example, a portion of the antibody may be human (e.g., a constant region) and another portion of the antibody may be non-human (e.g., a murine heavy or murine light chain variable region). Thus, an example of a chimeric antibody is an antibody in which different portions of the antibody are of different species origins. Unlike a humanized or primatized antibody, a chimeric antibody can have the different species sequences in any region of the antibody.

IL-10R antibodies and subsequences of the invention include those having at least partial sequence identity to a heavy or light chain constant or variable region sequence of 136C5, 136C8 or 136D29, or a heavy chain variable region sequence of any of SEQ ID NOs:29, 31 or 33, or a light chain variable region sequence of any of SEQ ID NOs:30, 32, or 34. The percent identity of such antibodies and subsequences thereof can be as little as 60%, or can be greater (e.g., 65%, 70%, 75%, 80%, 85%, 90%, 95%, 96%, 97%, 98%, 99%, etc.). The percent identity can extend over the entire sequence length of a heavy or light chain constant or variable region sequence of 136C5, 136C8 or 136D29, or a heavy chain variable region sequence of any of SEQ ID NOs:29, 31 or 33, or a light chain variable region sequence of any of SEQ ID NOs:30, 32, or 34. In particular aspects, the length of the sequence sharing the percent identity is 5 or more contiguous amino acids, e.g., 6, 7, 8, 9, 10, 11, 12, 13, 14, 15, 16, 17, 18, 19, 20, etc. contiguous amino acids. In additional particular aspects, the length of the sequence sharing the percent identity is 20 or more contiguous amino acids, e.g., 20, 21, 22, 23, 24, 25, 26, 27, 28, 29, 30, 31, 32, 33, 34, 35, etc. contiguous amino acids. In further particular aspects, the length of the sequence sharing the percent identity is 35 or more contiguous amino acids, e.g., 35, 36, 37, 38, 39, 40, 41, 42, 43, 44, 45, 45, 47, 48, 49, 50, etc., contiguous amino acids. In yet further particular aspects, the length of the sequence sharing the percent identity is 50 or more contiguous amino acids, e.g., 50-55, 55-60, 60-65, 65-70, 70-75, 75-80, 80-85, 85-90, 90-95, 95-100, 100-110, etc. contiguous amino acids.

The term "identity" and grammatical variations thereof, mean that two or more referenced entities are the same. Thus, where two antibody sequences are identical, such as heavy or light chain variable region sequences, they have the same amino acid sequence. The identity can be over a defined area (region or domain) of the sequence. "Areas, regions or domains" of homology or identity mean that a portion of two or more referenced entities share homology or are the same.

The extent of identity between two sequences can be ascertained using a computer program and mathematical algorithm known in the art. Such algorithms that calculate percent sequence identity (homology) generally account for sequence gaps and mismatches over the comparison region or area. For example, a BLAST (e.g., BLAST 2.0) search algorithm (see, e.g., Altschul et al., J. Mol. Biol. 215:403 (1990), publicly available through NCBI) has exemplary search parameters as follows: Mismatch-2; gap open 5; gap extension 2. For polypeptide sequence comparisons, a BLASTP algorithm is typically used in combination with a scoring matrix, such as PAM100, PAM 250, BLOSUM 62 or BLOSUM 50. FASTA (e.g., FASTA2 and FASTA3) and SSEARCH sequence comparison programs are also used to quantitate the extent of identity (Pearson et al., *Proc. Natl. Acad. Sci. USA* 85:2444 (1988); Pearson, *Methods Mol. Biol.* 132:185 (2000); and Smith et al., *J. Mol. Biol.* 147:195 (1981)). Programs for quantitating protein structural similarity using Delaunay-based topological mapping have also been developed (Bostick et al., *Biochem Biophys Res Commun.* 304:320 (2003)).

In accordance with the invention, there are provided antibodies and subsequences thereof that specifically bind IL-10R alpha protein and include one, two or all three CDRs of a heavy or a light chain variable region sequence of antibody designated 136C5, 136C8 or 136D29; one, two or all three CDRs of a heavy chain variable region sequence of any of SEQ ID NOs:29, 31 or 33; or one, two or all three CDRs of a light chain variable region sequence of any of SEQ ID NOs:30, 32, or 34. Exemplary heavy chain variable region CDR sequences (SEQ ID NOs:49-55) are as follows: SYSMN; YISTGSSTIYYADSVKG; ENYYGSGSYEDYFDY; YISTRSSTIYYADSVKG; ELSMH; GFDPDDGETIYAQKFQG; and GGYYGPVGMDV. Exemplary light chain variable region CDR sequences (SEQ ID NOs:56-61) are as follows: RASQSVSSYLA; DASNRAT; QQRSNWPIFT; RASQGISIWLA; AASSLQS; and QQYNSYPLT. In particular aspects, an antibody or a subsequence that specifically binds IL-10R alpha protein includes all three CDRs of a heavy chain variable region of 136C5, 136C8 or 136D29; or any of SEQ ID NOs:29, 31 or 33, and all three CDRs of a light chain variable region of 136C5, 136C8 or 136D29; or any of SEQ ID NOs:30, 32, or 34. For example, any of a heavy chain variable region sequence with CDR1 (SYSMN), CDR2 (YISTGSSTIYYADSVKG), and/or CDR3 (ENYYGSGSYEDYFDY) and a light chain variable region sequence with CDR1 (RASQSVSSYLA), CDR2 (DASNRAT), and/or CDR3 (QQRSNWPIFT); a heavy chain variable region sequence with CDR1 (SYSMN), CDR2 (YISTRSSTIYYADSVKG), and/or CDR3 (ENYYGSGSYEDYFDY) and a light chain variable region sequence with CDR1 (RASQSVSSYLA), CDR2 (DASNRAT), and/or CDR3 (QQRSNWPIFI); and heavy chain variable region sequence with CDR1 (ELSMH), CDR2 (GFDPDDGETIYAQKFQG), and/or CDR3 (GGYYGPVGMDV) and a light chain variable region sequence with CDR1 (RASQGISIWLA), CDR2 (AASSLQS), and/or CDR3 (QQYNSYPLT).

IL-10R antibodies and functional fragments can have substantially the same, greater or less relative activity or function than a reference antibody (e.g., 136C5, 136C8 or 136D29, or an antibody or subsequence thereof that includes a heavy chain variable region sequence of any of SEQ ID NOs:29, 31 or 33, and a light chain variable region sequence of any of SEQ ID NOs:30, 32, or 34). For example, an IL-10R antibody can have substantially the same, greater or less relative binding affinity or avidity for IL-10R than a reference antibody (e.g., 136C5, 136C8 or 136D29, or an antibody or subsequence thereof that includes a heavy chain variable region sequence of any of SEQ ID NOs:29, 31 or 33, and a light chain variable region sequence of any of SEQ ID NOs:30, 32, or 34). Such antibodies having measurable binding affinity for IL-10R compete for binding of the reference antibody (e.g., 136C5, 136C8 or 136D29, or an antibody or subsequence thereof that includes a heavy chain variable region sequence of any of SEQ ID NOs:29, 31 or 33, and a light chain variable region sequence of any of SEQ ID NOs:30, 32, or 34) to IL-10R. IL-10R antibodies and functional fragments therefore include those that compete with any of 136C5, 136C8 or 136D29 antibody, or an antibody or subsequence thereof that includes a heavy chain variable region sequence of any of SEQ ID NOs:29, 31 or 33, and a light chain variable region sequence of any of SEQ ID NOs:30, 32, or 34, for binding to IL-10R, and have substantially the same, greater or less relative binding affinity or avidity for binding to IL-10R as compared to a reference antibody (e.g., 136C5, 136C8 or 136D29, or an antibody or subsequence thereof that includes a heavy chain variable region sequence of any of SEQ ID NOs:29, 31 or 33, and a light chain variable region sequence of any of SEQ ID NOs:30, 32, or 34).

IL-10R antibodies and functional fragments can have a greater or less than 2-5, 5-10, 10-100, 100-1000 or 1000-10,000-fold binding affinity, KD, for binding to IL-10R, or any numerical value or range within or encompassing such values, than a reference antibody (e.g., within 2-5, 5-10, 10-100, 100-1000 or 1000-10,000-fold of the binding affinity, KD, of 136C5, 136C8 or 136D29, or an antibody or subsequence thereof that includes a heavy chain variable region sequence of any of SEQ ID NOs:29, 31 or 33, and a light chain variable region sequence of any of SEQ ID NOs:30, 32, or 34, for binding to IL-10R). In one embodiment, an antibody or a functional thereof has a binding affinity, KD, within about 1-1000 fold (more or less than) of a reference antibody (e.g., 136C5, 136C8 or 136D29, or an antibody or subsequence thereof that includes a heavy chain variable region sequence of any of SEQ ID NOs:29, 31 or 33, and a light chain variable region sequence of any of SEQ ID NOs:30, 32, or 34), for binding to IL-10R.

IL-10R antibodies and functional fragments can have substantially the same binding affinity, KD, for binding to IL-10R as a reference antibody. In particular embodiments, an IL-10R antibody has substantially the same binding affinity, KD, or avidity for IL-10R as 136C5, 136C8 or 136D29, or an antibody or subsequence thereof that includes a heavy chain variable region sequence of any of SEQ ID NOs:29, 31 or 33, and a light chain variable region sequence of any of SEQ ID NOs:30, 32, or 34, for binding to IL-10R.

The term "substantially the same" when used in reference to antibody or functional fragment binding affinity or avidity for antigen, means that the binding is within 100 fold (greater or less than) of the binding affinity of a reference antibody for the antigen (e.g., IL-10R). Binding affinity can be determined by association ($K_a$) and dissociation (KD or $K_d$) rate. Equilibrium affinity constant, K, is the ratio of $K_d/K_a$. Association ($K_a$) and dissociation (KD or $K_d$) rates can be measured using surface plasmon resonance (SPR) (Rich and Myszka, *Curr. Opin. Biotechnol.* 11:54 (2000); Englebienne, *Analyst.* 123: 1599 (1998)). Instrumentation and methods for real time detection and monitoring of binding rates are known and are commercially available (BiaCore 2000, Biacore AB, Upsala, Sweden; and Malmqvist, *Biochem. Soc. Trans.* 27:335 (1999)). Thus, for example, if binding of a reference antibody to IL-10R has a KD of $10^{-9}$ M, than an antibody which has substantially the same binding affinity as the reference antibody will have a KD within the range of $10^{-7}$ M to KD $10^{-11}$ M for binding to IL-10R.

IL-10R antibodies and functional fragments can have a binding affinity, KD, for binding to IL-10R within about KD $10^{-2}$ M to about KD $10^{-15}$ M, or within about KD $10^{-6}$ M to about KD $10^{-12}$ M. In particular embodiments, binding affinity, KD, for binding to IL-10R is less than $5\times10^{-2}$ M, $10^{-2}$ M, $5\times10^{-3}$ M, $10^{-3}$ M $5\times10^{-4}$ M, $10^{-4}$ M $5\times10^{-5}$ M, $10^{-5}$ M $5\times10^{-6}$ M, $10^{-6}$ M $5\times10^{-7}$ M, $10^{-7}$ M $5\times10^{-8}$ M, $10^{-8}$ M $5\times10^{-9}$ M, $10^{-9}$ M $5\times10^{-10}$ M, $10^{-10}$ M $5\times10^{-11}$ M, $10^{-11}$ M $5\times10^{-12}$ M, $10^{-12}$ M $5\times10^{-13}$ M, $10^{-13}$ M $5\times10^{-14}$ M, $10^{-14}$ M $5\times10^{-15}$ M, and $10^{-15}$ M.

In accordance with the invention, there are provided antibodies and subsequences that include modified and variant forms. As used herein, the terms "modify" or "variant" and grammatical variations thereof, mean that an antibody or subsequence thereof deviates from a reference antibody or subsequence thereof (e.g., 136C5, 136C8 or 136D29 antibody, or an antibody or subsequence thereof that includes a heavy chain variable region sequence of any of SEQ ID NOs:29, 31 or 33, or a light chain variable region sequence of any of SEQ ID NOs:30, 32, or 34). Modified and variant antibodies and subsequences thereof may have greater or less activity or function than a reference antibody or an activity or function distinct from a reference antibody, but at least retain partial activity or function of the reference antibody (e.g., 136C5, 136C8 or 136D29 antibody, or an antibody or subsequence thereof that includes a heavy chain variable region sequence of any of SEQ ID NOs:29, 31 or 33, and a light chain variable region sequence of any of SEQ ID NOs:30, 32, or 34).

Non-limiting examples of modifications include one or more amino acid substitutions (e.g., 1-3, 3-5, 5-10, 10-15, 15-20, 20-25, or more residues), additions (e.g., insertions) and deletions (e.g., subsequences or fragments) of antibody constant or variable region sequences. In particular embodiments, a modified or variant antibody retains at least part of a function or an activity of unmodified antibody, e.g., binding affinity (e.g., KD or $K_d$) or binding specificity to IL-10R in vitro or a cell expressing IL-10R, or an activity, such as an antagonist activity of IL-10R, IL-10 or IL-10/IL-10R signaling pathway. Such modified forms and variants can have less than, the same, or greater, but at least a part of, a function or activity of a reference antibody or subsequence thereof, for example, binding to IL-10R, to reduce, decrease inhibit, suppress, limit, prevent or abrogate an activity or function of IL-10 or IL-10R, or the IL-10/IL-10R signaling pathway.

Specific non-limiting examples of substitutions include conservative and non-conservative amino acid substitutions. Substitutions can be within or outside of a constant region, a complementary determining region (CDR) or a framework region (FR) of the antibody. In particular embodiments, a heavy or light chain CDR (CDR1, CDR2 or CDR3) or FR will have 1-8, 1-5, 1-3 or fewer (e.g., 1 or 2) amino acid substitutions. In an additional embodiment, a substitution within a variable region sequence is not within a CDR. In another embodiment, a substitution within a variable region sequence is not within an FR. A particular non-limiting example of an amino acid substitution is a conservative substitution within or outside of a constant region, a complementary determining region (CDR) or a framework region (FR), for example, a substitution of one or more amino acid residues of a constant region, or any heavy or light chain variable region sequence of 136C5, 136C8 or 136D29 antibodies, or any heavy chain variable region sequence of SEQ ID NOs:29, 31 or 33, or any light chain variable region sequence of SEQ ID NOs:30, 32, or 34.

A "conservative substitution" is the replacement of one amino acid by a biologically, chemically or structurally similar residue. Biologically similar means that the substitution does not destroy a biological activity. Structurally similar means that the amino acids have side chains with similar length, such as alanine, glycine and serine, or a similar size. Chemical similarity means that the residues have the same charge or are both hydrophilic or hydrophobic. Particular examples include the substitution of one hydrophobic residue, such as isoleucine, valine, leucine or methionine for another, or the substitution of one polar residue for another, such as the substitution of arginine for lysine, glutamic for aspartic acids, or glutamine for asparagine, serine for threonine, and the like.

The structural determinants that contribute to antigen binding, such as complementarity determining regions (CDR) and framework regions (FR) within hypervariable regions are known in the art. The location of additional regions, such as D- and J-regions are also known. Antibodies and subsequences thereof that include one or more CDR sequences, optionally with flanking FR sequences, will typically have sufficient sequence identity to a heavy or light chain variable region sequence exemplified herein so as to retain at least partial function or activity of an antibody that includes a heavy and a light chain sequence exemplified herein, e.g., binding affinity (e.g., KD), avidity or binding specificity or selectivity to IL-10R.

One or a few amino acid substitutions (e.g., 2, 3, 4 or 5) in heavy or light chain variable regions, within or outside a CDR, are likely to be tolerated. Non-conservative substitution of many amino acids in hypervariable regions is likely to affect binding activity, specificity or antibody function or activity. Regional mutability analysis can be used to predict the effect of particular substitutions in complementarity determining regions (CDR) and framework regions (FR) (Shapiro et al., *J Immunol.* 163:259 (1999)). In brief, sequence comparison indicates a hierarchy of mutability among di- and trinucleotide sequences located within Ig intronic DNA, which predicts regions that are more or less mutable. Quantitative structure-activity relationship (QSAR) can be used to identify the nature of the antibody recognition domain and, therefore, amino acids that participate in ligand binding. Predictive models based upon OSAR can in turn be used to predict the effect of substitutions (mutations). For example, the effect of mutations on the association and dissociation rate of an antibody interacting with its antigen has been used to construct quantitative predictive models for both kinetic ($K_a$ and $K_d$) constants, which can in turn be used to predict the effect of other mutations on the antibody (De Genst et al., *J Biol. Chem.* 277:29897 (2002)). The skilled artisan can therefore use such analysis to predict amino acid substitutions of antibodies and subsequences that are likely to result in an antibody or subsequence that retains at least partial activity or function of non-substituted antibody or subsequence.

An addition can be the covalent or non-covalent attachment of any type of molecule to the antibody. Specific examples of antibody additions include glycosylation, acetylation, phosphorylation, amidation, formylation, ubiquitination, and derivatization by protecting/blocking groups and any of numerous chemical modifications. Additional specific non-limiting examples of an addition is another amino acid sequence. In particular embodiments, an addition is a fusion (chimeric) sequence, an amino acid sequence having one or more molecules not normally present in a reference native (wild type) sequence covalently attached to the sequence. A particular example is an amino acid sequence of another antibody to produce an antibody multimer, such as a multi-specific antibody.

Another particular example of a modified antibody having an amino acid addition is one in which a second heterologous sequence, i.e., heterologous functional domain is attached (covalent or non-covalent binding) that confers a distinct or complementary function upon the antibody. Heterologous functional domains are not restricted to amino acid residues. Thus, a heterologous functional domain can consist of any of a variety of different types of small or large functional moieties. Such moieties include nucleic acid, peptide, carbohydrate, lipid or small organic compounds, such as a drug (e.g., an antiviral), a metal (gold, silver), radioisotope. For example, a tag such as T7 or polyhistidine can be attached to antibody in order to facilitate purification or detection of antigen. Thus, in other embodiments the invention provides antibodies and a heterologous domain, wherein the domain confers a distinct function, i.e. a heterologous functional domain, on the antibody.

Linkers, such as amino acid or peptidimimetic sequences may be inserted between the antibody sequence and the addition (e.g., heterologous functional domain) so that the two entities maintain, at least in part, a distinct function or activity. Linkers may have one or more properties that include a flexible conformation, an inability to form an ordered secondary structure or a hydrophobic or charged character which could promote or interact with either domain. Amino acids typically found in flexible protein regions include Gly, Asn and Ser. Other near neutral amino acids, such as Thr and Ala, may also be used in the linker sequence. The length of the linker sequence may vary without significantly affecting a function or activity of the fusion protein (see, e.g., U.S. Pat. No. 6,087,329). Linkers further include chemical moieties and conjugating agents, such as sulfo-succinimidyl derivatives (sulfo-SMCC, sulfo-SMPB), disuccinimidyl suberate (DSS), disuccinimidyl glutarate (DSG) and disuccinimidyl tartrate (DST).

Additional non-limiting examples of additions are detectable labels. Thus, in another embodiment, the invention provides IL-10R antibodies and subsequences thereof that are detectably labeled. Specific examples of detectable labels include fluorophores, chromophores, radioactive isotopes (e.g., $S^{35}$, $P^{32}$, $I^{125}$), electron-dense reagents, enzymes, ligands and receptors. Enzymes are typically detected by their activity. For example, horseradish peroxidase is usually detected by its ability to convert a substrate such as 3,3-', 5,5-'-tetramethylbenzidine (TMB) to a blue pigment, which can be quantified. Ligands may bind other molecules such as biotin, which may bind avidin or streptavidin, and IgG, which can bind protein A.

Another non-limiting example of an addition is an insertion of an amino acid within any sequence of 136C5, 136C8 or 136D29 antibodies, or in an antibody that includes a heavy chain variable region sequence of any of SEQ ID NOs:29, 31 or 33, and a light chain variable region sequence of any of SEQ ID NOs:30, 32, or 34. Insertions can occur within a constant or variable region, such as heavy or light chain variable region sequences, within or outside of a CDR or FR. Insertions within CDRs, such as CDR3, occur naturally during antibody affinity maturation. Amino acid insertions within CDRs, such as CDR3, of invention antibodies and subsequences thereof therefore need not destroy IL-10R binding affinity. In particular embodiments, an insertion is of one or more amino acid residues in any of 136C5, 136C8 or 136D29 antibodies, or in an antibody that includes a heavy chain variable region sequence of any of SEQ ID NOs:29, 31 or 33, and a light chain variable region sequence of any of SEQ ID NOs:30, 32, or 34.

Additional specific non-limiting examples of modifications and variants include antibody subsequences and fragments. The terms "functional subsequence" and "functional fragment" when referring to an antibody means a portion that retains at least a part of one or more functions or activities as full length or native antibody, e.g., a function or activity of IL-10R antibody, such as binding to IL-10R. Thus, for example, an antibody subsequence or fragment that binds to IL-10R, or a fragment of IL-10R is considered a functional subsequence. Antibody subsequences or fragments retain, at least a part of, a function or activity of an unmodified or a reference full length, native or intact antibody. Subsequences and fragments can have less than, the same, or greater binding affinity or avidity as full length native antibody, the binding specificity as full length native antibody, or one or more activities or functions of as a full length native antibody, e.g., a function or activity of an IL-10R antibody.

Exemplary subsequences and fragments include antibody subsequences and fragments that bind to IL-10R, such as an antibody with at least one fewer amino acid than a full length IL-10R antibody (e.g., one or more internal or terminal amino acid deletions from either amino or carboxy-termini of IL-10R antibody having two heavy chains and two light chains that bind to IL-10R). Antibody subsequences and fragments, including single-chain antibodies, can include all or a portion of heavy or light chain variable region sequences (e.g., CDR1, CDR2 or CDR3 in any of 136C5, 136C8 or 136D29 antibodies, or in a heavy chain variable region sequence of any of SEQ ID NOs:29, 31 or 33, or a light chain variable region sequence of any of SEQ ID NOs:30, 32, or 34, is an example) alone or in combination with all or a portion of one or more of the following: hinge region, CH1, CH2, and CH3 domains. Non-limiting representative fragments and subsequences of a full length antibody include but are not limited to Fab, Fab', F(ab')$_2$, Fv, Fd, single-chain Fv (scFv), disulfide-linked Fvs (sdFv), $V_L$, $V_H$, trispecific (Fab$_3$), bispecific (Fab$_2$), diabody (($V_L$-$V_H$)$_2$ or ($V_H$-$V_L$)$_2$), triabody (trivalent), tetrabody (tetravalent), minibody ((scF$_V$-C$_H$3)$_2$), bispecific single-chain Fv (Bis-scFv), IgGdeltaCH2, scFv-Fc, (scFv)$_2$-Fc and IgG4PE.

Antibody subsequences and fragments can be combined. For example, $V_L$ or $V_H$ subsequences can be joined by a linker sequence thereby forming a $V_L$-$V_H$ chimera. A combination of single-chain Fvs (scFv) subsequences can be joined by a linker sequence thereby forming an scFv-scFv chimera. Antibody subsequences and fragments include single-chain antibodies or variable region(s) alone or in combination with all or a portion of other antibody subsequences.

Functional fragments and subsequences also include all or a portion of a full length antibody heavy or light chain, or a heavy or light chain variable region, which includes one, two or three CDRs of a heavy or light chain variable region sequence, optionally with or without a flanking FR. In various aspects, a functional fragment or a subsequence of a full length antibody heavy or light chain, or a heavy or light chain variable region, has a length from about 20-30, 30-50, 50-100, 100-150, 150-200, 200-250, 250-300, 300-400, or 400-500, amino acid residues.

Another particular non-limiting example of a modification is where an antibody is altered to have a different isotype or subclass by, for example, substitution of the heavy chain constant region. An alteration of Ig subclass can result in a change or an improvement in a function or activity (e.g., an anti-IL-10R activity). Thus, modifications include deleting small and large regions of amino acid sequences from an antibody and substituting the deleted region with another amino acid sequence, whether the sequence is greater or shorter in length than the deleted region.

Modified polypeptides also include one or more D-amino acids substituted for L-amino acids (and mixtures thereof), structural and functional analogues, for example, peptidomimetics having synthetic or non-natural amino acids or amino acid analogues and derivatized forms. Modifications include cyclic structures such as an end-to-end amide bond between the amino and carboxy-terminus of the molecule or intra- or inter-molecular disulfide bond. Polypeptides may be modified in vitro or in vivo, e.g., post-translationally modified to include, for example, sugar residues, phosphate groups, ubiquitin, fatty acids, lipids, etc.

IL-10 receptor (IL-10R) antibodies and subsequences thereof include an antibody or subsequence thereof which functions as an antagonist of IL-10 or IL-10 receptor (IL-10R) signaling pathway. The term "antagonist" and grammatical variations thereof, when used in reference to IL-10 and IL-10 receptor (IL-10R), is an antibody or a subsequence thereof that directly or indirectly reduces, decreases, inhibits, suppresses, prevents, limits, blocks or abrogates an activity or function of IL-10, IL-10R, or IL-10 or IL-10R signaling activity or signaling pathway. Such invention antibodies and subsequences thereof detectably reduce, decrease, inhibit, suppress, prevent, limit, block or abrogate an activity or function of IL-10 or IL-10 receptor (IL-10R) signaling activity or signaling pathway. Thus, an IL-10 receptor (IL-10R) antibody or subsequence thereof antagonist detectably reduces, decreases, inhibits, suppresses, prevents, limits, blocks or abrogates one or more IL-10 or IL-10 receptor (IL-10R) activities or functions, which can include, for example, binding of IL-10 to IL-10R, IL-10 or IL-10R mediated signaling or expression, or an IL-10 or IL-10R-mediated or IL-10 or IL-10R-modulatable cell response, or another IL-10 or IL-10 receptor (IL-10R) activity or function as set forth herein or otherwise one that one skilled in the art would be apprised. Various assays for measuring activity or function of IL-10, IL-10R, or IL-10 or IL-10R signaling activity or signaling pathway, such as measuring TNF-alpha expression or secretion by PBMCs (e.g., human, chimpanzee or macaque) treated with LPS in vitro in the presence of IL-10, and determining an increase in TNF-alpha expression or secretion by the PBMCs, are disclosed herein and known to one of ordinary skill in the art.

In further embodiments, antibodies and subsequences thereof specifically bind to IL-10 Receptor alpha protein (IL-10Rα) and modulate an IL-10R/IL-10 signaling activity. In one aspect, an antibody or subsequence thereof reduces, inhibits, decreases, suppresses or limits an IL-10R/IL-10 signaling activity. In further aspects, an antibody or subsequence thereof specifically binds to a human, a chimpanzee or a cynomolgus macaque IL-10Rα, and reduces, inhibits, decreases, suppresses or limits an activity of human, chimpanzee or cynomolgus macaque IL-10Rα (e.g., IL-10R/IL-10 signaling). In still further particular aspects, an antibody or subsequence thereof specifically binds to a human IL-10Rα, and one or both of a chimpanzee IL-10Rα and cynomolgus macaque IL-10Rα, and reduces, inhibits, decreases, suppresses or limits an activity of human, chimpanzee or cynomolgus macaque IL-10Rα (e.g., IL-10R/IL-10 signaling).

Various non-limiting examples of IL-10 and IL-10R activities and functions which, when contacted with an invention antibody or subsequence thereof, can result in: stimulating, inducing, increasing, enhancing, augmenting, or promoting a proinflammatory (e.g., IL-2, IFN-gamma, IL-4, IL-5, TNF-alpha) or adaptive immune response, production or expression of a cytokine (e.g., IL-1alpha, IL-1beta, TNF-alpha, IL-6, IL-9, IL-12, IL-18, GM-CSF, etc.) or a chemokine (e.g., MCP1, MCP5, RANTES, IL-8, IP-10, MIP-2, etc.); stimulating, inducing, increasing, enhancing, augmenting, or promoting expression of MHC class II or costimulatory molecules (e.g., OX40L) or anti-pathogen cytokines or chemokines by antigen presenting cells; stimulating, inducing, increasing, enhancing, augmenting, or promoting proliferation, differentiation or expression of CD4 or CD8 T cells or CD4 or CD8 T cell effector responses; stimulating, inducing, increasing, enhancing, augmenting, or promoting macrophage activation or proliferation; reducing, decreasing, inhibiting or suppressing expression or activity of Jak/Stat pathway genes, MAPK or p38 pathways; and reducing, decreasing, inhibiting, suppressing, controlling or limiting pathogen proliferation, replication, pathology, adverse symptoms caused by or associated with the pathogen, reactivation of pathogen from latency and transmission of pathogen from one subject to another subject. Thus, an IL-10R antibody or subsequence thereof that reduces, decreases, suppresses, inhibits, prevents, limits, blocks or abrogates an IL-10 and IL-10R activity or function disclosed herein or known to the skilled artisan, can result in, for example, inducing, increasing, promoting, enhancing, augmenting, or stimulating cell proliferation, expansion or activation (e.g., CD4+ or CD8+ T cells, NKT cells, dendritic cells, neutrophils, eosinophils, monocytes, or macrophages), cell survival or apoptosis (e.g., lymphocytes such as naïve, activated, effector, or memory T cells), cytokines and interferon expression or production (in vivo or in vitro), proinflammatory or adaptive immune response against an pathogen, anti-apoptotic or pro-apoptotic protein expression or production (e.g., Bcl-xL, Bcl-2, Bad or Bim), and treatment, inhibition, reduction, decreasing, prevention, control, limiting or ameliorating one or more disorders, diseases, illnesses, physiological conditions, pathologies or adverse symptoms or complications associated with or caused by pathogen infection, reactivation from latency or transmission of pathogen from one subject to another subject.

The invention also provides heavy and light chain variable region sequences, which may be optionally isolated or purified as set forth herein. In particular embodiments, a heavy or light chain variable region sequence is a sequence identical to a heavy or light sequence of any of 136C5, 136C8 or 136D29 antibodies, a heavy chain variable region sequence of any of SEQ ID NOs:29, 31 or 33, or a light chain variable region sequence of any of SEQ ID NOs:30, 32, or 34. Such heavy and light chain sequences include variants, such as substitutions, additions and deletions of any of 136C5, 136C8 or 136D29 antibodies, SEQ ID NOs:29, 31 or 33, or SEQ ID NOs:30, 32, or 34, as well as sequences with less than 100% identity to the heavy and light chain variable regions sequences of 136C5, 136C8 or 136D29 antibodies, SEQ ID NOs:29, 31 or 33, and SEQ ID NOs:30, 32, or 34 (e.g., 60% or more, such as 65%, 70%, 75%, 80%, 85%, 90%, 95%, etc., identical to any heavy chain variable region sequence set forth as SEQ ID NOs:29, 31 or 33, or 60% or more, such as 65%, 70%, 75%, 80%, 85%, 90%, 95%, etc., identical to any light chain variable region sequence set forth as SEQ ID NOs:30, 32, or 34).

Methods of producing polyclonal and monoclonal antibodies are known in the art. For example, IL-10R or an immunogenic fragment thereof, optionally conjugated to a carrier such as keyhole limpet hemocyanin (KLH) or ovalbumin (e.g., BSA), or mixed with an adjuvant such as Freund's complete or incomplete adjuvant, and used to immunize an animal. Using hybridoma technology, splenocytes from immunized animals that respond to IL-10R can be isolated and fused with myeloma cells. Monoclonal antibodies produced by hybridomas can be screened for reactivity with IL-10R, or an immunogenic fragment thereof. Hybridoma, recombinant, and phage display methods are known in the art (see, for example, U.S. Pat. Nos. 4,902,614, 4,543,439, and 4,411,993; see, also *Monoclonal Antibodies, Hybridomas: A New Dimension in Biological Analyses*, Plenum Press, Kennett, McKearn, and Bechtol (eds.), 1980, and Harlow et al., *Antibodies: A Laboratory Manual*, Cold Spring Harbor Laboratory Press, 2nd ed. 1988).

Animals that may be immunized include primates, mice, rats, rabbits, goats, sheep, cattle, or guinea pigs. Initial and any optional subsequent immunization may be through intravenous, intraperitoneal, intramuscular, or subcutaneous routes. Additionally, to increase the immune response, antigen can be coupled to another protein such as ovalbumin or keyhole limpet hemocyanin (KLH), thyroglobulin and tetanus toxoid, or mixed with an adjuvant such as Freund's complete or incomplete adjuvant. Initial and any optional subsequent immunization may be through intraperitoneal, intramuscular, intraocular, or subcutaneous routes. Subsequent immunizations may be at the same or at different concentrations of antigen, and may be at regular or irregular intervals.

Animals include mammals genetically modified to include human gene loci, such as human immunoglobulin lambda or kappa light chain, which can be used to produce human antibodies. Transgenic (e.g., transchromosomic) animals with one or more human immunoglobulin genes are described, for example, in U.S. Pat. No. 5,939,598, WO 02/43478, and WO 02/092812. Human trans-chromosomic mice (KM Mice™) are described, for example, in WO 02/43478, WO 02/092812, and Ishida, et al., IBC's 11$^{th}$ Antibody Engineering Meeting. Abstract (2000)). Such animals include, for example, mice, rat, guinea pig, rabbit, sheep, cow pig and horse.

Humanized antibodies can be produced using techniques known in the art including, for example, CDR-grafting (EP 239,400; WO91/09967; U.S. Pat. Nos. 5,225,539; 5,530,101; and 5,585,089), veneering or resurfacing (EP 592,106; EP 519,596; Padlan, *Molecular Immunol.* 28:489 (1991); Studnicka et al., *Protein Engineering* 7:805 (1994); Roguska. et al., *Proc. Nat'l. Acad. Sci. USA* 91:969 (1994)), and chain shuffling (U.S. Pat. No. 5,565,332). Human consensus sequences (Padlan, *Mol. Immunol.* 31:169 (1994); and Padlan, *Mol. Immunol.* 28:489 (1991)) have previously used to produce humanized antibodies (Carter et al., *Proc. Natl. Acad. Sci. USA* 89:4285 (1992); and Presta et al., *J. Immunol.* 151:2623 (1993)). Additional methods for producing human polyclonal antibodies and human monoclonal antibodies are described (see, e.g., Kuroiwa et al., *Nat. Biotechnol.* 20:889 (2002); WO 98/24893; WO 92/01047; WO 96/34096; WO 96/33735; U.S. Pat. Nos. 5,413,923; 5,625,126; 5,633,425; 5,569,825; 5,661,016; 5,545,806; 5,814,318; 5,885,793; 5,916,771; and 5,939,598).

Methods for producing chimeric antibodies are known in the art (e.g., Morrison, *Science* 229:1202 (1985); Oi et al., *BioTechniques* 4:214 (1986); Gillies et al., *J. Immunol. Methods* 125:191 (1989); and U.S. Pat. Nos. 5,807,715; 4,816,567; and 4,816,397). Chimeric antibodies in which a variable domain from an antibody of one species is substituted for the variable domain of another species are described, for example, in Munro, *Nature* 312:597 (1984); Neuberger et al., *Nature* 312:604 (1984); Sharon et al., *Nature* 309:364 (1984); Morrison et al., *Proc. Nat'l. Acad. Sci. USA* 81:6851 (1984); Boulianne et al., *Nature* 312:643 (1984); Capon et al., *Nature* 337:525 (1989); and Traunecker et al., *Nature* 339:68 (1989)).

IL-10R protein suitable for generating antibodies can be produced by any of a variety of standard protein purification or recombinant expression techniques. Forms of IL-10R suitable for generating an immune response include IL-10R subsequences, such as an immunogenic fragment. Additional forms of IL-10R include IL-10R expressing cells, IL-10R containing preparations or cell extracts or fractions, partially purified IL-10R. For example, an IL-10R sequence can be produced by standard peptide synthesis techniques, such as solid-phase synthesis. A portion of the protein may contain an amino acid sequence such as a T7 tag or polyhistidine sequence to facilitate purification of expressed or synthesized protein. The protein may be expressed in a cell and purified. The protein may be expressed as a part of a larger protein (e.g., a fusion or chimera) by recombinant methods.

Suitable techniques that additionally may be employed in antibody methods include IL-10R-based affinity purification, non-denaturing gel purification, HPLC or RP-HPLC, size exclusion, purification on protein A column, or any combination of these techniques. Antibody isotype can be determined using an ELISA assay, for example, a human Ig can be identified using mouse Ig-absorbed anti-human Ig.

Polypeptide sequences including modified forms can be made using recombinant DNA technology via cell expression or in vitro translation. Polypeptide sequences including modified forms can also be produced by chemical synthesis using methods known in the art, for example, an automated peptide synthesis apparatus (see, e.g., Applied Biosystems, Foster City, Calif.).

Antibody subsequences and fragments can be prepared by proteolytic hydrolysis of antibody, for example, by pepsin or papain digestion of whole antibodies. Antibody subsequences and fragments produced by enzymatic cleavage with pepsin provide a 5S fragment denoted $F(ab')_2$. This fragment can be further cleaved using a thiol reducing agent to produce 3.5S Fab' monovalent fragments. Alternatively, an enzymatic cleavage using pepsin produces two monovalent Fab' fragments and the Fc fragment directly (see, e.g., U.S. Pat. Nos. 4,036,945 and 4,331,647; and Edelman et al., *Methods Enymol.* 1:422 (1967)). Other methods of cleaving antibodies, such as separation of heavy chains to form monovalent light-heavy chain fragments, further cleavage of fragments, or other enzymatic or chemical may also be used.

The invention also provides nucleic acids encoding heavy and light chain variable region sequences of IL-10R antibodies and subsequences thereof, optionally further encoding a constant region. In one embodiment, a nucleic acid encodes a sequence at least 60% or more (e.g., 65%, 70%, 75%, 80%, 85%, 90%, 95%, etc.) identical to a heavy chain variable region sequence of any of 136C5, 136C8 or 136D29 antibodies, or a heavy chain variable region sequence set forth as SEQ ID NOs:29, 31 or 33. In another embodiment, a nucleic acid encodes a sequence at least 60% or more (e.g., 65%, 70%, 75%, 80%, 85%, 90%, 95%, etc.) identical to a light chain variable region sequence of any of 136C5, 136C8 or 136D29 antibodies, or a light chain variable region sequence set forth as SEQ ID NOs:30, 32, or 34. In an additional embodiment, a nucleic acid encodes a sequence having one or more amino acid additions (insertions), deletions or substitutions of a constant region, or a heavy or light chain variable region sequence of any of 136C5, 136C8 or 136D29 antibodies, SEQ ID NOs: 29, 31 or 33, or SEQ ID NOs: 30, 32, or 34. In particular aspects, the nucleic acid encodes a constant region of an antibody (e.g., a mammalian constant region such as a primate or human).

The terms "nucleic acid" and "polynucleotide" and the like refer to at least two or more ribo- or deoxy-ribonucleic acid base pairs (nucleotides) that are linked through a phosphoester bond or equivalent. Nucleic acids include polynucleotides and polynucleosides. Nucleic acids include single, double or triplex, circular or linear, molecules. Exemplary nucleic acids include but are not limited to: RNA, DNA, cDNA, genomic nucleic acid, naturally occurring and non naturally occurring nucleic acid, e.g., synthetic nucleic acid.

Nucleic acids can be of various lengths. Nucleic acid lengths typically range from about 20 nucleotides to 20 Kb, or any numerical value or range within or encompassing such lengths, 10 nucleotides to 10 Kb, 1 to 5 Kb or less, 1000 to about 500 nucleotides or less in length. Nucleic acids can also be shorter, for example, 100 to about 500 nucleotides, or from about 12 to 25, 25 to 50, 50 to 100, 100 to 250, or about 250 to 500 nucleotides in length, or any numerical value or range or value within or encompassing such lengths. In particular aspects, a nucleic acid sequence has a length from about 10-20, 20-30, 30-50, 50-100, 100-150, 150-200, 200-250, 250-300, 300-400, 400-500, 500-1000, 1000-2000, nucleotides, or any numerical value or range within or encompassing such lengths. Shorter polynucleotides are commonly referred to as "oligonucleotides" or "probes" of single- or double-stranded DNA. However, there is no upper limit to the length of such oligonucleotides.

The invention also provides nucleic acid sequences that are complementary to all or a portion of a sequence that encodes a heavy or light chain variable region sequence of any of 136C5, 136C8 or 136D29 antibodies, SEQ ID NOs: 29, 31 or 33, or SEQ ID NOs: 30, 32, or 34, and nucleic acid sequences that specifically hybridize to all or a portion of a heavy or light chain variable region sequence of any of 136C5, 136C8 or 136D29 antibodies, SEQ ID NOs: 29, 31 or 33, or SEQ ID NOs: 30, 32, or 34, or a complementary or antisense sequence thereof.

The term "complementary" or "antisense" refers to a polynucleotide or peptide nucleic acid capable of binding to a specific DNA or RNA sequence. Antisense includes single, double, triple or greater stranded RNA and DNA polynucleotides and peptide nucleic acids (PNAs) that bind RNA transcript or DNA. Particular examples include RNA and DNA antisense that binds to sense RNA. For example, a single stranded nucleic acid can target a protein transcript that participates in metabolism, catabolism, removal or degradation of glycogen from a cell (e.g., mRNA). Antisense molecules are typically 95-100% complementary to the sense strand but can be "partially" complementary, in which only some of the nucleotides bind to the sense molecule (less than 100% complementary, e.g., 95%, 90%, 80%, 70% and sometimes less), or any numerical value or range within or encompassing such percent values.

The term "hybridize" and grammatical variations thereof refer to the binding between nucleic acid sequences. Hybridizing sequences will generally be more than about 50% complementary to a nucleic acid that encodes an amino acid sequence of a reference antibody or subsequence (e.g., an antibody heavy or light chain variable region sequence). The hybridization region between hybridizing sequences typically is at least about 12-15 nucleotides, 15-20 nucleotides, 20-30 nucleotides, 30-50 nucleotides, 50-100 nucleotides, 100 to 200 nucleotides or more, or any numerical value or range within or encompassing such lengths.

Nucleic acid sequences further include nucleotide and nucleoside substitutions, additions and deletions, as well as derivatized forms and fusion/chimeric sequences (e.g., encoding recombinant polypeptide). For example, due to the degeneracy of the genetic code, nucleic acids include sequences and subsequences degenerate with respect to nucleic acids that encode a sequence of any of 136C5, 136C8 or 136D29 antibodies, SEQ ID NOs: 29, 31, or 33, or SEQ ID NOs: 30, 32, or 34, and subsequences thereof, as well as variants and modifications thereof (e.g., substitutions, additions insertions and deletions).

Nucleic acids can be produced using various standard cloning and chemical synthesis techniques. Techniques include, but are not limited to nucleic acid amplification, e.g., polymerase chain reaction (PCR), with genomic DNA or cDNA targets using primers (e.g., a degenerate primer mixture) capable of annealing to antibody encoding sequence. Nucleic acids can also be produced by chemical synthesis (e.g., solid phase phosphoramidite synthesis) or transcription from a gene. The sequences produced can then be translated in vitro, or cloned into a plasmid and propagated and then expressed in a cell (e.g., a host cell such as eukaryote or mammalian cell, yeast or bacteria, in an animal or in a plant).

Nucleic acid may be inserted into a nucleic acid construct in which expression of the nucleic acid is influenced or regulated by an "expression control element." An "expression control element" refers to a nucleic acid sequence element that regulates or influences expression of a nucleic acid sequence to which it is operatively linked. Expression control elements include, as appropriate, promoters, enhancers, transcription terminators, gene silencers, a start codon (e.g., ATG) in front of a protein-encoding gene, etc.

An expression control element operatively linked to a nucleic acid sequence controls transcription and, as appropriate, translation of the nucleic acid sequence. Expression control elements include elements that activate transcription constitutively, that are inducible (i.e., require an external signal for activation), or derepressible (i.e., require a signal to turn transcription off; when the signal is no longer present, transcription is activated or "derepressed"), or specific for cell-types or tissues (i.e., tissue-specific control elements).

Nucleic acid may be inserted into a plasmid for propagation into a host cell and for subsequent genetic manipulation. A plasmid is a nucleic acid that can be propagated in a host cell, plasmids may optionally contain expression control elements in order to drive expression of the nucleic acid encoding IL-10R binding antibody, subsequence thereof or antigen (e.g., IL-10R alpha or beta chain) in the host cell. A vector is used herein synonymously with a plasmid and may also include an expression control element for expression in a host cell (e.g., expression vector). Plasmids and vectors generally contain at least an origin of replication for propagation in a cell and a promoter. Plasmids and vectors are therefore useful for genetic manipulation and expression of IL-10R binding antibodies and subsequences, as well as antibody constant, heavy and light chain variable regions as well as antigen (e.g., IL-10R). Accordingly, vectors that include nucleic acids encoding or complementary to IL-10R binding antibodies and subsequences thereof, as well as antibody constant, heavy and light chain variable regions are provided.

Nucleic acids encoding variable regions of IL-10R antibody heavy and light chains or subsequences thereof, or encoding full length IL-10R antibody heavy and light chains or subsequences thereof, can be produced synthetically or using recombinant methods, or isolated from a cell such as a hybridoma. Isolated nucleic acids may be inserted into a suitable expression vector, and introduced into suitable host cells (e.g., CHO, plant and other cells) which can be cultured for the production of recombinant IL-10R antibodies, heavy and light chains or subsequences thereof.

In accordance with the invention, there are provided host cells that express or are transformed with a nucleic acid that encodes a IL-10R antibodies and subsequences of the invention. Host cells include but are not limited to prokaryotic and eukaryotic cells such as bacteria, fungi (yeast), plant, insect, and animal (e.g., mammalian, including primate and human, CHO cells and hybridomas) cells. For example, bacteria transformed with recombinant bacteriophage nucleic acid, plasmid nucleic acid or cosmid nucleic acid expression vectors; yeast transformed with recombinant yeast expression vectors; plant cell systems infected with recombinant virus expression vectors (e.g., cauliflower mosaic virus, CaMV; tobacco mosaic virus, TMV) or transformed with recombinant plasmid expression vectors (e.g., Ti plasmid); insect cell systems infected with recombinant virus expression vectors (e.g., baculovirus); and animal cell systems infected with recombinant virus expression vectors (e.g., retroviruses, adenovirus, vaccinia virus), or transformed animal cell systems engineered for stable expression.

The cells may be a primary cell isolate, cell culture (e.g., passaged, established or immortalized cell line), or part of a plurality of cells, or a tissue or organ ex vivo or in a subject (in vivo). In particular embodiments, a host cell is a CHO cell, a hybridoma cell or a HEK293F cell.

The term "transformed" or "transfected" when used in reference to a cell (e.g., a host cell) or organism, means a genetic change in a cell following incorporation of an exogenous molecule, for example, a protein or nucleic acid (e.g., a transgene) into the cell. Thus, a "transfected" or "transformed" cell is a cell into which, or a progeny thereof in which an exogenous molecule has been introduced by the hand of man, for example, by recombinant DNA techniques.

The nucleic acid or protein can be stably or transiently transfected or transformed (expressed) in the cell and progeny thereof. The cell(s) can be propagated and the introduced protein expressed, or nucleic acid transcribed. A progeny of a transfected or transformed cell may not be identical to the parent cell, since there may be mutations that occur during replication.

Introduction of protein and nucleic acid into target cells (e.g., host cells) can also be carried out by methods known in the art such as osmotic shock (e.g., calcium phosphate), electroporation, microinjection, cell fusion, etc. Introduction of nucleic acid and polypeptide in vitro, ex vivo and in vivo can also be accomplished using other techniques. For example, a polymeric substance, such as polyesters, polyamine acids, hydrogel, polyvinyl pyrrolidone, ethylene-vinylacetate, methylcellulose, carboxymethylcellulose, protamine sulfate, or lactide/glycolide copolymers, polylactide/glycolide copolymers, or ethylenevinylacetate copolymers. A nucleic acid can be entrapped in microcapsules prepared by coacervation techniques or by interfacial polymerization, for example, by the use of hydroxymethylcellulose or gelatin-microcapsules, or poly (methylmethacrolate) microcapsules, respectively, or in a colloid system. Colloidal dispersion systems include macromolecule complexes, nano-capsules, microspheres, beads, and lipid-based systems, including oil-in-water emulsions, micelles, mixed micelles, and liposomes.

Liposomes for introducing various compositions into cells are known in the art and include, for example, phosphatidylcholine, phosphatidylserine, lipofectin and DOTAP (e.g., U.S. Pat. Nos. 4,844,904, 5,000,959, 4,863,740, and 4,975,282; and GIBCO-BRL, Gaithersburg, Md.). piperazine based amphilic cationic lipids useful for gene therapy also are known (see, e.g., U.S. Pat. No. 5,861,397). Cationic lipid systems also are known (see, e.g., U.S. Pat. No. 5,459,127). Polymeric substances, microcapsules and colloidal dispersion systems such as liposomes are collectively referred to herein as "vesicles." Accordingly, viral and non-viral vector means delivery into cells, tissue or organs, in vitro, in vivo and ex vivo are included.

The invention is also based at least in part on the role of the IL-10/IL-10R signaling in decreasing, reducing, inhibiting, preventing, blocking or suppressing anti-pathogen immune responses. In particular, IL-10 signaling during exposure to or contact with a pathogen, infection with a pathogen, or reactivation of a latent pathogen infection, appears to decrease, reduce, inhibit, prevent, block or suppress immune responses against the pathogen. Thus, a decrease, inhibition, reduction, suppression, or blockade of IL-10 or IL-10R signaling by an IL-10 receptor (IL-10R) antibody or subsequence thereof can be used to decrease, reduce, inhibit, prevent, block or suppress IL-10 or IL-10R signaling thereby providing therapeutic treatment or prophylactic (preventative) treatment of a pathogen infection. Binding IL-10R antibodies to IL-10R can therefore enhance, promote, stimulate, augment, induce or increase an immune response, such as a proinflammatory or adaptive response against a pathogen; decrease, reduce, inhibit, suppress, prevent, limit or control pathogen replication or proliferation; ameliorate (e.g., prevent, decrease, reduce, inhibit, suppress, control or limit) one or more pathologies or adverse symptoms associated with or caused by pathogen infection or reactivation from latency; enhance, promote, stimulate, augment, induce or increase pathogen clearance or removal; or decrease, reduce, inhibit, suppress, control or limit transmission of pathogen from one subject to another subject (e.g., to a susceptible host).

In accordance with the invention, there are provided methods of treating a subject for a pathogen infection (chronic or acute). In one embodiment, a method includes administering to a subject an amount of an invention IL-10R antibody or subsequence thereof sufficient to treat the subject for the pathogen infection (chronic or acute). In another embodiment, a method includes administering to a subject an amount of an IL-10R antibody or subsequence thereof and a pathogen antigen, live or attenuated pathogen, or a nucleic acid encoding all or a portion (e.g., an epitope) of any protein or proteinaceous pathogen antigen sufficient to treat the subject for a pathogen infection.

Pathogens are typically microorganisms that cause or are associated with adverse symptoms, pathologies, illnesses, complications or undesirable effects in a subject. Non-limiting examples of pathogens include viruses, bacteria, parasites and fungi.

Particular non-limiting examples of viruses include poxvirus, herpesvirus, hepatitis virus, immunodeficiency virus, flavivirus, papilloma virus (PV), polyoma virus, rhabdovirus, a myxovirus, an arenavirus, a coronavirus, adenovirus, reovirus, picornavirus, togavirus, bunyavirus, parvovirus and retrovirus.

Non-limiting examples of poxvirus include a vaccinia virus, Molluscum contagiosum, variola major or variola minor smallpox virus, cow pox, camel pox, sheep pox, and monkey pox.

Non-limiting examples of herpesvirus include an alpha-herpesvirus, beta-herpesvirus, gamma-herpesvirus, Epstein Bar Virus (EBV), Cytomegalovirus (CMV), varicella zoster virus (VZV/HHV-3), and human herpes virus 1, 2, 4, 5, 6, 7, and 8 (HHV-8, Kaposi's sarcoma-associated virus).

Non-limiting examples of hepatitis virus include hepatitis A, B, C, D, E and G.

Non-limiting examples of immunodeficiency virus include human immunodeficiency virus (HIV), such as HIV-1, HIV-2 and HIV-3.

Non-limiting examples of flavivirus include Hepatitis C virus, Yellow Fever virus, Dengue virus, Japanese Encephalitis and West Nile viruses.

Non-limiting examples of papilloma virus include a human papilloma virus (HPV), such as HPV strain 1, 6, 11, 16, 18, 30, 31, 42, 43, 44, 45, 51, 52, and 54.

Non-limiting examples of polyoma virus include BK virus (BKV) and JC virus (JCV).

Non-limiting examples of rhabdovirus include rabies virus and vesiculovirus.

Non-limiting examples of myxovirus include paramyxovirus and orthomyxovirus. Non-limiting examples of paramyxovirus include measles, mumps, pneumovirus and respiratory syncytial virus (RSV).

Non-limiting examples of orthomyxovirus include influenza virus, such as influenza A, influenza B and influenza C.

Non-limiting examples of arenavirus include lymphocytic choriomeningitis virus (LCMV), Junin virus, Lassa virus, Guanarito virus, Sabia virus and Machupo virus.

Non-limiting examples of coronavirus include a virus that causes a common cold, and severe acute respiratory syndrome (SARS).

Non-limiting examples of adenovirus include viral infections of bronchii, lung, stomach, intestine (gastroenteritis), eye (conjunctivitis), bladder (cystitis) and skin.

Non-limiting examples of reovirus include a rotavirus, cypovirus and orbivirus.

Non-limiting examples of picornavirus include a rhinovirus, apthovirus, hepatovirus, enterovirus, coxsackie B virus and cardiovirus. Rhinovirus can cause the common cold.

Non-limiting examples of togavirus include alphavirus, sindbus virus, and rubellavirus.

Non-limiting examples of bunyavirus include hantavirus, phlebovirus and nairovirus.

Non-limiting examples of retrovirus include an alpha, beta, delta, gamma, epsilon, lentivirus, spumavirus and human T-cell leukemia virus.

Non-limiting examples of lentivirus include an immunodeficiency virus, such as immunodeficiency virus (e.g., a bovine, porcine, equine, canine, feline or primate virus).

Non-limiting examples of human T-cell leukemia viruses include human T-cell leukemia virus 1 and 2 (HTLV-1 and HTLV-2).

Non-limiting examples of bacteria include a mycobacterium (e.g., tuberculosis and atypical mycobacterium), *listeria monocytogenes, helicobacter, Bordetella, streptococcus, salmonella* and *chlamydia*.

Non-limiting examples of parasites include a protozoa or nematode. Non-limiting examples of protozoa include a *Toxoplasma gondii, Leishmania, Plasmodium*, or *Trypanosoma cruzi*. Non-limiting examples of nematodes include a *Schistosoma mansoni*, or a *Heligmosomoides polygyrus*.

Non-limiting examples of fungus include *Candida albicans*.

In accordance with the invention, there are further provided therapeutic and prophylactic methods of treating a subject for a pathogen infection, for example, a subject at risk of a pathogen infection. Such methods include administering an IL-10 receptor (IL-10R) antibody or subsequence thereof to therapeutically or prophylactically (vaccinating or immunizing) treat a subject having or at risk of having a pathogen infection. Such methods can treat the infection or provide the subject with protection from a pathogen infection (e.g., prophylactic protection). In one embodiment, a method includes administering an amount of an IL-10 receptor (IL-10R) antibody or subsequence thereof to a subject in need thereof, sufficient to provide the subject with protection against a pathogen infection (chronic or acute). Pathogen antigens (e.g., protein or an epitope thereof), live or attenuated pathogen, inactivated pathogen, pathogen extract, nucleic acid encoding all or a portion (e.g., an epitope) of any protein or proteinaceous pathogen antigen are useful in the methods of the invention. Thus, in another embodiment, a method includes administering an amount of an IL-10 receptor (IL-10R) antibody or subsequence thereof to a subject in need thereof and a pathogen antigen, a live or attenuated pathogen or a nucleic acid encoding all or a portion (e.g., an epitope) of a pathogen antigen sufficient to vaccinate or immunize the subject against the pathogen infection (chronic or acute). IL-10 receptor (IL-10R) antibody or subsequence thereof can be administered as a combination composition with a pathogen antigen, a live or attenuated pathogen or a nucleic acid encoding a pathogen antigen or a portion of an antigen (e.g., an epitope), or administered separately, such as concurrently or sequentially (prior to or following) administering a pathogen antigen, a live or attenuated pathogen or a nucleic acid encoding a pathogen antigen or a portion of an antigen (e.g., an epitope), to a subject.

Pathogen antigens (e.g., protein or an epitope thereof) useful in accordance with the invention can be any antigen (e.g., pathogen extract), live or attenuated pathogen (e.g., inactivated pathogen). Pathogen antigens (e.g., protein or an epitope thereof) can be encoded by a nucleic acid. Nucleic acids can encode all or a portion (e.g., an epitope) of any protein or proteinaceous pathogen antigen.

Particular non-limiting examples of pathogen antigens, live or attenuated pathogen, or a nucleic acid encoding pathogen antigens or a portion of an antigen (e.g., an epitope) are virus, bacteria, parasite, or fungal antigen, live or attenuated virus, bacteria, parasite, or fungus, or a nucleic acid encoding a virus, bacteria, parasite, or fungal antigen or a portion of a virus, bacteria, parasite, or fungal antigen (e.g., an epitope). Such antigens are from any pathogen set forth herein or known to one of skill in the art, and include an antigen that increases, stimulates, enhances, promotes, augments or induces a proinflammatory or adaptive immune response, numbers or activation of an immune cell (e.g., T cell, natural killer T (NKT) cell, dendritic cell (DC), B cell, macrophage, neutrophil, eosinophil, mast cell, CD4+ or a CD8+ cell, B220+ cell, CD14+, CD11b+ or CD11c+ cells), an anti-pathogen CD4+ or CD8+ T cell response, production of a Th1 cytokine, a T cell mediated immune response, etc.

Non-limiting viral antigens include a poxvirus, herpesvirus, hepatitis virus, immunodeficiency virus, flavivirus, papilloma virus (PV), polyoma virus, rhabdovirus, a myxovirus, an arenavirus, a coronavirus, adenovirus, reovirus, picornavirus, togavirus, bunyavirus, parvovirus or a retrovirus antigen.

Poxvirus viral antigen (or nucleic acid encoding all or a portion of the antigen), live or attenuated virus include vaccinia virus (e.g., B8R, L4R, H3L, E9L, F15L, J4R, B5R, I1L, A3L, A8R, A23R, B2R and other poxvirus antigens), Molluscum contagiosum, variola major or variola minor smallpox virus, cow pox, camel pox, sheep pox, or monkey pox antigen.

Herpesvirus viral antigen (or nucleic acid encoding all or a portion of the antigen), live or attenuated virus include an alpha-herpesvirus, beta-herpesvirus, gamma-herpesvirus, Epstein Bar Virus (EBV), Cytomegalovirus (CMV), varicella zoster virus (VZV/HHV-3), or human herpes virus 1, 2, 4, 5, 6, 7, or 8 (HEV-8, Kaposi's sarcoma-associated virus) antigen.

Hepatitis viral antigen (or nucleic acid encoding all or a portion of the antigen), live or attenuated virus include a hepatitis A, B, C, D, E or G antigen.

Immunodeficiency viral antigen (or nucleic acid encoding all or a portion of the antigen), live or attenuated virus include a human immunodeficiency virus (HIV) antigen. Non-limiting examples of HIV viral antigen, or attenuated virus include HIV-1, HIV-2 or HIV-3 antigen.

Flavivirus viral antigen (or nucleic acid encoding all or a portion of the antigen), live or attenuated virus include a Hepatitis C virus (e.g., core, E1, E2, p7, NS2, NS3, NS4, NS5, or other virus antigen), Yellow Fever virus, Dengue virus, Japanese Encephalitis or West Nile virus antigen.

Papilloma viral antigen (or nucleic acid encoding all or a portion of the antigen), live or attenuated virus include a human papilloma virus (HPV) antigen. Non-limiting examples of human papilloma viral antigen, live or attenuated virus include a HPV strain 1, 6, 11, 16, 18, 30, 31, 42, 43, 44, 45, 51, 52, or 54 antigen.

Polyoma viral antigen (or nucleic acid encoding all or a portion of the antigen), live or attenuated virus include a BK virus (BKV) or JC virus (JCV) antigen.

Rhabdovirus viral antigen (or nucleic acid encoding all or a portion of the antigen), live or attenuated virus include a rabies virus or vesiculovirus antigen.

Myxovirus viral antigen (or nucleic acid encoding all or a portion of the antigen), live or attenuated virus include a paramyxovirus or orthomyxovirus antigen. Non-limiting examples of paramyxovirus a viral antigen, live or attenuated virus include a measles, mumps, pneumovirus or respiratory syncytial virus (RSV) antigen. Non-limiting examples of orthomyxovirus viral antigen, live or attenuated virus include an influenza virus antigen.

Influenza virus viral antigen (or nucleic acid encoding all or a portion of the antigen), live or attenuated virus include a influenza A, influenza B or influenza C antigen.

Arenavirus viral antigen (or nucleic acid encoding all or a portion of the antigen), live or attenuated virus include a lymphocytic choriomeningitis virus (LCMV), Junin virus, Lassa virus, Guanarito virus, Sabia virus or Machupo virus antigen.

Coronavirus viral antigen (or nucleic acid encoding all or a portion of the antigen), live or attenuated virus include an antigen of a virus that causes a common cold or severe acute respiratory syndrome (SARS).

Reovirus viral antigen (or nucleic acid encoding all or a portion of the antigen), live or attenuated virus include a rotavirus, cypovirus or orbivirus antigen.

Picornavirus viral antigen (or nucleic acid encoding all or a portion of the antigen), live or attenuated virus include a rhinovirus, apthovirus, hepatovirus, enterovirus, coxsackie B virus, or cardiovirus antigen.

Togavirus viral antigen (or nucleic acid encoding all or a portion of the antigen), live or attenuated virus include alphavirus, sindbus virus, or rubellavirus antigen.

Bunyavirus viral antigen (or nucleic acid encoding all or a portion of the antigen), live or attenuated virus include a hantavirus, phlebovirus or nairovirus antigen.

Retrovirus viral antigen (or nucleic acid encoding all or a portion of the antigen), live or attenuated virus include an alpha, beta, delta, gamma, epsilon, lentivirus, spumavirus or human T-cell leukemia virus antigen. Non-limiting examples of lentivirus viral antigen (or nucleic acid encoding all or a portion of the antigen), live or attenuated virus include an immunodeficiency virus antigen. Non-limiting examples of immunodeficiency viral antigen, live or attenuated virus include a bovine, porcine, equine, canine, feline or primate virus antigen. Non-limiting examples of human T-cell leukemia viral antigen (or nucleic acid encoding all or a portion of the antigen), live or attenuated virus include a human T-cell leukemia virus 1 or 2 (HTLV-1 and HTLV-2) antigen.

Bacteria antigens (or nucleic acid encoding all or a portion of the antigen), live or attenuated bacteria include a mycobacterium, *listeria monocytogenes, helicobacter, bordetella, streptococcus, salmonella* or *Chlamydia* antigen.

Parasite antigens (or nucleic acid encoding all or a portion of the antigen), live or attenuated parasite include a protozoa or nematode antigen. Exemplary protozoa antigens include a *Toxoplasma gondii, Leishmania, Plasmodium*, or *Trypanosoma cruzi* antigen.

Nematode pathogen antigens (or nucleic acid encoding all or a portion of the antigen), live or attenuated nematode include a *Schistosoma mansoni* or a helminth antigen.

Fungal pathogen antigens (or nucleic acid encoding all or a portion of the antigen), live or attenuated fungus include a *Candida albicans* antigen.

In additional various methods embodiments, an antibody or subsequence thereof and a second active, such as an antibody (agonist or antagonist) that binds to an immune regulatory molecule to modulate activity of an immune regulatory molecule, or an antibody that binds to a pathogen antigen, a pathogen nucleic acid, an agent or a drug are administered to a subject, one or more times, as a combination (e.g., an IL-10R antibody or subsequence thereof is administered as a combination composition with a second active, such as another antibody, agent or drug to a subject). In further various methods embodiments, an IL-10R antibody or subsequence thereof and a second active, such as a different antibody, an agent or a drug are administered to a subject, one or more times, sequentially (e.g., an IL-10R antibody or subsequence thereof and an agent or drug are administered separately to a subject, in a sequence). Additional method embodiments include, for example, second actives such as type I interferons, toll receptor ligands, T cell costimulatory molecules such as OX40, 4-1BB, agonists to these or other costimulatory molecules and antagonists to inhibitory receptors or ligands such as antibodies that bind to CTLA4, PD-1, PD-L1, CD160 and LAG3.

In particular methods embodiments, one or more disorders, diseases, physiological conditions, pathologies and symptoms associated with or caused by a pathogen infection or reactivation from latency will respond to treatment or therapy with an IL-10R binding antibody or a subsequence thereof. In particular methods embodiments, treatment methods reduce, decrease, suppress, limit, control or inhibit pathogen numbers or titer; reduce, decrease, suppress, limit, control or inhibit pathogen proliferation or replication; reduce, decrease, suppress, limit, control or inhibit the amount of a pathogen protein; or reduce, decrease, suppress, limit, control or inhibit the amount of a pathogen nucleic acid. In additional particular methods embodiments, treatment methods include an amount of IL-10R binding antibody or a subsequence thereof sufficient to increase, induce, enhance, augment, promote or stimulate an immune response against a pathogen; increase, induce, enhance, augment, promote or stimulate pathogen clearance or removal; decrease, reduce, inhibit, suppress, limit or control pathogen reactivation from latency (e.g., hepatitis or herpesvirus reactivation from latency); or decrease, reduce, inhibit, suppress, prevent, control, or limit transmission to another subject (e.g., transmission of pathogen from an infected subject to an uninfected subject). In further particular methods embodiments, treatment methods include an amount of IL-10R binding antibody or a subsequence thereof sufficient to protect a subject from a pathogen infection or pathology, or reactivation from latency, or reduce, decrease, limit, control or inhibit susceptibility to pathogen infection or pathology, Methods of the invention include treatment methods, which result in any therapeutic or beneficial effect. In various methods embodiments, pathogen infection, proliferation or pathogenesis is reduced, decreased, inhibited, limited, delayed or prevented, or a method decreases, reduces, inhibits, suppresses, prevents, controls or limits one or more adverse (e.g., physical) symptoms, disorders, illnesses, diseases or complications caused by or associated with chronic or acute pathogen infection, proliferation or replication, pathology or reactivation from latency. In additional various particular embodiments, treatment methods include reducing, decreasing, inhibiting, delaying or preventing onset, progression, frequency, duration, severity, probability or susceptibility of one or more adverse symptoms, disorders, illnesses, diseases or complications caused by or associated with chronic or acute pathogen infection, proliferation or replication, pathology or reactivation from latency. In further various particular embodiments, treatment methods include accelerating, facilitating, enhancing, augmenting, or hastening recovery of a subject from a pathogen infection, reactivation from latency or pathogenesis, or one or more adverse symptoms, disorders, illnesses, diseases or complications caused by or associated with chronic or acute pathogen infection, proliferation or replication, pathology or reactivation from latency. In yet additional various embodiments, treatment methods include stabilizing infection, proliferation, replication, pathogenesis, or an adverse symptom, disorder, illness, disease or complication caused by or associated with chronic or acute pathogen infection, proliferation or replication, pathology or reactivation from latency, or decreasing, reducing, inhibiting, suppressing, limiting or controlling transmission of a pathogen from an infected host to an uninfected host.

A therapeutic or beneficial effect of treatment is therefore any objective or subjective measurable or detectable improvement or benefit provided to a particular subject. A therapeutic or beneficial effect can but need not be complete ablation of all or any particular adverse symptom, disorder, illness, disease or complication caused by or associated with chronic or acute pathogen infection, proliferation or replication, pathology or reactivation from latency. Thus, a satisfactory clinical endpoint is achieved when there is an incremental improvement or a partial reduction in an adverse symptom, disorder, illness, disease or complication caused by or associated with chronic or acute pathogen infection, proliferation or replication, pathology or reactivation from latency, or an inhibition, decrease, reduction, suppression, prevention, limit or control of worsening or progression of one or more adverse symptoms, disorders, illnesses, diseases or complications caused by or associated with chronic or acute pathogen infection, pathogen numbers, titers, proliferation or replication, pathogen protein or nucleic acid, or pathogen pathology or reactivation from latency, over a short or long duration (hours, days, weeks, months, etc.).

A therapeutic or beneficial effect also includes reducing or eliminating the need, dosage frequency or amount of a second active such as another drug or other agent (e.g., small molecule, protein, antibody) used for treating a subject having or at risk of having a pathogen infection or pathogenesis. For example, reducing an amount of an adjunct therapy, for example, a reduction or decrease of a treatment for a pathogen infection, or reactivation from latency, or a vaccination or immunization protocol is considered a beneficial effect. In addition, reducing or decreasing an amount of a pathogen antigen used for vaccination or immunization of a subject to provide protection to the subject from a pathogen infection, or reactivation from latency, is considered a beneficial effect.

Adverse symptoms, conditions, side effects, pathologies and complications associated with pathogen infection, such as virus, bacteria, parasites and fungus, are known to the skilled artisan. Accordingly, one skilled in the art will be apprised of a variety of clinical indicia by which to ascertain treatment efficacy as well as a therapeutic or beneficial effect.

Adverse symptoms and complications associated with poxvirus (vaccinia virus) infection and pathogenesis include, for example, high fever, fatigue, headache, backache, malaise, rash (maculopapular, vesicular or pustular) or lesions, delirium, vomiting, diarrhea, and excess bleeding. Other symptoms of poxvirus infection or pathogenesis, including variola major and variola minor smallpox virus, monkeypox, cowpox, Molluscum Contagiosum and camelpox, are known in the art and treatment thereof in accordance with the invention is provided.

Adverse symptoms and complications associated with herpesvirus infection and pathogenesis include, for example, red skin, blisters, pustules, bumps, healing with skin regeneration, pain, burning or itching in affected area, swollen lymph glands, headache, muscle ache, fever, burning sensation during urination, lower back pain, pox (e.g., chickenpox). Other symptoms of herpesvirus infection or pathogenesis are known in the art and treatment thereof in accordance with the invention is provided.

Adverse symptoms and complications associated with hepatitis infection and pathogenesis include, for example, abdominal pain, jaundice, flu-like illness, nausea, vomiting, diarrhea, loss of appetite, weight loss, joint pain, fatigue, itchy skin, cirrhosis, liver failure and hepatocellular carcinoma. Other symptoms of hepatitis infection or pathogenesis are known in the art and treatment thereof in accordance with the invention is provided.

Adverse symptoms and complications associated with immunodeficiency virus (e.g., HIV) infection and pathogenesis include, for example, abdominal cramps, nausea, vomiting, diarrhea, enlarged lymph nodes, fever, headache, muscle ache or pain, skin rash, sore throat, weight loss, loss of T cells (CD4+), increased frequency of opportunistic infections, such as yeast and bacterial infections. Other symptoms of immunodeficiency virus infection or pathogenesis are known in the art and treatment thereof in accordance with the invention is provided.

Adverse symptoms and complications associated with flavivirus (e.g., West Nile virus) infection and pathogenesis include, for example, acute febrile illness, malaise, headache, flushing, and diarrhea. Other symptoms of flavivirus infection or pathogenesis are known in the art and treatment thereof in accordance with the invention is provided.

Adverse symptoms and complications associated with papillomavirus (PPV) infection and pathogenesis include, for example, warts (e.g., genital warts). Other symptoms of papillomavirus infection or pathogenesis are known in the art and treatment thereof in accordance with the invention is provided.

Adverse symptoms and complications associated with bacteria infection include, for example, inflammation, swelling, fever, lethargy, fatigue, sore muscles, aches, puss, discharge, redness or soreness, coughing, wheezing, nasal congestion discharge or drip, among others. Such adverse symptoms or conditions can affect a variety of cells, tissue or organs, such as skin, reproductive system (e.g., vagina, cervix, uterus, fallopian tubes) or urinary tract, mucosa (e.g., mouth), nervous system, digestive system, cardio-pulmonary system (lung or cardiac tissue), muscles or bone, kidney, liver, for example.

Adverse symptoms and complications associated with *mycobacteria tuberculosis* infection include, for example, cough lasting three or more weeks that may produce discolored or bloody sputum, weight loss, fatigue, fever, night sweats, chills, loss of appetite and pleurisy. Adverse symptoms and complications associated with atypical mycobacteria infection include, for example, abscesses, septic arthritis, and osteomyelitis (bone infection). Symptoms of *mycobacterium avium*, which frequently affects AIDS patients, includes lung disease. Symptoms of *mycobacterium marinum* are skin infections and swimming pool granuloma. Symptoms of mycobacterium ulcerans include skin infections. Symptoms of *mycobacterium kansasii* include lung disease.

For *listeria monocytogenes*, adverse symptoms include fever, muscle aches, gastrointestinal symptoms such as nausea or diarrhea, headache, stiff neck, confusion, loss of balance, or convulsions. Pregnant women can experience mild, flu-like illness, but during pregnancy can lead to miscarriage or stillbirth, premature delivery, or infection of the newborn.

For *helicobacter pylori*, adverse symptoms include heartburn, bloating, nausea, abdominal pain, gastritis (inflammation of the stomach), and ulcers in stomach or duodenum.

Adverse symptoms and complications associated with symptoms of *Bordetella pertussis* and parapertussis, which cause whooping cough, include paroxysmal coughing, whooping and vomiting, nocturnal coughing and contact anamnesis.

Adverse symptoms and complications associated with *Streptococcus pyogenes*, which causes strep throat include fever, pain, redness, and swelling of the throat or tonsil.

Adverse symptoms and complications associated with *salmonella* include nausea, vomiting, diarrhea, fever, and abdominal cramps.

For *Chlamydia*, three quarters of infected women and half of infected men have no apparent symptoms. When adverse symptoms and complications associated with chlamydia do appear, they include abnormal vaginal discharge or a burning when urinating. After infection spreads from cervix to fallopian tubes, there may still be no signs or symptoms, but there may be lower abdominal pain, low back pain, nausea, fever, pain during intercourse, and bleeding between menstrual periods. Symptoms may not be apparent until complications develop.

Adverse symptoms and complications associated with *Toxoplasma gondii* resemble a mild case of mononucleosis, such as lack of energy, headache, fatigue, loss of appetite or chills.

Adverse symptoms and complications associated with cutaneous *Leishmania* include skin sores, which can change in size and appearance over time, and may be covered by a scab. The sores can be painless or painful. Swollen glands may be near the sores (for example, under the arm if the sores are on the arm or hand). Adverse symptoms and complications associated with visceral *Leishmania* include fever, weight loss, an enlarged spleen or liver, swollen glands, low blood counts, such as a low red blood cell count (anemia), low white blood cell count, or low platelet count.

Adverse symptoms and complications associated with *Plasmodium*, which can cause malaria, include shaking chills, high fever, sweating, fatigue, headache, dizziness, nausea, vomiting, abdominal cramps, dry cough, muscle or joint pain, back ache and cerebral malaria death.

Adverse symptoms and complications associated with *Trypanosoma cruzi*, which causes Chagas' disease, include, in the acute phase, typically inflammation, swelling or chagoma, as well as fever, hepatosplenomegaly, adenopathy and myocarditis sinus tachycardia and cardiomegaly; and in the intermediate phase or chronic phase, lesions of internal organs such as the heart, esophagus and colon as well as the peripheral nervous system and in severe cases heart failure.

Adverse symptoms and complications associated with *Schistosoma mansoni*, which can cause Schistosomiasis include an initial rash following infection that mimics scabies or other types of rashes, followed within two to ten weeks later by symptoms that include fever, aching, cough, diarrhea, or gland enlargement. Katayama fever may also develop from infection, as well as fever, lethargy, the eruption of pale temporary bumps associated with severe itching (urticarial) rash, liver and spleen enlargement, and bronchospasm, which if left untreated is followed by intestinal schistosomiasis, leading to an immune system reaction called a granulomatous reaction, which can lead to obstruction of the colon and blood loss. Eggs can also become lodged in the liver, leading to high blood pressure through liver, enlarged spleen, fluid buildup in the abdomen, and dilations or swollen areas in the esophagus or gastrointestinal tract that can tear and bleed profusely (esophageal varices).

Adverse symptoms and complications associated with fungal infection include, for example, for *Candida albicans*, discomfort, swelling, itching, burning, rash or blisters in or around mucosal tissues, vaginal discharge, vaginitis, pelvic pain, cramps and/or menstrual irregularities, premenstrual tension, prostatitis, urinary urgency or frequency, burning on urination, fatigue, lethargy, dry or sore throat, cough, bronchitis, rash or blisters in mouth or tongue, mouth infections/thrush, white coating on tongue, mucus in stool, rectal itch, muscle weakness or aches, nasal congestion or discharge, nasal itching, sinusitis, pain and swelling in joints, and canker sores.

Additional adverse symptoms, conditions, complications, disorders, diseases, pathologies, and illnesses associated with or caused by a pathogen infection will of course depend upon the particular type, stage of pathogen, the particular subject infected, etc. Specific adverse symptoms, conditions, complications, disorders, diseases, pathologies, and illnesses associated with or caused by a pathogen infection are known to the skilled artisan.

Methods and compositions of the invention include administration of an amount of IL-10R antibody or subsequence thereof to a subject with or at risk of a pathogen infection or reactivation from latency. In a particular aspect, a subject is administered an IL-10R antibody or subsequence alone or in combination with pathogen antigen, live or attenuated pathogen, or a nucleic acid encoding all or a portion (e.g., an epitope) of any protein or proteinaceous pathogen antigen, thereby increasing numbers or activation of an immune cell (e.g., natural killer T (NKT) cells, dendritic cells, macrophages, neutrophils, eosinophils, mast cells, CD4+ or CD8+ cells, CD14+, CD11b+, CD11c+ cells etc.). In another particular aspect, a subject is administered an IL-10R antibody or subsequence alone or in combination with pathogen antigen, live or attenuated pathogen, or a nucleic acid encoding all or a portion (e.g., an epitope) of any protein or proteinaceous pathogen antigen, prior to, substantially contemporaneously with or following vaccination or immunization of the subject against the pathogen infection, as well as administration prior to, substantially contemporaneously with or after a subject has been contacted by, exposed to or infected with a pathogen, acute or chronic, or pathogen reactivation from latency.

Methods and compositions of the invention also include increasing, stimulating, promoting, enhancing, augmenting or inducing an anti-pathogen CD8+ or CD4+ T cell response in a subject with or at risk of a pathogen infection or reactivation from latency. In one embodiment, a method includes administering to a subject an amount of IL-10R antibody or subsequence thereof sufficient to increase, stimulate, promote, enhance, augment or induce anti-pathogen CD8+ or CD4+ T cell response in the subject. In another embodiment, a method includes administering to a subject an amount of an IL-10 receptor alpha (IL-10R alpha) antibody or subsequence thereof and administering a pathogen antigen, live or attenuated pathogen, or a nucleic acid encoding all or a portion (e.g., an epitope) of any protein or proteinaceous pathogen antigen sufficient to increase, stimulate, promote, enhance, augment or induce anti-pathogen CD8+ or CD4+ T cell response in the subject.

Methods of the invention additionally include, among other things, increasing production of a Th1 cytokine (e.g., interferon gamma, IL-1alpha, IL-1beta, IL-2, TNF-alpha, IL-6, IL-8, IL-12, GM-CSF, etc.). In one embodiment, a method includes administering to a subject in need thereof an amount of IL-10 receptor (IL-10R) antibody or subsequence thereof sufficient to increase production of a Th1 cytokine in the subject (e.g., interferon gamma, IL-1 alpha, IL-1beta, IL-2, TNF-alpha, IL-6, IL-8, IL-12, GM-CSF, etc.). In another embodiment, a method includes administering to a subject an amount of an IL-10 receptor alpha (IL-10R alpha) antibody or subsequence thereof and administering a pathogen antigen, live or attenuated pathogen, or a nucleic acid encoding all or a portion (e.g., an epitope) of any protein or proteinaceous pathogen antigen, sufficient to increase production of a Th1 cytokine in the subject (e.g., interferon gamma, IL-1alpha, IL-1beta, IL-2, TNF-alpha, IL-6, IL-8, IL-12, GM-CSF, etc.).

Methods and compositions of the invention further include administration of IL-10R antibody or subsequence thereof to a subject prior to contact, substantially contemporaneously with or following administration of a pathogen antigen, live or attenuated pathogen, or a nucleic acid encoding all or a portion (e.g., an epitope) of any protein or proteinaceous pathogen antigen, to the subject. A subject can be administered IL-10R antibody or subsequence thereof alone or in combination with pathogen antigen, live or attenuated pathogen, or a nucleic acid encoding all or a portion (e.g., an epitope) of any protein or proteinaceous pathogen antigen, prior to contact, substantially contemporaneously with or following contact, exposure or infection by a pathogen. IL-10R antibody or subsequence thereof can therefore be administered to a subject in a combination with a pathogen antigen, live or attenuated pathogen or a nucleic acid encoding all or a portion (e.g., an epitope) of any protein or proteinaceous pathogen antigen, or separately, i.e., the IL-10R antibody or subsequence thereof and antigen, live or attenuated pathogen or nucleic acid encoding all or a portion (e.g., an epitope) of any protein or proteinaceous pathogen antigen are administered sequentially to a subject, i.e IL-10R antibody or subsequence thereof is administered followed by administering a pathogen antigen, live or attenuated pathogen or a nucleic acid encoding all or a portion (e.g., an epitope) of any protein or proteinaceous pathogen antigen.

Methods and compositions of the invention include administration of an IL-10R antibody or subsequence thereof to a subject prior to contact, exposure or infection by a pathogen, administration prior to, substantially contemporaneously with or after a subject has been contacted by, exposed to or infected with a pathogen, acute or chronic, and administration prior to, substantially contemporaneously with or after pathogen reactivation from latency. Methods and compositions of the invention also include administration of an IL-10R antibody or subsequence thereof to a subject prior to, substantially contemporaneously with or following a pathology or adverse symptom, disorder, illness or disease caused by or associated with a pathogen infection, or reactivation from latency. A subject infected with a pathogen may have an acute infection or be chronically infected over a period of days, months, or years, or may be chronically affected that may over time be relatively asymptomatic but may suffer from acute incidents of reactivation from latency.

Invention compositions (e.g., antibodies or subsequences thereof) and methods can be combined with any compound, agent, drug, treatment or other therapeutic regimen or protocol having a desired therapeutic, beneficial, additive, synergistic or complementary activity or effect. Exemplary treatments and therapies include second actives, such as anti-pathogen compounds, agents and drugs, as well as agents that assist, promote, stimulate or enhance efficacy. Such anti-pathogen drugs, agents, treatments and therapies can be administered or performed prior to, substantially contemporaneously with or following any other method of the invention, for example, a therapeutic method of treating a subject for a pathogen infection or reactivation from latency, or a method of prophylactic treatment of a subject for a pathogen infection.

Combination methods embodiments include, for example, second actives such as anti-pathogen drugs, such as protease inhibitors, reverse transcriptase inhibitors, virus fusion inhibitors and virus entry inhibitors, antibodies to pathogen proteins, live or attenuated pathogen, or a nucleic acid encoding all or a portion (e.g., an epitope) of any protein or proteinaceous pathogen antigen, immune stimulating agents, etc., and include contact with, administration in vitro or in vivo, with another compound, agent, treatment or therapeutic regimen appropriate for pathogen infection, vaccination or immunization Specific non-limiting examples of antivirals include AK602, AMD070, APV, ATV, ATZ, AVX754, AZT, Abacavir, Acyclovir, Adefovir dipivoxil, Adriamycin, Agenerase, Aldesleukin, Alovudine, AmBisome, Amdoxovir, Amphocin, Amphotec, Amphotericin B, Ampligen, Amprenavir, Androderm, Androgel, Aptivus, Atazanavir, Azithromycin, BMS-488043, Bactrim, Baraclude, Biaxin, BufferGel, C31G, CD4-IgG2, CPV, CS, Calanolide A, Capravirine, Carbopol 974P, Carrageenan, Carraguard, Cellulose sulfate, Cidofivir, Clarithromycin, Combivir, Copegus, Cotrimoxazole, Crixivan, Cyanovirin-N, Cytovene, DAPD, DLV, DPC 817, DS, Delavirdine, Depo-Testosterone, Dextran sulfate, Didanosine, Diflucan, Doxil, Doxorubicin, Dronabinol, Duofilm, EFV, Efavirenz, Elvucitabine, Emtricitabine, Emtriva, Enfuvirtide, Entecavir, Epivir, Epoetin alfa, Epogen, Epzicom, Etopophos (phosphate salt), Etoposide, Etravirine, Fluconazole, Fortovase, Fosamprenavir, Fungizone, Fuzeon, GSK-873,140 (aplaviroc), GW433908, Gammar-P, Ganciclovir, Growth hormone, Human growth hormone, HEC, Hepsera, Hivid, Hydroxyethyl cellulose, IDV, IGIV, Imiquimod cream, Interleukin-2 (IL-2), INH, Immune Globulin, Indinavir, Interferon alfa-2, Interferon alfa-2b, Intron A (2b), Invirase, Isoniazid, Itraconazole, KP-1461, Kaletra, L-000870810, LPV/RTV, Lamivudine, Lexiva, Marinol, Megace, Megestrol, Mycobutin, NFV, NVP, Naphthalene 2-sulfonate polymer, Nebupent, Nelfinavir, Neutrexin, Nevirapine, New-Fill, Norvir, Nydrazid, Occlusal, Onxol, Oseltamivir, PA-457, PMPA, PRO 2000, PRO542, Paclitaxel, Paxene, Pegasys (2a), Pentamidine, Peptide T, pleconaril, podofilox, podophyllin, Poly(I)-Poly(C12U), Poly-L-lactic acid, Polygam S/D, Procrit, Proleukin, RCV, RTV, RVT, Racivir, Rebetol, Rescriptor, Retrovir, Reverset, Reyataz, Ribavirin, Rifabutin, Rifadin, Rifampin, Rimactane, Ritonavir, Roferon-A (2a), SCH-C, SCH-D (vicriviroc), SQV, Saquinavir, Savvy, Sculptra, Septra, Serostim, Somatropin, Sporanox, Stavudine, Sulfamethoxazole, Sustanon, Sustiva, T-20, TDF, THC, TMC114, TMC125, TNX-355, Taxol, Tenofovir, Tenofovir disoproxil fumarate, Testosterone, Tipranavir, Toposar, TransVer-Sal, Trichloroacetic acid (TCA), Trimethoprim, Trimetrexate, Trizivir, Truvada, UC-781, UK-427,857 (maraviroc), Ushercell, Valcyte, Valganciclovir, Valproic acid, VePesid, Vicriviroc, Videx, Viracept, Viranol, Viramune, Virazole, Viread, Vitrasert, ZDV, Zalcitabine, Zerit, Ziagen, Zidovudine, Zithromax, Zovirax, D4T, ddC, β-LFddC, P-LFd4C, DDI, f-APV, 3TC, 5-FU and human erythropoietin (EPO).

Specific non-limiting examples of anti-bacterials include antibiotics. Antibiotics can be first, second, third, fourth, fifth or subsequent generations. Antibiotics include, for example, aminoglycosides (e.g., gentamycin, kanamycin, streptomycin, etc.), Carbapenems (e.g., cilastatin), cephalasporins (e.g., cefalexin, cefoxitin, cefdinir, cefapime, etc.), glycopeptides (e.g., vancomycin), macrolides (erythromycin), monbactams (e.g., aztreonam), penicillins (e.g., ampicillin, amopxicillin, oxacillin, etc.), quinolones (e.g., ciprofloxacin), sulfanomides (e.g., Mafenide, Sulfasalazine, etc.), tetracyclines (e.g., doxycycline, tetracyclone, etc.) and others such as chloramphenicol, rifampicin, etc.

Specific non-limiting examples of anti-parasites include albendazole, mebendazole, thiabendazole, metronidazole, nitazoxanide, niclosamide, oxamniquine, praziquantel, pyrantel, and pyantel pamoate.

Specific non-limiting examples of anti-fungals include clotrimazole, econazole, fenticonazole, miconazole, sulconazole, tioconazole, amphotericin, nystatin terbinafine, itraconazole, fluconazole, ketoconazole and griselfulvin.

The invention provides combinations in which a method of the invention is used in a combination with any compound, agent, drug, therapeutic regimen, treatment protocol, process, remedy or composition, such as an anti-pathogen or immune stimulating, enhancing or augmenting protocol, or pathogen vaccination or immunization (e.g., prophylaxis) set forth herein or known in the art. The compound, agent, drug, therapeutic regimen, treatment protocol, process, remedy or composition can be administered or performed prior to, substantially contemporaneously with or following administration of IL-10R antibody or subsequence thereof, pathogen antigen, live or attenuated pathogen, or a nucleic acid encoding all or a portion (e.g., an epitope) of any protein or proteinaceous pathogen antigen, to a subject. Specific non-limiting examples of combination embodiments therefore include the foregoing or other compound, agent, drug, therapeutic regimen, treatment protocol, process, remedy or composition, known to the skilled artisan.

Treatments such as steroidal and non-steroidal anti-inflammatory drugs such as acetaminophen, ibuprofen, naproxen, indomethacin, piroxicam, ketoprofen and pyrancarboxylic acid (Lodine). Further additional exemplary treatments include pathogen protein, antibody that binds to a pathogen antigen, pathogen nucleic acid, passive immunoglobulin therapy, such as VIG.

Methods of the invention also include, among other things, methods that result in a reduced need or use of another compound, agent, drug, therapeutic regimen, treatment protocol, process, or remedy. For example, for a pathogen infection, reactivation from latency, vaccination or immunization, a method of the invention has a therapeutic benefit if in a given subject a less frequent or reduced dose or elimination of an anti-pathogen treatment or therapy results. Thus, in accordance with the invention, methods of reducing need or use of a treatment or therapy for a pathogen infection, reactivation from latency, or vaccination or immunization, are provided.

In invention methods in which there is a desired outcome, such as a therapeutic or prophylactic method that provides a benefit from treatment or vaccination or immunization of a pathogen infection or pathogenesis, an IL-10R antibody or subsequence thereof alone or in combination with each other or another composition or method, such as a pathogen antigen, live or attenuated pathogen, or a nucleic acid encoding all or a portion (e.g., an epitope) of any protein or proteinaceous pathogen antigen, can be administered in a sufficient or effective amount. As used herein, a "sufficient amount" or "effective amount" or an "amount sufficient" or an "amount effective" refers to an amount that provides, in single or multiple doses, alone or in combination with one or more other compounds, treatments, therapeutic regimens or agents (e.g., a drug), a long term or a short term detectable or measurable improvement in a given subject or any objective or subjective benefit to a given subject of any degree or for any time period or duration (e.g., for minutes, hours, days, months, years, or cured).

An amount sufficient or an amount effective can but need not be provided in a single administration and can but need not be achieved by IL-10R antibody or subsequence thereof alone, in a combination composition or method that includes a pathogen antigen, live or attenuated pathogen, or a nucleic acid encoding all or a portion (e.g., an epitope) of any protein or proteinaceous pathogen antigen. In addition, an amount sufficient or an amount effective need not be sufficient or effective if given in single or multiple doses without a second or additional administration or dosage, since additional doses, amounts or duration above and beyond such doses, or additional antigens, compounds, drugs, agents, treatment or therapeutic regimens may be included in order to provide a given subject with a detectable or measurable improvement or benefit to the subject.

An amount sufficient or an amount effective need not be therapeutically or prophylactically effective in each and every subject treated, nor a majority of subjects treated in a given group or population. An amount sufficient or an amount effective means sufficiency or effectiveness in a particular subject, not a group of subjects or the general population. As is typical for such methods, different subjects will exhibit varied responses to treatment.

The term "subject" refers to an animal, typically a mammalian animal, such as a non human primate (apes, gibbons, gorillas, chimpanzees, orangutans, macaques), a domestic animal (dogs and cats), a farm animal (poultry such as chickens and ducks, horses, cows, goats, sheep, pigs), experimental animal (mouse, rat, rabbit, guinea pig) and humans. Subjects include animal disease models, for example, mouse and other animal models of pathogen infection and reactivation from latency known in the art.

Subjects appropriate for treatment include those having or at risk of having a pathogen infection or pathogenesis, or reactivation from latency. Target subjects therefore include subjects that have been exposed to or contacted with a pathogen, or that have an ongoing infection and have developed one or more adverse symptoms caused by or associated with pathogen infection or pathogenesis, regardless of the type, timing or degree of onset, progression, severity, frequency, duration of the symptoms, or subjects that are chronically infected and may not exhibit apparent adverse symptoms but are at risk of pathogen reactivation from latency.

Target subjects also include those at risk of pathogen exposure, contact, infection or pathogenesis or at risk of having or developing a pathogen infection or pathogenesis. The invention methods are therefore applicable to treating a subject who is at risk of pathogen exposure, contact, infection or pathogenesis, but has not yet been exposed to or contacted with pathogen. Prophylactic methods are therefore included. Target subjects for prophylaxis can be at increased risk (probability or susceptibility) of pathogen exposure, contact, infection or pathogenesis, as set forth herein and known in the art. Such subjects are considered in need of treatment due to such a risk.

Target subjects for prophylaxis need not be at increased risk but may be from the general population in which it is desired to vaccinate or immunize a subject against a pathogen infection, for example, a child such as an infant or toddler in which it is desired to vaccinate or immunize against a pathogen can be administered an IL-10R antibody or subsequence thereof and an appropriate antigen. In another non-limiting example, a subject that is not specifically at risk of exposure to or contact with a pathogen, but nevertheless does wish to protect against pathogen infection, such as a measles or mumps virus, or papilloma virus, can be administered an IL-10R antibody or subsequence thereof and an appropriate antigen. Such subjects are also considered in need of treatment.

At risk subjects appropriate for treatment also include subjects exposed to other subjects having a pathogen infection or having been exposed to another subject having a pathogen infection (e.g., at risk of pathogen infection due to transmission from one subject to another). Subjects appropriate for treatment therefore include human subjects exposed to or at risk of exposure to other humans that may have a pathogen infection, or are at risk of a pathogen infection. At risk subjects appropriate for treatment also include subjects where the risk of pathogen infection or pathogenesis is increased due to changes in pathogen infectivity or cell tropism, environmental factors, or immunological susceptibility (e.g., an immune-suppressed, immunocompromised, or HIV-positive subject). Such subjects are also considered in need of treatment due to such a risk.

"Prophylaxis" and grammatical variations thereof mean a method in which contact, administration or in vivo delivery to a subject is prior to contact with or exposure to or infection with a pathogen. In certain situations it may not be known that a subject has been contacted with or exposed to pathogen, but administration or in vivo delivery to a subject can be performed prior to pathogen infection or manifestation of pathogenesis (or an associated adverse symptom, condition, complication, etc. caused by or associated with a pathogen). For example, a subject can be immunized or vaccinated with a pathogen antigen, live or attenuated pathogen, or a nucleic acid encoding all or a portion (e.g., an epitope) of any protein or proteinaceous pathogen antigen, and administered an IL-10R antibody or subsequence thereof. In such case, a method can eliminate, prevent, inhibit, suppress, limit, decrease or reduce the probability of or susceptibility towards a pathogen infection or pathogenesis, or an adverse symptom, condition or complication associated with or caused by or associated with a pathogen infection, pathogenesis or reactivation from latency.

Treatment of an acute or chronic (persistent) infection can be at any time during the infection. A chronic infection may or may not be latent. Non-limiting examples of chronic (persistent) infections that are not considered latent are hepatitis B and C viruses. In such non-latent chronic infections, pathogen continues to proliferate or replicate at reduced levels and to induce adverse events, but evades clearance due to immune suppression or repression, for example, by IL-10 or IL-10 analogs produced by the pathogen. Latency refers to a quiescent phase of an infection in which there is no viral production or symptoms and detection of the pathogen is difficult. Reactivation from latency refers to reactivation and subsequent proliferation of a pathogen, which is triggered by an event, such as immune suppression, stress, etc. An example of an infection that can become latent is an acute herpesvirus infection that after the initial acute infection is controlled by the immune system, becomes a latent persistent infection.

Methods of the invention may be practiced by any mode of administration or delivery, or by any route, systemic, regional and local administration or delivery. Exemplary administration and delivery routes include intravenous (i.v.), intraperitoneal (i.p.), intrarterial, intramuscular, parenteral, subcutaneous, intra-pleural, topical, dermal, intradermal, transdermal, transmucosal, intra-cranial, intra-spinal, rectal, oral (alimentary), mucosal, inhalation, respiration, intranasal, intubation, intrapulmonary, intrapulmonary instillation, buccal, sublingual, intravascular, intrathecal, intracavity, iontophoretic, intraocular, ophthalmic, optical, intraglandular, intraorgan, intralymphatic.

IL-10R antibody or subsequence thereof can be administered as a combination (e.g., with an antigen, live or attenuated pathogen, or a nucleic acid encoding all or a portion (e.g., an epitope) of any protein or proteinaceous pathogen antigen), or separately concurrently or in sequence (sequentially) in accordance with the methods as a single or multiple dose e.g., one or more times hourly, daily, weekly, monthly or annually or between about 1 to 10 weeks, or for as long as appropriate, for example, to achieve a reduction in the onset, progression, severity, frequency, duration of one or more symptoms or complications associated with or caused by pathogen infection, pathology, or an adverse symptom, condition or complication associated with or caused by a pathogen. Thus, a method can be practiced one or more times (e.g., 1-10, 1-5 or 1-3 times) an hour, day, week, month, or year. The skilled artisan will know when it is appropriate to delay or discontinue administration. A non-limiting dosage schedule is 1-7 times per week, for 1, 2, 3, 4, 5, 6, 7, 8, 9, 10, 15, 20 or more weeks, and any numerical value or range or value within such ranges.

Doses can be based upon current existing protocols, empirically determined, using animal disease models or optionally in human clinical trials. Initial study doses can be based upon animal studies set forth herein, for a mouse, which weighs about 30 grams, and the amount of IL-10R antibody or subsequence thereof administered that is determined to be effective. Exemplary non-limiting amounts (doses) are in a range of about 0.1 mg/kg to about 100 mg/kg, and any numerical value or range or value within such ranges. Greater or lesser amounts (doses) can be administered, for example, 0.01-500 mg/kg, and any numerical value or range or value within such ranges. The dose can be adjusted according to the mass of a subject, and will generally be in a range from about 1-10 ug/kg, 10-25 ug/kg, 25-50 ug/kg, 50-100 ug/kg, 100-500 ug/kg, 500-1,000 ug/kg, 1-5 mg/kg, 5-10 mg/kg, 10-20 mg/kg, 20-50 mg/kg, 50-100 mg/kg, 100-250 mg/kg, 250-500 mg/kg, or more, two, three, four, or more times per hour, day, week, month or annually. A typical range will be from about 0.3 mg/kg to about 50 mg/kg, 0-25 mg/kg, or 1.0-10 mg/kg, or any numerical value or range or value within such ranges.

Doses can vary and depend upon whether the treatment is prophylactic or therapeutic, the onset, progression, severity, frequency, duration probability of or susceptibility of the symptom, condition, pathology or complication the type of pathogen infection or pathogenesis, reactivation from latency or vaccination or immunization to which treatment is directed, the clinical endpoint desired, previous or simultaneous treatments, the general health, age, gender, race or immunological competency of the subject and other factors that will be appreciated by the skilled artisan. The skilled artisan will appreciate the factors that may influence the dosage and timing required to provide an amount sufficient for providing a therapeutic or prophylactic benefit.

Typically, for therapeutic treatment, IL-10R antibody or subsequence thereof will be administered as soon as practical, typically within 1-2, 2-4, 4-12, 12-24 or 24-72 hours after a subject is exposed to or contacted with a pathogen, or within 1-2, 2-4, 4-12, 12-24 or 24-48 hours after onset or development of one or more adverse symptoms, conditions, pathologies, complications, etc., associated with or caused by a pathogen infection or reactivation from latency. For prophylactic treatment in connection with vaccination or immunization, IL-10R antibody or subsequence thereof and an antigen, live or attenuated pathogen, or a nucleic acid encoding a pathogen antigen, can be administered for a duration of 0-4 weeks, e.g., 2-3 weeks, prior to exposure to, contact or infection with pathogen, or at least within 1-2, 2-4, 4-12, 12-24, 24-48 or 48-72 hours prior to exposure to, contact or infection with pathogen. For a chronic infection, such as a latent pathogen infection in a subject that has or is at risk of reactivation from latency, IL-10R antibody or subsequence thereof is administered at any appropriate time.

The dose amount, number, frequency or duration may be proportionally increased or reduced, as indicated by the status of the subject. For example, whether the subject has a pathogen infection, whether the subject has been exposed to, contacted or infected with pathogen or is merely at risk of pathogen contact, exposure or infection, whether the subject is or is at risk of suffering from reactivation from latency or whether the subject is a candidate for or will be vaccinated or immunized. The dose amount, number, frequency or duration may be proportionally increased or reduced, as indicated by any adverse side effects, complications or other risk factors of the treatment or therapy.

IL-10R antibodies and subsequences thereof, optionally in combination with an antigen, live or attenuated pathogen, or a nucleic acid encoding a pathogen antigen, can be incorporated into pharmaceutical compositions, e.g., a pharmaceutically acceptable carrier or excipient. Such pharmaceutical compositions are useful for, among other things, administration to a subject in vivo or ex vivo.

As used herein the term "pharmaceutically acceptable" and "physiologically acceptable" mean a biologically acceptable formulation, gaseous, liquid or solid, or mixture thereof, which is suitable for one or more routes of administration, in vivo delivery or contact. Such formulations include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions.

Pharmaceutical compositions can be formulated to be compatible with a particular route of administration. Thus, pharmaceutical compositions include carriers, diluents, or excipients suitable for administration by various routes. Exemplary routes of administration for contact or in vivo delivery which a composition can optionally be formulated include inhalation, respiration, intranasal, intubation, intrapulmonary instillation, oral, buccal, intrapulmonary, intradermal, topical, dermal, parenteral, sublingual, subcutaneous, intravascular, intrathecal, intraarticular, intracavity, transdermal, iontophoretic, intraocular, opthalmic, optical, intravenous (i.v.), intramuscular, intraglandular, intraorgan, intralymphatic.

Formulations suitable for parenteral administration comprise aqueous and non-aqueous solutions, suspensions or emulsions of the active compound, which preparations are typically sterile and can be isotonic with the blood of the intended recipient. Non-limiting illustrative examples include water, saline, dextrose, fructose, ethanol, animal, vegetable or synthetic oils.

For transmucosal or transdermal administration (e.g., topical contact), penetrants can be included in the pharmaceutical composition. Penetrants are known in the art, and include, for example, for transmucosal administration, detergents, bile salts, and fusidic acid derivatives. For transdermal administration, the active ingredient can be formulated into aerosols, sprays, ointments, salves, gels, or creams as generally known in the art. For contact with skin, pharmaceutical compositions typically include ointments, creams, lotions, pastes, gels, sprays, aerosols, or oils. Carriers which may be used include Vaseline, lanolin, polyethylene glycols, alcohols, transdermal enhancers, and combinations thereof.

Cosolvents and adjuvants may be added to the formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Adjuvants include, for example, surfactants such as, soya lecithin and oleic acid; sorbitan esters such as sorbitan trioleate; and polyvinylpyrrolidone.

Supplementary compounds (e.g., preservatives, antioxidants, antimicrobial agents including biocides and biostats such as antibacterial, antiviral and antifungal agents) can also be incorporated into the compositions. Pharmaceutical compositions may therefore include preservatives, anti-oxidants and antimicrobial agents.

Preservatives can be used to inhibit microbial growth or increase stability of ingredients thereby prolonging the shelf life of the pharmaceutical formulation. Suitable preservatives are known in the art and include, for example, EDTA, EGTA, benzalkonium chloride or benzoic acid or benzoates, such as sodium benzoate. Antioxidants include, for example, ascorbic acid, vitamin A, vitamin E, tocopherols, and similar vitamins or provitamins.

An antimicrobial agent or compound directly or indirectly inhibits, reduces, delays, halts, eliminates, arrests, suppresses or prevents contamination by or growth, infectivity, replication, proliferation, reproduction, of a pathogenic or non-pathogenic microbial organism. Classes of antimicrobials include, antibacterial, antiviral, antifungal and antiparasitics. Antimicrobials include agents and compounds that kill or destroy (-cidal) or inhibit (-static) contamination by or growth, infectivity, replication, proliferation, reproduction of the microbial organism.

Exemplary antibacterials (antibiotics) include penicillins (e.g., penicillin G, ampicillin, methicillin, oxacillin, and amoxicillin), cephalosporins (e.g., cefadroxil, ceforanid, cefotaxime, and ceftriaxone), tetracyclines (e.g., doxycycline, chlortetracycline, minocycline, and tetracycline), aminoglycosides (e.g., amikacin, gentamycin, kanamycin, neomycin, streptomycin, netilmicin, paromomycin and tobramycin), macrolides (e.g., azithromycin, clarithromycin, and erythromycin), fluoroquinolones (e.g., ciprofloxacin, lomefloxacin, and norfloxacin), and other antibiotics including chloramphenicol, clindamycin, cycloserine, isoniazid, rifampin, vancomycin, aztreonam, clavulanic acid, imipenem, polymyxin, bacitracin, amphotericin and nystatin.

Particular non-limiting classes of anti-virals include reverse transcriptase inhibitors; protease inhibitors; thymidine kinase inhibitors; sugar or glycoprotein synthesis inhibitors; structural protein synthesis inhibitors; nucleoside analogues; and viral maturation inhibitors. Specific non-limiting examples of anti-virals include nevirapine, delavirdine, efavirenz, saquinavir, ritonavir, indinavir, nelfinavir, amprenavir, zidovudine (AZT), stavudine (d4T), lamivudine (3TC), didanosine (DDI), zalcitabine (ddC), abacavir, acyclovir, penciclovir, ribavirin, valacyclovir, ganciclovir, 1,-D-ribofuranosyl-1,2,4-triazole-3 carboxamide, 9->2-hydroxyethoxy methylguanine, adamantanamine, 5-iodo-2'-deoxyuridine, trifluorothymidine, interferon and adenine arabinoside.

Pharmaceutical formulations and delivery systems appropriate for the compositions and methods of the invention are known in the art (see, e.g., *Remington: The Science and Practice of Pharmacy* (2003) 20$^{th}$ ed., Mack Publishing Co., Easton, Pa.; *Remington's Pharmaceutical Sciences* (1990) 18$^{th}$ ed., Mack Publishing Co., Easton, Pa.; *The Merck Index* (1996) 12$^{th}$ ed., Merck Publishing Group, Whitehouse, N.J.; *Pharmaceutical Principles of Solid Dosage Forms* (1993), Technonic Publishing Co., Inc., Lancaster, Pa.; Ansel and Stoklosa, *Pharmaceutical Calculations* (2001) 11$^{th}$ ed., Lippincott Williams & Wilkins, Baltimore, Md.; and Poznansky et al., *Drug Delivery Systems* (1980), R. L. Juliano, ed., Oxford, N.Y., pp. 253-315).

IL-10R antibody and subsequences thereof, along with any adjunct agent, compound drug, composition, whether active or inactive, etc., can be packaged in unit dosage form (capsules, tablets, troches, cachets, lozenges) for ease of administration and uniformity of dosage. A "unit dosage form" as used herein refers to physically discrete units suited as unitary dosages for the subject to be treated; each unit containing a predetermined quantity of active ingredient optionally in association with a pharmaceutical carrier (excipient, diluent, vehicle or filling agent) which, when administered in one or more doses, is calculated to produce a desired effect (e.g., prophylactic or therapeutic effect). Unit dosage forms also include, for example, ampules and vials, which may include a composition in a freeze-dried or lyophilized state; a sterile liquid carrier, for example, can be added prior to administration or delivery in vivo. Unit dosage forms additionally include, for example, ampules and vials with liquid compositions disposed therein. Individual unit dosage forms can be included in multi-dose kits or containers. Pharmaceutical formulations can be packaged in single or multiple unit dosage form for ease of administration and uniformity of dosage.

The invention provides kits comprising IL-10R antibodies and subsequences thereof, optionally with a pathogen antigen, live or attenuated pathogen, combination compositions and pharmaceutical formulations thereof, packaged into suitable packaging material. A kit typically includes a label or packaging insert including a description of the components or instructions for use in vitro, in vivo, or ex vivo, of the components therein. A kit can contain a collection of such components, e.g., IL-10R antibody or subsequence thereof and optionally a pathogen antigen, live or attenuated pathogen, alone (individual vessel or pack) or in combination (e.g., mixture), or another compound, agent, drug or composition.

The term "packaging material" refers to a physical structure housing the components of the kit. The packaging material can maintain the components sterilely, and can be made of material commonly used for such purposes (e.g., paper, corrugated fiber, glass, plastic, foil, ampules, vials, tubes, etc.).

Kits of the invention can include labels or inserts. Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a disk (e.g., floppy diskette, hard disk, flash memory), optical disk such as CD- or DVD-ROM/RAM, DVD, MP3, magnetic tape, or an electrical storage media such as RAM and ROM or hybrids of these such as magnetic/optical storage media, FLASH media or memory type cards.

Labels or inserts can include identifying information of one or more components therein, dose amounts, clinical pharmacology of the active ingredient(s) including mechanism of action, pharmacokinetics and pharmacodynamics. Labels or inserts can include information identifying manufacturer information, lot numbers, manufacturer location and date.

Labels or inserts can include information on a condition, disorder or disease (e.g., viral infection, vaccination or immunization) for which a kit component may be used. Labels or inserts can include instructions for the clinician or subject for using one or more of the kit components in a method, or treatment protocol or therapeutic regimen. Instructions can include dosage amounts, frequency or duration, and instructions for practicing any of the methods, treatment protocols or prophylactic or therapeutic regimes described herein. Exemplary instructions include, instructions for treating a pathogen infection or pathology, and instructions for providing a subject with protection against pathogen infection, pathology or reactivation from latency.

Labels or inserts can include information on any benefit that a component may provide, such as a prophylactic or therapeutic benefit. Labels or inserts can include information on potential adverse side effects, complications or reactions, such as warnings to the subject or clinician regarding situations where it would not be appropriate to use a particular composition. Adverse side effects or complications could also occur when the subject has, will be or is currently taking one or more other medications that may be incompatible with the composition, or the subject has, will be or is currently undergoing another treatment protocol or therapeutic regimen which would be incompatible with the composition and, therefore, instructions could include information regarding such incompatibilities.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All applications, publications, patents and other references, GenBank citations and ATCC citations cited herein are incorporated by reference in their entirety. In case of conflict, the specification, including definitions, will control.

As used herein, the singular forms "a," "and," and "the" include plural referents unless the context clearly indicates otherwise. Thus, for example, reference to an "IL-10 antibody" or a "pathogen" includes a plurality of antibodies or pathogens and reference to an "activity or function" such as "an IL-10 activity or function" or "an IL-10R activity or function" can include reference to one or more IL-10R activities or functions, including any activity or function of any component of the IL-10/IL-10R signaling pathway or activity, and so forth.

As used herein, all numerical values or ranges include fractions of the values and integers within such ranges and fractions of the integers within such ranges unless the context clearly indicates otherwise. Thus, to illustrate, reference to a numerical range, such as a percentage range, 90-100%, includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and so forth. Reference to a range of 1-5 fold therefore includes 1, 2, 3, 4, 5, 6, 7, 8, 9, 10, 11, 12, 13, 14, 15, 16, 17, 18, 19, 20, fold, etc., as well as 1.1, 1.2, 1.3, 1.4, 1.5, fold, etc., 2.1, 2.2, 2.3, 2.4, 2.5, fold, etc., and so forth.

The invention is generally disclosed herein using affirmative language to describe the numerous embodiments and aspects. The invention also specifically includes embodiments in which particular subject matter is excluded, in full or in part, such as substances or materials, method steps and conditions, protocols, procedures, assays or analysis. For example, in certain embodiments or aspects of the invention, antibodies or other materials and method steps are excluded. In certain embodiments and aspects of the invention, for example, an IL-10R antibody or pathogen antigen is excluded. Thus, even though the invention is generally not expressed herein in terms of what is not included, embodiments and aspects that expressly exclude compositions (e.g., antibodies or pathogen antigens) or method steps are nevertheless disclosed and included in the invention.

A number of embodiments of the invention have been described. Nevertheless, it will be understood that various modifications may be made without departing from the spirit and scope of the invention. Accordingly, the following examples are intended to illustrate but not limit the scope of invention described in the claims.

EXAMPLES

Example 1

This example includes a description of various materials and methods.

Human IL-10Rα cloning: The full length IL-10Rα MGC clone in pCMVsport6 (Accession number BE272922) was purchased from Invitrogen Corp. (Carlsbad, Calif.) and the full-length IL-10Rα open reading frame was subcloned by polymerase chain reaction [primers: hIL-10Ra F48 EcoRI and hIL-10Ra R1857 NotI (Table 1)] from the MGC clone. The amplified product was digested with EcoRI and NotI restriction enzymes and subcloned into pcDNA3.1(+) (Invitrogen Corp.) previously digested with EcoRI and NotI. The sequence encoding the human IL-10Rα extracellular domain was amplified from pCMVsport6 vector by polymerase chain reaction [primers: hIL-10R Forward and hIL-10R Reverse (Table 1)]. The amplified product was digested with EcoRI and BglII restriction enzymes, which were included in the primers, and the human IgG1 Fc sequence was excised from the pV11392.fc vector using BglII and NotI restriction enzymes. The shIL-10Rα (EcoRI-BglII) and hFc (BglII-NotI) fragments were subcloned into the pcDNA3.1(+) expression vector previously digested with EcoRI and NotI to generate a hIL-10Rα:hFc expression vector.

Nucleotide sequence of full-length human IL-10Rα from initiation codon (ATG) through the IL-10Rα stop codon (underlined): SEQ ID NO:1

```
ATGCTGCCGT GCCTCGTAGT GCTGCTGGCG GCGCTCCTCA GCCTCCGTCT TGGCTCAGAC    60

GCTCATGGGA CAGAGCTGCC CAGCCCTCCG TCTGTGTGGT TTGAAGCAGA ATTTTTCCAC   120

CACATCCTCC ACTGGACACC CATCCCAAAT CAGTCTGAAA GTACCTGCTA TGAAGTGGCA   180

CTCCTGAGGT ATGGAATAGA GTCCTGGAAC TCCATCTCCA ACTGTAGCCA GACCCTGTCC   240

TATGACCTTA CCGCAGTGAC CTTGGACCTG TACCACAGCA ATGGCTACCG GGCCAGAGTG   300

CGGGCTGTGG ACGGCAGCCG GCACTCCAAC TGGACCGTCA CCAACACCCG CTTCTCTGTG   360

GATGAAGTGA CTCTGACAGT TGGCAGTGTG AACCTAGAGA TCCACAATGG CTTCATCCTC   420

GGGAAGATTC AGCTACCCAG GCCCAAGATG GCCCCCGCAA ATGACACATA TGAAAGCATC   480

TTCAGTCACT TCCGAGAGTA TGAGATTGCC ATTCGCAAGG TGCCGGGAAA CTTCACGTTC   540

ACACACAAGA AAGTAAAACA TGAAAACTTC AGCCTCCTAA CCTCTGGAGA AGTGGGAGAG   600

TTCTGTGTCC AGGTGAAACC ATCTGTCGCT TCCCGAAGTA CAAGGGGAT GTGGTCTAAA   660

GAGGAGTGCA TCTCCCTCAC CAGGCAGTAT TTCACCGTGA CCAACGTCAT CATCTTCTTT   720

GCCTTTGTCC TGCTGCTCTC CGGAGCCCTC GCCTACTGCC TGGCCCTCCA GCTGTATGTG   780

CGGCGCCGAA AGAAGCTACC CAGTGTCCTG CTCTTCAAGA AGCCCAGCCC CTTCATCTTC   840

ATCAGCCAGC GTCCCTCCCC AGAGACCCAA GACACCATCC ACCCGCTTGA TGAGGAGGCC   900

TTTTTGAAGG TGTCCCCAGA GCTGAAGAAC TTGGACCTGC ACGGCAGCAC AGACAGTGGC   960

TTTGGCAGCA CCAAGCCATC CCTGCAGACT GAAGAGCCCC AGTTCCTCCT CCCTGACCCT  1020

CACCCCCAGG CTGACAGAAC GCTGGGAAAC GGGGAGCCCC CTGTGCTGGG GGACAGCTGC  1080

AGTAGTGGCA GCAGCAATAG CACAGACAGC GGGATCTGCC TGCAGGAGCC CAGCCTGAGC  1140

CCCAGCACAG GGCCCACCTG GGAGCAACAG GTGGGGAGCA ACAGCAGGGG CCAGGATGAC  1200

AGTGGCATTG ACTTAGTTCA AAACTCTGAG GGCCGGGCTG GGGACACACA GGGTGGCTCG  1260

GCCTTGGGCC ACCACAGTCC CCCGGAGCCT GAGGTGCCTG GGGAAGAAGA CCCAGCTGCT  1320
```

```
GTGGCATTCC AGGGTTACCT GAGGCAGACC AGATGTGCTG AAGAGAAGGC AACCAAGACA   1380

GGCTGCCTGG AGGAAGAATC GCCCTTGACA GATGGCCTTG GCCCCAAATT CGGGAGATGC   1440

CTGGTTGATG AGGCAGGCTT GCATCCACCA GCCCTGGCCA AGGGCTATTT GAAACAGGAT   1500

CCTCTAGAAA TGACTCTGGC TTCCTCAGGG GCCCCAACGG GACAGTGGAA CCAGCCCACT   1560

GAGGAATGGT CACTCCTGGC CTTGAGCAGC TGCAGTGACC TGGGAATATC TGACTGGAGC   1620

TTTGCCCATG ACCTTGCCCC TCTAGGCTGT GTGGCAGCCC CAGGTGGTCT CCTGGGCAGC   1680

TTTAACTCAG ACCTGGTCAC CCTGCCCCTC ATCTCTAGCC TGCAGTCAAG TGAGTGA     1740
```

Amino acid sequence of full-length human IL-10Rα from the start Met to the terminal amino acid: SEQ ID NO:2

```
MLPCLVVLLA ALLSLRLGSD AHGTELPSPP SVWFEAEFFH HILHWTPIPN QSESTCYEVA    60

LLRYGIESWN SISNCSQTLS YDLTAVTLDL YHSNGYRARV RAVDGSRHSN WTVTNTRFSV   120

DEVTLTVGSV NLEIHNGFIL GKIQLPRPKM APANDTYESI FSHFREYEIA IRKVPGNFTF   180

THKKVKHENF SLLTSGEVGE FCVQVKPSVA SRSNKGMWSK EECISLTRQY FTVTNVIIFF   240

AFVLLLSGAL AYCLALQLYV RRRKKLPSVL LFKKPSPFIF ISQRPSPETQ DTIHPLDEEA   300

FLKVSPELKN LDLHGSTDSG FGSTKPSLQT EEPQFLLPDP HPQADRTLGN GEPPVLGDSC   360

SSGSSNSTDS GICLQEPSLS PSTGPTWEQQ VGSNSRGQDD SGIDLVQNSE GRAGDTQGGS   420

ALGHHSPPEP EVPGEEDPAA VAFQGYLRQT RCAEEKATKT GCLEEESPLT DGLGPKFGRC   480

LVDEAGLHPP ALAKGYLKQD PLEMTLASSG APTGQWNQPT EEWSLLALSS CSDLGISDWS   540

FAHDLAPLGC VAAPGGLLGS FNSDLVTLPL ISSLQSSE                          600
```

Nucleotide sequence of human IL-10Rα:human IgG1 fusion protein from initiation codon (ATG) through human IL-10Rα extracellular domain to end of human Fc sequence (underlined): SEQ ID NO:3

```
                              ATGGTGCCGT GCCTCGTAGT GCTGCTGGCG GCGCTCCTCA GCCTCCGTCT TGGCTCAGAC     60

GCTCATGGGA CAGAGCTGCC CAGCCCTCCG TCTGTGTGGT TTGAAGCAGA ATTTTTCCAC    120

CACATCCTCC ACTGGACACC CATCCCAAAT CAGTCTGAAA GTACCTGCTA TGAAGTGGCG    180

CTCCTGAGGT ATGGAATAGA GTCCTGGAAC TCCATCTCCA ACTGTAGCCA GACCCTGTCC    240

TATGACCTTA CCGCAGTGAC CTTGGACCTG TACCACAGCA ATGGCTACCG GGCCAGAGTG    300

CGGGCTGTGG ACGGCAGCCG GCACTCCAAC TGGACCGTCA CCAACACCCG CTTCTCTGTG    360

GATGAAGTGA CTCTGACAGT TGGCAGTGTG AACCTAGAGA TCCACAATGG CTTCATCCTC    420

GGGAAGATTC AGCTACCCAG GCCCAAGATG GCCCCCGCGA ATGACACATA TGAAAGCATC    480

TTCAGTCACT TCCGAGAGTA TGAGATTGCC ATTCGCAAGG TGCCGGGAAA CTTCACGTTC    540

ACACACAAGA AAGTAAAACA TGAAAACTTC AGCCTCCTAA CCTCTGGAGA AGTGGGAGAG    600

TTCTGTGTCC AGGTGAAACC ATCTGTCGCT TCCCGAAGTA ACAAGGGGAT GTGGTCTAAA    660

GAGGAGTGCA TCTCCCTCAC CAGGCAGTAT TTCACCGTGA CCAACAGATC TTGTGACAAA    720

ACTCACACAT GCCCACCGTG CCCAGCACCT GAACTCCTGG GGGACCGTC AGTCTTCCTC    780

TTCCCCCCAA AACCCAAGGA CACCCTCATG ATCTCCCGGA CCCCTGAGGT CACATGCGTG    840

GTGGTGGACG TGAGCCACGA AGACCCTGAG GTCAAGTTCA ACTGGTACGT GGACGGCGTG    900

GAGGTGCATA ATGCCAAGAC AAAGCCGCGG GAGGAGCAGT ACAACAGCAC GTACCGTGTG    960

GTCAGCGTCC TCACCGTCCT GCACCAGGAC TGGCTGAATG GCAAGGAGTA CAAGTGCAAG   1020
```

```
GTCTCCAACA AAGCCCTCCC AGCCCCCATC GAGAAAACCA TCTCCAAAGC CAAAGGGCAG    1080

CCCCGAGAAC CACAGGTGTA CACCCTGCCC CCATCCCGGG ATGAGCTGAC CAAGAACCAG    1140

GTCAGCCTGA CCTGCCTGGT CAAAGGCTTC TATCCCAGCG ACATCGCCGT GGAGTGGGAG    1200

AGCAATGGGC AGCCGGAGAA CAACTACAAG ACCACGCCTC CCGTGCTGGA CTCCGACGGC    1260

TCCTTCTTCC TCTACAGCAA GCTCACCGTG GACAAGAGCA GGTGGCAGCA GGGGAACGTC    1320

TTCTCATGCT CCGTGATGCA TGAGGCTCTG CACAACCACT ACACGCAGAA GAGCCTCTCC    1380

CTGTCTCCGG GTAAATGA                                                   1440
```

Amino acid sequence of human IL-10Rα-extracellular domain fused to the Fc portion of human IgG1 (underlined): SEQ ID NO:4

```
MVPCLVVLLA ALLSLRLGSD AHGTELPSPP SVWFEAEFFH HILHWTPIPN QSESTCYEVA     60

LLRYGIESWN SISNCSQTLS YDLTAVTLDL YHSNGYRARV RAVDGSRHSN WTVTNTRFSV    120

DEVTLTVGSV NLEIHNGFIL GKIQLPRPKM APANDTYESI FSHFREYEIA IRKVPGNFTF    180

THKKVKHENF SLLTSGEVGE FCVQVKPSVA SRSNKGMWSK EECISLTRQY FTVTNRSCDK    240

THTCPPCPAP ELLGGPSVFL FPPKPKDTLM ISRTPEVTCV VVDVSHEDPE VKFNWYVDGV    300

EVHNAKTKPR EEQYNSTYRV VSVLTVLHQD WLNGKEYKCK VSNKALPAPI EKTISKAKGQ    360

PREPQVYTLP PSRDELTKNQ VSLTCLVKGF YPSDIAVEWE SNGQPENNYK TTPPVLDSDG    420

SFFLYSKLTV DKSRWQQGNV FSCSVMHEAL HNHYTQKSLS LSPGK                    480
```

Pan troglodyte (chimpanzee) IL-10Rα cloning: The predicted amino acid sequence of the extracellular region of Pan troglodyte IL-10Rα contains two amino acid differences from the human amino acid sequence of IL-10Rα: arginine at amino acid position 92 instead of histidine, and valine at amino acid position 224 instead of isoleucine (Accession number NC_006478.2). The amino acid change at position 224 (V224I) is a recognized single nucleotide polymorphism (SNP) in human IL-10Rα sequence. The DNA sequence of human IL-10Rα was mutated within the codons for amino acid His92 [nucleotide 275 (adenine) was changed to guanine (A275G)], and amino acid Val224 [nucleotide 670 (adenine) was changed to guanine (A670G)] using polymerase chain reaction [primers hIL-10R Forward, IL-10Ra NotI R1857, IL-10R-a275g-F, IL-10R-a275g-R, IL-10R-a670g-F, and IL-10R-a670g-R (Table 1)]. The amplified product was cloned into vector pCR-BluntII-Topo (Invitrogen Corp.) using a Zero Blunt TOPO PCR Cloning Kit (Invitrogen Corp.). Clones were then sequenced and verified to contain the mutations designed. The modified sequence encoding the modified full length human IL-10Rα (referred to as cIL-10Rα-FL) was subcloned into mammalian expression vector pcDNA3.1(+) previously digested with EcoRI and NotI.

A construct coding for a fusion protein consisting of the extracellular region of Pan troglodyte IL-10Rα fused to the Fc portion of human IgG1 was constructed as follows. The DNA sequence encoding the extracellular domain of the Pan troglodyte-modified human IL-10Rα (cIL-10Ra-EX) from amino acid Met1 through Asp235 was amplified by polymerase chain reaction using cIL-10Rα-FL as template. The restriction site for BamHI was integrated into the 3' primer and placed directly after the codon for Asp235. Polymerase chain reaction was performed [primers hIL-10Ra Forward, hIL-10Ra Reverse (Table 1)]. The amplified product was digested with EcoRI and BamHI. The Fc portion of human IgG1 was excised from the human IL-10Rα:hFc expression vector construct with restriction enzymes (BglII at the 5' end, and NotI at the 3' end). The cIL-10Rα-EX and human IgG1 Fc were subcloned into the mammalian expression vector pcDNA3.1(+) previously digested with EcoRI and NotI.

Nucleotide sequence of Pan troglodyte IL-10Rα:human IgG1 fusion protein from initiation codon (ATG) through Pan troglodyte IL-10Rα extracellular domain to end of human Fc sequence (underlined): SEQ ID NO:5

```
ATGGTGCCGT GCCTCGTAGT GCTGCTGGCG GCGCTCCTCA GCCTCCGTCT TGGCTCAGAC   60

GCTCATGGGA CAGAGCTGCC CAGCCCTCCG TCTGTGTGGT TTGAAGCAGA ATTTTTCCAC  120

CACATCCTCC ACTGGACACC CATCCCAAAT CAGTCTGAAA GTACCTGCTA TGAAGTGGCA  180

CTCCTGAGGT ATGGAATAGA GTCCTGGAAC TCCATCTCCA ACTGTAGCCA GACCCTGTCC  240

TATGACCTTA CCGCAGTGAC CTTGGACCTG TACCGCAGCA ATGGCTACCG GGCCAGAGTG  300
```

```
CGGGCTGTGG ACGGCAGCCG GCACTCCAAC TGGACCGTCA CCAACACCCG CTTCTCTGTG    360

GATGAAGTGA CTCTGACAGT TGGCAGTGTG AACCTAGAGA TCCACAATGG CTTCATCCTC    420

GGGAAGATTC AGCTACCCAG GCCCAAGATG GCCCCCGCAA ATGACACATA TGAAAGCATC    480

TTCAGTCACT TCCGAGAGTA TGAGATTGCC ATTCGCAAGG TGCCGGGAAA CTTCACGTTC    540

ACACACAAGA AAGTAAAACA TGAAAACTTC AGCCTCCTAA CCTCTGGAGA AGTGGGAGAG    600

TTCTGTGTCC AGGTGAAACC ATCTGTCGCT TCCCGAAGTA ACAAGGGGAT GTGGTCTAAA    660

GAGGAGTGCG TCTCCCTCAC CAGGCAGTAT TTCACCGTGA CCAACAGATC TTGTGACAAA    720

ACTCACACAT GCCCACCGTG CCCAGCACCT GAACTCCTGG GGGGACCGTC AGTCTTCCTC    780

TTCCCCCCAA AACCCAAGGA CACCCTCATG ATCTCCCGGA CCCCTGAGGT CACATGCGTG    840

GTGGTGGACG TGAGCCACGA AGACCCTGAG GTCAAGTTCA ACTGGTACGT GGACGGCGTG    900

GAGGTGCATA ATGCCAAGAC AAAGCCGCGG GAGGAGCAGT ACAACAGCAC GTACCGTGTG    960

GTCAGCGTCC TCACCGTCCT GCACCAGGAC TGGCTGAATG GCAAGGAGTA CAAGTGCAAG   1020

GTCTCCAACA AAGCCCTCCC AGCCCCCATC GAGAAAACCA TCTCCAAAGC CAAAGGGCAG   1080

CCCCGAGAAC CACAGGTGTA CACCCTGCCC CCATCCCGGG AGGAGATGAC CAAGAACCAG   1140

GTCAGCCTGA CCTGCCTGGT CAAAGGCTTC TATCCCAGCG ACATCGCCGT GGAGTGGGAG   1200

AGCAATGGGC AGCCGGAGAA CAACTACAAG ACCACGCCTC CCGTGCTGGA CTCCGACGGC   1260

TCCTTCTTCC TCTATAGCAA GCTCACCGTG GACAAGAGCA GGTGGCAGCA GGGGAACGTC   1320

TTCTCATGCT CCGTGATGCA TGAGGCTCTG CACAACCACT ACACGCAGAA GAGCCTCTCC   1380

CTGTCTCCGG GTAAATGA                                                 1440
```

Amino acid sequence of Pan troglodyte IL-10Rα-extracellular domain fused to the Fc portion of human IgG1 (underlined), the amino acid corresponding to the human SNP is bold: SEQ ID NO: 6

```
MVPCLVVLLA ALLSLRLGSD AHGTELPSPP SVWFEAEFFH HILHWTPIPN QSESTCYEVA    60

LLRYGIESWN SISNCSQTLS YDLTAVTLDL YRSNGYRARV RAVDGSRHSN WTVTNTRFSV   120

DEVTLTVGSV NLEIHNGFIL GKIQLPRPKM APANDTYESI FSHFREYEIA IRKVPGNFTF   180

THKKVKHENF SLLTSGEVGE FCVQVKPSVA SRSNKGMWSK EECVSLTRQY FTVTNRSCDK   240

THTCPPCPAP ELLGGPSVFL FPPKPKDTLM ISRTPEVTCV VVDVSHEDPE VKFNWYVDGV   300

EVHNAKTKPR EEQYNSTYRV VSVLTVLHQD WLNGKEYKCK VSNKALPAPI EKTISKAKGQ   360

PREPQVYTLP PSREEMTKNQ VSLTCLVKGF YPSDIAVEWE SNGQPENNYK TTPPVLDSDG   420

SFFLYSKLTV DKSRWQQGNV FSCSVMHEAL HNHYTQKSLS LSPGK                   480
```

Cynomolgus macaque IL-10Rα cloning: Full length cynomolgus macaque IL-10Rα was cloned from purified cynomolgus T cells activated for 41 hours with 1 ng/ml phorbol myristic acid (PMA) (Sigma, St. Louis, Mo.) and 500 ng/ml ionomycin (Calbiochem, San Diego, Calif.). The T cells were purified from peripheral blood mononuclear cells using a Pan T cell negative isolation kit from Miltenyi Biotec (Auburn, Calif.) and following the manufacturer's instructions. RNA was isolated from $2 \times 10^6$ cells using an RNAeasy kit (QIAGEN, Frankfurt, Germany) and first strand cDNA was made by reverse transcription using a SuperScriptII kit (Invitrogen Corp.). The predicted sequence for rhesus IL-10Rα (Accession number XM_001092376) was initially used to design primers for amplification of the cynomolgus IL-10Rα, however, amplification with this primer set was unsuccessful. Analysis of the predicted sequence suggested a miscalculation in the splice site that disrupted the forward primer binding sequence. Therefore a forward primer designed from the Pan troglodytes sequence and a rhesus IL-10α reverse primer [chIL-10RaF1 and rhIL-10Ra_R2098 (Table 1)] were used. The amplified product was put into pCR®-Blunt II-TOPO® using a Zero Blunt® TOPO® PCR Cloning Kit and was sequenced. The full-length cyIL-10Rα was then amplified using polymerase chain reaction [primers hIL-10Ra Forward, M13R (Table 1)] and subcloned into pcDNA 3.1 (+) previously digested with EcoRI. The construct was verified by restriction digest and sequencing.

Nucleotide sequence of cynomolgus IL-10Rα full-length protein from initiation codon (ATG) through cynomolgus IL-10Rα stop codon sequence (underlined): SEQ ID NO:7

```
ATGCTGCCGT GCCTCGTAGT GCTGCTGGCG GCGTTCCTCA GTCGCCGTCT TGGCTCAGAC    60
GCTCATGGGA CAGAGCTGCC CAGCCCGCCA TCTGTGTGGT TTGAAGCAGA ATTTTTCCAC   120
CACATCCTCC ACTGGACACC CATCCCAAAT CAGTCTGAAA GTACCTGCTA TGAAGTGGCA   180
CTCCTGAGGT ATGGAACAGG GCGCTGGAAC TCCATCTCCA ACTGTAGCCA GGCCCTGTCC   240
TATGACCTTA CCGCGGTGAC CTTGGACCTG TACCGCAGCA ATGGCTACCG GGCCAGAGTG   300
CGTGCTGTGG ACGGCAGCCG GCACTCCAAC TGGACCGTCA CCAACACCCG CTTCTCTTTG   360
GATGAAGTGA CTCTGACAGT TGGCAGTGTG AAGCTAGAGA TCCACAATGG CTTCATCCTT   420
GGGAAGATTC AGCCCCCCAG GCCCAAGATG GCTCCTGCAA ATGACACATA TGAAAGCATC   480
TTCAGTCACT TCCGAGAGTA TGAGATTGCC ATTCGCAAGG TGCCGGGAAA CTTTACGTTC   540
ACACACAAGA AAGTAAAACA TGAAAACTTC AGCCTCCTAA CCTCTGGAGA AGTGGGAGAG   600
TTCTGTGTCC AGGTGAAACC ATCTGTCACT TCCCGAACCA ACAAGGGGAT GTGGTCTAAA   660
GAGGAGTGCG TCTCCCTCAC CAGGCAGTAT TTCACCGTGA CCAACGTCAT CATCTTCTTT   720
GCCTTTGTCC TGCTGCTCTC CGGAGCCCTG GCCTACTGCC TGGCCCTCCA GCTGTATGTG   780
CGGCGCCGAA AGAAGCTGCC CAGGGTCCTG CTCTTCAAGA AGCCCAACGC CTTCATCTTC   840
ATCAGCCAGC GTCCCTCCCC AGAGACCCAA GACACCATCC ACCCGCTTGA TGAGGAGGCC   900
TTCCTGAAGG TGTCACCAGA GCTGAGGAAC TCGGACCTGC ATGGCAGCAC GGACAGTGGC   960
TTTGGCAGTA CCAAACCATC CCTGCAGACC GAAGAGCCCC AGTTCCTCCT CCCTGACCCT  1020
CACCCCCAGG CTGACAGAAC GCTGGGAAAC GGAGAGCCCC CTGAGCTGGG CGACAGCTGC  1080
AGTAGTGGCA GCAGCAATAG CACGGACAGC GGGATCTGCC TGCAGGAGCC AGCCTGAGC   1140
CCCAGCACTG GCCCACCTG GGAGCAGCAG GTGGGGAGCG ACAGCAGGGG CCAGGATGAC   1200
AGTGGCATTG GCCTAGTTCA AAACTCTGAG GGCCAGGCTG GGGACACACA GGGTGGCTCA  1260
GCCTTGGGCC ACGACAGTCC CCCAGAGCCT GAGGTGCCTG CGGAACAAGA CCCAACTGCT  1320
GTGGTATTCC GGGGCTACCT GAGGCAGACC AGATGCGCTG AGGAGAAGGC AACCAAGACA  1380
GGCTGCCTGG AGGAAGAATT GCCCCTGACA GGTGGCCTTG GCCCAAATT CAGGGGATGC   1440
CTGGATGACG AAGCAGGCTT GCATCCATCA GCCCTGGCCA AGGGCTATTT GAAACAGGAT  1500
CCCCTAGAAA TGACTCTGGC TTCCTCGGGG GCCCCAGCTG AACAGTGGAA CCAGCCCACT  1560
GAGGAATGGT CACTCCTGGC CTTGAGCAGC TGCAGTGACC TGGAACATC TGACTGGAGC   1620
TTTGCCCATG ACCTTGCCCC TCTAGGCTGT GTGGCAGCCC AGATGGTCT CCTGGGCAGC   1680
TTTAACTCAG ACCTGGTCAC CCTGCCCCTC ATCTCTAGCC TGCACTCGAG TGACTCGAGC  1740
TGA                                                                1800
```

Amino acid sequence of cynomolgus macaque IL-10Rα
full-length protein from the start Met through the terminal
amino acid: SEQ ID NO: 8

```
MLPCLVVLLA AFLSRRLGSD AHGTELPSPP SVWFEAEFFH HILHWTPIPN QSESTCYEVA    60
LLRYGTGRWN SISNCSQALS YDLTAVTLDL YRSNGYRARV RAVDGSRHSN WTVTNTRFSL  120
DEVTLTVGSV KLEIHNGFIL GKIQPPRPKM APANDTYESI FSHFREYEIA IRKVPGNFTF  180
THKKVKHENF SLLTSGEVGE FCVQVKPSVT SRTNKGMWSK EECVSLTRQY FTVTNVIIFF  240
AFVLLLSGAL AYCLALQLYV RRRKKLPRVL LFKKPNAFIF ISQRPSPETQ DTIHPLDEEA  300
FLKVSPELRN SDLHGSTDSG FGSTKPSLQT EEPQFLLPDP HPQADRTLGN GEPPELGDSC  360
SSGSSNSTDS GICLQEPSLS PSTGPTWEQQ VGSDSRGQDD SGIGLVQNSE GQAGDTQGGS  420
```

-continued

```
ALGHDSPPEP EVPAEQDPTA VVFRGYLRQT RCAEEKATKT GCLEEELPLT GGLGPKFRGC    480

LDDEAGLHPS ALAKGYLKQD PLEMTLASSG APAEQWNQPT EEWSLLALSS CSDLGTSDWS    540

FAHDLAPLGC VAAPDGLLGS FNSDLVTLPL ISSLHSSDSS                          600
```

A construct expressing the cynomolgus macaque IL-10Rα extracellular region fused to the Fc portion of human IgG1 (cyIL-10Rα) was fabricated using the same method described for making the hIL-10Rα:hFC fusion construct.

Nucleotide sequence of cynomolgus macaque IL-10Rα: human IgG1 fusion protein from initiation codon (ATG) through cynomolgus macaque IL-10Rα extracellular domain to end of human Fc sequence (underlined): SEQ ID NO: 9

```
ATGGTGCCGT GCCTCGTAGT GCTGCTGGCG GCGTTCCTCA GTCGCCGTCT TGGCTCAGAC    60

GCTCATGGGA CAGAGCTGCC CAGCCCGCCA TCTGTGTGGT TTGAAGCAGA ATTTTTCCAC   120

CACATCCTCC ACTGGACACC CATCCCAAAT CAGTCTGAAA GTACCTGCTA TGAAGTGGCA   180

CTCCTGAGGT ATGGAACAGG GCGCTGGAAC TCCATCTCCA ACTGTAGCCA GGCCCTGTCC   240

TATGACCTTA CCGCGGTGAC CTTGGACCTG TACCGCAGCA ATGGCTACCG GGCCAGAGTG   300

CGTGCTGTGG ACGGCAGCCG GCACTCCAAC TGGACCGTCA CCAACACCCG CTTCTCTTTG   360

GATGAAGTGA CTCTGACAGT TGGCAGTGTG AAGCTAGAGA TCCACAATGG CTTCATCCTT   420

GGGAAGATTC AGCCCCCCAG GCCCAAGATG GCTCCTGCAA ATGACACATA TGAAAGCATC   480

TTCAGTCACT TCCGAGAGTA TGAGATTGCC ATTCGCAAGG TGCCGGGAAA CTTTACGTTC   540

ACACACAAGA AAGTAAAACA TGAAAACTTC AGCCTCCTAA CCTCTGGAGA AGTGGGAGAG   600

TTCTGTGTCC AGGTGAAACC ATCTGTCACT TCCCGAACCA ACAAGGGGAT GTGGTCTAAA   660

GAGGAGTGCG TCTCCCTCAC CAGGCAGTAT TTCACCGTGA CCAACAGATC TTGTGACAAA   720

ACTCACACAT GCCCACCGTG CCCAGCACCT GAACTCCTGG GGGGACCGTC AGTCTTCCTC   780

TTCCCCCCAA AACCCAAGGA CACCCTCATG ATCTCCCGGA CCCCTGAGGT CACATGCGTG   840

GTGGTGGACG TGAGCCACGA AGACCCTGAG GTCAAGTTCA ACTGGTACGT GGACGGCGTG   900

GAGGTGCATA ATGCCAAGAC AAAGCCGCGG GAGGAGCAGT ACAACAGCAC GTACCGTGTG   960

GTCAGCGTCC TCACCGTCCT GCACCAGGAC TGGCTGAATG GCAAGGAGTA CAAGTGCAAG  1020

GTCTCCAACA AAGCCCTCCC AGCCCCCATC GAGAAAACCA TCTCCAAAGC CAAAGGGCAG  1080

CCCCGAGAAC CACAGGTGTA CACCCTGCCC CCATCCCGGG AGGAGATGAC CAAGAACCAG  1140

GTCAGCCTGA CCTGCCTGGT CAAAGGCTTC TATCCCAGCG ACATCGCCGT GGAGTGGGAG  1200

AGCAATGGGC AGCCGGAGAA CAACTACAAG ACCACGCCTC CCGTGCTGGA CTCCGACGGC  1260

TCCTTCTTCC TCTATAGCAA GCTCACCGTG GACAAGAGCA GGTGGCAGCA GGGGAACGTC  1320

TTCTCATGCT CCGTGATGCA TGAGGCTCTG CACAACCACT ACACGCAGAA GAGCCTCTCC  1380

CTGTCTCCGG GTAAATGA                                                1440
```

Amino acid sequence of cynomolgus macaque IL-10Rα-extracellular domain fused to the Fc portion of human IgG1 (underlined): SEQ ID NO:10

```
MVPCLVVLLA AFLSRRLGSD AHGTELPSPP SVWFEAEFFH HILHWTPIPN QSESTCYEVA    60

LLRYGTGRWN SISNCSQALS YDLTAVTLDL YRSNGYRARV RAVDGSRHSN WTVTNTRFSL   120

DEVTLTVGSV KLEIHNGFIL GKIQPPRPKM APANDTYESI FSHFREYEIA IRKVPGNFTF   180

THKKVKHENF SLLTSGEVGE FCVQVKPSVT SRTNKGMWSK EECVSLTRQY FTVTNRSCDK   240

THTCPPCPAP ELLGGPSVFL FPPKPKDTLM ISRTPEVTCV VVDVSHEDPE VKFNWYVDGV   300

EVHNAKTKPR EEQYNSTYRV VSVLTVLHQD WLNGKEYKCK VSNKALPAPI EKTISKAKGQ   360
```

```
PREPQVYTLP PSREEMTKNQ VSLTCLVKGF YPSDIAVEWE SNGQPENNYK TTPPVLDSDG    420

SFFLYSKLTV DKSRWQQGNV FSCSVMHEAL HNHYTQKSLS LSPGK                   480
```

Human IL10Ra SNP Variant Cloning: Five mammalian expression vectors were constructed, each expressing one of five known single nucleotide polymorphism (SNP) variants of the extracellular domain of hIL-10Rα (705 nucleotides coding for amino acids 1-235 when including signal peptide) fused with human IgG1 Fc. The SNP variants are designated L61V, V113I, S159G, R212E, and V233M where the first letter denotes the consensus amino acid, the number denotes the amino acid number when counting from the start methionine of hIL-10Rα, and the second letter denotes the amino acid of the SNP after mutation. The constructs were designed such that the vector, and protein produced thereof, should be identical to the hIL-10Rα:hFc vector and protein except at the site of SNP mutation. In general, mutation of L61V, V113I, S159G, and R212E were performed in a two-step PCR reaction followed by cloning of the complete expression construct, which was performed using the same method as the hIL-10Rα:hFC fusion construct.

Specifically, L61V will be used as an example for V113I, S159G and R212E, which were generated using the same technique with their own unique primers for mutation (Table 1). cDNA coding for hIL-10Rα was used as template for two separate PCR reactions: Rxn1 (primers hIL10R Forward, IL10Ra-R-L61V) amplified the N-term cDNA from the start ATG to 13 nucleotides 3' of the SNP site; Rxn2 (primers IL10Ra-F-L61V, hIL10R Reverse) amplified from 13 nucleotides 5' of the SNP site through Asp235 of hIL-10Rα (nucleotide 705). Primer "hIL10R Forward" adds a restriction enzyme recognition site for EcoRI 5' of the sense strand immediately preceding the start methionine, and primer "hIL10R Reverse" adds the restriction enzyme recognition site for BglII at the 3' end of the sense strand immediately following Asp235. Primers "IL10Ra-F-L61V" and "IL10Ra-R-L61V" are 100% complementary for each other and contain the nucleotide mutation responsible for conversion of the consensus amino acid to the SNP variant near the center of the primers. The PCR products were purified by gel electrophoresis, and added at roughly equimolar ratios to a standard PCR mix containing no primers. Three cycles of PCR thermal cycling were performed such that the complementary regions of each PCR product, Rxn 1 and Rxn2, "primed" the reverse strand of the other reaction product allowing for elongation of the sense and antisense strands to the full length of the hIL-10Rα extracellular domain. This reaction was used as template in a second PCR reaction with primers "hIL10R Forward" and "hIL10R Reverse." The amplified product was digested with EcoRI and BglII restriction enzymes, which were included in the primers, and the human IgG1 Fc sequence was excised from the pV11392.fc vector using BglII and NotI restriction enzymes. The shIL-10Rα (EcoRI-BglII) and hFc (BglII-NotI) fragments were subcloned into the pcDNA3.1(+) expression vector previously digested with EcoRI and NotI to generate a hIL-10Rα-L61V-hFc expression vector.

Construction of the SNP variants V1131, S159G and R212E all used the common primers "hIL10R Forward" and "hIL10R Reverse." Unique primers (Table 1) containing the SNP nucleotide mutation are: V113I (IL10Ra-F-V 113I, IL10Ra-R-V113I), S159G (IL10Ra-F-S159G, IL10Ra-R-S159G) and R212E (IL10Ra-F-R212E, IL10Ra-R-R212E).

Construction of hIL-10Rα variant V233M was done with a single PCR step (primers "hIL10R Forward", "hIL-10_V233M_R"), followed by a restriction cloning method identical to that described for construction of the hIL-10Rα:hFC vector. Primer "hIL10_V233M_R" contains the SNP mutation and the BglII restriction site for fusion to hFc. Each construct was verified by DNA sequencing.

Nucleotide sequence of SNP variant L61V (codon bolded) of human IL-10Rα:human IgG1 fusion protein from initiation codon (ATG) through human IL-10Rα extracellular domain to end of human Fc sequence (underlined): SEQ ID NO:62

```
ATGGTGCCGT GCCTCGTAGT GCTGCTGGCG GCGCTCCTCA GCCTCCGTCT TGGCTCAGAC   60

GCTCATGGGA CAGAGCTGCC CAGCCCTCCG TCTGTGTGGT TTGAAGCAGA ATTTTTCCAC  120

CACATCCTCC ACTGGACACC CATCCCAAAT CAGTCTGAAA GTACCTGCTA TGAAGTGGCG  180

GTCCTGAGGT ATGGAATAGA GTCCTGGAAC TCCATCTCCA ACTGTAGCCA GACCCTGTCC  240

TATGACCTTA CCGCAGTGAC CTTGGACCTG TACCACAGCA ATGGCTACCG GGCCAGAGTG  300

CGGGCTGTGG ACGGCAGCCG GCACTCCAAC TGGACCGTCA CCAACACCCG CTTCTCTGTG  360

GATGAAGTGA CTCTGACAGT TGGCAGTGTG AACCTAGAGA TCCACAATGG CTTCATCCTC  420

GGGAAGATTC AGCTACCCAG GCCCAAGATG GCCCCCGCGA ATGACACATA TGAAAGCATC  480

TTCAGTCACT TCCGAGAGTA TGAGATTGCC ATTCGCAAGG TGCCGGGAAA CTTCACGTTC  540

ACACACAAGA AAGTAAAACA TGAAAACTTC AGCCTCCTAA CCTCTGGAGA AGTGGGAGAG  600

TTCTGTGTCC AGGTGAAACC ATCTGTCGCT TCCCGAAGTA ACAAGGGGAT GTGGTCTAAA  660

GAGGAGTGCA TCTCCCTCAC CAGGCAGTAT TTCACCGTGA CCAACAGATC TTGTGACAAA  720

ACTCACACAT GCCCACCGTG CCCAGCACCT GAACTCCTGG GGGGACCGTC AGTCTTCCTC  780

TTCCCCCCAA AACCCAAGGA CACCCTCATG ATCTCCCGGA CCCCTGAGGT CACATGCGTG  840

GTGGTGGACG TGAGCCACGA AGACCCTGAG GTCAAGTTCA ACTGGTACGT GGACGGCGTG  900
```

-continued

```
GAGGTGCATA ATGCCAAGAC AAAGCCGCGG GAGGAGCAGT ACAACAGCAC GTACCGTGTG    960

GTCAGCGTCC TCACCGTCCT GCACCAGGAC TGGCTGAATG GCAAGGAGTA CAAGTGCAAG   1020

GTCTCCAACA AAGCCCTCCC AGCCCCCATC GAGAAAACCA TCTCCAAAGC CAAAGGGCAG   1080

CCCCGAGAAC CACAGGTGTA CACCCTGCCC CCATCCCGGG ATGAGCTGAC CAAGAACCAG   1140

GTCAGCCTGA CCTGCCTGGT CAAAGGCTTC TATCCCAGCG ACATCGCCGT GGAGTGGGAG   1200

AGCAATGGGC AGCCGGAGAA CAACTACAAG ACCACGCCTC CCGTGCTGGA CTCCGACGGC   1260

TCCTTCTTCC TCTACAGCAA GCTCACCGTG GACAAGAGCA GGTGGCAGCA GGGGAACGTC   1320

TTCTCATGCT CCGTGATGCA TGAGGCTCTG CACAACCACT ACACGCAGAA GAGCCTCTCC   1380

CTGTCTCCGG GTAAATGA                                                 1440
```

Amino acid sequence of SNP variant L61V (amino acid bolded) of human IL-10Rα-extracellular domain fused to the Fc portion of human IgG1 (underlined): SEQ ID NO:63

```
MVPCLVVLLA ALLSLRLGSD AHGTELPSPP SVWFEAEFFH HILHWTPIPN QSESTCYEVA    60

VLRYGIESWN SISNCSQTLS YDLTAVTLDL YHSNGYRARV RAVDGSRHSN WTVTNTRFSV   120

DEVTLTVGSV NLEIHNGFIL GKIQLPRPKM APANDTYESI FSHFREYEIA IRKVPGNFTF   180

THKKVKHENF SLLTSGEVGE FCVQVKPSVA SRSNKGMWSK EECISLTRQY FTVTNRSCDK   240

THTCPPCPAP ELLGGPSVFL FPPKPKDTLM ISRTPEVTCV VVDVSHEDPE VKFNWYVDGV   300

EVHNAKTKPR EEQYNSTYRV VSVLTVLHQD WLNGKEYKCK VSNKALPAPI EKTISKAKGQ   360

PREPQVYTLP PSRDELTKNQ VSLTCLVKGF YPSDIAVEWE SNGQPENNYK TTPPVLDSDG   420

SFFLYSKLTV DKSRWQQGNV FSCSVMHEAL HNHYTQKSLS LSPGK                   480
```

Nucleotide sequence of SNP variant V113I (codon bolded) of human IL-10Rα:human IgG1 fusion protein from initiation codon (ATG) through human IL-10Rα extracellular domain to end of human Fc sequence (underlined): SEQ ID NO:64

```
ATGGTGCCGT GCCTCGTAGT GCTGCTGGCG GCGCTCCTCA GCCTCCGTCT TGGCTCAGAC    60

GCTCATGGGA CAGAGCTGCC CAGCCCTCCG TCTGTGTGGT TTGAAGCAGA ATTTTTCCAC   120

CACATCCTCC ACTGGACACC CATCCCAAAT CAGTCTGAAA GTACCTGCTA TGAAGTGGCG   180

CTCCTGAGGT ATGGAATAGA GTCCTGGAAC TCCATCTCCA ACTGTAGCCA GACCCTGTCC   240

TATGACCTTA CCGCAGTGAC CTTGGACCTG TACCACAGCA ATGGCTACCG GGCCAGAGTG   300

CGGGCTGTGG ACGGCAGCCG GCACTCCAAC TGGACCATCA CCAACACCCG CTTCTCTGTG   360

GATGAAGTGA CTCTGACAGT TGGCAGTGTG AACCTAGAGA TCCACAATGG CTTCATCCTC   420

GGGAAGATTC AGCTACCCAG GCCCAAGATG GCCCCCGCGA ATGACACATA TGAAAGCATC   480

TTCAGTCACT TCCGAGAGTA TGAGATTGCC ATTCGCAAGG TGCCGGGAAA CTTCACGTTC   540

ACACACAAGA AAGTAAAACA TGAAAACTTC AGCCTCCTAA CCTCTGGAGA AGTGGGAGAG   600

TTCTGTGTCC AGGTGAAACC ATCTGTCGCT TCCCGAAGTA ACAAGGGGAT GTGGTCTAAA   660

GAGGAGTGCA TCTCCCTCAC CAGGCAGTAT TTCACCGTGA CCAACAGATC TTGTGACAAA   720

ACTCACACAT GCCCACCGTG CCCAGCACCT GAACTCCTGG GGGGACCGTC AGTCTTCCTC   780

TTCCCCCCAA AACCCAAGGA CACCCTCATG ATCTCCCGGA CCCCTGAGGT CACATGCGTG   840

GTGGTGGACG TGAGCCACGA AGACCCTGAG GTCAAGTTCA ACTGGTACGT GGACGGCGTG   900
```

```
GAGGTGCATA ATGCCAAGAC AAAGCCGCGG GAGGAGCAGT ACAACAGCAC GTACCGTGTG    960

GTCAGCGTCC TCACCGTCCT GCACCAGGAC TGGCTGAATG GCAAGGAGTA CAAGTGCAAG   1020

GTCTCCAACA AAGCCCTCCC AGCCCCCATC GAGAAAACCA TCTCCAAAGC CAAAGGGCAG   1080

CCCCGAGAAC CACAGGTGTA CACCCTGCCC CCATCCCGGG ATGAGCTGAC CAAGAACCAG   1140

GTCAGCCTGA CCTGCCTGGT CAAAGGCTTC TATCCCAGCG ACATCGCCGT GGAGTGGGAG   1200

AGCAATGGGC AGCCGGAGAA CAACTACAAG ACCACGCCTC CCGTGCTGGA CTCCGACGGC   1260

TCCTTCTTCC TCTACAGCAA GCTCACCGTG GACAAGAGCA GGTGGCAGCA GGGGAACGTC   1320

TTCTCATGCT CCGTGATGCA TGAGGCTCTG CACAACCACT ACACGCAGAA GAGCCTCTCC   1380

CTGTCTCCGG GTAAATGA                                                 1440
```

Amino acid sequence of SNP variant V113I (amino acid bolded) of human IL-10Rα-extracellular domain fused to the Fc portion of human IgG1 (underlined): SEQ ID NO:65

```
MVPCLVVLLA ALLSLRLGSD AHGTELPSPP SVWFEAEFFH HILHWTPIPN QSESTCYEVA    60

LLRYGIESWN SISNCSQTLS YDLTAVTLDL YHSNGYRARV RAVDGSRHSN WTITNTRFSV   120

DEVTLTVGSV NLEIHNGFIL GKIQLPRPKM APANDTYESI FSHFREYEIA IRKVPGNFTF   180

THKKVKHENF SLLTSGEVGE FCVQVKPSVA SRSNKGMWSK EECISLTRQY FTVTNRSCDK   240

THTCPPCPAP ELLGGPSVFL FPPKPKDTLM ISRTPEVTCV VVDVSHEDPE VKFNWYVDGV   300

EVHNAKTKPR EEQYNSTYRV VSVLTVLHQD WLNGKEYKCK VSNKALPAPI EKTISKAKGQ   360

PREPQVYTLP PSRDELTKNQ VSLTCLVKGF YPSDIAVEWE SNGQPENNYK TTPPVLDSDG   420

SFFLYSKLTV DKSRWQQGNV FSCSVMHEAL HNHYTQKSLS LSPGK                   480
```

Nucleotide sequence of SNP variant S159G (codon bolded) of human IL-10Rα:human IgG1 fusion protein from initiation codon (ATG) through human IL-10Rα extracellular domain to end of human Fc sequence (underlined): SEQ ID NO:66

```
ATGGTGCCGT GCCTCGTAGT GCTGCTGGCG GCGCTCCTCA GCCTCCGTCT TGGCTCAGAC    60

GCTCATGGGA CAGAGCTGCC CAGCCCTCCG TCTGTGTGGT TTGAAGCAGA ATTTTTCCAC   120

CACATCCTCC ACTGGACACC CATCCCAAAT CAGTCTGAAA GTACCTGCTA TGAAGTGGCG   180

CTCCTGAGGT ATGGAATAGA GTCCTGGAAC TCCATCTCCA ACTGTAGCCA GACCCTGTCC   240

TATGACCTTA CCGCAGTGAC CTTGGACCTG TACCACAGCA ATGGCTACCG GGCCAGAGTG   300

CGGGCTGTGG ACGGCAGCCG GCACTCCAAC TGGACCGTCA CCAACACCCG CTTCTCTGTG   360

GATGAAGTGA CTCTGACAGT TGGCAGTGTG AACCTAGAGA TCCACAATGG CTTCATCCTC   420

GGGAAGATTC AGCTACCCAG GCCCAAGATG GCCCCCGCGA ATGACACATA TGAAGGCATC   480

TTCAGTCACT TCCGAGAGTA TGAGATTGCC ATTCGCAAGG TGCCGGGAAA CTTCACGTTC   540

ACACACAAGA AAGTAAAACA TGAAAACTTC AGCCTCCTAA CCTCTGGAGA AGTGGGAGAG   600

TTCTGTGTCC AGGTGAAACC ATCTGTCGCT TCCCGAAGTA ACAAGGGGAT GTGGTCTAAA   660

GAGGAGTGCA TCTCCCTCAC CAGGCAGTAT TTCACCGTGA CCAACAGATC TTGTGACAAA   720

ACTCACACAT GCCCACCGTG CCCAGCACCT GAACTCCTGG GGGGACCGTC AGTCTTCCTC   780

TTCCCCCCAA AACCCAAGGA CACCCTCATG ATCTCCCGGA CCCCTGAGGT CACATGCGTG   840

GTGGTGGACG TGAGCCACGA AGACCCTGAG GTCAAGTTCA ACTGGTACGT GGACGGCGTG   900

GAGGTGCATA ATGCCAAGAC AAAGCCGCGG GAGGAGCAGT ACAACAGCAC GTACCGTGTG   960
```

```
GTCAGCGTCC TCACCGTCCT GCACCAGGAC TGGCTGAATG GCAAGGAGTA CAAGTGCAAG    1020

GTCTCCAACA AAGCCCTCCC AGCCCCCATC GAGAAAACCA TCTCCAAAGC CAAAGGGCAG    1080

CCCCGAGAAC CACAGGTGTA CACCCTGCCC CCATCCCGGG ATGAGCTGAC CAAGAACCAG    1140

GTCAGCCTGA CCTGCCTGGT CAAAGGCTTC TATCCCAGCG ACATCGCCGT GGAGTGGGAG    1200

AGCAATGGGC AGCCGGAGAA CAACTACAAG ACCACGCCTC CCGTGCTGGA CTCCGACGGC    1260

TCCTTCTTCC TCTACAGCAA GCTCACCGTG GACAAGAGCA GGTGGCAGCA GGGGAACGTC    1320

TTCTCATGCT CCGTGATGCA TGAGGCTCTG CACAACCACT ACACGCAGAA GAGCCTCTCC    1380

CTGTCTCCGG GTAAATGA                                                   1440
```

Amino acid sequence of SNP variant S159G (amino acid bolded) of human IL-10Rα-extracellular domain fused to the Fc portion of human IgG1 (underlined): SEQ ID NO:67

```
MVPCLVVLLA ALLSLRLGSD AHGTELPSPP SVWFEAEFFH HILHWTPIPN QSESTCYEVA     60

LLRYGIESWN SISNCSQTLS YDLTAVTLDL YHSNGYRARV RAVDGSRHSN WTVTNTRFSV    120

DEVTLTVGSV NLEIHNGFIL GKIQLPRPKM APANDTYEGI FSHFREYEIA IRKVPGNFTF    180

THKKVKHENF SLLTSGEVGE FCVQVKPSVA SRSNKGMWSK EECISLTRQY FTVTNRSCDK    240

THTCPPCPAP ELLGGPSVFL FPPKPKDTLM ISRTPEVTCV VVDVSHEDPE VKFNWYVDGV    300

EVHNAKTKPR EEQYNSTYRV VSVLTVLHQD WLNGKEYKCK VSNKALPAPI EKTISKAKGQ    360

PREPQVYTLP PSRDELTKNQ VSLTCLVKGF YPSDIAVEWE SNGQPENNYK TTPPVLDSDG    420

SFFLYSKLTV DKSRWQQGNV FSCSVMHEAL HNHYTQKSLS LSPGK                    480
```

Nucleotide sequence of SNP variant R212E (codon bolded) of human IL-10Rα:human IgG1 fusion protein from initiation codon (ATG) through human IL-10Rα extracellular domain to end of human Fc sequence (underlined): SEQ ID NO:68

```
ATGGTGCCGT GCCTCGTAGT GCTGCTGGCG GCGCTCCTCA GCCTCCGTCT TGGCTCAGAC     60

GCTCATGGGA CAGAGCTGCC CAGCCCTCCG TCTGTGTGGT TTGAAGCAGA ATTTTTCCAC    120

CACATCCTCC ACTGGACACC CATCCCAAAT CAGTCTGAAA GTACCTGCTA TGAAGTGGCG    180

CTCCTGAGGT ATGGAATAGA GTCCTGGAAC TCCATCTCCA ACTGTAGCCA GACCCTGTCC    240

TATGACCTTA CCGCAGTGAC CTTGGACCTG TACCACAGCA ATGGCTACCG GGCCAGAGTG    300

CGGGCTGTGG ACGGCAGCCG GCACTCCAAC TGGACCGTCA CCAACACCCG CTTCTCTGTG    360

GATGAAGTGA CTCTGACAGT TGGCAGTGTG AACCTAGAGA TCCACAATGG CTTCATCCTC    420

GGGAAGATTC AGCTACCCAG GCCCAAGATG GCCCCCGCGA ATGACACATA TGAAAGCATC    480

TTCAGTCACT TCCGAGAGTA TGAGATTGCC ATTCGCAAGG TGCCGGGAAA CTTCACGTTC    540

ACACACAAGA AAGTAAAACA TGAAAACTTC AGCCTCCTAA CCTCTGGAGA AGTGGGAGAG    600

TTCTGTGTCC AGGTGAAACC ATCTGTCGCT TCCGAAAGTA CAAGGGGAT GTGGTCTAAA    660

GAGGAGTGCA TCTCCCTCAC CAGGCAGTAT TTCACCGTGA CCAACAGATC TTGTGACAAA    720

ACTCACACAT GCCCACCGTG CCCAGCACCT GAACTCCTGG GGGGACCGTC AGTCTTCCTC    780

TTCCCCCCAA AACCCAAGGA CACCCTCATG ATCTCCCGGA CCCCTGAGGT CACATGCGTG    840

GTGGTGGACG TGAGCCACGA AGACCCTGAG GTCAAGTTCA ACTGGTACGT GGACGGCGTG    900

GAGGTGCATA ATGCCAAGAC AAAGCCGCGG GAGGAGCAGT ACAACAGCAC GTACCGTGTG    960
```

```
GTCAGCGTCC TCACCGTCCT GCACCAGGAC TGGCTGAATG GCAAGGAGTA CAAGTGCAAG    1020

GTCTCCAACA AAGCCCTCCC AGCCCCCATC GAGAAAACCA TCTCCAAAGC CAAAGGGCAG    1080

CCCCGAGAAC CACAGGTGTA CACCCTGCCC CCATCCCGGG ATGAGCTGAC CAAGAACCAG    1140

GTCAGCCTGA CCTGCCTGGT CAAAGGCTTC TATCCCAGCG ACATCGCCGT GGAGTGGGAG    1200

AGCAATGGGC AGCCGGAGAA CAACTACAAG ACCACGCCTC CCGTGCTGGA CTCCGACGGC    1260

TCCTTCTTCC TCTACAGCAA GCTCACCGTG GACAAGAGCA GGTGGCAGCA GGGGAACGTC    1320

TTCTCATGCT CCGTGATGCA TGAGGCTCTG CACAACCACT ACACGCAGAA GAGCCTCTCC    1380

CTGTCTCCGG GTAAATGA                                                  1440
```

Amino acid sequence of SNP variant R212E (amino acid bolded) of human IL-10Rα-extracellular domain fused to the Fc portion of human IgG1 (underlined): SEQ ID NO:69

```
MVPCLVVLLA ALLSLRLGSD AHGTELPSPP SVWFEAEFFH HILHWTPIPN QSESTCYEVA     60

LLRYGIESWN SISNCSQTLS YDLTAVTLDL YHSNGYRARV RAVDGSRHSN WTVTNTRFSV    120

DEVTLTVGSV NLEIHNGFIL GKIQLPRPKM APANDTYESI FSHFREYEIA IRKVPGNFTF    180

THKKVKHENF SLLTSGEVGE FCVQVKPSVA SESNKGMWSK EECISLTRQY FTVTNRSCDK    240

THTCPPCPAP ELLGGPSVFL FPPKPKDTLM ISRTPEVTCV VVDVSHEDPE VKFNWYVDGV    300

EVHNAKTKPR EEQYNSTYRV VSVLTVLHQD WLNGKEYKCK VSNKALPAPI EKTISKAKGQ    360

PREPQVYTLP PSRDELTKNQ VSLTCLVKGF YPSDIAVEWE SNGQPENNYK TTPPVLDSDG    420

SFFLYSKLTV DKSRWQQGNV FSCSVMHEAL HNHYTQKSLS LSPGK                    480
```

Nucleotide sequence of SNP variant V233M (codon bolded) of human IL-10Rα:human IgG1 fusion protein from initiation codon (ATG) through human IL-10Rα extracellular domain to end of human Fc sequence (underlined): SEQ ID NO:70

```
ATGGTGCCGT GCCTCGTAGT GCTGCTGGCG GCGCTCCTCA GCCTCCGTCT TGGCTCAGAC     60

GCTCATGGGA CAGAGCTGCC CAGCCCTCCG TCTGTGTGGT TTGAAGCAGA ATTTTTCCAC    120

CACATCCTCC ACTGGACACC CATCCCAAAT CAGTCTGAAA GTACCTGCTA TGAAGTGGCG    180

CTCCTGAGGT ATGGAATAGA GTCCTGGAAC TCCATCTCCA ACTGTAGCCA GACCCTGTCC    240

TATGACCTTA CCGCAGTGAC CTTGGACCTG TACCACAGCA ATGGCTACCG GGCCAGAGTG    300

CGGGCTGTGG ACGGCAGCCG GCACTCCAAC TGGACCGTCA CCAACACCCG CTTCTCTGTG    360

GATGAAGTGA CTCTGACAGT TGGCAGTGTG AACCTAGAGA TCCACAATGG CTTCATCCTC    420

GGGAAGATTC AGCTACCCAG GCCCAAGATG GCCCCCGCGA ATGACACATA TGAAAGCATC    480

TTCAGTCACT TCCGAGAGTA TGAGATTGCC ATTCGCAAGG TGCCGGGAAA CTTCACGTTC    540

ACACACAAGA AAGTAAAACA TGAAAACTTC AGCCTCCTAA CCTCTGGAGA AGTGGGAGAG    600

TTCTGTGTCC AGGTGAAACC ATCTGTCGCT TCCCGAAGTA ACAAGGGGAT GTGGTCTAAA    660

GAGGAGTGCA TCTCCCTCAC CAGGCAGTAT TTCACCATGA CCAACAGATC TTGTGACAAA    720

ACTCACACAT GCCCACCGTG CCCAGCACCT GAACTCCTGG GGGGACCGTC AGTCTTCCTC    780

TTCCCCCCAA AACCCAAGGA CACCCTCATG ATCTCCCGGA CCCCTGAGGT CACATGCGTG    840

GTGGTGGACG TGAGCCACGA AGACCCTGAG GTCAAGTTCA ACTGGTACGT GGACGGCGTG    900

GAGGTGCATA ATGCCAAGAC AAAGCCGCGG GAGGAGCAGT ACAACAGCAC GTACCGTGTG    960

GTCAGCGTCC TCACCGTCCT GCACCAGGAC TGGCTGAATG GCAAGGAGTA CAAGTGCAAG   1020
```

-continued

```
GTCTCCAACA AAGCCCTCCC AGCCCCCATC GAGAAAACCA TCTCCAAAGC CAAAGGGCAG  1080

CCCCGAGAAC CACAGGTGTA CACCCTGCCC CCATCCCGGG ATGAGCTGAC CAAGAACCAG  1140

GTCAGCCTGA CCTGCCTGGT CAAAGGCTTC TATCCCAGCG ACATCGCCGT GGAGTGGGAG  1200

AGCAATGGGC AGCCGGAGAA CAACTACAAG ACCACGCCTC CCGTGCTGGA CTCCGACGGC  1260

TCCTTCTTCC TCTACAGCAA GCTCACCGTG GACAAGAGCA GGTGGCAGCA GGGGAACGTC  1320

TTCTCATGCT CCGTGATGCA TGAGGCTCTG CACAACCACT ACACGCAGAA GAGCCTCTCC  1380

CTGTCTCCGG GTAAATGA                                                1440
```

Amino acid sequence of SNP variant V233M (amino acid bolded) of human IL-10Rα-extracellular domain fused to the Fc portion of human IgG1 (underlined): SEQ ID NO:71

```
MVPCLVVLLA ALLSLRLGSD AHGTELPSPP SVWFEAEFFH HILHWTPIPN QSESTCYEVA   60

LLRYGIESWN SISNCSQTLS YDLTAVTLDL YHSNGYRARV RAVDGSRHSN WTVTNTRFSV  120

DEVTLTVGSV NLEIHNGFIL GKIQLPRPKM APANDTYESI FSHFREYEIA IRKVPGNFTF  180

THKKVKHENF SLLTSGEVGE FCVQVKPSVA SRSNKGMWSK EECISLTRQY FTMTNRSCDK  240

THTCPPCPAP ELLGGPSVFL FPPKPKDTLM ISRTPEVTCV VVDVSHEDPE VKFNWYVDGV  300

EVHNAKTKPR EEQYNSTYRV VSVLTVLHQD WLNGKEYKCK VSNKALPAPI EKTISKAKGQ  360

PREPQVYTLP PSRDELTKNQ VSLTCLVKGF YPSDIAVEWE SNGQPENNYK TTPPVLDSDG  420

SFFLYSKLTV DKSRWQQGNV FSCSVMHEAL HNHYTQKSLS LSPGK                  480
```

TABLE 1

DNA primers for cloning IL-10Rα

| SEQ ID NO | Name | Sequence 5' to 3' | Length |
|---|---|---|---|
| 11 | hIL-10Ra_F48_EcorI | GAGAGAGAGAGAATTCGCCCAGGATGCTGCCGTGC | 35-mer |
| 12 | IL-10Ra_NotI_1857 | AGAGAGAGAGCGGCCGCGGCAGAGGAGCAGGCATGGC | 37-mer |
| 13 | hIL-10R_Forward | AAACCGGAATTCCCACCATGGTGCCGTGCCTCGTAGTGCTG | 41-mer |
| 14 | hIL-10R_Reverse | AAAGGAAGATCTGTTGGTCACGGTGAAATACTGCCT | 36-mer |
| 15 | IL-10R-a275g-F | CCTTGGACCTGTACCGCAGCAATGGCTACCG | 31-mer |
| 16 | IL-10R-a275g-R | CGGTAGCCATTGCTGCGGTACAGGTCCAAGG | 31-mer |
| 17 | IL-10R-a670g-F | TCTAAAGAGGAGTGCGTCTCCCTCACCAGGC | 31-mer |
| 18 | IL-10R-a670g-R | GCCTGGTGAGGGAGACGCACTCCTCMAGA | 31-mer |
| 19 | chIL-10R-Bgl2-R | ACACAGATCTGTTGGTCACGGTGAAATACTGCCTGGTGAGGGAGATGCAC | 50-mer |
| 20 | chIL-10Ra_F1 | ATGCTGCCGTGCCTCGTAGTGCTGC | 25-mer |
| 21 | rhIL-10Ra_R2098 | ATGGTTCCCCTGAGCAAATAATCC | 24-mer |
| 22 | M13R | CAGGAAACAGCTATGAC | 17-mer |
| 72 | IL10Ra-F-L61V | CTATGAAGTGGCGGTCCTGAGGTATGG | 27-mer |
| 73 | IL10Ra-R-L61V | CCATACCTCAGGACCGCCACTTCATAG | 27-mer |
| 74 | IL10Ra-F-V113I | CTCCAACTGGACCATCACCAACACCC | 26-mer |
| 75 | IL10Ra-R-V113I | GGGTGTTGGTGATGGTCCAGTTGGAG | 26-mer |
| 76 | hIL10_S159G_F | CAAATGACACATATGAAGGCATCTTCAGTCACTTC | 35-mer |

TABLE 1 -continued

DNA primers for cloning IL-10Rα

| SEQ ID NO | Name | Sequence 5' to 3' | Length |
|---|---|---|---|
| 77 | hIL10_S159G_R | GAAGTGACTGAAGATGCCTTCATATGTGTCATTTG | 35-mer |
| 78 | IL10Ra-F-R212E | CCATCTGTCGCTTCCGAAAGTAACAAGGGGATG | 33-mer |
| 79 | IL10Ra-R-R212E | CATCCCCTTGTTACTTTCGGAAGCGACAGATGG | 33-mer |
| 80 | hIL10_V233M_R | GTCACAAGATCTGTTGGTCATGGTGAAATACTGCCTGG | 38-mer |

Protein Expression: Protein was expressed by transient expression in Freestyle 293F cells (Invitrogen Corp.) transfected using 293fectin (Invitrogen Corp.) following the manufacturer's instructions.

Generation of stable lines: The full-length human and chimpanzee IL-10Rα pcDNA3.1 expression vectors were individually transfected into EL-4 (ATCC TIB-39) cells using lipofectamine 2000 (Invitrogen, Corp.) according to the manufacturer's instructions. Stable transfectants were selected using geneticin (Invitrogen, Corp.). CHO-K1 (ATCC CCL-61) human IL-10Rα stable transfectants were generated using the Amaxa nucleofector system (Amaxa, Gaithersburg, Md.) according to the manufacturer's instructions. In all cases after two weeks under selection, the cells expressing a high level of IL-10Rα based on staining with an IL-10Rα antibody were sorted using a FACS Aria (Becton Dickinson Bioscience, Palo Alto, Calif.).

Mice: Human trans-chromosomic KM Mice™ [WO 02/43478; WO 02/092812; Ishida and Lonberg, IBC's 11$^{th}$ Antibody Engineering Meeting. Abstract (2000); and Kataoka, S. IBC's 13$^{th}$ Antibody Engineering Meeting. Abstract (2002)] harboring human chromosome fragments encoding the human immunoglobulin region were obtained from Kirin Pharma Co., Ltd. An overview of the technology for producing human antibodies is described in Lonberg and Huszar [*Int Rev. Immunol* 13:65 (1995)]. Transgenic animals with one or more human immunoglobulin genes (kappa or lambda) that do not express endogenous immunoglobulins are described, for example in, U.S. Pat. No. 5,939,598. Additional methods for producing human antibodies and human monoclonal antibodies are described (see, e.g., WO 98/24893; WO 92/01047; WO 96/34096; WO 96/33735; U.S. Pat. Nos. 5,413,923; 5,625,126; 5,633,425; 5,569,825; 5,661, 016; 5,545,806; 5,814,318; 5,885,793; 5,916,771; and 5,939, 598). Development of bovine carrying human immunoglobulin genes, transchromosomic (TC) cows, is described, for example, in Ishida and Lonberg [IBC's 11$^{th}$ Antibody Engineering Meeting. Abstract (2000)].

Immunization: Soluble human IL-10Rα:hFc recombinant protein was mixed 1:1 with an equal volume of RIBI adjuvant (Corixa, Seattle, Wash.) and an emulsion was prepared. Mice were immunized with 20 μg of soluble hIL-10Rα:hFc recombinant protein intraperitoneally and were boosted intraperitoneally with 20 μg of protein mixed 1:1 with RIBI adjuvant (Corixa) at 2-week intervals for 3 boosts. A final intraperitoneal injection of 20 μg of soluble hIL-10Rα:hFc without adjuvant was given 3 days prior to fusion. A second group of mice was immunized in a similar manner, but were boosted at 1-week intervals for 4 boosts.

Hybridoma production: The mice with the highest anti-human IL-10Rα IgG specific antibody titer in their serum were selected for the production of monoclonal antibodies. Human anti-human IL-10Rα IgG antibodies were confirmed by flow cytometric analysis. The spleens were harvested and single cell suspensions were fused with a myeloma cell line (SP2/O-Ag14) (ATCC, Rockville, Md.) at a ratio of 5:1 with 100% polyethylene glycol (Roche, Basel, Switzerland). The fusions were plated into 96 well flat bottom plates at an optimal density and cultured in DMEM (Dulbecco's Modified Engle's Media, Invitrogen, Corp.) with 10% fetal bovine serum (FBS, Hyclone, Ogden, Utah), 100 mg/L sodium pyruvate (Invitrogen, Corp.), 4.5 g/L D-glucose (Invitrogen, Corp.), 2 mM L-glutamine (Sigma), 100 U/ml penicillin (Sigma), 100 μg/ml streptomycin sulfate (Sigma), 55 μM 2-mercaptoethanol (Invitrogen, Corp.), HAT supplement (Sigma), and 5 ng/ml human IL-6 (Kirin Pharma Co., Ltd., Takasaki, Japan) in a 10% $CO_2$, 37° C. incubator. Approximately 2000 wells from 2 fusions were screened by ELISA for human IgG containing human IL-10Rα specific antibodies. Human anti-human IL-10Rα IgG antibodies were confirmed by flow cytometric analysis. Positive wells were expanded and subjected to 2 rounds of limiting dilution cloning to obtain monoclonal antibodies.

Antibody and protein purification: For antibody purification, hybridomas were cultured in 2-liter roller bottles at 300-350 milliliter per bottle with hybridoma-SFM medium (Invitrogen, Corp.). Soluble hIL-10Rα:hFc, chimp IL-10Rα: hFc and cynomolgus IL-10Rα:hFc recombinant proteins were generated by transient expression in FreeStyle™ HEK293F cells following manufacturer's protocols (Invitrogen, Corp.). Human monoclonal antibodies and the IL-10Rα: hFc recombinant proteins were purified from culture media using HiTrap MAb Select SuRe Protein A resin (Amersham, Piscataway, N.J.). In cases when supernatant volume exceeded 1 L, conditioned medium was first concentrated using a Sartorius tangential flow filtration system (Sartorius Stedim, Goettingen, Germany). The conditioned medium was filtered with a 0.22 μm vacuum filter unit (Millipore, Bedford, Mass.) and loaded onto the Protein A column of a size appropriate for the amount of the target protein in the medium. The column was washed thoroughly with 6 column volumes of PBS and the bound protein was eluted with appropriate buffer (0.1 M Gly-HCl, pH 3.4, 0.15 M NaCl for the antibody or ice cold 50 mM Citrate/NaCltrate pH 3.5, 0.15 M NaCl for the recombinant fusion protein). Eluted fractions were immediately neutralized with 1M Tris-HCl, pH 8.0. The fractions with high absorbance at 280 nm were pooled and concentrated with a centrifugal concentrator (Vivaspin, 10,000 MWCO: Sartorius). Concentrated samples were then loaded into 12 mL or 30 mL Slide-A-Lyzer dialysis cassettes (3,500 MWCO: Pierce, Rockford, Ill.), and dialyzed against 4 L PBS, pH 7.4 (Sigma, St. Louis, Mo.). Following the dialysis the proteins were filter sterilized using 0.22 μm syringe filters and their concentrations were determined by the Lowry method. Pyrogen content was quantitatively determined using the Endosafe Portable Testing System unit (Charles River, Charleston, S.C.) with high sensitivity Limulus Amebocyte Lysate (LAL) test cartridges. The samples were considered endotoxin-negative if the test result was less than 0.05 EU/mg (the assay limit of detection).

Human IgG Quantitation ELISA: To determine the amount of human antibody present in supernatants and purified stocks the following protocol was used. Goat anti-human Fcγ specific antibody (Jackson Immunoresearch Laboratories, West Grove, Pa.) was coated onto 96 well plates (Nunc, Denmark) in carbonate buffer (pH9.4) at 0.5 µg/well for 1 hour at 37° C. The plates were then blocked with Superblock (Pierce) for 30 minutes followed by addition of the samples to the plates. Standard curves were generated using total human IgG (Sigma) or purified human IgG1 or IgG4 (Kirin Pharma Co. Ltd.). The plates were incubated for 1 hour at 37° C., washed in PBS/1% BSA/0.1% Tween20 (Sigma), and the bound antibody was detected with goat anti-human Fcγ specific antibody conjugated to horseradish peroxidase (HRP, Jackson Immunoresearch) for 1 hour at 37° C. The TMB substrate (Sigma) was added for 10 minutes and the reaction was stopped with $H_2SO_4$ (LabChem, Pittsburgh, Pa.). The optical density (OD) was measured at 450 nm on a microplate reader and the antibody concentration calculations were computed using SoftMax Pro software (Molecular Devices, Sunnyvale, Calif.).

IL-10Rα Specific Antibody Detection ELISA: Antibody titers, specificity, and production by hybridomas were determined by ELISA. In brief, 96 well flat bottom Maxisorb plates were coated with 50 µl of hIL-10Rα (R&D Systems, Minneapolis, Minn.) at 1 µg/ml in carbonate buffer (pH 9.4) overnight at 4° C. or at 37° C. for 1 hour. After washing three times with PBS/0.05% Tween 20, plates were blocked with Superblock blocking buffer in TBS (Pierce) at room temperature for 30 minutes. The serum, supernatant, or purified antibody was diluted in blocking buffer, added to the wells, and the plates were incubated for 1 hour at room temperature. The plates were washed 3 times with PBS/0.05% Tween 20 and peroxidase-conjugated goat anti-human IgG (Fcγ specific), anti-rat IgG, or anti-mouse IgG detection antibodies (Jackson Immunoresearch) were added at a dilution of 1:5000. Multiple lots of anti-rat and anti-mouse IgG antibodies were used in different assays. These secondary antibodies demonstrated variable binding to 3F9, SPM466 and 37607. Following a 1 hour incubation at room temperature, the plates were washed and the TMB (Sigma) substrate was added and incubated at room temperature for 5 to 10 minutes. The reaction was stopped with $H_2SO_4$ (LabChem) and the optical density was measured at 450 nm by a microplate reader. A second ELISA protocol using soluble human, chimp and cynomolgus IL-10Rα:hFc recombinant proteins as the coating antigens was also employed. In this assay, binding of specific human IgG were detected with a peroxidase labeled sheep anti-human kappa antibody (The Binding Site, Birmingham, UK).

Flow Cytometry: Antibody titers, specificity, and relative binding affinities were determined by flow cytometric analysis using human IL-10Rα stable CHO-K1 transfectants, EL-4 transfectants, RPMI-8226 cells (ATCC, CCL-155) or total human peripheral blood mononuclear cells (PBMC). The cells were washed once in staining buffer: PBS+2% FBS+ 0.01% $NaN_3$+10 mM EDTA, then blocked with 20 µg/ml rabbit IgG (Jackson Immunoresearch), resuspended in serum, supernatant, purified anti-human IL-10Rα antibodies, or isotype control antibodies in a final volume of 50 µl. The cells were incubated with the antibodies on ice for 20 minutes, washed twice in staining buffer then resuspended in an anti-human IgG secondary antibody for 20 minutes. Two different antibodies were used, goat anti-human IgG biotin (Jackson Immunoresearch) or anti-human IgG PE (Southern Biotech Associates, Birmingham, Ala.). If the biotinylated antibody was used, antibody binding was detected by labeling with streptavidin-phycoerythrin (SA-PE) for 20 minutes. Binding of rat and mouse anti-hIL-10Rα antibodies were detected with either biotinylated or PE conjugated anti-rat or anti-mouse IgG antibodies from multiple sources (Jackson Immunoresearch; Southern Biotech Associates; and BD Pharmingen, San Diego, Calif.). The cells were then washed once and fixed 10 minutes with 1% paraformaldehyde. After a final wash the cells were resuspended in staining buffer and the samples were acquired using a FACS Calibur flow cytometer (Becton Dickinson Biosciences, Palo Alto, Calif.) and the data were analyzed using Cellquest (Becton Dickinson Biosciences) or FlowJo (TreeStar, Inc., San Carlos, Calif.) softwares.

IL-10 Blocking Assay: To determine if the anti-human IL-10Rα antibodies were blocked by binding of IL-10 to the receptor on the cell surface, a flow cytometric protocol was used. In the flow cytometric assay, RPMI-8226 cells were washed and resuspended in staining buffer and then incubated with biotinylated human IL-10 or a negative control protein (R&D Systems) for 30 minutes on ice. The anti-IL-10Rα antibodies were then added to the cells for an additional 30 minutes. The cells were washed and incubated with anti-human IgG conjugated to PE (Southern Biotech Associates) for 30 minutes. After another wash, the cells were fixed with 1% paraformaldehyde and analyzed on a FACS Calibur. The fold reduction in antibody binding was determined using the geometric mean fluorescence intensity in the following formula: Fold reduction=geometric mean fluorescence intensity in the absence of IL-10/geometric mean fluorescence intensity binding in presence of IL-10.

Anti-IL-10Rα Antibody Competition ELISA: In order to determine if the antibodies bind the same "epitope" of human IL-10Rα an ELISA protocol was used. Nunc 96 well flat bottom ELISA plates were coated with the human anti-human IL-10Rα antibodies 136C5, 136C8, 136D29, mouse anti-human IL-10Rα 37607 (R&D Systems) or rat anti-human IL-10Rα 3F9 (Biolegend, San Diego, Calif.) in carbonate buffer at 2 µg/ml for 1 hour at 37° C. The plates were washed and then blocked with PBS/1% BSA/Tween 20. Soluble anti-human IL-10Rα antibodies were pre-incubated with biotinylated recombinant human IL-10Rα:hFc fusion protein for 30 minutes at room temperature. The in-house generated human IL-10Rα:hFc recombinant protein was biotinylated using the NHS-PEO4-biotin labeling kit (Pierce, Rockford, Ill.) according to the manufacturer's instructions. The combinations of antibody-IL-10Rα:hFc-biotin were added to the plate and incubated for 1 hour at 37° C. After 3 washes, bound IL-10Rα:hFc-biotin was detected with streptavidin-horseradish peroxidase (Southern Biotech Associates). The ELISA was completed as described above. The percent inhibition was determined using the OD of each sample in the following formula: percent inhibition=100− [(experimental sample OD/maximum binding OD)*100].

Methods to detect antibody binding to peptides derived from the human IL-10Rα sequence: Multiple methods were employed to detect binding of anti-human IL-10Rα antibodies to peptides derived from the extracellular domain of human IL-10Rα that have been reported by Reineke, et al. (Reineke, et al., *Protein Sci* 7:951 (1998)) to be included in the IL-10 binding site of the receptor. The following amide synthesized peptides were tested: Ac-YHSNGYRARVRA-NH2, Ac-TVTNTRFSVD-NH2, Ac-SIFSHFREYE-NH2, Ac-GNFTFTHKKV-NH2, Ac-SVASRSNKGM-NH2 (SEQ ID NO. 81-85). In addition, the following biotinylated peptides were tested: Biotin-SGSTLDLYHSNGY-RARVRAVDG-NH2, Biotin-SGSTYSIFSHFREYEI-AIRKV-NH2 (SEQ ID NO. 86-87). The amide peptides were synthesized by A&A Labs, LLC (San Diego, Calif.) and the biotinylated peptides were synthesized by GenScript (Piscataway, N.J.) both at >95% purity and reconstituted at 20 mg/ml in DMSO. In one assay design peptides were spotted at 5 µg/spot in PBS onto PVDF membranes or nitrocellulose membranes that had been prepared according to the manufacturer's instructions. The membranes were incubated with anti-IL-10Rα antibodies using standard Western blotting methods (e.g. Towbin, et al., Proc Natl Acad Sci 76:4350 (1979)). Native human IL-10Ra:hFc and heat denatured human IL-10Ra:hFc were also spotted at 1 µg/spot on the membranes as controls. Negative controls included an irrelevant peptide and isotype controls. 136C5, 136C8, 136D29, 3F9, and 37607 only bound to native human IL-10Ra:hFc. None of the antibodies bound to the spotted denatured protein or to any of the peptides derived from the human IL-10Ra extracellular domain or the irrelevant peptide.

Multiple ELISA methods were also employed to detect binding of anti-IL-10Rα antibodies to IL-10Rα, derived peptides. The biotinylated IL-10Rα derived peptides (SEQ ID NO. 86-87) were diluted to 1 µg/ml in TBS/BSA/0.05% Tween 20 and added to Extravidin or Neutravidin pre-coated ELISA plates (Pierce) for 2 hours at room temperature. After washing three times with TBS/BSA/0.05% Tween 20. The purified anti-human IL-10Rα antibodies were diluted in TBS/BSA/0.05% Tween 20 and added to the wells. The plates were incubated for 1 hour at room temperature. The plates were washed 3 times with TBS/0.05% Tween 20 and peroxidase-conjugated goat anti-human IgG (Fcγ specific), anti-rat IgG, or anti-mouse IgG detection antibodies (Jackson Immunoresearch) were added. Following 1 hour incubation at room temperature, the plates were washed and the TMB (Sigma) substrate was added and incubated at room temperature for 5 to 10 minutes. The reaction was stopped with $H_2SO_4$ (LabChem) and the optical density was measured at 450 nm using a microplate reader. An OD reading above background wells with no primary antibody is indicative of antibody binding to the peptides. 136C5, 136C8, 136D29, 3F9, or 37607 did not bind to any of the IL-10Rα derived peptides in this assay system. The antibodies only bound the positive control biotinylated recombinant human IL-10Rα:hFc protein. In a second ELISA, the IL-10Rα amide peptides (SEQ ID NO. 81-85) were tested for their ability to block the anti-IL10Rα antibodies from binding to coated human IL-10Rα. The peptides were pre-incubated with 136C5, 136C8, 136D29, 3F9 or 37607 at 200 µg/ml peptide: 0.1 µg/ml antibody for 30 minutes. The peptide antibody mixture was then added IL-10Rα coated ELISA plates. Antibody binding was detected with species-specific anti-IgG-HRP secondary antibodies. None of the IL-10Rα derived peptides reduced the binding of the anti-IL-10Rα antibodies to the coated IL-10Rα protein. These data demonstrate that the antibodies disclosed herein do not bind linear epitopes of the sequences described in SEQ ID NO. 81-87. Using the conditions described here, we could not confirm the binding of 37607 that was previously reported by Reineke, et al. (Reineke, et al., Protein Sci 7:951 (1998)).

Purification of human peripheral blood mononuclear cells (PBMC) from whole blood: Whole blood was collected from healthy donors between the ages of 18 and 50 by the normal blood donor program at Scripps Green Hospital (La Jolla, Calif.). Heparin was added to prevent clotting. No race, ethnicity, or gender was specified. The blood was diluted in PBS and then underlayed with Ficoll-Paque Plus (Amersham Biosciences). The mononuclear cells were separated from the serum and platelets by centrifugation at 1800 RPM without the brake. The interface containing the PBMC was collected and washed two times with PBS.

TNF-α Enhancement Assay: Human, chimpanzee or cynomolgus peripheral blood mononuclear cells (PBMC) were plated at $4 \times 10^5$ cells per well in a 96 well flat-bottom plate with and without 10 ng/ml LPS (Sigma) and recombinant human IL-10 (R&D Systems) at 3 ng/ml (human, chimpanzee) and 5 ng/ml (cynomolgus), and the anti-human IL-10Rα antibodies at various concentrations in a final volume of 200 µl. AIM-V media (Invitrogen) supplemented with 1% human AB serum (MP Biomedicals, Solon, Ohio) was used as the culture media, and cells were cultured for 20 hr and 48 hr at 37° C., 5% $CO_2$. Samples from each time point were stored in a −20° C. freezer until analyzed. In some experiments with human PBMC recombinant cytomegalovirus (CMV) IL-10 (R&D Systems) was used at 10 ng/ml to suppress LPS induced TNF-α.

NKT Cell Assay: Human natural killer T (NKT) cell lines generated as described in Rogers, et al. (J Immunol Meth 285:197 (2004)) that are specific for α-galactosylceramide (KRN700, Kirin Pharma Company, Ltd. (Kawano, et al., Science 278:1626 (1997); Kobayashi, et al., Oncol Res 7:529 (1995)) were plated at $2 \times 10^5$ cells per well with $1 \times 10^6$ total allogeneic PBMC and 100 ng/ml KRN7000 in the presence or absence of anti-IL-10Rα antibodies or control antibodies. Following a 1 hr incubation at 37° C., 10 ng/ml of IL-10 was added to the wells and the cells were cultured for 48 to 72 hrs at 37° C. with 5% $CO_2$. Supernatants were removed at 48 and 72 hrs and cytokine specific ELISAs were used to measure cytokine production.

Detection of HLA-DR expression: Human PBMC were incubated at $1 \times 10^6$/ml with 10 µg/ml of anti-IL-10Rα antibodies for 30 min prior to the addition of 10 ng/ml IL-10. The culture media was RPMI-1640 (Invitrogen) supplemented with 5% fetal bovine serum (FBS) (Hyclone), 1% L-glutamine, 1% penicillin/streptomycin, 1% HEPES, and 0.1% β-mercaptoethanol. Following an overnight incubation at 37° C. with 5% $CO_2$ the cells were labeled with anti-HLA-DR-PE (Immunotech, Marseilles, France) using standard methods. Staining was detected by flow cytometric analysis on a FACS Calibur. The mean fluorescence intensity (MFI) was determined using Cell Quest or Flow Jo softwares.

Detection of STAT3 phosphorylation: Human PBMC were diluted to $1 \times 10^7$/ml in media containing 10% FBS, 1% penicillin/streptomycin, 1% L-Glutamine, 1% HEPES in RPMI 1640 media. Cells were treated with IL-10 at 10 ng/ml in the presence or absence of titrated anti-IL-10Rα or control antibody starting at 3 ug/ml for 15 min at 37° C. Untreated cells were also included as a control. A fraction of the samples were treated with anti-IL-10Rα plus goat anti-human IgG (Jackson ImmunoResearch) to crosslink the antibody in the absence of IL-10 for 0, 15 or 30 min. The stimulation was stopped by transfer of the samples to ice. The cells were then lysed using NP-40 lysis buffer: 150 mM NaCl, 50 mM Tris-HCL pH8.0, 1% NP-40 (Calbiochem, San Diego, Calif.), 1× Protease Inhibitor Cocktail (Roche Applied Science, Indianapolis, Ind.) in $dH_2O$, and homogenized. Protein concentrations were determined using the Lowry method with bovine gamma globulin (Pierce) as protein standards and Lowry reagent solutions from BioRad. Approximately 15 ug of lysate samples were loaded on 4-20% Tris-Glycine SDS-PAGE gels (Invitrogen), transferred to PVDF membranes (Invitrogen) and probed with anti-phospho-STAT3 and anti-STAT3 (Cell Signaling Technology, Danvers, Mass.). Antibody binding was detected with anti-rabbit-IgG-HRP (Jackson ImmunoResearch) and ECL reagents (Amersham Biosciences, Piscataway, N.J.) using standard western blotting protocols.

Cytokine ELISAs: Nunc 96 well flat bottom ELISA plates were coated overnight with anti-human TNF-α (Biolegend) or anti-IFN-γ (eBioscience, San Diego, Calif.) at 2 μg/ml or 1 μg/ml respectively, in carbonate buffer. The following day, plates were washed three times in ELISA wash buffer (1×PBS plus 0.05% Tween 20.) The plates were blotted dry and incubated for 30 minutes at room temperature with 250 μl of Blocking Buffer (1×PBS plus 1% BSA.) Samples were thawed and 50 μl were added to the 96 well plates, in duplicate, along with recombinant human TNF-α (eBioscience) or recombinant human IFN-γ (R&D Systems) standard dilutions. After 3 washes, biotinylated anti-human TNF-α or anti-human IFN-γ (Biolegend) at 1 ug/ml or 0.5 μg/ml, respectively, was incubated for 1 hr at RT. Plates were washed 3 times and then streptavidin-horseradish peroxidase (Southern Biotech Associates) at 1:2000 was added to the wells for 30 minutes. Following three washes, 100 μl TMB substrate was added for 3 to 10 minutes. The reaction was stopped with 50 μl $H_2SO_4$ and the plates were immediately read at 450 nm. The optical density (OD) of the experimental samples was used to calculate the amount of cytokine secreted based on the standard curve using Softmax Pro software.

Example 2

This example includes a description of exemplary antibodies that bind to IL-10Rα.

Isolation of Human Anti-IL-10Rα Antibody Genes: Cultured hybridoma cells (136C5, 136C8 or 136D29), which produce 136C5 (IgG1), 136C8 (IgG2) or 136D29 (IgG4) antibodies respectively, were collected by centrifugation. Total RNA was purified from these cells using RNeasy kit (QIAGEN Inc., Valencia, Calif.) following the manufacturer's instructions. SMART RACE cDNA Amplification Kit (Clontech Co., Ltd., Palo Alto, Calif.) and the reverse transcriptase SuperScriptll (Invitrogen Corp.) were used for cloning of cDNA that encodes the variable region of the immunoglobulin genes from total hybridoma cell RNA. Briefly, first strand cDNA was prepared by reverse transcriptase from 2 microgram of RNA. This cDNA was used as a template for polymerase chain reaction (PCR) to amplify the variable region and a part of the constant region of heavy and light chains (VH and VL, respectively). The amplified sequences also contained the leader sequences. The reaction was as follows: 1 U KOD Hot Start DNA polymerase (EMD, Novagen Brand, Madison, Wis.); 0.2 μM 3' Primer [for Heavy chain: IgG1p, for Light chain: hk5, (Table 1); 1× Universal Primer Mix A for the 5' end (UMP primer Mix A included in the SMART RACE Kit); 200 μM dNTP mix; 1 mM $MgCl_2$; KOD Hot Start Buffer (final concentration is 1×); and cDNA template. The thermocycling program was 1 cycle of 94° C.×4 min: 35 cycles of: 94° C.×30 sec, 55° C.×30 sec, 68° C.×1.5 min. followed by an extension at 72° C.×7 min.

Amplified DNA fragments were collected by agarose gel electrophoresis, and purified by QIAquick Gel Extraction Kit (Qiagen Co., Ltd., Germany). Purified DNA fragments of VH and VL were integrated into PCR BluntII-TOPO vector using the Zero Blunt TOPO PCR Cloning Kit, and each construct plasmid was transformed into E. coli, and then cloned. Nucleotide sequences of each insert (VH and VL) in the construct plasmids were analyzed using specific primers (M13F, M13R, Table 1). Based on the sequence obtained from VH and VL, oligonucleotide primers (Table 2) were designed to amplify 136C5 VH (136C$_5$H_F, 136C$_5$H_R) and VL (136C$_5$H_R, 12k1 reverse BsiWI), 136C8 VH (136C$_8$H_F, 136C5H) and VL (136C5K1_F, 12k1 reverse BsiWI), or 136D29 VH (136D29H_F, 14h1 reverse NheI) and VL #1 (136C5K1_F, 136D29K1_R), and VL #2 (136D29K2_F, 136D29K1_R).

Due to the nature of the KM Mice™, multiple kappa chain genes may be rearranged and expressed in a single B cell. This was the case for the 136D29 hybridoma. Two kappa chain genes were cloned. Recombinant antibodies with the two potential kappa chains paired with the single heavy chain were generated and the correct light chain gene, 136D29 light chain #2 was identified as the correct kappa chain and paired with the 136D29 heavy chain to yield an antibody with human IL-10Rα specificity.

CDRs were defined using the Kabat method. CDR-1 and CDR-2 were identified automatically by BLAST (NCBI website, www.ncbi.nlm.nih.gov/igblast/), and CDR-3 was identified by manual analysis using the following Kabat rules. The CDR-H3 is 3 to 25 amino acids in length, starts exactly 33 residues after the CDR-H2 and the preceding amino acids are always cysteine followed by two amino acids, typically the sequence will be cysteine-alanine-arginine; the end of CDR-H3 is always followed by the sequence tryptophan, glycine, any amino acid, glycine. CDR-L3 is 7 to 11 residues in length, always starts 33 residues after the end of the CDR-L2, which is always a cysteine; the end of CDR-L3 is always followed by phenylalanine-glycine-any amino acid-glycine. The VH and VL CDR1 and CDR2 sequences of 136C5, 136C8, and 136D29 were compared to the genomic sequence of human VH and VL genes using NCBI Ig BLAST. Changes in the amino acid sequences between the human anti-human IL-10Rα VH and VL and the germline amino acid sequences were identified and noted in the sequences below. The CDR3-sequences arise from joining of the variable, diversity and joining gene segments in the case of VH and variable and joining gene segments for VL. Therefore this region is prone to insertions and deletions and cannot be compared with germline sequences.

Nucleotide sequence of cDNA of 136C5 heavy chain variable region (VH) (from initiation codon (ATG) to the end of variable region). The CDR sequences are in bold text. SEQ ID NO:23

```
ATGGACTTGG GGCTGTGCTG GGTTTTCCTT GTTGCTATTT TAGAAGGTGT CCAGTGTGAG   60

GTGCAGCTGG TGGAGTCTGG GGGAGGCTTG GTACAGCCTG GGGGGTCCCT GAGACTCTCC  120

TGTGCAGCCT CTGGATTCAC CTTCAGTAGC TATAGCATGA ACTGGGTCCG CCAGGCTCCA  180

GGGAAGGGGC TGGAGTGGGT TTCATACATT AGTACTGGTA GTAGTACCAT ATACTACGCA  240

GACTCTGTGA AGGGCCGATT CACCATCTCC AGAGACAATG CCAAGAACTC ACTGTATCTG  300
```

```
CAAATGAACA GCCTGAGAGA CGAGGACACG GCTGTGTATT ACTGTGCGAG AGAGAATTAC  360

TATGGTTCGG GGAGTTATGA AGACTACTTT GACTACTGGG GCCAGGGAAC CCTGGTCACC  420

GTCTCCTCA                                                         480
```

Nucleotide sequence of cDNA of 136C5 light chain variable region (VL) (from initiation codon (ATG) to the end of variable region). The CDR sequences are in bold text. SEQ ID NO:24

```
ATGGAAGCCC CAGCTCAGCT TCTCTTCCTC CTGCTACTCT GGCTCCCAGA TACCACCGGA  60

GAAATTGTGT TGACACAGTC TCCAGCCACC CTGTCTTTGT CTCCAGGGGA AAGAGCCACC  120

CTCTCCTGCA GGGCCAGTCA GAGTGTTAGC AGCTACTTAG CCTGGTACCA ACAGAAACCT  180

GGCCAGGCTC CCAGGCTCCT CATCTATGAT GCATCCAACA GGGCCACTGG CATCCCAGCC  240

AGGTTCAGTG GCAGTGGGTC TGGGACAGAC TTCACTCTCA CCATCAGCAG CCTAGAGCCT  300

GAAGATTTTG CAGTTTATTA CTGTCAGCAG CGTAGCAACT GGCCCATATT CACTTTCGGC  360

CCTGGGACCA AAGTGGATAT CAAA                                        420
```

Nucleotide sequence of cDNA of 136C8 heavy chain variable region (VH) [from initiation codon (ATG) to the end of variable region]. The CDR sequences are in bold text. SEQ ID NO:25

```
ATGGAGTTGG GGCTGTGCTG GGTTTTCCTT GTTGCTATTT TAGAAGGTGT CCAGTGTGAG  60

GTGCAGCTGG TGGAGTCTGG GGGAGGCTTA GTACAGCCTG GGGGGTCCCT GAGACTCTCC  120

TGTGCAGCCT CTGGATTCAC CTTCAGTAGC TATAGCATGA ACTGGGTCCG CCAGGCTCCA  180

GGGAAGGGGC TGGAGTGGGT TTCATACATT AGTACTAGGA GTAGTACCAT ATACTACGCA  240

GACTCTGTGA AGGGCCGATT CACCATCTCC AGAGACAATG CCAAGAACTC ACTGTATCTG  300

CAAATGAACA GCCTGAGAGA CGAGGACACG GCTGTGTATT ACTGTGCGAG AGAGAATTAC  360

TATGGTTCGG GGAGTTATGA AGACTACTTT GACTACTGGG GCCAGGGAAC CCTGGTCACC  420

GTCTCCTCA                                                         480
```

Nucleotide sequence of cDNA of 136C8 light chain variable region (VL) [from initiation codon (ATG) to the end of variable region]. The CDR sequences are in bold text. SEQ ID NO:26

```
ATGGAAGCCC CAGCTCAGCT TCTCTTCCTC CTGCTACTCT GGCTCCCAGA TACCACCGGA  60

GAAATTGTGT TGACACAGTC TCCAGCCACC CTGTCTTTGT CTCCAGGGGA AAGAGCCACC  120

CTCTCCTGCA GGGCCAGTCA GAGTGTTAGC AGCTACTTAG CCTGGTACCA ACAGAAACCT  180

GGCCAGGCTC CCAGGCTCCT CATCTATGAT GCATCCAACA GGGCCACTGG CATCCCAGCC  240

AGGTTCAGTG GCAGTGGGTC TGGGACAGAC TTCACTCTCA CCATCAGCAG CCTAGAGCCT  300

GAAGATTTTG CAGTTTATTA CTGTCAGCAG CGTAGCAACT GGCCCATATT CACTTTCGGC  360

CCTGGGACCA AAGTGGATAT CAAA                                        420
```

Nucleotide sequence of cDNA of 136D29 heavy chain variable region (VH) [from initiation codon (ATG) to the end of variable region]. The CDR sequences are in bold text. SEQ ID NO:27

```
ATGGACTGCA CCTGGAGGAT CCTCTTCTTG GTGGCAGCAG CTACAGGCAC CCACGCCCAG  60

GTCCAGCTGG TACAATCTGG GGCTGAGGTG AAGAAGCCTG GGGCCTCAGT GAAGGTCTCC  120
```

```
TGCAAGGTTT CCGGATTCAC CCTCACTGAA TTATCCATGC ACTGGGTGCG ACAGGCTCCT  180

GGAAAAGGGC TTGAATGGAT GGGAGGTTTT GATCCTGACG ATGGTGAAAC AATCTACGCA  240

CAGAAGTTCC AGGGCAGAGT CTCCATGACC GAGGACACAT CTACAGACAC AGCCTACATG  300

GAGCTGAGCA GCCTGAGATC TGAGGACACG GCCGTGTATT ACTGTGCAAC AGGGGGGTAC  360

TATGGTCCTG TCGGTATGGA CGTCTGGGGC CAAGGGACCA CGGTCACCGT CTCCTCA    420
```

Nucleotide sequence of cDNA of 136D29 light chain #2 variable region (VL2) [from initiation codon (ATG) to the end of variable region]. The CDR sequences are in bold text. SEQ ID NO:28

```
ATGGACATGA GGGTCCTCGC TCAGCTCCTG GGGCTCCTGC TGCTCTGTTT CCCAGGTGCC  60

AGATGTGACA TCCAGATGAC CCAGTCTCCA TCCTCACTGT CTGCATCTGT AGGAGACAGA  120

GTCACCATCA CTTGTCGGGC GAGTCAGGGT ATTAGCATCT GGTTAGCCTG GTATCAGCAG  180

AAACCAGAGA AAGCCCCTAA GTCCCTGATC TATGCTGCAT CCAGTTTGCA AAGTGGGGTC  240

CCATCAAGGT TCAGCGGCAG TGGATCTGGG ACAGATTTCA CTCTCACCAT CAGCAGCCTG  300

CAGCCTGAAG ATTTTGCAAC TTATTACTGC CAACAGTATA ATAGTTACCC GCTCACTTTC  360

GGCGGAGGGA CCAAGGTGGA GATCAAA                                     420
```

Amino acid sequence of cDNA of 136C5 heavy chain variable region (VH) [leader sequence (italics) and variable region.] The CDR sequences are in bold text and changes from the germline sequence are underlined. SEQ ID NO:29

```
MDLGLCWVFL VAILEGVQCE VQLVESGGGL VQPGGSLRLS CAASGFTFSS YSMNWVRQAP  60

GKGLEWVSYI STGSSTIYYA DSVKGRFTIS RDNAKNSLYL QMNSLRDEDT AVYYCARENY  120

YGSGSYEDYF DYWGQGTLVT VSS                                         180
```

Amino acid sequence of cDNA of 136C5 kappa light chain variable region (VL) [leader sequence (italics) and variable region]. The CDR sequences are in bold text and changes from the germline sequence are underlined. SEQ ID NO:30

```
MEAPAQLLFL LLLWLPDTTG EIVLTQSPAT LSLSPGERAT LSCRASQSVS SYLAWYQQKP  60

GQAPRLLIYD ASNRATGIPA RFSGSGSGTD FTLTISSLEP EDFAVYYCQQ RSNWPIFTFG  120

PGTKVDIK                                                           180
```

Amino acid sequence of cDNA of 136C8 heavy chain variable region (VH) [leader sequence (italics) and variable region]. The CDR sequences are in bold text and changes from the germline sequence are underlined. SEQ ID NO:31

```
MELGLCWVFL VAILEGVQCE VQLVESGGGL VQPGGSLRLS CAASGFTFSS YSMNWVRQAP  60

GKGLEWVSYI STRSSTIYYA DSVKGRFTIS RDNAKNSLYL QMNSLRDEDT AVYYCARENY  120

YGSGSYEDYF DYWGQGTLVT VSS                                         180
```

Amino acid sequence of cDNA of 136C8 kappa light chain variable region (VL) [leader sequence (bold) and variable region]. The CDR sequences are in bold text and changes from the germline sequence are underlined. SEQ ID NO:32

*MEAPAQLLFL LLLWLPDTTG* EIVLTQSPAT LSLSPGERAT LSCRASQSVS SYLAWYQQKP 60

GQAPRLLIYD ASNRATGIPA RFSGSGSGTD FTLTISSLEP EDFAVYYCQQ RSNWPIFTFG 120

PGTKVDIK 180

Amino acid sequence of cDNA of 136D29 heavy chain variable region (VH) [leader sequence (bold) and variable region]. The CDR sequences are in bold text and changes from the germline sequence are underlined. SEQ ID NO:33

*MDCTWRILFL VAAATGTHAQ* VQLVQSGAEV KKPGASVKVS CKVSG<u>F</u>TLTE LSMHWVRQAP 60

GKGLEWMGGF DP<u>D</u>DGETIYA QKFQGRV<u>S</u>MT EDTSTDTAYM ELSSLRSEDT AVYYCATGGY 120

YGPVGMDVWG QGTTVTVSS 180

Amino acid sequence of cDNA of 136D29 kappa light chain #2 variable region (VL2) [leader sequence (bold) and variable region]. The CDR sequences are in bold text and changes from the germline sequence are underlined. SEQ ID NO: 34

*MDMRVLAOLL GLLLLCFPGA R*CDIQMTQSP SSLSASVGDR VTITCRASQG IS<u>I</u>WLAWYQQ 60

KPEKAPKSLI YAASSLQSGV PSRFSGSGSG TDFTLTISSL QPEDFATYYC QQYNSYPLTF 120

GGGTKVEIK 180

136C5, 136C8 or 136D29 VH and VL were cloned into the IgG4PE expression vector. Briefly, oligonucleotide primers, containing 5'-SalI and 3'-NheI restriction enzyme recognition sites were designed to amplify the variable region of the Heavy chain (VH) by PCR. PCR was performed using pTopoC5VH miniprep DNA as a template, 136C5H_F and 136C5H_R as primers (Table 2) with KOD Hot Start DNA polymerase. After digestion of the PCR product with NheI and SalI, a 424 bp fragment was subcloned into the IgG4PE expression vector pN5KG4PE-Lark (IDEC Pharmaceuticals, U.S. Pat. No. 6,001,358) that was pre-digested with NheI and SalI (8.9 kilobases DNA fragment). The existence of variable region of the Heavy chain (VH) was analyzed by restriction digest and verified by DNA sequencing.

As the second step, VL was inserted into N5KG4PE Lark-VH vector as follows: the DNA vector was digested by two DNA restriction enzymes, BglII and BsiWI. The 9.1 kb DNA fragment was isolated. Similarly to the Heavy chain construct, a primer set for PCR of VL was designed to contain the recognition sites for 5'BglI and 3'BsiWi. These primers (Table 2), 136C5K1_F and 12k1 reverse BsiWI, were used to amplify VL from the pTopoC5VL miniprep plasmid DNA. The PCR product was digested with BglII and BsiWI and isolated by agarose gel electrophoresis and gel purification. This fragment, containing C5VL, was ligated to the prepared 9.1 kb vector with T4 DNA ligase and used to transform Top10 cells (Invitrogen). Positive *E. coli* transformants were selected. This expression vector, pN5KG4PE136C5, was purified, and the presence of both C5VL and C5VH regions were confirmed by restriction analysis.

Generation of vectors to produce recombinant 136C5G4PE and 136D29G4PE antibodies was performed in the same manner. The resulting vectors, pN5KG4PE136C8 and pN5KG4PE136D29k1, and pN5KG4PE136D29k2, were confirmed by restriction enzyme digest and sequencing.

These recombinant antibodies are variants of human IgG4 isotype in which serine 228 was replaced with a proline (S228P). This change in the Fc region of IgG4 reduces heterogeneity observed with hIgG4 and extends the serum half-life (Angal et al., *Mol Immunol* 30:105 (1993)). A second mutation that replaces leucine 235 with a glutamic acid (L235E) eliminates the residual FcR binding and complement binding activities (Alegre et al., *J Immunol* 148:3461 (1992)). The resulting antibody with both mutations is referred to as IgG4PE. The numbering of the hIgG4 amino acids was derived from Kabat at al., *Sequences of Proteins of Immunological Interest*, Fifth Edition (1991).

TABLE 2

Primers for Human VH and VL cloning

| SEQ ID NO | Name | Sequence 5' to 3' | Length |
|---|---|---|---|
| 35 | RACEUPS5' | CTAATACGACTCACTATAGGGC | 22-mer |
| 36 | IgG1p | TCTTGTCCACCTTGGTGTTGCTGGGCTTGTG | 31-mer |
| 37 | HK5 | AGGCACACAACAGAGGCAGTTCCAGATTTC | 30-mer |
| 38 | M13F | GTAAAACGACGGCCAGTG | 18-mer |

TABLE 2 -continued

Primers for Human VH and VL cloning

| SEQ ID NO | Name | Sequence 5' to 3' | Length |
|---|---|---|---|
| 39 | M13R | CAGGAAACAGCTATGAC | 17-mer |
| 40 | 136C5H_F | AGAGAGAGAGGTCGACTCACCATGGACTTGGGGCTGTG | 38-mer |
| 41 | 136C5H_R | AGAGAGAGAGGCTAGCTGAGGAGACGGTGACCAGGGTTC | 39-mer |
| 42 | 136C5K1_F | AGAGAGAGAGAGATCTGAACCATGGAAGCCCCAGCTCA | 38-mer |
| 43 | 12k1 reverse BsiWI | AGAGAGAGAGCGTACGTTTGATATCCACTTTGGTCCCAGG | 40-mer |
| 44 | 136C8H_F | AGAGAGAGAGGTCGACTCACCATGGAGTTGGGGCTGTG | 38-mer |
| 45 | 136D29H_F | AGAGAGAGAGGTCGACTCACCATGGACTGCACCTGGAG | 38-mer |
| 46 | 14h1 reverse NheI | AGAGAGAGAGGCTAGCTGAGGAGACGGTGACCGTGGT | 37-mer |
| 47 | 136D29K2_F | AGAGAGAGAGAGATCTACAGCATGGACATGAGGGTCC | 37-mer |
| 48 | 136D29K1_R | AGAGAGAGAGCGTACGTTTGATCTCCACCTTGGTCCCTCC | 40-mer |

Production of recombinant human anti-hIL-10Rα antibody from 293F cells: Suspension cultures of 293F cells were maintained in Freestyle 293 expression medium while shaking at ~120 rpm/min in an 8% CO$_2$ humidified incubator at 37° C. For transient expression of recombinant antibodies, $3 \times 10^7$ 293F cells were transfected with 30 µg of each plasmid encoding the recombinant IgG4PE versions of either the 136C5, 136C8 or 136D29 anti-hIL-10Rα antibodies using 293-fectin (Invitrogen Corp.) following the manufacturer's instructions. Transfectants were allowed to grow in suspension in 30 mL of Freestyle 293 expression medium for 7 days under normal growth conditions. Growth medium was harvested and cells removed by centrifugation at a speed of 300×g followed by filtration through a 0.22 µm filter. The antibody concentration present in this unpurified material determined by hIgG quantitation ELISA and used for in vitro assays to assess the functional properties of the subclass switched antibodies.

Example 3

This example includes a description of characterization of human monoclonal antibodies that bind to IL-10Rα.

KM Mice™ were immunized with soluble recombinant hIL-10Rα:hFc in RIBI. Several of the mice raised anti-human IL-10Rα specific antibodies, with a range in human IgG IL-10Rα specific titers. Splenocytes from the highest responders were fused with myeloma cells to generate human anti-human IL-10Rα producing hybridomas. The production of anti-IL-10Rα antibodies was determined by both ELISA and flow cytometry using recombinant soluble hIL-10Rα and CHO-hIL-10Rα transfectants, respectively. The positive hybridomas were cloned by limiting dilution to yield monoclonal hybridomas. Three human antibodies were further characterized for relative binding affinity for human IL-10Rα, the ability to be blocked by human IL-10 binding to the receptor in vitro, competition with each other, cross-reactivity with non-human primate IL-10Rα, and neutralization of IL-10 in vitro. These antibodies were also compared with commercially available anti-human IL-10Rα antibodies, 3F9 (Biolegend), SPM466 (Spring Biosystems) and 37607 (R&D Systems) (Table 3).

TABLE 3

Characteristics of Anti-Human IL-10Rα Monoclonal Antibodies

| Antibody | Original Subclass | Binding Group^ | Binding to shIL-10Rα KD | Binding to shIL-10Rα BMAX | Fold Reduction by IL-10 | In vitro neutralizing activity Human | In vitro neutralizing activity Chimp | In vitro neutralizing activity Macaque |
|---|---|---|---|---|---|---|---|---|
| 136C5# | hIgG1 | A | 0.038 | 1.79 | 1.88 | + | + | + |
| 136C8# | hIgG2 | A | 0.047 | 1.77 | 1.98 | + | + | + |
| 136D29# | hIgG4 | B | 0.058 | 1.68 | 1.98 | + | + | ND |
| 3F9* | Rat IgG2a | C | 0.034 | 2.08 | 2.37 | + | + | ND |
| SPM466* | Rat IgG | C | 0.043 | 1.71 | NT | + | NT | ND |
| 37607* | Mouse IgG2a | C | 0.071 | 0.63 | NT | + | NT | ND |

Figure 2A:
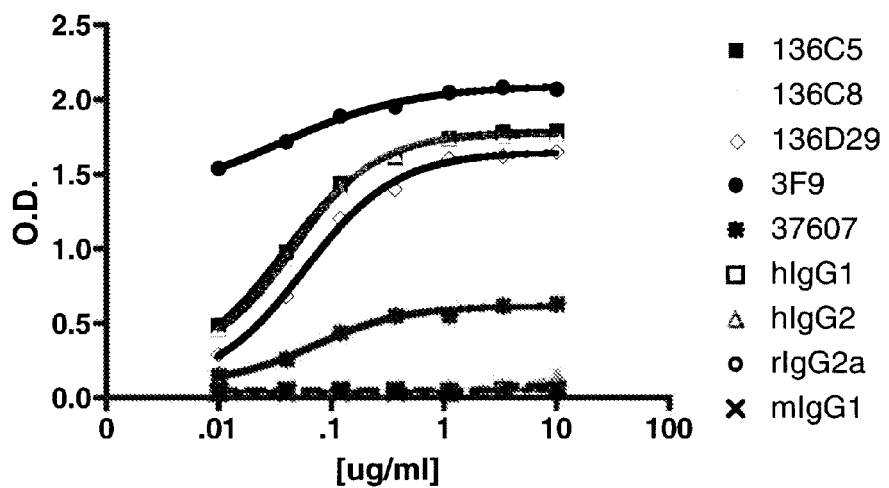
FIGS. 2A-2B show relative binding affinity of anti-human IL-10R antibodies for human IL-10Rα. A) Titration of anti-IL-10Rα antibodies binding to coated human IL-10Rα:hFc. Binding was detected with anti-human kappa-HRP, anti-mouse IgG-HRP, or anti-rat IgG-HRP. These data were used to determine the KD and BMAX (Tables 3 and 5); B) Binding to human IL-10Rα on the surface of the B cell line RPMI-8226 by the human anti-human IL-10Rα monoclonal antibodies. RPMI-8226 cells were labeled with anti-human IL-10Rα antibodies at various concentrations and detected with anti-human IgG-PE. The commercial rat anti-human IL-10Rα antibody 3F9 was detected with anti-rat IgG-PE. The geometric mean fluorescence intensity (geo mean) data are shown.
Figure 2B:
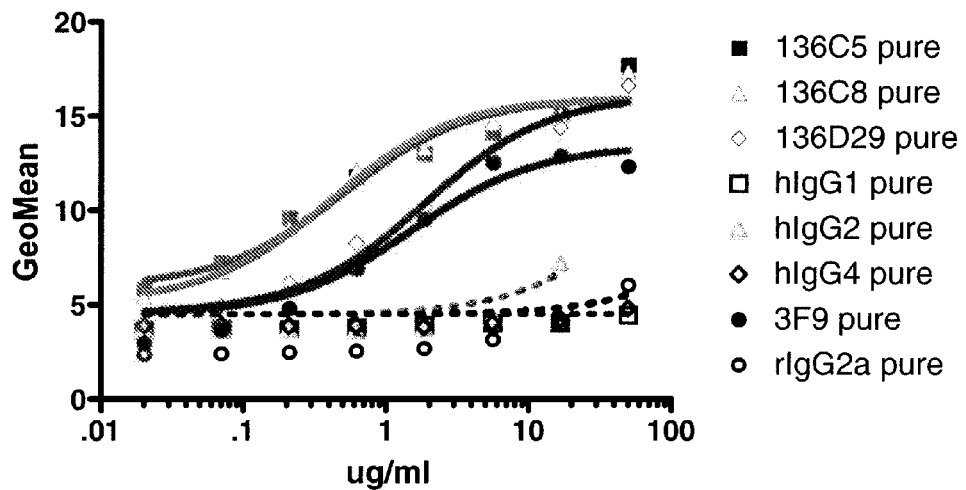

Human anti-human IL-10Rα antibodies
*commercial rat or mouse anti-human IL-10Rα antibodies
^Binding group defined by all parameters measured including cross-blocking, cross-reactivity, and neutralizing activity
NT: not tested
ND: no neutralizing activity detected Antibodies 136C5, 136C8, and 136D29 all bound specifically to human IL-10Rα expressed on monocytes and lymphocytes found in human peripheral blood. Binding could be inhibited by pre-incubation with soluble human IL-10Rα: hFc (FIG. 1). The binding of these human anti-human IL-10Rα antibodies was saturable and the KD and maximum binding (BMAX) of each antibody was determined by titrating the amount of antibody needed to bind to recombinant human IL-10Rα coated on an ELISA plate (FIG. 2A and Table 3). These results were confirmed using a flow cytometry based assay and the human B cell line RPMI-8226. (FIG. 2B). Binding of 37607 to this cell line is barely detectable above isotype control staining. The relative binding affinities of 136C5, 136C8, 136D29, and 3F9 were not significantly different from each other, all demonstrated approximately three-fold higher relative binding affinities than 37607 in the ELISA. Binding of a third commercial antibody, SPM466, was very similar to 3F9 in both assays. The KD value is equal to the effective concentration of half maximal binding (EC50) and was determined by non-linear regression analysis of the sigmoidal dose response in the ELISA and flow cytometric assays using the following equation. Y=bottom+(Top−Bottom)/(1+10^((LogEC50−X))). X is the logarithm of concentration. Y is the response. Y starts at Bottom and goes to Top with a sigmoid shape (Graphpad Prism 4 Software, San Diego, Calif.). The BMAX is the highest OD or geometric mean fluorescence intensity (geo mean) observed for an individual antibody. The binding max can be variable depending on the source and lot of the secondary antibody used to detect the anti-human IL-10Rα antibodies.

Figures 3A, 3B:
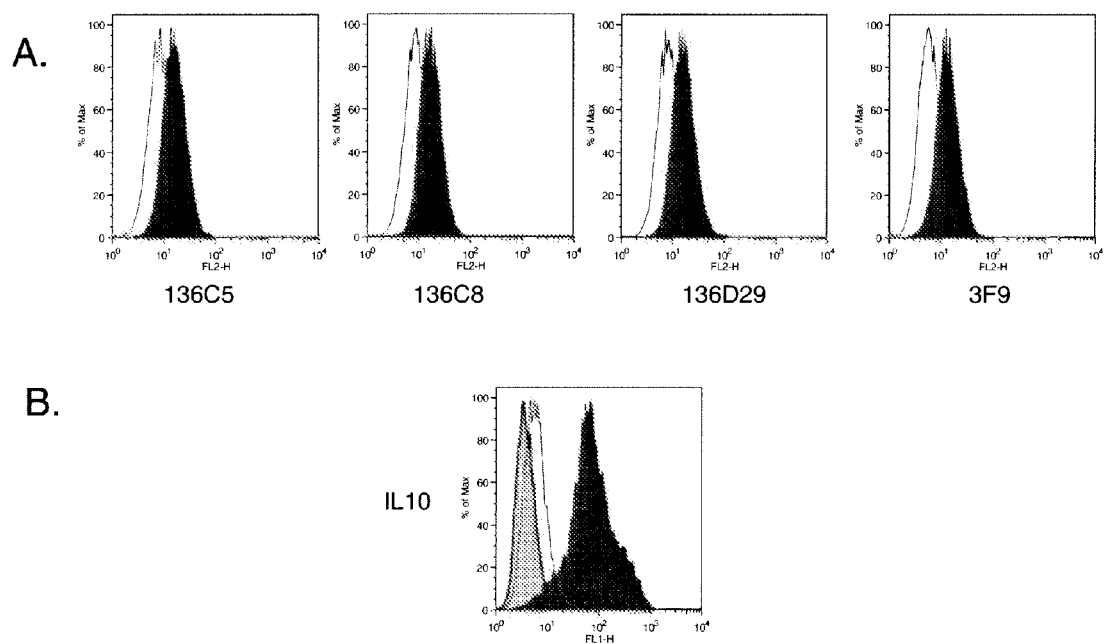
FIGS. 3A-3B show data indicating that binding of anti-human IL-10Rα cells to human IL-10Rα is blocked by pre-binding of human IL-10 to the IL-10 receptor. RPMI-8226 cells were stained with human IL-10 biotin followed by anti-human IL-10Rα antibodies, and binding of antibodies was detected with anti-human IgG-PE or anti-rat IgG-PE. A) Filled histograms represent the maximum binding of the antibodies in the absence of IL-10, the open histograms are in the presence of human IL-10; B) Maximum IL-10 binding (closed histogram) is inhibited by anti-IL-10 (open histogram.) The shaded histogram represents binding of a negative control protein. Binding of IL-10 was detected with streptavidin-FITC.
Figure 4:
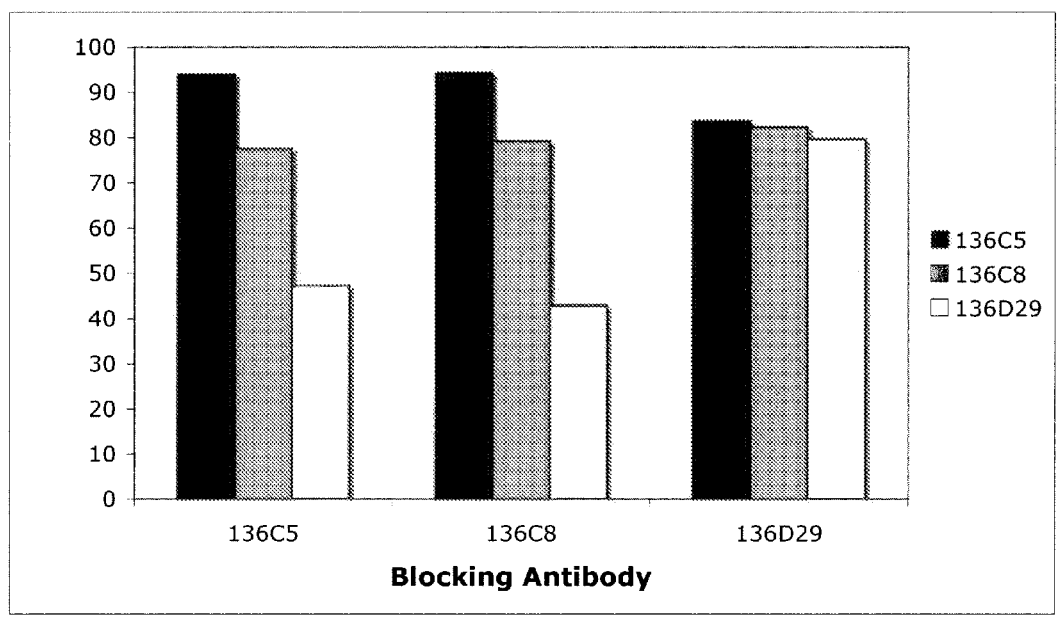
FIG. 4 shows data indicating that three human antibodies can be divided into two groups based on competition for binding to IL-10Rα. Individual antibodies were coated in the wells of a 96 well plate. Biotinylated hIL-10Rα:hFc was pre-incubated with soluble anti-IL-10Rα antibodies and then added to coated wells. Binding of hIL-10Rα:hFc to the coated antibody was detected with streptavidin-HRP. Percent inhibition (y-axis) was determined using the following formula (100−(OD study sample/OD maximum binding sample))*100.

Recombinant IL-10 binding to the IL-10R expressed by RPMI-8226 cells reduced binding of the anti-human IL-10Rα antibodies (FIG. 3A). The reduction in antibody binding was similar for all antibodies tested. FIG. 3B illustrates the binding of IL-10 to the RPMI-8226 cells. The fold reduction in binding by IL-10 (Table 3) was determined by dividing the geo mean of the antibody binding in the absence of IL-10 by the geo mean in the presence of IL-10. These data show that 136C5, 136C8, 136D29, and 3F9 recognize sequences within the IL-10 binding site. Blockade of antibody binding by IL-10 was not complete because saturating amounts of IL-10 were not used.

Figures 12A, 12B, 12C, 12D, 12E, 12F, 12G:
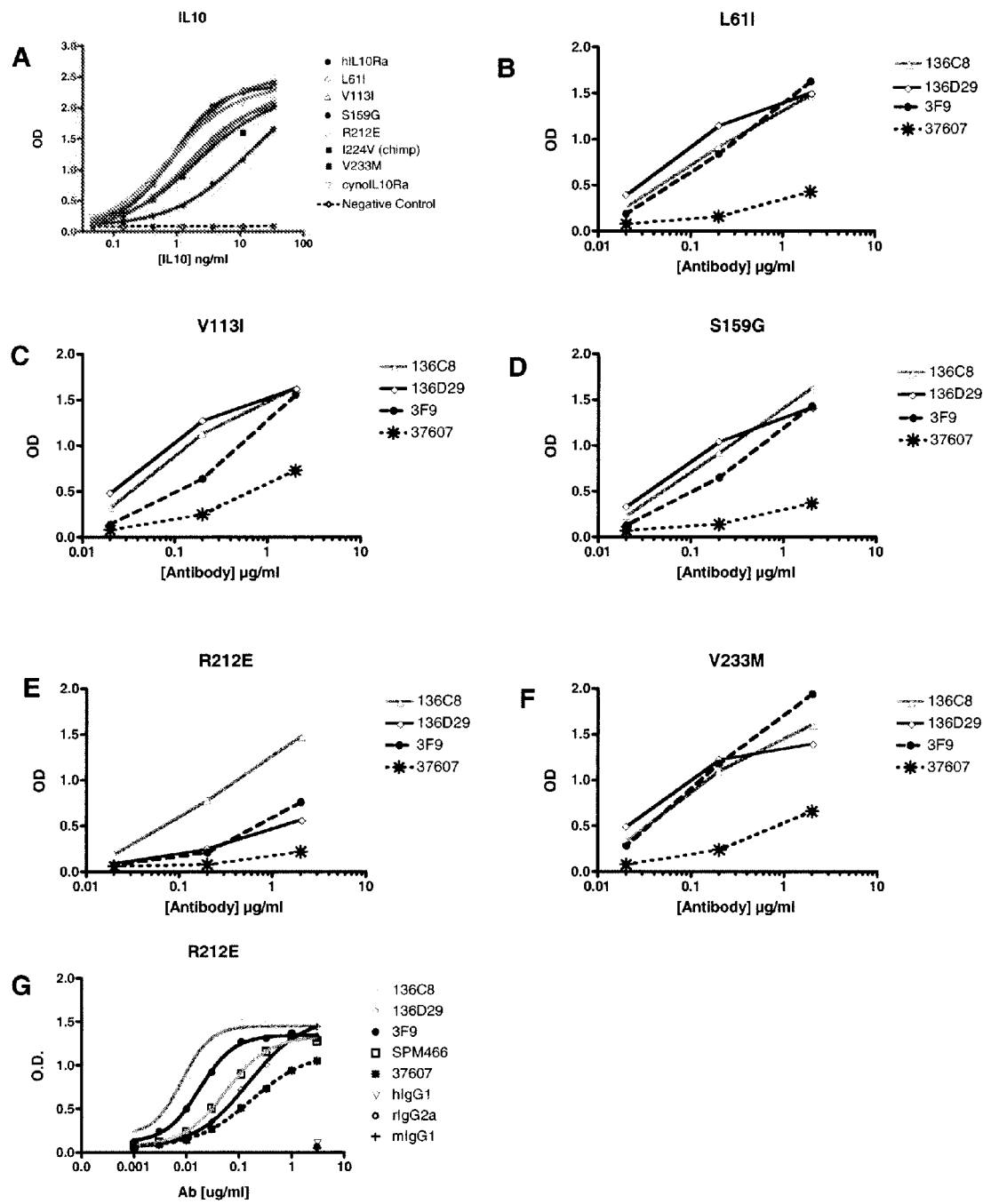
FIGS. 12A-12G show binding of the anti-human IL-10Rα antibodies, 136C8 (▲), 136D29 (♦), 3F9 (■), 37607 (*) and SPM466 (□, last panel only), to IL-10 itself (A) or single nucleotide polymorphism variants of human IL-10Rα, namely B, L61I, C, V113I, D, S159G, E, R212E, F, V233M, and G, R212E.

Several single nucleotide polymorphisms (SNP) have been identified in the extracellular domain of human IL-10Rα (Gasche, et al., *J Immunol* 170:5578 (2003)). The SNP that result in changes to the amino acid sequence of human IL-10Rα have the potential to affect the binding of anti-human IL-10Rα antibodies. This possibility was assessed by generating recombinant-Fc fusion proteins of each of the extracellular human IL-10Rα SNP variants that result in amino acid changes (SEQ ID NO. 63, 64, 65, 67, 69, 72) and testing their binding to IL-10 and to anti-IL-10Rα antibodies by ELISA (FIG. 12). IL-10 binding to variant S159G (SEQ ID NO. 67) was reduced as was previously reported (Gasche, et al., *J Immunol* 170:5578 (2003)). Binding of 136C5, 136C8, 136D29, 3F9, and SPM466 to all variants is superior than 37607, similar to binding to the consensus human protein. 136C8 shows significantly better binding to IL-10Rα variant R212E (SEQ ID NO. 69) than 136D29, 3F9, SPM466 and 37607 binding to IL-10Rα variant R212E (SEQ ID NO. 69). These results demonstrate unique binding of antibody 136C8 compared to other described antibodies, and that therapeutic use of an antibody that binds to R212E, such as 136C8, would cover a broader population. Individual antibody binding to L611 (SEQ ID NO. 63) and V233M (SEQ ID NO. 71) variants is similar to binding to the consensus human IL-10Rα for all antibodies tested. 3F9 binding to V113I (SEQ ID NO. 65) and 1224V (chimp) (SEQ ID NO. 6) is reduced compared with 136C8 and 136D29. These changes are due to the nature of different secondary anti-rat antibodies used to detect 3F9 in different assays as these data differ from FIG. 7A, where a different lot of anti-rat IgG was used to detect binding of 3F9.

Example 4

This example includes a description of cross block studies.

The antibodies were evaluated by ELISA to determine if they compete with each other for binding to soluble human IL-10Rα as a means of determining how many antibody reactivities or epitopes are recognized by this panel of antibodies. Three epitopes groups (Groups I, II and III), were identified by the ability of the antibodies to completely (>70%, Group I), partially (>50%-<70%, Group II), or marginally (<50%, Group III) inhibit binding of each other (FIG. 4, Table 4). Using this criteria 136C5 and 136C8 are in the same group (I). 136D29 is closely related to 136C5 and 136C8, but distinct (group II) in that binding of 136D29 is only marginally affected by the other antibodies. The commercial antibody 3F9 binds to a third epitope (group III). Assignment of SPM466 to an epitope group by this method is difficult. Its ability to block the other antibodies is similar to 3F9, which it partially blocks, but SPM466 binding is inhibited by all other antibodies. The blocking by 136C5, 136C8, and 136D29 may be due to steric hindrance. Assignment of antibody 37607 to an epitope group is difficult due to its apparent low affinity. Antibody 37607 binding to IL-10Rα is completely blocked by all the antibodies tested here, but 37607 only partially or marginally affected binding of 136C5, 136C8, 136D29 and 3F9 antibodies. Complete blockade of SPM466 suggests a shared or overlapping epitope.

The epitope is not the only parameter that can affect antibody binding in this experimental approach, the affinities and avidities of the antibodies for hIL-10Rα will affect how they compete with one another for binding. An example of this is that 37607 has a relatively low binding affinity for human IL-10R (FIG. 2 and Table 3), in this assay 37607 is significantly inhibited by the human anti-human IL-10R antibodies, yet it only partially or marginally affects the binding of the human anti-IL-10Rα antibodies. In addition, steric hindrance due to binding of the antibodies to close or overlapping sequences will also lead to competition, this can also be affected by the subclass of the antibody as some isotypes, such as IgG4, are more flexible than others. The IL-10 binding site of the IL-10Rα protein has been mapped (Reineke, et al. *Protein Sci* 7:951 (1998)). In their paper, Reineke, et al. describe that the IL-10 binding site on IL-10Rα is composed of 5 non-contiguous peptides that form the three-dimensional IL-10 binding site and that the 37607 antibody binds to 2 of 5 peptides. If the human anti-human IL-10Rα antibodies described here bind to just one of the two peptides recognized by 37607 as described by Reineke, et al., they would reduce binding of 37607 in our assay. This model suggests that antibodies could compete with each other but not share the exact same binding site. We used ELISA and dot blot methods to test the binding of 37607 and 136C8 to peptides that overlap the IL-10 binding sites of IL-10Rα described by Reineke, et al. By the methods we employed we were unable confirm Reineke's data for binding of the commercial antibody 37607 to any of the peptides that comprise the reported IL-10 binding site of IL-10Rα (SEQ ID NO 81-87). We also did not detect binding of 136C5, 136C8, 136D29, or 3F9 to these peptides. Furthermore, our data demonstrate that these antibodies only recognize native protein and not reduced or denatured IL-10Rα as demonstrated by dot blot and western blot analyses. These results demonstrate that the exemplary antibodies disclosed herein, 136C5, 136C8, and 136D29, recognize conformational epitopes, and not linear epitopes.

TABLE 4

Percent IL-10Rα binding inhibition by anti-IL-10Rα antibodies.

| Coated Ab | 136C5 | 136C8 | 136D29 | 3F9 | SPM466 | 37607 |
|---|---|---|---|---|---|---|
| 136C5# | 93.93 | 77.91 | 48.00 | 40.36 | 83.22 | 78.80 |
| 136C8# | 94.21 | 79.52 | 43.81 | 34.42 | 83.32 | 79.08 |
| 136D29# | 83.43 | 82.54 | 80.00 | 46.50 | 84.56 | 74.21 |
| 3F9* | 67.20 | 77.60 | 58.00 | 69.40 | 90.25 | 70.78 |
| SPM466* | 72.10 | 64.55 | 55.04 | 52.16 | 90.59 | 74.38 |
| 37607* | 59.30 | 65.20 | 38.70 | 1 | 84.38 | 74.20 |

Blocking Ab
Grey highlight = antibody's blockade of self
Human anti-human IL-10Rα antibodies
*commercial rat or mouse anti-human IL-10Rα antibodies Example 5

This example includes a description of in vitro functional analysis of the human anti-human IL-10Rα antibodies.

Figure 5A:
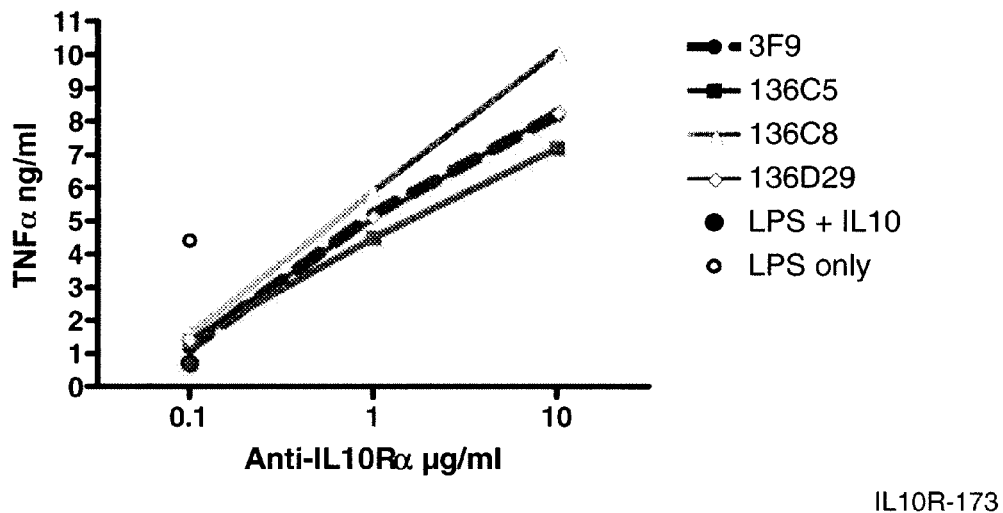
FIGS. 5A-5B show data indicating that neutralization of IL-10 enhances TNF-α secretion by human PBMC. A) LPS treatment induces TNF-α secretion by human PBMC (open circle), IL-10 blocks TNF-α secretion (gray circle). Addition of anti-human IL-10Rα antibodies increases TNF-α secretion in a dose dependent manner. Panel representative of 10 studies with six donors. B) Effectiveness of human anti-human IL-10Rα antibody 136C8 compared with commercial antibodies. Antibody 136C8 neutralizes IL-10 blockade of TNF-α more robustly than commercial IL-10Rα antibodies 3F9 and 37607.
Figure 5B:
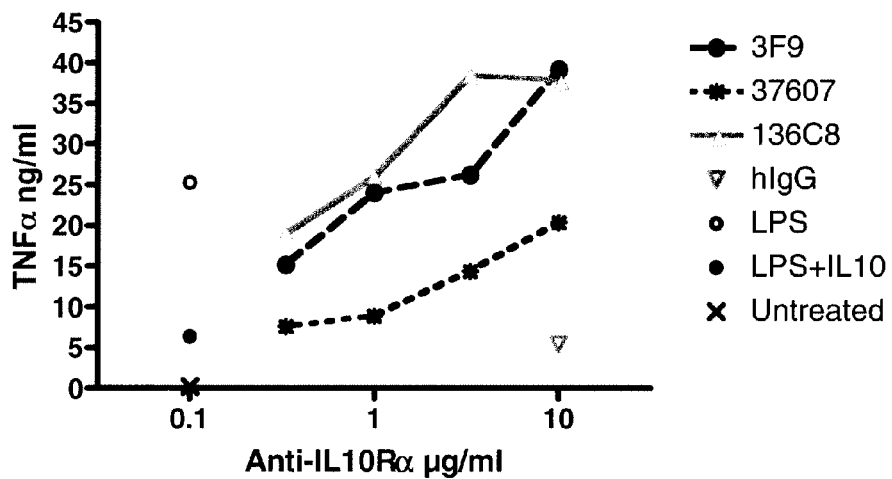

To study the in vitro neutralization activity of the anti-human IL-10Rα antibodies, human peripheral blood mononuclear cells (PBMC) were treated with lipopolysaccharide (LPS) to induce secretion of TNF-α. Addition of recombinant human IL-10 blocks TNF-α secretion. If addition of an anti-human IL-10Rα antibody to the culture restores or enhances TNF-α secretion, then the antibody is considered to have IL-10 neutralizing activity. This was observed with the human and commercial anti-human IL-10Rα antibodies (FIG. 5). At the 20 (FIG. 5) and 48 hour timepoints, 136C5, 136C8, 136D29, 3F9 and SPM466 (not shown) all enhanced TNF-α secretion from PBMC treated with LPS and IL-10 with similar dose responses. The mouse anti-human IL-10Rα antibody 37607 was less effective, but still neutralized (i.e., inhibited, reduced, antagonized, prevented or blocked) IL-10. PBMC treated with LPS also produce IL-10 and at 48 hours this amount of endogenous TL-10 reduces TNF-α secretion. The anti-human IL-10Rα antibodies effectively enhanced TNF-α secretion in the presence of endogenous IL-10 as well as in the presence of exogenous IL-10. LPS treatment of PBMC also induces production of IFN-gamma, IL-6 and IL-1β which are suppressed by addition of IL-10. Neutralization (i.e., inhibition, reduction, antagonism, prevention, or blockade) of IL-10 with 136C5, 136C8, 136D29, 3F9, SPM466, and 37607 restored production of IFN-gamma, IL-6, and IL-1β from the LPS treated PBMC with similar efficacy as observed for restoration of TNF-α. These results demonstrate the ability of invention antibodies to enhance production of TNF-α, IL-6, IL-1β, and IFN-γ secretion in the presence of exogenous IL-10, which results increased immune responses.

LL-10 has been described as an immunosuppressive agent that reduces the cytokine production by activated T cells (de Waal Malefyt, et al., *J Exp Med* 174:1209 (1991); Fiorentino, et al., *J Immunol* 146:3444 (1991); Matsuda, et al., *J Exp Med* 180:2371 (1994)). Natural Killer T (NKT) cells are a subset of T cells that express NK cell markers such as CD56 and CD161. Approximately 10-25% of human T cells in the peripheral blood express NK cell markers (Lanier, et al., *J Immunol* 153:2417 (1994); Kronenberg, *Annu Rev Immunol* 23:877 (2005)). Within the NKT cell population there exists a very small subset of cells, 0.01-0.5%, that expresses the Vα24 chain of the T cell receptor. These invariant NKT cells are activated by and expand in the presence of a synthetic glycolipid, α-galactosylceramide, (also known as KRN7000, which was originally discovered by Kirin Brewery Co. Ltd. (Kawano, et al., *Science*, 278:1626 (1997); Kobayashi, et al., *Oncol Res* 7:259 (1995))). Stimulation of human NKT cell lines with KRN7000 bound to CD1d expressed on antigen presenting cells results in secretion of large amounts of cytokines such as IFN-γ, TNF-α, GM-CSF, IL-4 and IL-5 and induces cytotoxic activity against target cells that present KRN7000. IL-10 inhibits cytokine secretion from these invariant NKT cells.

Figures 10A, 10B:
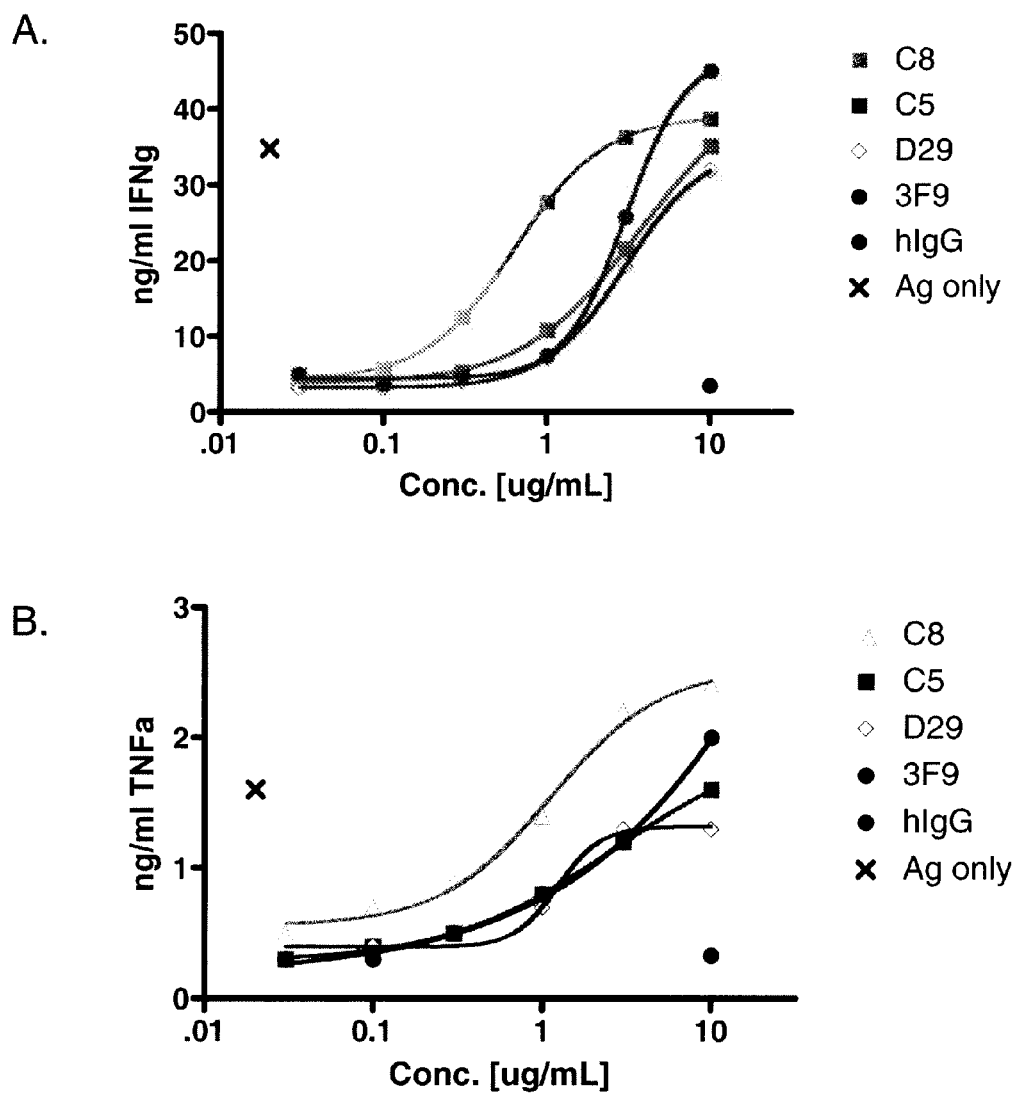
FIGS. 10A-10B show data demonstrating the ability of the anti-IL-10Rα antibodies to restore antigen-induced cytokine secretion from a human NKT cell line treated with IL-10. KRN7000 (Ag only, X symbol) induction of IFN-γ (A) and TNF-α (B) was inhibited by human IL-10 (gray circle). Addition of 136C5, 136C8, 136D29 and 3F9 neutralized IL-10 and restored IFN-γ and TNF-α secretion in a dose dependent manner. Data representative of responses by two human NKT cell lines.

The ability of the human IL-10Rα antibodies to neutralize this function of IL-10 was studied using NKT cell lines previously described by Rogers, et al. (Rogers, et al., *J Immunol Meth* 285:197 (2004)). NKT cell lines were stimulated with the antigen KRN7000 and allogeneic PBMC, in the presence or absence of IL-10. Antigen stimulation resulted in secretion of IFN-γ and TNF-α at 24 and 48 hours and was inhibited by IL-10. 136C5, 136C8, 136D9, and 3F9 all restored secretion of these cytokines in a dose dependent manner (FIG. 10). GM-CSF and IL-5 secretion were also restored by neutralization of IL-10 by the human anti-human IL-10Rα antibodies. These data show that human antibody 136C8 has superior neutralizing (i.e., inhibiting, reducing, antagonizing, preventing or blocking) activity compared to the other antibodies. Restoration or enhancement of cytokine secretion, whether induced by Toll Like Receptor (TLR) ligands such as LPS or by antigen stimulation, will lead to increased immune responses that are beneficial in appropriate physiological settings, such as a chronic viral infection.

Figure 11A:
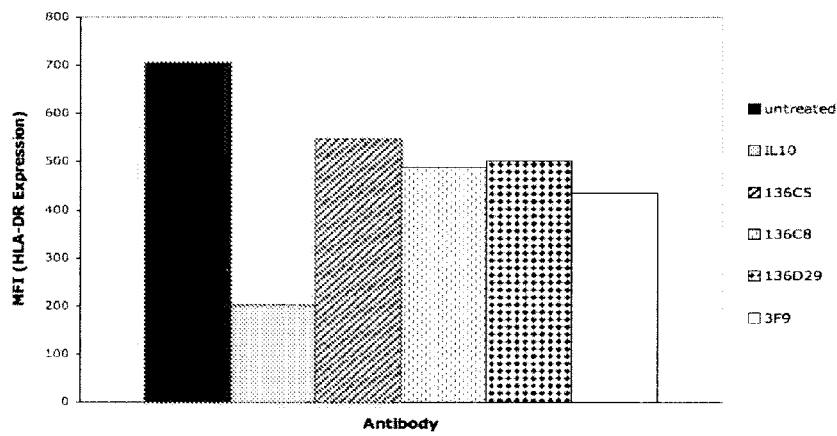
FIGS. 11A-11C show the additional antagonist activity of the human anti-human IL-10Rα antibodies and the lack of agonist activity. A. HLA-DR expression on human PBMC (solid black bar) is decreased by treatment with IL-10 (solid gray bar). Anti-human IL-10Rα antibodies restore HLA-DR expression on PBMC treated with IL-10. Levels of expression are represented as Geometric mean fluorescence intensity. B-C. STAT3 is phosphorylated in human PBMC following treatment with IL-10. B. Left and middle panels. Incubation with 136C8 or a negative control antibody in the presence of IL-10 prevents STAT3 phosphorylation in a dose dependent manner. Doses were 3, 1.5, 0.75, and 0.38 µg/ml. Right panel. Incubation with 3 µg/ml 136C8, 37607, or SPM466 in the presence of IL-10 show different levels of inhibition of STAT3 phosphorylation. C. Incubation with 136C8 in the presence of a crosslinking antibody, anti-hIgG1, and in the absence of IL-10 does not induce STAT3 phosphorylation.

In addition to suppression of cytokine secretion, IL-10 induces the down-regulation of MHC class II and co-stimulatory molecules (de Waal Malefyt, et al., *J Exp Med* 174:1209 (1991); de Waal Malefyt, et al., *J Exp Med* 174:915 (1991)). Treatment of human PBMC with the anti-human IL-10Rα antibodies in the presence of IL-10 partially restored expression of the HLA-DR MHC class II molecule (FIG. 11A). Thus, these antibodies may restore or enhance antigen presentation of IL-10 suppressed antigen presenting cells. Treatment of the PBMC with the antibodies alone had no effect on the level of HLA-DR expression indicating that the antibodies were not agonistic in nature.

Figure 11B:
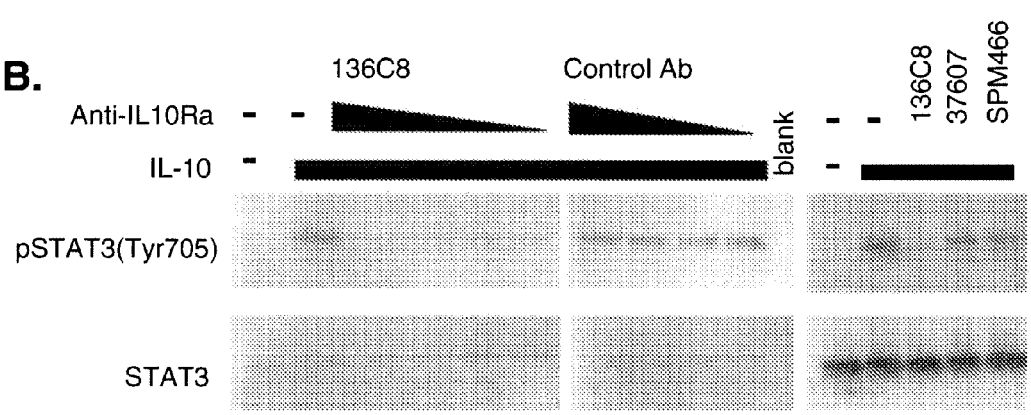
Figure 11C:
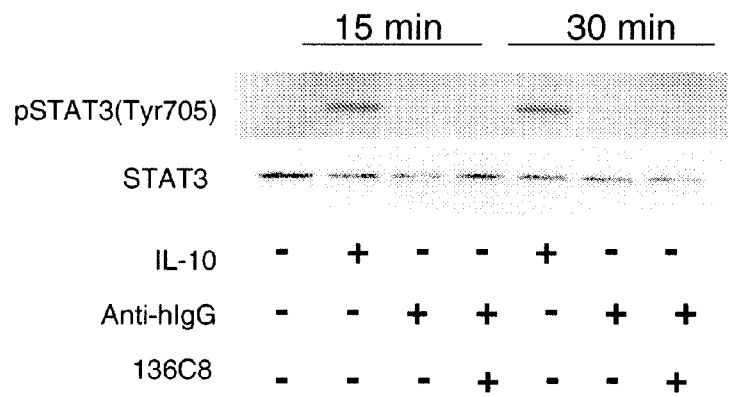

Signaling through the IL-10R results in activation of STAT3, which can be measured by detecting phosphorylation of Tyrosine 705 (phosphoSTAT3) (O'Farrell, et al., *Embo J* 17:1006 (1998); O'Farrell, et al., *J Immunol* 164:4607 (2000); Rahimi, et al., *J Immunol* 174:7823 (2005)). Western blot analysis of lysates from human PBMC stimulated with IL-10 confirmed activation of STAT3. Treatment with the anti-human IL-10Rα antibodies blocked IL-10 induced phosphorylation of STAT3 in a dose dependent manner (FIG. 11B, left panel) and IL-10 inhibition by 136C8 was greater than inhibition by 37607 or SPM466 at the highest dose tested, 3 μg/ml (right panel). These data show that human antibody 136C8 has superior neutralizing (i.e., inhibiting, reducing, antagonizing, preventing or blocking) activity compared to the other antibodies. The antibodies alone did not induce STAT3 activation even when crosslinked with an anti-human IgG antibody (FIG. 11C). These data demonstrate that the anti-human IL-10Rα antibodies can neutralize (i.e., inhibit, reduce, antagonize, prevent or block) many of the pleiotropic effects of IL-10, including TNF-α and IFN-γ induction, HLA-DR expression, and STAT3 activation. In the absence of exogenously added IL-10 the antibodies retain their neutralizing activity and despite binding to IL-10R do not induce the signaling pathways resulting from IL-10 binding to IL-10R.

Example 6

This example includes a description of cross-reactivity with non-human IL-10Rα

Figures 6A, 6B, 6C:
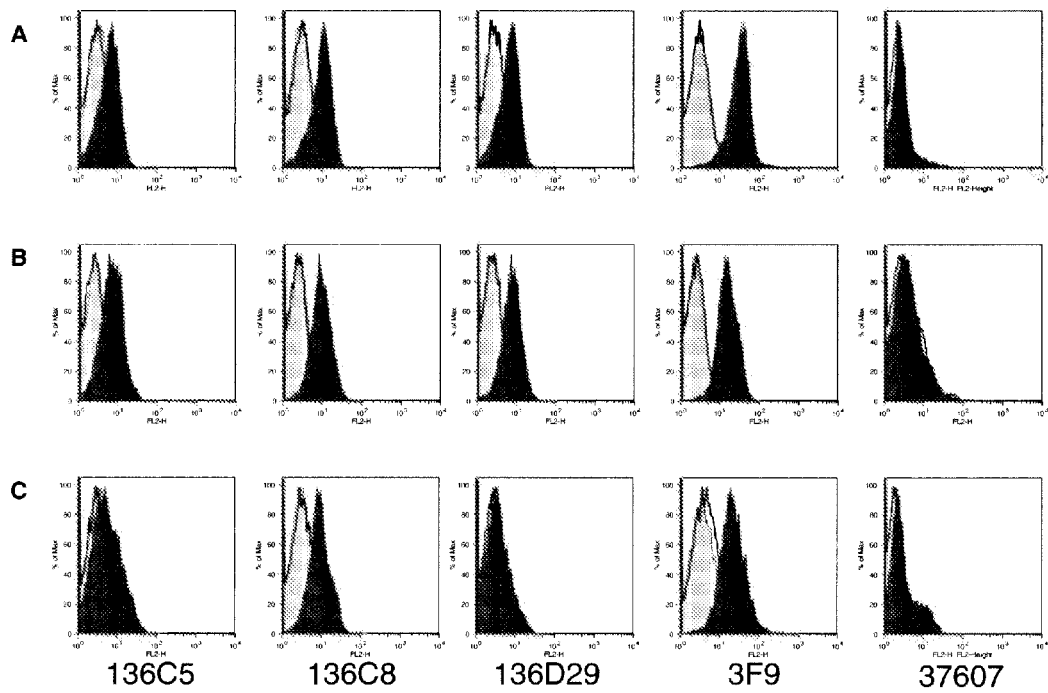
Figures 7A, 7B:
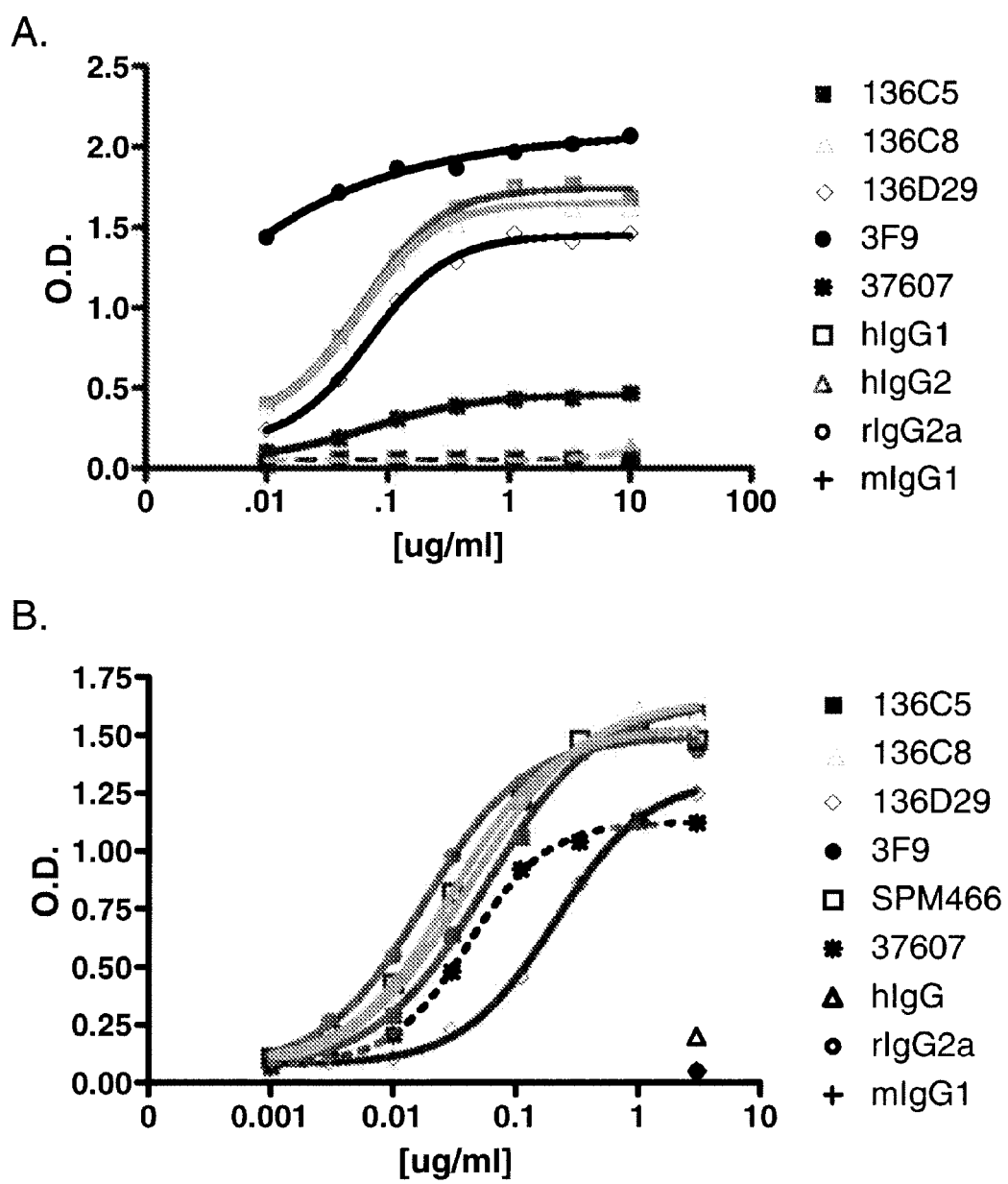
FIG. 7A-7B shows data indicating relative binding affinity of anti-human IL-10R antibodies for chimp IL-10Rα:hFc (panel A) and cynomolgus macaque IL-10Rα:hFc (panel B), as determined by ELISA. Titration of anti-IL-10Rα antibodies binding to coated chimp or cynomolgus IL-10Rα:hFc. Binding was detected with anti-human kappa-HRP, anti-mouse IgG-HRP, or anti-rat IgG-HRP. Different anti-rat-IgG HRP and anti-mouse IgG antibodies were used to generate the data in panels A and B. The nature of these secondary antibodies can affect the results and lead to different maximum binding (BMAX). The BMAX from these studies are described in Table 5.

Additional information about the binding specificity of the human anti-human IL-10Rα monoclonal antibodies was obtained by evaluating the ability of the antibodies to bind to rodent, chimpanzee, and cynomolgus macaque IL-10Rα on primary peripheral blood mononuclear cells (PBMC). Neither the human or commercial anti-human IL-10Rα monoclonal antibodies bound to IL-10Rα on mouse or rat splenocytes. 136C5, 136C8, 136D29 and 3F9 bound to IL-10Rα on the surface of chimpanzee and cynomolgus lymphocytes (FIG. 6) and monocytes. Binding could be inhibited by pre-incubation with recombinant soluble human IL-10Rα:hFc, demonstrating the specific cross-reactivity of the antibodies. Binding of 37607 to human, chimpanzee, and cynomolgus macaque IL-10Rα was barely detectable above the isotype control staining. Binding of 136C5, 136C8, 136D29, 3F9, and 37607 to soluble chimp IL-10Rα:hFc was tested by ELISA and was found to be similar for all antibodies to binding to human IL-10Rα:hFc (FIG. 7A and Table 5). Binding to cynomolgus macaque recombinant IL-10Rα:hFc confirmed the reduced binding of 136D29 and 37607 compared with binding of this antibody to human and chimp IL-10Rα (FIG. 7B and Table 5). In contrast to the flow cytometry data, SPM466 and 3F9 bound well to the soluble recombinant form of cynomolgus IL-10Rα:hFc, indicating differences between the conformation of soluble and surface expressed IL-10Rα and further confirming the uniqueness of the human anti-human IL-10Rα antibodies disclosed herein compared with previously described antibodies.

TABLE 5

Binding (BMAX) of anti-human IL-10Rα monoclonal antibodies to human, chimp, and cynomolgus IL-10Rα

|  | Human | Chimp | Cynomolgus |
|---|---|---|---|
| 136C5[#] | 1.789 | 1.743 | 1.643 |
| 136C8[#] | 1.764 | 1.654 | 1.656 |
| 136D29[#] | 1.646 | 1.449 | 1.315 |
| 3F9* | 2.094 | 2.10 | 1.493 |
| SPM466* | 1.71 | NT | 1.536 |
| 37607* | 0.61 | 0.46 | 1.126 |

Figure 8:
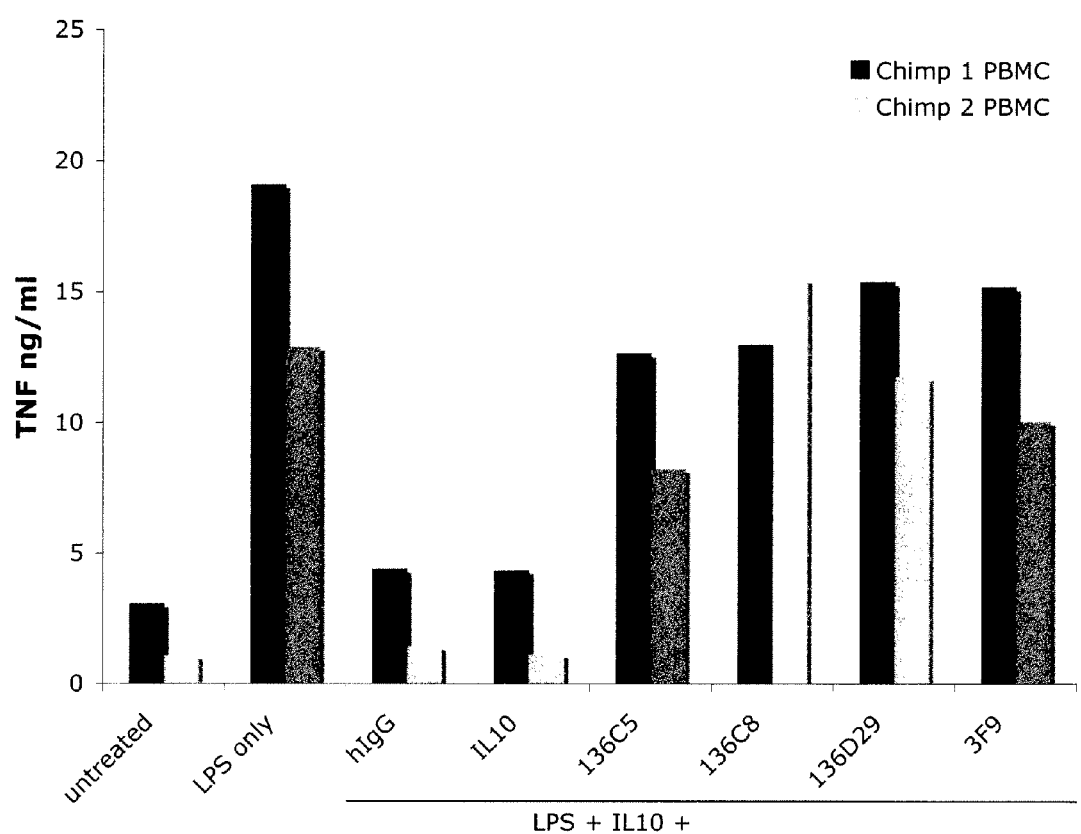
FIG. 8 shows data indicating that anti-IL-10Rα antibodies cross-react with chimpanzee IL-10Rα. LPS induction of TNF-α secretion by chimpanzee PBMC was inhibited by human IL-10. Addition of anti-IL-10Rα neutralized IL-10 suppression of TNF-α secretion. This study was repeated twice with two different donors.
Figures 9A, 9B:
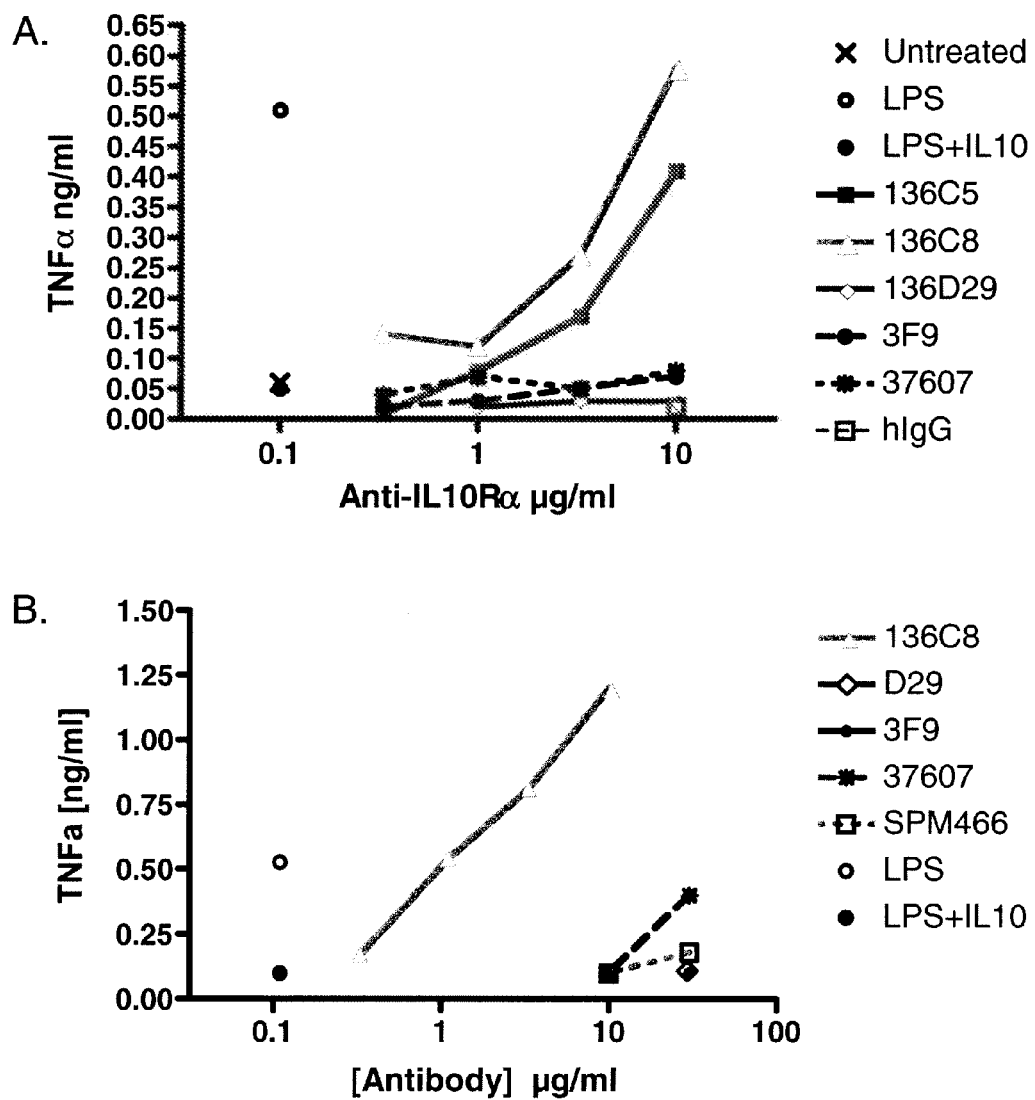
FIGS. 9A-9B show data indicating a subset of IL-10Rα antibodies functionally cross-react with cynomolgus macaque IL-10Rα. LPS induction of TNF-α by cynomolgus PBMC (open circle) was inhibited by human IL-10 (gray circle). Addition of 136C5 and 136C8 neutralized IL-10 and enhanced TNF-α secretion, while 136D29, 3F9, SPM466, and 37607 did not detectably block IL-10 suppression. Panels A and B represent results from two different animals. Similar results have been observed with 5 different donors.

[#]Human anti-human IL-10Rα antibodies
*commercial rat or mouse anti-human IL-10Rα antibodies Antibody binding does not insure functional cross-reactivity. The antibodies were tested in the TNF-α enhancement assay using chimpanzee (FIG. 8) or cynomolgus (FIG. 9) PBMC and recombinant human IL-10. Human IL-10 inhibited LPS induced TNF-α secretion from both chimpanzee and cynomolgus PBMC. 136C5, 136C8, 136D29, and 3F9 neutralized (i.e., inhibited, reduced, antagonized, prevented or blocked) the effects of human IL-10 on chimpanzee TNF-α secretion. These data demonstrate the functional cross-reactivity of the anti-human IL-10Rα monoclonal antibodies with chimpanzee IL-10Rα. The 37607 and SPM466 antibodies were not evaluated in this assay. Differences were observed in the ability of the antibodies to functionally cross-react with cynomolgus IL-10Rα (FIG. 9A-B). Only the human anti-human IL-10Rα monoclonal antibodies 136C5 and 136C8 neutralized the effect of human IL-10 on cynomolgus PBMC. In contrast, 136D29, 3F9, SPM466 and 37607 antibodies did not significantly enhance TNF-α secretion. These results demonstrate that 136C5 and 136C8 functionally neutralize (i.e., inhibit, reduce, antagonize, prevent or block one or more functions) cynomolgus macaque IL-10Rα, while 136D29, 3F9, and 37607 do not neutralize cynomolgus macaque IL-10Rα responses. This is in agreement with the epitope mapping performed by competition ELISA (Table 4), in which 136C5 and 136C8 are in a different group (I) than the other antibodies and clearly demonstrates unique characteristics of these antibodies, placing them in a unique binding group designated group (A). This difference in binding will enable in vivo pre-clinical safety and efficacy studies to be performed in cynomolgus macaques, which will aid in clinical development of anti-IL-10Rα antibody.

Figures 13A, 13B:
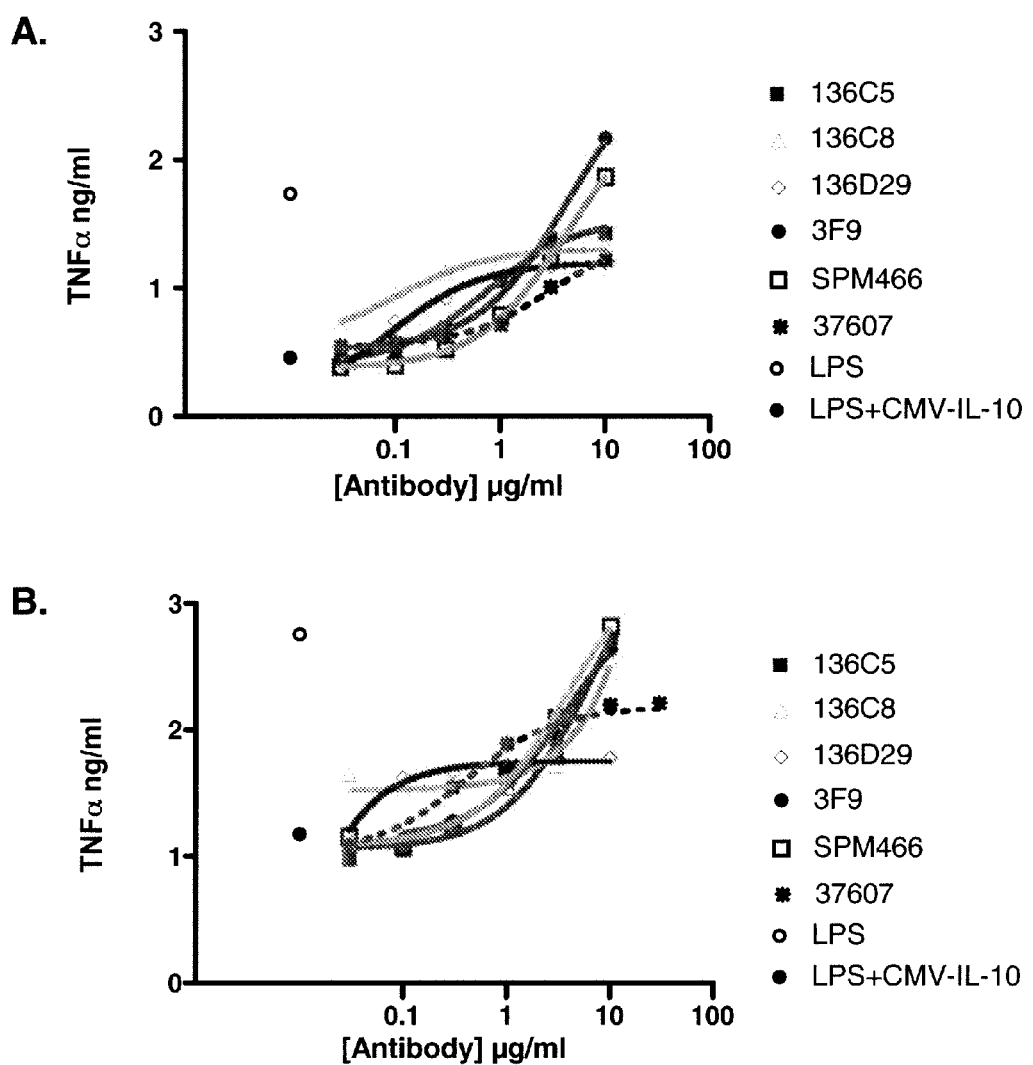
FIG. 13A-13B show data demonstrating the neutralizing activity of anti-human IL-10Rα antibodies for cytomegalovirus IL-10. Addition of 136C5, 136C8, 136D29, 3F9, SPM466, or 37607 to human PBMC treated with LPS+CMV IL-10 restored TNF-α production from two different healthy donors. Panels A and B are data from two donors.

Blockade of viral IL-10 suppression. Human and murine cytomegaloviruses (CMV) encode homologues of IL-10, which are capable of binding IL-10Rα and suppressing immune responses (Redpath, et al., *J Immunol* 162:6701 (1999); Jones, et al., *Proc Natl Acad Sci USA* 99:9404 (2002); Spencer, et al., *J Virol* 76:1285 (2002); Chang, et al., *J Virol* 78:8720 (2004)). IL-10Rα antibodies were tested for their ability to neutralize recombinant CMV IL-10 suppression of LPS-induced TNF-α secretion from PBMC isolated from two donors (FIG. 13A-B). All of the antibodies studies neutralized suppressive activity of CMV IL-10 in vitro. The ability of the antibodies of the invention to neutralize CMV IL-10 indicates that the antibodies can be used as a therapeutic for treatment of latent or acute CMV infection.

---

What is claimed is:

1. An isolated or purified antibody, or fragment thereof, that specifically binds to an Interleukin-10 Receptor alpha protein (IL-10Rα),
   wherein said isolated or purified antibody reduces, inhibits, or competes for, the binding of an antibody selected from the group consisting of (a) and (b) to said IL-10Rα:
   (a) an antibody comprising a heavy chain variable (VH) region with three complementarity determining regions (CDRs) and a light chain variable (VL) region with three CDRs, wherein CDR1, CDR2 and CDR3 of the VH region comprise the amino acid sequences of SEQ ID NOs: 49, 50 and 51, respectively, and wherein CDR1, CDR2 and CDR3 of the VL region comprise the amino acid sequences of SEQ ID NOs: 56, 57 and 58, respectively; and
   (b) an antibody comprising a VH region with three CDRs and a VL region with three CDRs, wherein CDR1, CDR2 and CDR3 of the VH region comprise the amino acid sequences of SEQ ID NOs: 49, 52 and 51, respectively, and wherein CDR1, CDR2 and CDR3 of the VL region comprise the amino acid sequences of SEQ ID NOs: 56, 57 and 58, respectively,
   and wherein said isolated or purified antibody or fragment thereof binds to an epitope distinct from the epitope to which the antibody designated as 3F9 binds.

2. The isolated or purified antibody, or fragment thereof, of claim 1, wherein said isolated or purified antibody, or fragment thereof, reduces, inhibits or competes for, the binding of an antibody selected from the group consisting of (a) and (b) to said IL-10Rα:
   (a) an antibody designated 136C5 or 136C8; and
   (b) an antibody comprising a VH region and a VL region, wherein the VH region comprises the amino acid sequence of SEQ ID NO: 29 or 31, and wherein the VL region comprises the amino acid sequence of SEQ ID NO: 30 or 32.

3. The isolated or purified antibody, or fragment thereof, of claim 1, wherein said isolated or purified antibody, or fragment thereof, is selected from the group consisting of (a) and (b):
   (a) an antibody comprising a VH region with three CDRs and a VL region with three CDRs, wherein CDR1, CDR2 and CDR3 of the VH region comprise the amino acid sequences of SEQ ID NOs: 49, 50 and 51, respectively, and wherein CDR1, CDR2 and CDR3 of the VL region comprise the amino acid sequences of SEQ ID NOs: 56, 57 and 58, respectively; and (b) an antibody comprising a VH region with three CDRs and a VL region with three CDRs, wherein CDR1, CDR2 and CDR3 of the VH region comprise the amino acid sequences of SEQ ID NOs: 49, 52 and 51, respectively, and wherein CDR1, CDR2 and CDR3 of the VL region comprise the amino acid sequences of SEQ ID NOs: 56, 57 and 58, respectively.

4. The isolated or purified antibody, or fragment thereof, of claim 1, wherein said isolated or purified antibody, or fragment thereof, comprises a VH region with an amino acid sequence at least 95% identical to the amino acid sequence of SEQ ID NO: 29 or 31, and a VL region with an amino acid sequence at least 95% identical to the amino acid sequence of SEQ ID NO: 30 or 32.

5. The isolated or purified antibody, or fragment thereof, of claim 1, wherein said IL-10Rα is a human, a chimp, or a macaque IL-10Rα.

6. The isolated or purified antibody, or fragment thereof, of claim 5, wherein said isolated or purified antibody, or fragment thereof binds to an extracellular domain of said IL-10Rα.

7. The isolated or purified antibody, or fragment thereof, of claim 1, wherein said isolated or purified antibody, or fragment thereof, reduces or inhibits interleukin-10 (IL-10) signaling activity.

8. The isolated or purified antibody, or fragment thereof, of claim 7, wherein the IL-10 signaling activity is the activity to increase or induce tumor necrosis factor-alpha (TNF-alpha) or interferon-gamma (IFN-gamma) expression by peripheral blood mononuclear cells (PBMC) or natural killer (NK) T cells in the presence of IL-10, at least partially restore expression of the HLA-DR MI-IC class II molecule in the presence of IL-10, or to inhibit or reduce IL-10 induced phosphorylation of Signal Transducer and Activator of Transcription 3 (STAT3).

9. An isolated or purified antibody, or fragment thereof, that specifically binds to an extracellular domain of a human, a chimp, or a macaque Interleukin-10 Receptor alpha protein (IL-10Rα),
wherein said isolated or purified antibody reduces, inhibits, or competes for, the binding of an antibody selected from the group consisting of (a) and (b) to said IL-10Rα:
(a) an antibody comprising a heavy chain variable (VH) region with three complementarity determining regions (CDRs) and a light chain variable (VL) region with three CDRs, wherein CDR1, CDR2 and CDR3 of the VH region comprise the amino acid sequences of SEQ ID NOs: 49, 50 and 51, respectively, and wherein CDR1, CDR2 and CDR3 of the VL region comprise the amino acid sequences of SEQ ID NOs: 56, 57 and 58, respectively; and
(b) an antibody comprising a VH region with three CDRs and a VL region with three CDRs, wherein CDR1, CDR2 and CDR3 of the VH region comprise the amino acid sequences of SEQ ID NOs: 49, 52 and 51, respectively, and wherein CDR1, CDR2 and CDR3 of the VL region comprise the amino acid sequences of SEQ ID NOs: 56, 57 and 58, respectively,
and wherein said isolated or purified antibody or fragment thereof binds to or recognizes a conformational epitope, and not a linear epitope.

10. An isolated or purified antibody, or fragment thereof, that specifically binds to an Interleukin-10 Receptor alpha protein (IL-10Rα),
wherein said isolated or purified antibody reduces, inhibits, or competes for, the binding of an antibody selected from the group consisting of (a) and (b) to said IL-10Rα:
(a) an antibody comprising a heavy chain variable (VH) region with three complementarity determining regions (CDRs) and a light chain variable (VL) region with three CDRs, wherein CDR1, CDR2 and CDR3 of the VH region comprise the amino acid sequences of SEQ ID NOs: 49, 50 and 51, respectively, and wherein CDR1, CDR2 and CDR3 of the VL region comprise the amino acid sequences of SEQ ID NOs: 56, 57 and 58, respectively; and
(b) an antibody comprising a VH region with three CDRs and a VL region with three CDRs, wherein CDR1, CDR2 and CDR3 of the VH region comprise the amino acid sequences of SEQ ID NOs: 49, 52 and 51, respectively, and wherein CDR1, CDR2 and CDR3 of the VL region comprise the amino acid sequences of SEQ ID NOs: 56, 57 and 58, respectively,
and wherein said isolated or purified antibody or fragment thereof binds to all known IL-10Rα single nucleotide polymorphism (SNP) variants.

11. An isolated or purified antibody, or fragment thereof, that specifically binds to an Interleukin-10 Receptor alpha protein (IL-10Rα),
wherein said isolated or purified antibody reduces, inhibits, or competes for, the binding of an antibody selected from the group consisting of (a) and (b) to said IL-10Rα:
(a) an antibody comprising a heavy chain variable (VH) region with three complementarity determining regions (CDRs) and a light chain variable (VL) region with three CDRs, wherein CDR1, CDR2 and CDR3 of the VH region comprise the amino acid sequences of SEQ ID NOs: 49, 50 and 51, respectively, and wherein CDR1, CDR2 and CDR3 of the VL region comprise the amino acid sequences of SEQ ID NOs: 56, 57 and 58, respectively; and
(b) an antibody comprising a VH region with three CDRs and a VL region with three CDRs, wherein CDR1, CDR2 and CDR3 of the VH region comprise the amino acid sequences of SEQ ID NOs: 49, 52 and 51, respectively, and wherein CDR1, CDR2 and CDR3 of the VL region comprise the amino acid sequences of SEQ ID NOs: 56, 57 and 58, respectively,
and wherein said antibody or fragment thereof binds to IL-10Rα variant R212E with greater affinity than an antibody selected from the group consisting of 136D29, 3F9, SPM466 and 37607.

12. An isolated or purified antibody, or fragment thereof, that specifically binds to an Interleukin-10 Receptor alpha protein (IL-10Rα),
wherein said isolated or purified antibody reduces, inhibits, or competes for, the binding of an antibody selected from the group consisting of (a) and (b) to said IL-10Rα:
(a) an antibody comprising a heavy chain variable (VH) region with three complementarity determining regions (CDRs) and a light chain variable (VL) region with three CDRs, wherein CDR1, CDR2 and CDR3 of the VH region comprise the amino acid sequences of SEQ ID NOs: 49, 50 and 51, respectively, and wherein CDR1, CDR2 and CDR3 of the VL region comprise the amino acid sequences of SEQ ID NOs: 56, 57 and 58, respectively; and
(b) an antibody comprising a VH region with three CDRs and a VL region with three CDRs, wherein CDR1, CDR2 and CDR3 of the VH region comprise the amino acid sequences of SEQ ID NOs: 49, 52 and 51, respectively, and wherein CDR1, CDR2 and CDR3 of the VL region comprise the amino acid sequences of SEQ ID NOs: 56, 57 and 58, respectively, and wherein said isolated or purified antibody or fragment thereof reverses or inhibits the interleukin-10 (IL-10) inhibition of tumor necrosis factor-alpha (TNF alpha) expression or secretion by human peripheral blood mononuclear cells (PBMC) treated with lipopolysaccharide (LPS).

13. An isolated or purified antibody, or fragment thereof, that specifically binds to an Interleukin-10 Receptor alpha protein (IL-10Rα), wherein said isolated or purified antibody reduces, inhibits, or competes for, the binding of an antibody selected from the group consisting of (a) and (b) to said IL-10Rα:

(a) an antibody comprising a heavy chain variable (VH) region with three complementarity determining regions (CDRs) and a light chain variable (VL) region with three CDRs, wherein CDR1, CDR2 and CDR3 of the VH region comprise the amino acid sequences of SEQ ID NOs: 49, 50 and 51, respectively, and wherein CDR1, CDR2 and CDR3 of the VL region comprise the amino acid sequences of SEQ ID NOs: 56, 57 and 58, respectively; and (b) an antibody comprising a VH region with three CDRs and a VL region with three CDRs, wherein CDR1, CDR2 and CDR3 of the VH region comprise the amino acid sequences of SEQ ID NOs: 49, 52 and 51, respectively, and wherein CDR1, CDR2 and CDR3 of the VL region comprise the amino acid sequences of SEQ ID NOs: 56, 57 and 58, respectively, and wherein said isolated or purified antibody or fragment thereof increases tumor necrosis factor-alpha (TNF-alpha), interleukin-6 (IL-6), interleukin-1 β(IL-1 β) or interferon-gamma (IFN-gamma) expression, or secretion by human, chimpanzee or macaque peripheral blood mononuclear cells (PBMCs) treated with lipopolysaccharide (LPS) in vitro in the presence of interleukin-10 (IL-10).

* * * * *